(12) United States Patent
Baron et al.

(10) Patent No.: US 9,938,229 B2
(45) Date of Patent: *Apr. 10, 2018

(54) POLYMERISABLE COMPOUNDS AND THE USE THEREOF IN LIQUID-CRYSTAL DISPLAYS

(71) Applicant: MERCK PATENT GMBH, Darmstadt (DE)

(72) Inventors: Eveline Baron, Darmstadt (DE); Julian Vogt, Griesheim (DE); Qiong Tong, Darmstadt (DE); Constanze Brocke, Gross-Gerau (DE); Helga Haas, Lampertheim (DE); Alexander Hahn, Biebesheim (DE)

(73) Assignee: MERCK PATENT GMBH, Darmstadt (DE)

( * ) Notice: Subject to any disclaimer, the term of this patent is extended or adjusted under 35 U.S.C. 154(b) by 69 days.

This patent is subject to a terminal disclaimer.

(21) Appl. No.: 14/812,070

(22) Filed: Jul. 29, 2015

(65) Prior Publication Data

US 2016/0032189 A1 Feb. 4, 2016

(30) Foreign Application Priority Data

Jul. 30, 2014 (EP) .................... 14002646

(51) Int. Cl.
| | | |
|---|---|---|
| *G02F 1/1333* | (2006.01) | |
| *C07C 69/65* | (2006.01) | |
| *C09K 19/30* | (2006.01) | |
| *C08F 222/20* | (2006.01) | |
| *C08F 222/10* | (2006.01) | |
| *C07C 69/54* | (2006.01) | |
| *C09K 19/04* | (2006.01) | |
| *C09K 19/12* | (2006.01) | |
| *C09K 19/06* | (2006.01) | |
| *C07C 69/653* | (2006.01) | |
| *C07C 69/94* | (2006.01) | |
| *C09K 19/54* | (2006.01) | |
| *G02F 1/137* | (2006.01) | |

(52) U.S. Cl.
CPC .............. *C07C 69/65* (2013.01); *C07C 69/54* (2013.01); *C07C 69/653* (2013.01); *C07C 69/94* (2013.01); *C08F 222/10* (2013.01); *C08F 222/20* (2013.01); *C09K 19/04* (2013.01); *C09K 19/062* (2013.01); *C09K 19/12* (2013.01); *C09K 19/30* (2013.01); *C09K 19/3003* (2013.01); *C09K 19/3066* (2013.01); *C09K 19/3098* (2013.01); *C09K 2019/0448* (2013.01); *C09K 2019/0481* (2013.01); *C09K 2019/122* (2013.01); *C09K 2019/123* (2013.01); *C09K 2019/301* (2013.01); *C09K 2019/3004* (2013.01); *C09K 2019/3009* (2013.01); *C09K 2019/3016* (2013.01); *C09K 2019/3027* (2013.01); *C09K 2019/548* (2013.01); *G02F 2001/13775* (2013.01)

(58) Field of Classification Search
CPC ............ C09K 19/3003; C09K 19/3066; C09K 19/3098; C09K 19/04; C09K 19/12; C09K 19/30; C09K 19/062; C09K 2019/3004; C09K 2019/3009; C09K 2019/301; C09K 2019/3016; C09K 2019/548; C09K 2019/0448; C09K 2019/0481; C09K 2019/122; C09K 2019/123; C09K 2019/3027; G02F 1/1333; G02F 2001/13775; C07C 69/65; C07C 69/54; C07C 69/653; C07C 69/94; C08F 222/10; C08F 222/20
USPC ........................ 252/299.01, 299.6; 428/1.1
See application file for complete search history.

(56) References Cited

U.S. PATENT DOCUMENTS

| | | | |
|---|---|---|---|
| 6,124,908 A | 9/2000 | Kobayashi et al. | |
| 2010/0304015 A1 | 12/2010 | Kim et al. | |
| 2013/0277609 A1 | 10/2013 | Goto et al. | |
| 2015/0070609 A1* | 3/2015 | Baron .................... | C09K 19/12 349/33 |

FOREIGN PATENT DOCUMENTS

| | | |
|---|---|---|
| EP | 2848676 A2 | 3/2015 |
| JP | 2013 148712 A | 8/2013 |
| JP | 2014 196265 A | 10/2014 |
| WO | 2014174929 A1 | 10/2014 |

OTHER PUBLICATIONS

Search Report dated Oct. 16, 2015 issued in corresponding application EP 15 00 2149 (pp. 1-3).
Y. Qiu, et al., "Application of organic electroluminescent material", Chemical Abstracts Service, XP002746801, pp. 1.
Y. Furusato, et al., "Liquid crystal composition and liquid crystal display element containing it", Chemical Abstracts Service, XP002746802, pp. 1-2.
M. Kobayashi, et al., "Linearly aligned ring polymerizable compounds, polymerizable compositions containing them, liquid crystal composites and optical isomers prepared from them, their use, and liquid crystal displays using them", Chemical Abstracts Service, XP002746803, pp. 1-2.

* cited by examiner

*Primary Examiner* — Geraldina Visconti
(74) *Attorney, Agent, or Firm* — Millen White Zelano and Branigan, PC; Csaba Henter

(57) ABSTRACT

The present invention relates to polymerizable compounds, to processes and intermediates for the preparation thereof, to liquid-crystal (LC) media comprising them, and to the use of the polymerizable compounds and LC media for optical, electro-optical and electronic purposes, in particular in LC displays, especially in LC displays of the polymer sustained alignment type.

25 Claims, No Drawings

POLYMERISABLE COMPOUNDS AND THE USE THEREOF IN LIQUID-CRYSTAL DISPLAYS

The present invention relates to polymerisable compounds, to processes and intermediates for the preparation thereof, to liquid-crystal (LC) media comprising them, and to the use of the polymerisable compounds and LC media for optical, electro-optical and electronic purposes, in particular in LC displays, especially in LC displays of the polymer sustained alignment type.

BACKGROUND OF THE INVENTION

The liquid-crystal displays (LC displays) used at present are usually those of the TN ("twisted nematic") type. However, these have the disadvantage of a strong viewing-angle dependence of the contrast.

In addition, so-called VA ("vertically aligned") displays are known which have a broader viewing angle. The LC cell of a VA display contains a layer of an LC medium between two transparent electrodes, where the LC medium usually has a negative dielectric anisotropy. In the switched-off state, the molecules of the LC layer are aligned perpendicular to the electrode surfaces (homeotropically) or have a tilted homeotropic alignment. On application of an electrical voltage to the two electrodes, a realignment of the LC molecules parallel to the electrode surfaces takes place.

Furthermore, OCB ("optically compensated bend") displays are known which are based on a birefringence effect and have an LC layer with a so-called "bend" alignment and usually positive dielectric anisotropy. On application of an electrical voltage, a realignment of the LC molecules perpendicular to the electrode surfaces takes place. In addition, OCB displays normally contain one or more birefringent optical retardation films in order to prevent undesired transparency to light of the bend cell in the dark state. OCB displays have a broader viewing angle and shorter response times compared with TN displays.

Also known are so-called IPS ("in-plane switching") displays, which contain an LC layer between two substrates, where the two electrodes are arranged on only one of the two substrates and preferably have intermeshed, comb-shaped structures. On application of a voltage to the electrodes, an electric field which has a significant component parallel to the LC layer is thereby generated between them. This causes realignment of the LC molecules in the layer plane.

Furthermore, so-called FFS ("fringe-field switching") displays have been reported (see, inter alia, S. H. Jung et al., Jpn. J. Appl. Phys., Volume 43, No. 3, 2004, 1028), which contain two electrodes on the same substrate, one of which structured in a comb-shaped manner and the other is unstructured. A strong, so-called "fringe field" is thereby generated, i.e. a strong electric field close to the edge of the electrodes, and, throughout the cell, an electric field which has both a strong vertical component and also a strong horizontal component. FFS displays have a low viewing-angle dependence of the contrast. FFS displays usually contain an LC medium with positive dielectric anisotropy, and an alignment layer, usually of polyimide, which provides planar alignment to the molecules of the LC medium.

FFS displays can be operated as active-matrix or passive-matrix displays. In the case of active-matrix displays, individual pixels are usually addressed by integrated, non-linear active elements, such as, for example, transistors (for example thin-film transistors ("TFTs")), while in the case of passive-matrix displays, individual pixels are usually addressed by the multiplex method, as known from the prior art.

Furthermore, FFS displays have been disclosed (see S. H. Lee et al., Appl. Phys. Lett. 73(20), 1998, 2882-2883 and S. H. Lee et al., Liquid Crystals 39(9), 2012, 1141-1148), which have similar electrode design and layer thickness as FFS displays, but comprise a layer of an LC medium with negative dielectric anisotropy instead of an LC medium with positive dielectric anisotropy. The LC medium with negative dielectric ansiotropy shows a more favourable director orientation that has less tilt and more twist orientation compared to the LC medium with positive dielectric anisotropy, as a result of which these displays have a higher transmission. The displays further comprise an alignment layer, preferably of polyimide provided on at least one of the substrates that is in contact with the LC medium and induces planar alignment of the LC molecules of the LC medium. These displays are also known as "Ultra Brightness FFS (UB-FFS)" mode displays. These displays require an LC medium with high reliability.

The term "reliability" as used hereinafter means the quality of the performance of the display during time and with different stress loads, such as light load, temperature, humidity, voltage, and comprises display effects such as image sticking (area and line image sticking), mura, yogore etc. which are known to the skilled person in the field of LC displays. As a standard parameter for categorising the reliability usually the voltage holding ration (VHR) value is used, which is a measure for maintaining a constant electrical voltage in a test display. The higher the VHR value, the better the reliability of the LC medium.

In VA displays of the more recent type, uniform alignment of the LC molecules is restricted to a plurality of relatively small domains within the LC cell. Disclinations may exist between these domains, also known as tilt domains. VA displays having tilt domains have, compared with conventional VA displays, a greater viewing-angle independence of the contrast and the grey shades. In addition, displays of this type are simpler to produce since additional treatment of the electrode surface for uniform alignment of the molecules in the switched-on state, such as, for example, by rubbing, is no longer necessary. Instead, the preferential direction of the tilt or pretilt angle is controlled by a special design of the electrodes.

In so-called MVA ("multidomain vertical alignment") displays, this is usually achieved by the electrodes having protrusions which cause a local pretilt. As a consequence, the LC molecules are aligned parallel to the electrode surfaces in different directions in different, defined regions of the cell on application of a voltage. "Controlled" switching is thereby achieved, and the formation of interfering disclination lines is prevented. Although this arrangement improves the viewing angle of the display, it results, however, in a reduction in its transparency to light. A further development of MVA uses protrusions on only one electrode side, while the opposite electrode has slits, which improves the transparency to light. The slitted electrodes generate an inhomogeneous electric field in the LC cell on application of a voltage, meaning that controlled switching is still achieved. For further improvement of the transparency to light, the separations between the slits and protrusions can be increased, but this in turn results in a lengthening of the response times. In so-called PVA ("patterned VA") displays, protrusions are rendered completely superfluous in that both electrodes are structured by means of slits on the opposite sides, which results in increased contrast and improved transparency to light, but is technologically difficult and makes the display more sensitive to mechanical influences ("tapping", etc.). For many applications, such as, for example, monitors and especially TV screens, however, a shortening of the response times and an improvement in the contrast and luminance (transmission) of the display are demanded.

A further development are displays of the so-called PS ("polymer sustained") or PSA ("polymer sustained alignment") type, for which the term "polymer stabilised" is also occasionally used. In these, a small amount (for example 0.3% by weight, typically <1% by weight) of one or more polymerisable, compound(s), preferably polymerisable monomeric compound(s), is added to the LC medium and, after filling the LC medium into the display, is polymerised or crosslinked in situ, usually by UV photopolymerisation, optionally while a voltage is applied to the electrodes of the display. The polymerisation is carried out at a temperature where the LC medium exhibits a liquid crystal phase, usually at room temperature. The addition of polymerisable mesogenic or liquid-crystalline compounds, also known as reactive mesogens or "RMs", to the LC mixture has proven particularly suitable.

Unless indicated otherwise, the term "PSA" is used hereinafter when referring to displays of the polymer sustained alignment type in general, and the term "PS" is used when referring to specific display modes, like PS-VA, PS-TN and the like.

Also, unless indicated otherwise, the term "RM" is used hereinafter when referring to a polymerisable mesogenic or liquid-crystalline compound.

In the meantime, the PS(A) principle is being used in various conventional LC display modes. Thus, for example, PS-VA, PS-OCB, PS-IPS, PS-FFS, PS-UB-FFS and PS-TN displays are known. The polymerisation of the RMs preferably takes place with an applied voltage in the case of PS-VA and PS-OCB displays, and with or without, preferably without, an applied voltage in the case of PS-IPS displays. As can be demonstrated in test cells, the PS(A) method results in a pretilt in the cell. In the case of PS-OCB displays, for example, it is possible for the bend structure to be stabilised so that an offset voltage is unnecessary or can be reduced. In the case of PS-VA displays, the pretilt has a positive effect on response times. For PS-VA displays, a standard MVA or PVA pixel and electrode layout can be used. In addition, however, it is also possible, for example, to manage with only one structured electrode side and no protrusions, which significantly simplifies production and at the same time results in very good contrast at the same time as very good transparency to light.

Furthermore, the so-called posi-VA displays ("positive VA") have proven to be a particularly suitable mode. Like in classical VA displays, the initial orientation of the LC molecules in posi-VA displays is homeotropic, i.e. substantially perpendicular to the substrates, in the initial state when no voltage is applied. However, in contrast to classical VA displays, in posi-VA displays LC media with positive dielectric anisotropy are used. Like in the usually used IPS displays, the two electrodes in posi-VA displays are arranged on only one of the two substrates, and preferably exhibit intermeshed and comb-shaped (interdigital) structures. By application of a voltage to the interdigital electrodes, which create an electrical field that is substantially parallel to the layer of the LC medium, the LC molecules are transferred into an orientation that is substantially parallel to the substrates. In posi-VA displays polymer stabilisation, by addition of RMs to the LC medium which are polymerised in the display, has also proven to be advantageous, as a significant reduction of the switching times could thereby be realised.

PS-VA displays are described, for example, in EP 1 170 626 A2, U.S. Pat. No. 6,861,107, U.S. Pat. No. 7,169,449, US 2004/0191428 A1, US 2006/0066793 A1 and US 2006/0103804 A1. PS-OCB displays are described, for example, in T.-J-Chen et al., Jpn. J. Appl. Phys. 45, 2006, 2702-2704 and S. H. Kim, L.-C-Chien, Jpn. J. Appl. Phys. 43, 2004, 7643-7647. PS-IPS displays are described, for example, in U.S. Pat. No. 6,177,972 and Appl. Phys. Lett. 1999, 75(21), 3264. PS-TN displays are described, for example, in Optics Express 2004, 12(7), 1221.

Like the conventional LC displays described above, PSA displays can be operated as active-matrix or passive-matrix displays. In the case of active-matrix displays, individual pixels are usually addressed by integrated, non-linear active elements, such as, for example, transistors (for example thin-film transistors ("TFTs")), while in the case of passive-matrix displays, individual pixels are usually addressed by the multiplex method, as known from the prior art.

The PSA display may also comprise an alignment layer on one or both of the substrates forming the display cell. The alignment layer is usually applied on the electrodes (where such electrodes are present) such that it is in contact with the LC medium and induces initial alignment of the LC molecules. The alignment layer may comprise or consist of, for example, a polyimide, which may also be rubbed, or may be prepared by a photoalignment method.

In particular for monitor and especially TV applications, optimisation of the response times, but also of the contrast and luminance (thus also transmission) of the LC display continues to be demanded. The PSA method can provide significant advantages here. In particular in the case of PS-VA, PS-IPS, PS-FFS and PS-posi-VA displays, a shortening of the response times, which correlate with a measurable pretilt in test cells, can be achieved without significant adverse effects on other parameters.

Prior art has suggested biphenyl diacrylates or dimethacrylates, which are optionally fluorinated as RMs for use in PSA displays However, the problem arises that not all combinations consisting of an LC mixture and one or more RMs are suitable for use in PSA displays because, for example, an inadequate tilt or none at all becomes established or since, for example, the so-called "voltage holding ratio" (VHR or HR) is inadequate for TFT display applications. In addition, it has been found that, on use in PSA displays, the LC mixtures and RMs known from the prior art do still have some disadvantages. Thus, not every known RM which is soluble in LC mixtures is suitable for use in PSA displays. In addition, it is often difficult to find a suitable selection criterion for the RM besides direct measurement of the pretilt in the PSA display. The choice of suitable RMs becomes even smaller if polymerisation by means of UV light without the addition of photoinitiators is desired, which may be advantageous for certain applications.

In addition, the selected combination of LC host mixture/RM should have the lowest possible rotational viscosity and the best possible electrical properties. In particular, it should have the highest possible VHR. In PSA displays, a high VHR after irradiation with UV light is particularly necessary since UV exposure is a requisite part of the display production process, but also occurs as normal exposure during operation of the finished display.

In particular, it would be desirable to have available novel materials for PSA displays which produce a particularly small pretilt angle. Preferred materials here are those which produce a lower pretilt angle during polymerisation for the same exposure time than the materials known to date, and/or through the use of which the (higher) pretilt angle that can be achieved with known materials can already be achieved after a shorter exposure time. The production time ("tact time") of the display could thus be shortened and the costs of the production process reduced.

A further problem in the production of PSA displays is the presence or removal of residual amounts of unpolymerised RMs, in particular after the polymerisation step for production of the pretilt angle in the display. For example, unreacted RMs of this type may adversely affect the properties of the display by, for example, polymerising in an uncontrolled manner during operation after finishing of the display.

Thus, the PSA displays known from the prior art often exhibit the undesired effect of so-called "image sticking" or "image burn", i.e. the image produced in the LC display by temporary addressing of individual pixels still remains visible even after the electric field in these pixels has been switched off or after other pixels have been addressed.

This "image sticking" can occur on the one hand if LC host mixtures having a low VHR are used. The UV component of daylight or the backlighting can cause undesired decomposition reactions of the LC molecules therein and thus initiate the production of ionic or free-radical impurities. These may accumulate, in particular, at the electrodes or the alignment layers, where they may reduce the effective applied voltage. This effect can also be observed in conventional LC displays without a polymer component.

In addition, an additional "image sticking" effect caused by the presence of unpolymerised RMs is often observed in PSA displays. Uncontrolled polymerisation of the residual RMs is initiated here by UV light from the environment or by the backlighting. In the switched display areas, this changes the tilt angle after a number of addressing cycles. As a result, a change in transmission in the switched areas may occur, while it remains unchanged in the unswitched areas.

It is therefore desirable for the polymerisation of the RMs to proceed as completely as possible during production of the PSA display and for the presence of unpolymerised RMs in the display to be excluded as far as possible or reduced to a minimum. Thus, RMs and LC mixtures are required which enable or support highly effective and complete polymerisation of the RMs. In addition, controlled reaction of the residual RM amounts would be desirable. This would be simpler if the RM polymerised more rapidly and effectively than the compounds known to date.

A further problem that has been observed in the operation of PSA displays is the stability of the pretilt angle. Thus, it was observed that the pretilt angle, which was generated during display manufacture by polymerising the RM as described above, does not remain constant but can deteriorate after the display was subjected to voltage stress during its operation. This can negatively affect the display performance, e.g. by increasing the black state transmission and hence lowering the contrast.

Another problem to be solved is that the RMs of prior art do often have high melting points, and do only show limited solubility in many currently common LC mixtures, and therefore frequently tend to spontaneously crystallise out of the mixture. In addition, the risk of spontaneous polymerisation prevents the LC host mixture being warmed in order to dissolve the polymerisable component, meaning that the best possible solubility even at room temperature is necessary. In addition, there is a risk of separation, for example on introduction of the LC medium into the LC display (chromatography effect), which may greatly impair the homogeneity of the display. This is further increased by the fact that the LC media are usually introduced at low temperatures in order to reduce the risk of spontaneous polymerisation (see above), which in turn has an adverse effect on the solubility.

Another problem observed in prior art is that LC media for use in PSA displays, including but not limited to displays of the PSA type, do often exhibit high viscosities and, as a consequence, high switching times. In order to reduce the viscosity and switching time of the LC medium, it has been suggested in prior art to add LC compounds with an alkenyl group. However, it was observed that LC media containing alkenyl compounds often show a decrease of the reliability and stability, and a decrease of the VHR especially after exposure to UV radiation. Especially for use in PSA displays this is a considerable disadvantage, because the photopolymerisation of the RMs in the PSA display is usually carried out by exposure to UV radiation, which may cause a VHR drop in the LC medium.

There is thus still a great demand for PSA displays and LC media and polymerisable compounds for use in such displays, which do not show the drawbacks as described above, or only do so to a small extent, and have improved properties. In particular, there is a great demand for PSA displays, and LC media and polymerisable compounds for use in such PSA displays, which enable a high specific resistance at the same time as a large working-temperature range, short response times, even at low temperatures, and a low threshold voltage, a low pretilt angle, a multiplicity of grey shades, high contrast and a broad viewing angle, have high reliability and high values for the "voltage holding ratio" (VHR) after UV exposure, and, in case of the polymerisable compounds, have low melting points and a high solubility in the LC host mixtures.

The invention is based on the object of providing novel suitable materials, in particular RMs and LC media comprising same, for use in PSA displays, which do not have the disadvantages indicated above or do so to a reduced extent, polymerise as rapidly and completely as possible, enable a low pretilt angle to be established as quickly as possible, reduce or prevent the occurrence of "image sticking" in the display, and preferably at the same time enable very high specific resistance values, high VHR values, low threshold voltages and short response times, and have a high solubility in the LC media which are typically used as host mixtures in PSA displays.

A further object of the invention is the provision of novel RMs, in particular for optical, electro-optical and electronic applications, and of suitable processes and intermediates for the preparation thereof.

In particular, the invention is based on the object of providing polymerisable compounds like RMs for use in PSA displays, which do not have the disadvantages indicated above or do so to a reduced extent, polymerise as rapidly and completely as possible, enable a low pretilt angle to be established as quickly as possible, show a high stability of the pretilt even after longer time and/or after UV exposure, reduce or prevent the occurrence of "image sticking" in the display, and preferably at the same time enable very high specific resistance values, high VHR values, high reliability, low threshold voltages and short response times, show good UV absorption especially at longer wavelengths, preferably in the range 320-360 nm, and have a high solubility in the LC media which are typically used as host mixtures in PSA displays.

A further object of the invention is the provision of novel RMs, in particular for optical, electro-optical and electronic applications, and of suitable processes and intermediates for the preparation thereof.

This object has been achieved in accordance with the present invention by materials and processes as described in the present application. In particular, it has been found, surprisingly, that the use of RMs of formula I as described hereinafter in PSA displays facilitates a quick polymerisation reaction, fast establishment of a stable tilt angle, and a high VHR value after UV photopolymerisation.

It was found that the use of RMs according to the present invention enable quick generation of a stable pretilt even without the addition of photoinitiator, and show high VHR values after irradiation with UV light and high reliability, especially when used in LC host mixtures containing LC compounds with an alkenyl group. The use of the RMs according to the present invention in such LC host mixtures enables high VHR values. In addition, the RMs compounds according to the invention have a good solubility in a wide range of LC media, especially in commercially available LC host mixtures for PSA use, and have a low tendency to crystallisation. Besides, they show good absorption at longer UV wavelengths, especially in the range from 300-380 nm, in particular at wavelengths of 340 nm or higher, and enable a quick and complete polymerisation with small amounts of residual, unreacted RMs in the cell.

SUMMARY OF THE INVENTION

The invention relates to polymerisable compounds of formula I

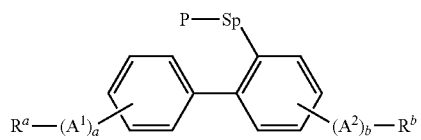

I in which the individual radicals have the following meanings $A^1$, $A^2$ denote, independently of each other, aryl or heteroaryl having 4 to 30 ring atoms, which is mono- or polycyclic and may also contain further substituents, $R^a$, $R^b$ denote, independently of each other, P-Sp-, H, F, Cl, CN, or straight chain, branched or cyclic alkyl having 1 to 25 C atoms, wherein one or more non-adjacent $CH_2$-groups are optionally replaced by —O—, —S—, —CO—, —CO—O—, —O—CO—, —O—CO—O— in such a manner that O- and/or S-atoms are not directly connected with each other, and wherein one or more H atoms are each optionally replaced by F, Cl or P-Sp-, Sp denotes, on each occurrence identically or differently, a spacer group or a single bond, P denotes, on each occurrence identically or differently, a polymerisable group, a, b denote, independently of each other, 0, 1 or 2, wherein all the benzene groups in the compound of formula I are optionally substituted by one or more groups L, wherein L denotes P—, P-Sp-, F, Cl, —CN, —$NO_2$, —NCO, —NCS, —OCN, —SCN, —C(=O)N($R^x$)$_2$, —C(=O) $Y^1$, —C(=O)$R^x$, —N($R^x$)$_2$, optionally substituted silyl, optionally substituted aryl or heteroaryl having 5 to 20 ring atoms, or straight-chain or branched alkyl having 1 to 25 C atoms, in which one or more non-adjacent $CH_2$ groups are optionally each replaced, independently of one another, by —C($R^0$)=C($R^{00}$)—, —C≡C—, —N($R^0$)—, —O—, —S—, —CO—, —CO—O—, —O—CO—, or —O—CO—O— in such a way that O and/or S atoms are not linked directly to one another, and in which one or more H atoms are optionally replaced by F, Cl, CN, P— or P-Sp-, $R^x$ denotes H, F, Cl, CN, or a straight chain, branched or cyclic alkyl having 1 to 25 C atoms, wherein one or more non-adjacent $CH_2$-groups are optionally replaced by —O—, —S—, —CO—, —CO—O—, —O—CO—, or —O—CO—O— in such a manner that O- and/or S-atoms are not directly connected with each other, and wherein one or more H atoms are each optionally replaced by F, Cl, P— or P-Sp-, $R^0$ and $R^{00}$ each, independently of one another, denote H or alkyl having 1 to 20 C atoms, and $Y^1$ is halogen.

The invention further relates to the use of compounds of formula I as polymerisable compounds in LC media and LC displays, especially in the LC medium, active layer or alignment layer of an LC display, wherein the LC displays are preferably PSA displays.

The invention further relates to methods for preparing compounds of formula I, and to novel intermediates used or obtained in these methods.

The invention furthermore relates to an LC medium comprising one or more compounds of formula I.

The invention furthermore relates to an LC medium comprising one or more polymerisable compounds, at least one of which is a compound of formula I.

The invention furthermore relates to an LC medium comprising
a polymerisable component A) comprising, preferably consisting of, one or more polymerisable compounds, at least one of which is a compound of formula I, and
a liquid-crystalline component B), hereinafter also referred to as "LC host mixture", comprising, preferably consisting of, one or more mesogenic or liquid-crystalline compounds.

The liquid-crystalline component B) of an LC medium according to the present invention is hereinafter also referred to as "LC host mixture", and preferably comprises, or consists of, one or more, preferably at least two mesogenic or LC compounds selected from low-molecular-weight compounds which are unpolymerisable.

The invention furthermore relates to an LC medium as described above and below, wherein the LC host mixture or component B comprises at least one mesogenic or LC compound comprising an alkenyl group.

The invention furthermore relates to an LC medium or LC display as described above, wherein the compounds of formula I are polymerised.

The invention furthermore relates to a process for preparing an LC medium as described above and below, comprising the steps of mixing one or more mesogenic or LC compounds, or an LC host mixture or LC component B) as described above and below, with one or more compounds of formula I, and optionally with further LC compounds and/or additives.

The invention furthermore relates to the use of compounds of formula I and LC media according to the invention in PSA displays, in particular the use in PSA displays containing an LC medium, for the production of a tilt angle in the LC medium by in-situ polymerisation of the compound(s) of the formula I in the PSA display, preferably in an electric or magnetic field.

The invention furthermore relates to an LC display comprising one or more compounds of formula I or an LC medium according to the invention, in particular a PSA display, particularly preferably a PS-VA, PS-OCB, PS-IPS, PS-FFS, PS-UB-FFS, PS-posi-VA or PS-TN display.

The invention furthermore relates to an LC display comprising a polymer obtainable by polymerisation of one or more compounds of formula I or of a polymerisable component A) as described above, or comprising an LC medium according to the invention, which is preferably a PSA display, very preferably a PS-VA, PS-OCB, PS-IPS, PS-FFS, PS-UB-FFS, PS-posi-VA or PS-TN display.

The invention furthermore relates to an LC display of the PSA type comprising two substrates, at least one which is transparent to light, an electrode provided on each substrate or two electrodes provided on only one of the substrates, and located between the substrates a layer of an LC medium that comprises one or more polymerisable compounds and an LC component as described above and below, wherein the polymerisable compounds are polymerised between the substrates of the display.

The invention furthermore relates to a process for manufacturing an LC display as described above and below, comprising the steps of filling or otherwise providing an LC medium, which comprises one or more polymerisable compounds as described above and below, between the substrates of the display, and polymerising the polymerisable compounds.

The PSA displays according to the invention have two electrodes, preferably in the form of transparent layers, which are applied to one or both of the substrates. In some displays, for example in PS-VA, PS-OCB or PS-TN displays, one electrode is applied to each of the two substrates. In other displays, for example in PS-posi-VA, PS-IPS or PS-FFS or PS-UB-FFS displays, both electrodes are applied to only one of the two substrates.

In a preferred embodiment the polymerisable component is polymerised in the LC display while a voltage is applied to the electrodes of the display.

The polymerisable compounds of the polymerisable component are preferably polymerised by photo-polymerisation, very preferably by UV photo-polymerisation.

DETAILED DESCRIPTION OF THE INVENTION

Unless stated otherwise, the compounds of formula I are preferably selected from achiral compounds.

As used herein, the terms "active layer" and "switchable layer" mean a layer in an electrooptical display, for example an LC display, that comprises one or more molecules having structural and optical anisotropy, like for example LC molecules, which change their orientation upon an external stimulus like an electric or magnetic field, resulting in a change of the transmission of the layer for polarized or unpolarized light.

As used herein, the terms "tilt" and "tilt angle" will be understood to mean a tilted alignment of the LC molecules of an LC medium relative to the surfaces of the cell in an LC display (here preferably a PSA display). The tilt angle here denotes the average angle (<90°) between the longitudinal molecular axes of the LC molecules (LC director) and the surface of the plane-parallel outer plates which form the LC cell. A low value for the tilt angle (i.e. a large deviation from the 90° angle) corresponds to a large tilt here. A suitable method for measurement of the tilt angle is given in the examples. Unless indicated otherwise, tilt angle values disclosed above and below relate to this measurement method.

As used herein, the terms "reactive mesogen" and "RM" will be understood to mean a compound containing a mesogenic or liquid crystalline skeleton, and one or more functional groups attached thereto which are suitable for polymerisation and are also referred to as "polymerisable group" or "P".

Unless stated otherwise, the term "polymerisable compound" as used herein will be understood to mean a polymerisable monomeric compound.

As used herein, the term "low-molecular-weight compound" will be understood to mean to a compound that is monomeric and/or is not prepared by a polymerisation reaction, as opposed to a "polymeric compound" or a "polymer".

As used herein, the term "unpolymerisable compound" will be understood to mean a compound that does not contain a functional group that is suitable for polymerisation under the conditions usually applied for the polymerisation of the RMs.

The term "mesogenic group" as used herein is known to the person skilled in the art and described in the literature, and means a group which, due to the anisotropy of its attracting and repelling interactions, essentially contributes to causing a liquid-crystal (LC) phase in low-molecular-weight or polymeric substances. Compounds containing mesogenic groups (mesogenic compounds) do not necessarily have to have an LC phase themselves. It is also possible for mesogenic compounds to exhibit LC phase behaviour only after mixing with other compounds and/or after polymerisation. Typical mesogenic groups are, for example, rigid rod- or disc-shaped units. An overview of the terms and definitions used in connection with mesogenic or LC compounds is given in *Pure Appl. Chem.* 2001, 73(5), 888 and C. Tschierske, G. Pelzl, S. Diele, *Angew. Chem.* 2004, 116, 6340-6368.

The term "spacer group", hereinafter also referred to as "Sp", as used herein is known to the person skilled in the art and is described in the literature, see, for example, *Pure Appl. Chem.* 2001, 73(5), 888 and C. Tschierske, G. Pelzl, S. Diele, *Angew. Chem.* 2004, 116, 6340-6368. As used herein, the terms "spacer group" or "spacer" mean a flexible group, for example an alkylene group, which connects the mesogenic group and the polymerisable group(s) in a polymerisable mesogenic compound.

Above and below,

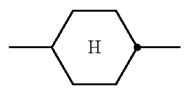

denotes a trans-1,4-cyclohexylene ring, and

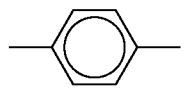

denotes a 1,4-phenylene ring.

Above and below "organic group" denotes a carbon or hydrocarbon group.

"Carbon group" denotes a mono- or polyvalent organic group containing at least one carbon atom, where this either contains no further atoms (such as, for example, —C≡C—) or optionally contains one or more further atoms, such as, for example, N, O, S, B, P, Si, Se, As, Te or Ge (for example carbonyl, etc.). The term "hydrocarbon group" denotes a carbon group which additionally contains one or more H atoms and optionally one or more heteroatoms, such as, for example, N, O, S, B, P, Si, Se, As, Te or Ge.

"Halogen" denotes F, Cl, Br or I.

—CO—, —C(=O)— and —C(O)— denote a carbonyl group, i.e.

A carbon or hydrocarbon group can be a saturated or unsaturated group. Unsaturated groups are, for example, aryl, alkenyl or alkynyl groups. A carbon or hydrocarbon radical having more than 3 C atoms can be straight-chain, branched and/or cyclic and may also contain spiro links or condensed rings.

The terms "alkyl", "aryl", "heteroaryl", etc., also encompass polyvalent groups, for example alkylene, arylene, heteroarylene, etc.

The term "aryl" denotes an aromatic carbon group or a group derived therefrom. The term "heteroaryl" denotes "aryl" as defined above, containing one or more heteroatoms, preferably selected from N, O, S, Se, Te, Si and Ge.

Preferred carbon and hydrocarbon groups are optionally substituted, straight-chain, branched or cyclic, alkyl, alkenyl, alkynyl, alkoxy, alkylcarbonyl, alkoxycarbonyl, alkylcarbonyloxy and alkoxycarbonyloxy having 1 to 40, preferably 1 to 20, very preferably 1 to 12, C atoms, optionally substituted aryl or aryloxy having 5 to 30, preferably 6 to 25, C atoms, or optionally substituted alkylaryl, arylalkyl, alkylaryloxy, arylalkyloxy, arylcarbonyl, aryloxycarbonyl, arylcarbonyloxy and aryloxycarbonyloxy having 5 to 30, preferably 6 to 25, C atoms, wherein one or more C atoms may also be replaced by hetero atoms, preferably selected from N, O, S, Se, Te, Si and Ge.

Further preferred carbon and hydrocarbon groups are $C_1$-$C_{20}$ alkyl, $C_2$-$C_{20}$ alkenyl, $C_2$-$C_{20}$ alkynyl, $C_3$-$C_{20}$ allyl, $C_4$-$C_{20}$ alkyldienyl, $C_4$-$C_{20}$ polyenyl, $C_6$-$C_{20}$ cycloalkyl, $C_4$-$C_{15}$ cycloalkenyl, $C_6$-$C_{30}$ aryl, $C_6$-$C_{30}$ alkylaryl, $C_6$-$C_{30}$ arylalkyl, $C_6$-$C_{30}$ alkylaryloxy, $C_6$-$C_{30}$ arylalkyloxy, $C_2$-$C_{30}$ heteroaryl, $C_2$-$C_{30}$ heteroaryloxy.

Particular preference is given to $C_1$-$C_{12}$ alkyl, $C_2$-$C_{12}$ alkenyl, $C_2$-$C_{12}$ alkynyl, $C_6$-$C_{25}$ aryl and $C_2$-$C_{25}$ heteroaryl.

Further preferred carbon and hydrocarbon groups are straight-chain, branched or cyclic alkyl having 1 to 20, preferably 1 to 12, C atoms, which are unsubstituted or mono- or polysubstituted by F, Cl, Br, I or CN and in which one or more non-adjacent $CH_2$ groups may each be replaced, independently of one another, by —C($R^{xx}$)=C($R^{xx}$)—, —C≡C—, —N($R^{xx}$)—, —O—, —S—, —CO—, —CO—O—, —O—CO—, —O—CO—O— in such a way that O and/or S atoms are not linked directly to one another.

$R^{xx}$ preferably denotes H, F, Cl, CN, a straight-chain, branched or cyclic alkyl chain having 1 to 25 C atoms, in which, in addition, one or more non-adjacent C atoms may be replaced by —O—, —S—, —CO—, —CO—O—, —O—CO—, —O—CO—O— and in which one or more H atoms may be replaced by F or Cl, or denotes an optionally substituted aryl or aryloxy group with 6 to 30 C atoms, or an optionally substituted heteroaryl or heteroaryloxy group with 2 to 30 C atoms.

Preferred alkyl groups are, for example, methyl, ethyl, n-propyl, isopropyl, n-butyl, isobutyl, s-butyl, t-butyl, 2-methylbutyl, n-pentyl, s-pentyl, cyclopentyl, n-hexyl, cyclohexyl, 2-ethylhexyl, n-heptyl, cycloheptyl, n-octyl, cyclooctyl, n-nonyl, n-decyl, n-undecyl, n-dodecyl, dodecanyl, trifluoromethyl, perfluoro-n-butyl, 2,2,2-trifluoroethyl, perfluorooctyl, perfluorohexyl, etc.

Preferred alkenyl groups are, for example, ethenyl, propenyl, butenyl, pentenyl, cyclopentenyl, hexenyl, cyclohexenyl, heptenyl, cycloheptenyl, octenyl, cyclooctenyl, etc.

Preferred alkynyl groups are, for example, ethynyl, propynyl, butynyl, pentynyl, hexynyl, octynyl, etc.

Preferred alkoxy groups are, for example, methoxy, ethoxy, 2-methoxy-ethoxy, n-propoxy, i-propoxy, n-butoxy, i-butoxy, s-butoxy, t-butoxy, 2-methylbutoxy, n-pentoxy, n-hexoxy, n-heptoxy, n-octoxy, n-nonoxy, n-decoxy, n-undecoxy, n-dodecoxy, etc.

Preferred amino groups are, for example, dimethylamino, methylamino, methylphenylamino, phenylamino, etc.

Aryl and heteroaryl groups can be monocyclic or polycyclic, i.e. they can contain one ring (such as, for example, phenyl) or two or more rings, which may also be fused (such as, for example, naphthyl) or covalently bonded (such as, for example, biphenyl), or contain a combination of fused and linked rings. Heteroaryl groups contain one or more heteroatoms, preferably selected from O, N, S and Se.

Particular preference is given to mono-, bi- or tricyclic aryl groups having 6 to 25 C atoms and mono-, bi- or tricyclic heteroaryl groups having 5 to 25 ring atoms, which optionally contain fused rings and are optionally substituted. Preference is furthermore given to 5-, 6- or 7-membered aryl and heteroaryl groups, in which, in addition, one or more CH groups may be replaced by N, S or O in such a way that O atoms and/or S atoms are not linked directly to one another.

Preferred aryl groups are, for example, phenyl, biphenyl, terphenyl, [1,1':3',1"]terphenyl-2'-yl, naphthyl, anthracene, binaphthyl, phenanthrene, 9,10-dihydro-phenanthrene, pyrene, dihydropyrene, chrysene, perylene, tetracene, pentacene, benzopyrene, fluorene, indene, indenofluorene, spirobifluorene, etc.

Preferred heteroaryl groups are, for example, 5-membered rings, such as pyrrole, pyrazole, imidazole, 1,2,3-triazole, 1,2,4-triazole, tetrazole, furan, thiophene, selenophene, oxazole, isoxazole, 1,2-thiazole, 1,3-thiazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 6-membered rings, such as pyridine, pyridazine, pyrimidine, pyrazine, 1,3,5-triazine, 1,2,4-triazine, 1,2,3-triazine, 1,2,4,5-tetrazine, 1,2,3,4-tetrazine, 1,2,3,5-tetrazine, or condensed groups, such as indole, isoindole, indolizine, indazole, benzimidazole, benzotriazole, purine, naphthimidazole, phenanthrimidazole, pyridimidazole, pyrazinimidazole, quinoxalinimidazole, benzoxazole, naphthoxazole, anthroxazole, phenanthroxazole, isoxazole, benzothiazole, benzofuran, isobenzofuran, dibenzofuran, quinoline, isoquinoline, pteridine, benzo-5,6-quinoline, benzo-6,7-quinoline, benzo-7,8-quinoline, benzoisoquinoline, acridine, phenothiazine, phenoxazine, benzopyridazine, benzopyrimidine, quinoxaline, phenazine, naphthyridine, azacarbazole, benzocarboline, phenanthridine, phenanthroline, thieno[2,3b]thiophene, thieno[3,2b]thiophene, dithienothiophene, isobenzothiophene, dibenzothiophene, benzothiadiazothiophene, or combinations of these groups.

The aryl and heteroaryl groups mentioned above and below may also be substituted by alkyl, alkoxy, thioalkyl, fluorine, fluoroalkyl or further aryl or heteroaryl groups.

The (non-aromatic) alicyclic and heterocyclic groups encompass both saturated rings, i.e. those containing exclusively single bonds, and also partially unsaturated rings, i.e. those which may also contain multiple bonds. Heterocyclic rings contain one or more heteroatoms, preferably selected from Si, O, N, S and Se.

The (non-aromatic) alicyclic and heterocyclic groups can be monocyclic, i.e. contain only one ring (such as, for example, cyclohexane), or polycyclic, i.e. contain a plurality of rings (such as, for example, decahydronaphthalene or bicyclooctane). Particular preference is given to saturated groups. Preference is furthermore given to mono-, bi- or tricyclic groups having 5 to 25 ring atoms, which optionally contain fused rings and are optionally substituted. Preference is furthermore given to 5-, 6-, 7- or 8-membered carbocyclic groups, in which, in addition, one or more C atoms may be replaced by Si and/or one or more CH groups may be replaced by N and/or one or more non-adjacent $CH_2$ groups may be replaced by —O— and/or —S—.

Preferred alicyclic and heterocyclic groups are, for example, 5-membered groups, such as cyclopentane, tetrahydrofuran, tetrahydrothiofuran, pyrrolidine, 6-membered groups, such as cyclohexane, silinane, cyclohexene, tetrahydropyran, tetrahydrothiopyran, 1,3-dioxane, 1,3-dithiane, piperidine, 7-membered groups, such as cycloheptane, and fused groups, such as tetrahydronaphthalene, decahydronaphthalene, indane, bicyclo[1.1.1]-pentane-1,3-diyl, bicyclo[2.2.2]octane-1,4-diyl, spiro[3.3]heptane-2,6-diyl, octahydro-4,7-methanoindane-2,5-diyl.

Preferred substituents are, for example, solubility-promoting groups, such as alkyl or alkoxy, electron-withdrawing groups, such as fluorine, nitro or nitrile, or substituents for increasing the glass transition temperature (Tg) in the polymer, in particular bulky groups, such as, for example, t-butyl or optionally substituted aryl groups.

Preferred substituents, hereinafter also referred to as "L", are, for example, F, Cl, Br, I, —CN, —$NO_2$, —NCO, —NCS, —OCN, —SCN, —C(=O)N($R^x$)$_2$, —C(=O)$Y^1$, —C(=O)$R^x$, —N($R^x$)$_2$, straight-chain or branched alkyl, alkoxy, alkylcarbonyl, alkoxycarbonyl, alkylcarbonyloxy or alkoxycarbonyloxy each having 1 to 25 C atoms, in which one or more H atoms may optionally be replaced by F or Cl, optionally substituted silyl having 1 to 20 Si atoms, or optionally substituted aryl having 6 to 25, preferably 6 to 15, C atoms,
wherein $R^x$ denotes H, F, Cl, CN, or straight chain, branched or cyclic alkyl having 1 to 25 C atoms, wherein one or more non-adjacent $CH_2$-groups are optionally replaced by —O—, —S—, —CO—, —CO—O—, —O—CO—, —O—CO—O— in such a manner that O- and/or S-atoms are not directly connected with each other, and wherein one or more H atoms are each optionally replaced by F, Cl, P— or P-Sp-, and
$Y^1$ denotes halogen.

"Substituted silyl or aryl" preferably means substituted by halogen, —CN, $R^0$, —$OR^0$, —CO—$R^0$, —CO—O—$R^0$, —O—CO—$R^0$ or —O—CO—O—$R^0$, wherein $R^0$ denotes H or alkyl with 1 to 20 C atoms.

Particularly preferred substituents L are, for example, F, Cl, CN, $NO_2$, $CH_3$, $C_2H_5$, $OCH_3$, $OC_2H_5$, $COCH_3$, $COC_2H_5$, $COOCH_3$, $COOC_2H_5$, $CF_3$, $OCF_3$, $OCHF_2$, $OC_2F_5$, furthermore phenyl.

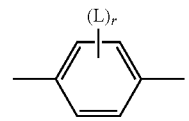

is preferably

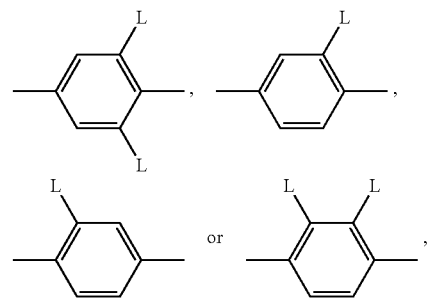

in which L has one of the meanings indicated above.

The polymerisable group P is a group which is suitable for a polymerisation reaction, such as, for example, free-radical or ionic chain polymerisation, polyaddition or polycondensation, or for a polymer-analogous reaction, for example addition or condensation onto a main polymer chain. Particular preference is given to groups for chain polymerisation, in particular those containing a C=C double bond or —C≡C— triple bond, and groups which are suitable for polymerisation with ring opening, such as, for example, oxetane or epoxide groups.

Preferred groups P are selected from the group consisting of $CH_2$=$CW^1$—CO—O—, $CH_2$=$CW^1$—CO—,

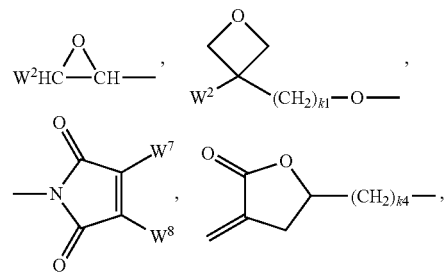

$CH_2$=$CW^2$—(O)$_{k3}$—, $CW^1$=CH—CO—(O)$_{k3}$—, $CW^1$=CH—CO—NH—, $CH_2$=$CW^1$—CO—NH—, $CH_3$—CH=CH—O—, ($CH_2$=CH)$_2$CH—OCO—, ($CH_2$=CH—$CH_2$)$_2$CH—OCO—, ($CH_2$=CH)$_2$CH—O—, ($CH_2$=CH—$CH_2$)$_2$N—, ($CH_2$=CH—$CH_2$)$_2$N—CO—, HO—$CW^2W^3$—, HS—$CW^2W^3$—, $HW^2$N—, HO—$CW^2W^3$—NH—, $CH_2$=$CW^1$—CO—NH—, $CH_2$=CH—(COO)$_{k1}$-Phe-(O)$_{k2}$—, $CH_2$=CH—(CO)$_{k1}$-Phe-(O)$_{k2}$—, Phe-CH=CH—, HOOC—, OCN— and $W^4W^5W^6$Si—, in which $W^1$ denotes H, F, Cl, CN, $CF_3$, phenyl or alkyl having 1 to 5 C atoms, in particular H, F, Cl or $CH_3$, $W^2$ and $W^3$ each, independently of one another, denote H or alkyl having 1 to 5 C atoms, in particular H, methyl, ethyl or n-propyl, $W^4$, $W^5$ and $W^6$ each, independently of one another, denote Cl, oxaalkyl or oxacarbonylalkyl having 1 to 5 C atoms, $W^7$ and $W^8$ each, independently of one another, denote H, Cl or alkyl having 1 to 5 C atoms, Phe denotes 1,4-phenylene, which is optionally substituted by one or more radicals L as defined above which are other than P-Sp-, $k_1$, $k_2$ and $k_3$ each, independently of one another, denote 0 or 1, $k_3$ preferably denotes 1, and $k_4$ denotes an integer from 1 to 10.

Very preferred groups P are selected from the group consisting of $CH_2=CW^1—CO—O—$, $CH_2=CW^1—CO—$,

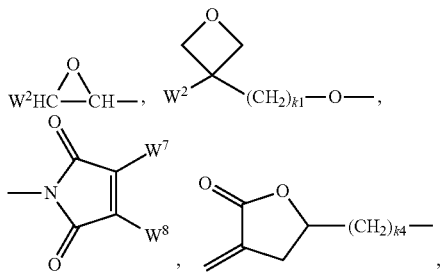

$CH_2=CW^2—O—$, $CH_2=CW^2—$, $CW^1=CH—CO—(O)_{k3}—$, $CW^1=CH—CO—NH—$, $CH_2=CW^1—CO—NH—$, $(CH_2=CH)_2CH—OCO—$, $(CH_2=CH—CH_2)_2CH—OCO—$, $(CH_2=CH)_2CH—O—$, $(CH_2=CH—CH_2)_2N—$, $(CH_2=CH—CH_2)_2N—CO—$, $CH_2=CW^1—CO—NH—$, $CH_2=CH—(COO)_{k1}$-Phe-$(O)_{k2}—$, $CH_2=CH—(CO)_{k1}$-Phe-$(O)_{k2}—$, Phe-$CH=CH—$ and $W^4W^5W^6Si—$, in which $W^1$ denotes H, F, Cl, CN, $CF_3$, phenyl or alkyl having 1 to 5 C atoms, in particular H, F, Cl or $CH_3$, $W^2$ and $W^3$ each, independently of one another, denote H or alkyl having 1 to 5 C atoms, in particular H, methyl, ethyl or n-propyl, $W^4$, $W^5$ and $W^6$ each, independently of one another, denote Cl, oxaalkyl or oxacarbonylalkyl having 1 to 5 C atoms, $W^7$ and $W^8$ each, independently of one another, denote H, Cl or alkyl having 1 to 5 C atoms, Phe denotes 1,4-phenylene, $k_1$, $k_2$ and $k_3$ each, independently of one another, denote 0 or 1, $k_3$ preferably denotes 1, and $k_4$ denotes an integer from 1 to 10.

Very particularly preferred groups P are selected from the group consisting of $CH_2=CW^1—CO—O—$, in particular $CH_2=CH—CO—O—$, $CH_2=C(CH_3)—CO—O—$ and $CH_2=CF—CO—O—$, furthermore $CH_2=CH—O—$, $(CH_2=CH)_2CH—O—CO—$, $(CH_2=CH)_2CH—O—$,

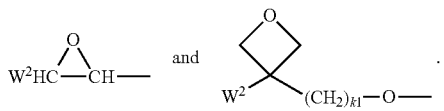

Further preferred polymerisable groups P are selected from the group consisting of vinyloxy, acrylate, methacrylate, fluoroacrylate, chloroacrylate, oxetane and epoxide, most preferably from acrylate and methacrylate.

If Sp is different from a single bond, it is preferably of the formula Sp"-X", so that the respective radical P-Sp- conforms to the formula P-Sp"-X"—, wherein Sp" denotes alkylene having 1 to 20, preferably 1 to 12, C atoms, which is optionally mono- or polysubstituted by F, Cl, Br, I or CN and in which, in addition, one or more non-adjacent $CH_2$ groups may each be replaced, independently of one another, by —O—, —S—, —NH—, —N(R⁰)—, —Si(R⁰R⁰⁰)—, —CO—, —CO—O—, —O—CO—, —O—CO—O—, —S—CO—, —CO—S—, —N(R⁰⁰)—CO—O—, —O—CO—N(R⁰)—, —N(R⁰)—CO—N(R⁰⁰)—, —CH=CH— or —C≡C— in such a way that O and/or S atoms are not linked directly to one another, X" denotes —O—, —S—, —CO—, —CO—O—, —O—CO—, —O—CO—O—, —CO—N(R⁰)—, —N(R⁰)—CO—, —N(R⁰)—CO—N(R⁰⁰)—, —OCH₂—, —CH₂O—, —SCH₂—, —CH₂S—, —CF₂O—, —OCF₂—, —CF₂S—, —SCF₂—, —CF₂CH₂—, —CH₂CF₂—, —CF₂CF₂—, —CH=N—, —N=CH—, —N=N—, —CH=CR⁰—, —CY²=CY³—, —C≡C—, —CH=CH—CO—O—, —O—CO—CH=CH— or a single bond, R⁰ and R⁰⁰ each, independently of one another, denote H or alkyl having 1 to 20 C atoms, and $Y^2$ and $Y^3$ each, independently of one another, denote H, F, Cl or CN.

X" is preferably —O—, —S—, —CO—, —COO—, —OCO—, —O—COO—, —CO—NR⁰—, —NR⁰—CO—, —NR⁰—CO—NR⁰⁰— or a single bond.

Typical spacer groups Sp and -Sp"-X"— are, for example, —(CH₂)$_{p1}$—, —(CH₂CH₂O)$_{q1}$—CH₂CH₂—, —CH₂CH₂—S—CH₂CH₂—, —CH₂CH₂—NH—CH₂CH₂— or —(SiR⁰R⁰⁰—O)$_{p1}$—, in which p1 is an integer from 1 to 12, q1 is an integer from 1 to 3, and R⁰ and R⁰⁰ have the meanings indicated above.

Particularly preferred groups Sp and -Sp"-X"— are —(CH₂)$_{p1}$—, —(CH₂)$_{p1}$—O—, —(CH₂)$_{p1}$—O—CO—, —(CH₂)$_{p1}$—CO—O—, —(CH₂)$_{p1}$—O—CO—O—, in which p1 and q1 have the meanings indicated above.

Particularly preferred groups Sp" are, in each case straight-chain, ethylene, propylene, butylene, pentylene, hexylene, heptylene, octylene, nonylene, decylene, undecylene, dodecylene, octadecylene, ethyleneoxyethylene, methyleneoxybutylene, ethylenethioethylene, ethylene-N-methylimino-ethylene, 1-methylalkylene, ethenylene, propenylene and butenylene.

In the compounds of formula I $A^1$ and $A^2$ denote an aromatic or heteroaromatic group which is monocyclic or polycyclic, has 4 to 30 ring atoms, and is unsubstituted or substituted by one or more substituents, said substituents preferably selected from L, wherein L denotes P-Sp-, F, Cl, —CN, —NO₂, —NCO, —NCS, —OCN, —SCN, —C(=O)N(R$^x$)₂, —C(=O)Y¹, —C(=O)R$^x$, —N(R$^x$)₂, optionally substituted silyl, optionally substituted aryl or heteroaryl having 5 to 20 ring atoms, or straight-chain or branched alkyl having 1 to 25, particularly preferably 1 to 10, C atoms, in which, in addition, one or more non-adjacent $CH_2$ groups may each be replaced, independently of one another, by —C(R⁰)=C(R⁰⁰)—, —C≡C—, —N(R⁰)—, —O—, —S—, —CO—, —CO—O—, —O—CO—, —O—CO—O— in such a way that O and/or S atoms are not linked directly to one another, and in which, in addition, one or more H atoms may be replaced by F, Cl, CN, P— or P-Sp-, R$^x$ denotes H, F, Cl, CN, or straight chain, branched or cyclic alkyl having 1 to 25 C atoms, wherein one or more non-adjacent $CH_2$-groups are optionally replaced by —O—, —S—, —CO—, —CO—O—, —O—CO—, —O—CO—O— in such a manner that O- and/or S-atoms are not directly connected with each other, and wherein one or more H atoms are each optionally replaced by F, Cl, P— or P-Sp-, and R⁰ and R⁰⁰ each, independently of one another, denote H or alkyl having 1 to 20 C atoms, and $Y^1$ is halogen.

Preferably A¹ and A¹ are selected from benzene and naphthalene which are optionally substituted by one or more groups L.

Preferred compounds of formula I are those wherein at least one of $R^a$ and $R^b$, very preferably both $R^a$ and $R^b$, denote P-Sp-. Accordingly these preferred compounds are selected from the following subformulae

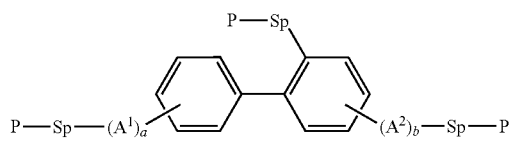

IA

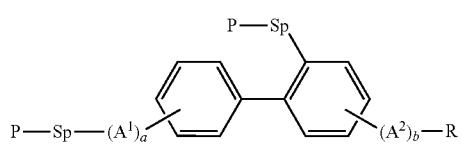

IB

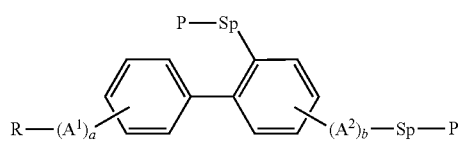

IC wherein P, Sp, A¹, A², a and b are as defined in formula I. Very preferred compounds are those of formula IA.

Preferred compounds of formula I are selected from the following formulae

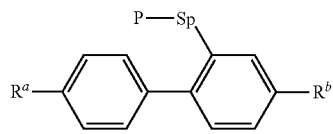

I1

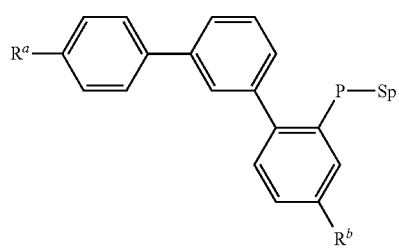

I2

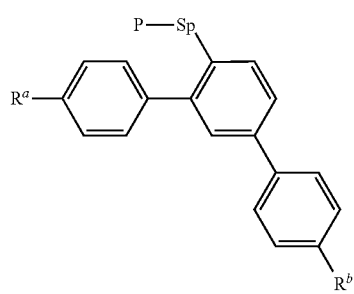

I3

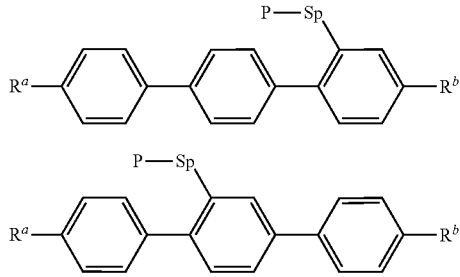

I4

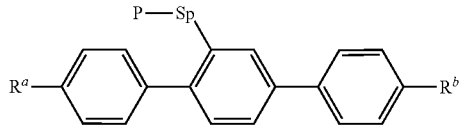

I5 wherein $R^a$, $R^b$, P and Sp are as defined in formula I, and the benzene rings are optionally substituted by one or more groups L as defined above, and preferably at least one of $R^a$ and $R^b$, very preferably both $R^a$ and $R^b$ denote P-Sp-.

Very preferred compounds of formula I are selected from the following subformulae:

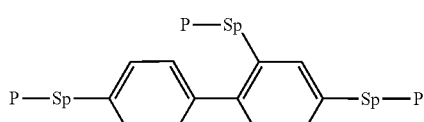

I1a

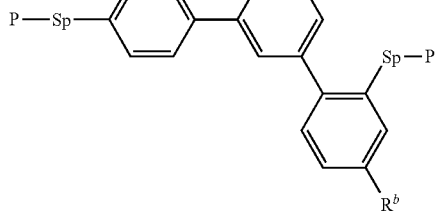

I2a

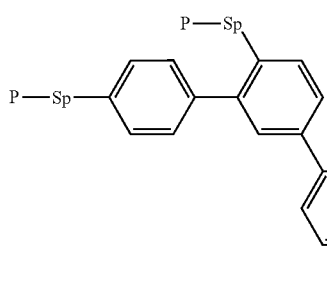

I3a

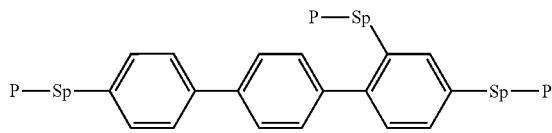

I4a

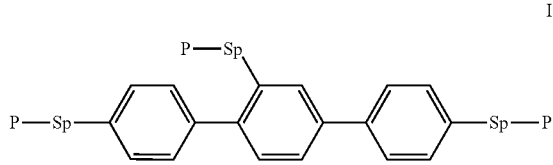

I5a wherein P and Sp are as defined in formula I, and the benzene rings are optionally substituted by one or more groups L as defined above.

Further preferred compounds of formula I are selected from the following subformulae:

I1a1 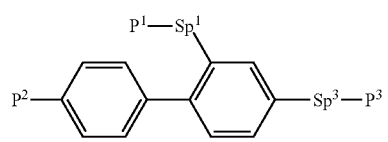
I1a2 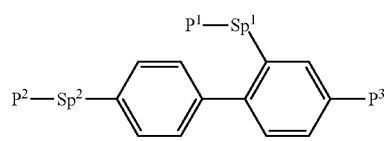
I1a3 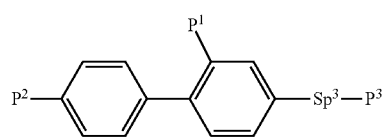
I1a4 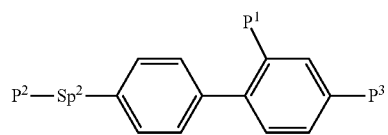
I1a5 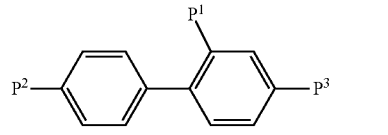
I2a1 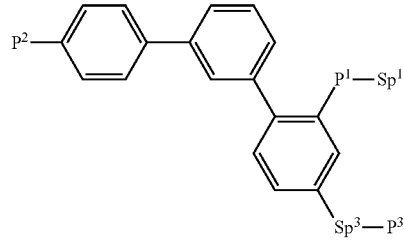
I2a2 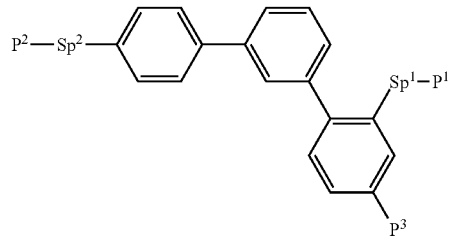
I2a3 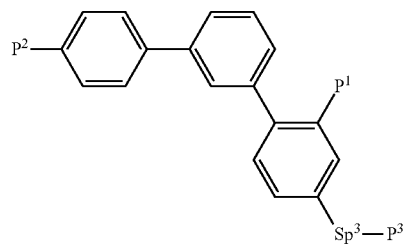
I2a4 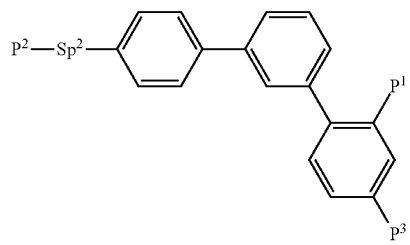
I2a5 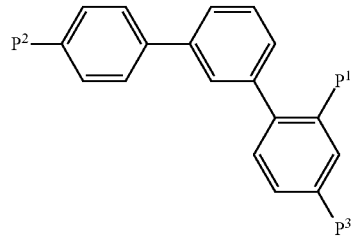
I3a1 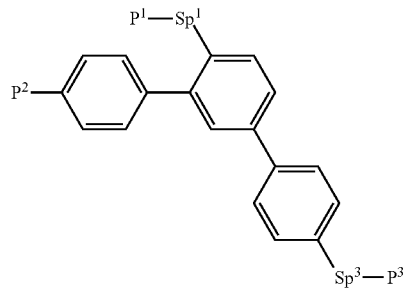
I3a2 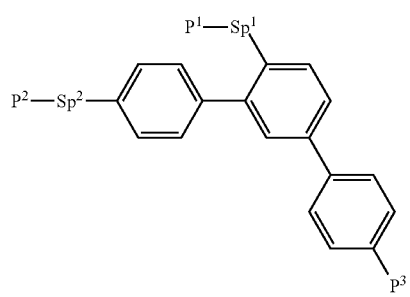
I3a3 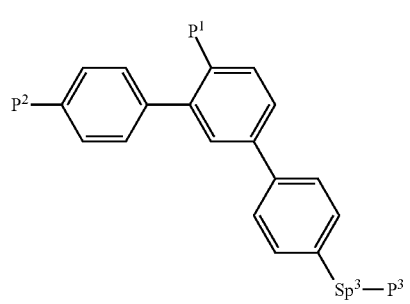

-continued

I3a4
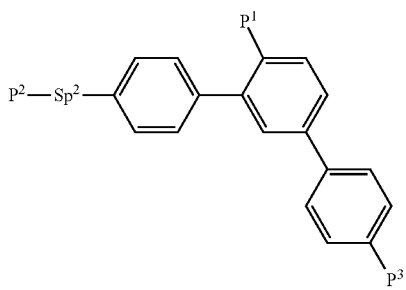

I3a5
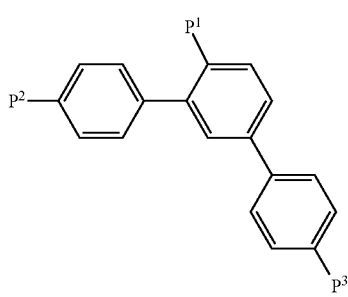

I4a1
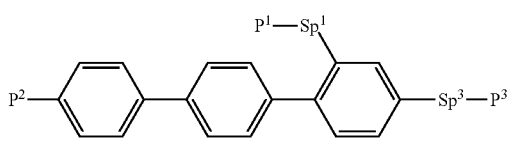

I4a2
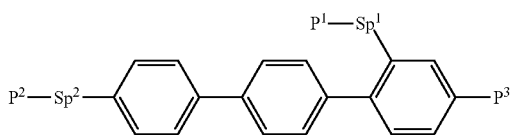

I4a3
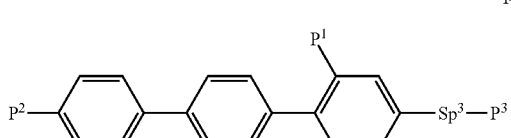

I4a4
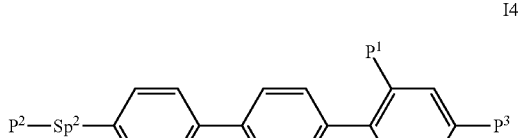

I4a5
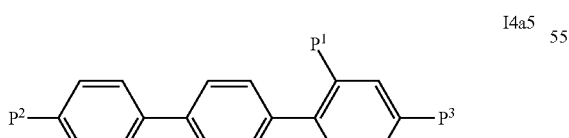

I5a1
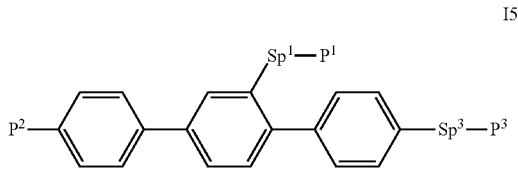

-continued

I5a2
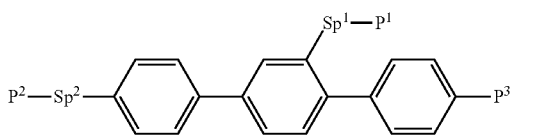

I5a3
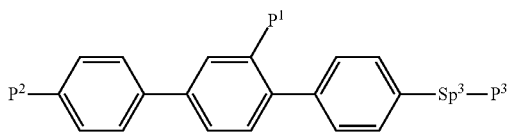

I5a4
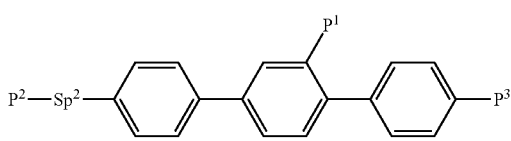

wherein $P^1$, $P^2$ and $P^3$ independently of each other have one of the meanings given for P in formula I or of its preferred meanings given above and below, and $Sp^1$, $Sp^2$ and $Sp^3$ independently of each other have one of the meanings given for Sp in formula I, or of its preferred meanings given above and below, which is different from a single bond. Especially preferably in these preferred formulae $P^1$, $P^2$ and $P^3$ are independently of each other selected from acrylate and methacrylate groups, and $Sp^1$, $Sp^2$ and $Sp^3$ are independently of each other selected from ethylene, n-propylene, n-butylene, n-pentylene and n-hexylene.

Very preferred are compounds of formulae I1a1, I1a2, I2a5, I3a5, I4a1, I4a2, I5a1 and I5a2.

Further preferred compounds of formula I and its subformulae IA-IC, I1-I5, I1a-I5a and I1a1-I5a4 are those selected from the following preferred embodiments, including any combination thereof:

a is 0 and b is 1, or a is 1 and b is 0,
a is 0 and b is 0,
P, $P^1$, $P^2$ and $P^3$ are selected from the group consisting of acrylate, methacrylate and oxetane,
at least one group Sp is different from a single bond,
one or two groups Sp are different from a single bond,
the compounds contain exactly three polymerisable groups (represented by the groups P or $P^1$, $P^2$ and $P^3$),
L does not denote or contain a polymerisable group,
L does not denote or contain a group P-Sp-,
at least one of the benzene rings in formula I and its subformulae is substituted by a group L that denotes P-Sp-,
at least one of the benzene rings in formula I and its subformulae is substituted by a group L that is different from P-Sp- and is not polymerisable, and is preferably selected from F, Cl, —CN and straight-chain or branched alkyl having 1 to 25, particularly preferably 1 to 10, C atoms, in which, in addition, one or more non-adjacent CH$_2$ groups may each be replaced, independently of one another, by —C(R$^{00}$)═C(R$^{000}$)—, —C≡C—, —N(R$^{00}$)—, —O—, —S—, —CO—, —CO—O—, —O—CO—, —O—CO—O— in such a way that O and/or S atoms are not linked directly to one another, and in which, in addition, one or more H atoms may be replaced by F, Cl, Br, I or CN,
at least one of the benzene rings in formula I and its subformulae is substituted by one or two substituents selected from F, CN, and alkyl or alkoxy with 1 to 6 C atoms that is optionally fluorinated.

The invention furthermore relates to compounds of formula II

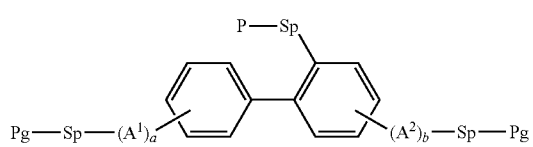

wherein Sp, $A^1$, $A^2$, a and b are as defined in formula I, and Pg denotes OH, a protected hydroxyl group or a masked hydroxyl group.

Preferred compounds of formula II are selected from subformulae IA-IC, I1-I5, I1a-I5a and I1a1-I5a4 as defined above, wherein P is replaced by Pg.

Suitable protected hydroxyl groups Pg are known to the person skilled in the art. Preferred protecting groups for hydroxyl groups are alkyl, alkoxyalkyl, acyl, alkylsilyl, arylsilyl and arylmethyl groups, especially 2-tetrahydropyranyl, methoxymethyl, methoxyethoxymethyl, acetyl, triisopropylsilyl, tert-butyl-dimethylsilyl or benzyl.

The term "masked hydroxyl group" is understood to mean any functional group that can be chemically converted into a hydroxyl group. Suitable masked hydroxyl groups Pg are known to the person skilled in the art.

The compounds of formula II are suitable as intermediates for the preparation of compounds of the formula I and its subformulae.

The invention further relates to the use of the compounds of formula II as intermediates for the preparation of compounds of the formula I and its subformulae.

The compounds and intermediates of the formulae I and II and sub-formulae thereof can be prepared analogously to processes known to the person skilled in the art and described in standard works of organic chemistry, such as, for example, in Houben-Weyl, Methoden der organischen Chemie [Methods of Organic Chemistry], Thieme-Verlag, Stuttgart.

For example, compounds of formula I can be synthesised by esterification or etherification of the intermediates of formula II, wherein Pg denote OH, using corresponding acids, acid derivatives, or halogenated compounds containing a polymerisable group P.

For example, acrylic or methacrylic esters can be prepared by esterification of the corresponding alcohols with acid derivatives like, for example, (meth)acryloyl chloride or (meth)acrylic anhydride in the presence of a base like pyridine or triethyl amine, and 4-(N,N-dimethylamino)pyridine (DMAP). Alternatively the esters can be prepared by esterification of the alcohols with (meth)acrylic acid in the presence of a dehydrating reagent, for example according to Steglich with dicyclohexylcarbodiimide (DCC), N-(3-dimethylaminopropyl)-N'-ethylcarbodiimide (EDC) or N-(3-dimethylaminopropyl)-N'-ethylcarbodiimide hydrochloride and DMAP.

Further suitable methods are shown in the Examples.

For the production of PSA displays, the polymerisable compounds contained in the LC medium are polymerised or crosslinked (if one compound contains two or more polymerisable groups) by in-situ polymerisation in the LC medium between the substrates of the LC display, optionally while a voltage is applied to the electrodes.

The structure of the PSA displays according to the invention corresponds to the usual geometry for PSA displays, as described in the prior art cited at the outset. Geometries without protrusions are preferred, in particular those in which, in addition, the electrode on the colour filter side is unstructured and only the electrode on the TFT side has slots. Particularly suitable and preferred electrode structures for PS-VA displays are described, for example, in US 2006/0066793 A1.

A preferred PSA type LC display of the present invention comprises:
a first substrate including a pixel electrode defining pixel areas, the pixel electrode being connected to a switching element disposed in each pixel area and optionally including a micro-slit pattern, and optionally a first alignment layer disposed on the pixel electrode,
a second substrate including a common electrode layer, which may be disposed on the entire portion of the second substrate facing the first substrate, and optionally a second alignment layer,
an LC layer disposed between the first and second substrates and including an LC medium comprising a polymerisable component A and a liquid crystal component B as described above and below, wherein the polymerisable component A may also be polymerised.

The first and/or second alignment layer controls the alignment direction of the LC molecules of the LC layer. For example, in PS-VA displays the alignment layer is selected such that it imparts to the LC molecules homeotropic (or vertical) alignment (i.e. perpendicular to the surface) or tilted alignment. Such an alignment layer may for example comprise a polyimide, which may also be rubbed, or may be prepared by a photoalignment method.

The LC layer with the LC medium can be deposited between the substrates of the display by methods that are conventionally used by display manufacturers, for example the so-called one-drop-filling (ODF) method. The polymerisable component of the LC medium is then polymerised for example by UV photopolymerisation. The polymerisation can be carried out in one step or in two or more steps.

The PSA display may comprise further elements, like a colour filter, a black matrix, a passivation layer, optical retardation layers, transistor elements for addressing the individual pixels, etc., all of which are well known to the person skilled in the art and can be employed without inventive skill.

The electrode structure can be designed by the skilled person depending on the individual display type. For example for PS-VA displays a multi-domain orientation of the LC molecules can be induced by providing electrodes having slits and/or bumps or protrusions in order to create two, four or more different tilt alignment directions.

Upon polymerisation the polymerisable compounds form a crosslinked polymer, which causes a certain pretilt of the LC molecules in the LC medium. Without wishing to be bound to a specific theory, it is believed that at least a part of the crosslinked polymer, which is formed by the polymerisable compounds, will phase-separate or precipitate from the LC medium and form a polymer layer on the substrates or electrodes, or the alignment layer provided thereon. Microscopic measurement data (like SEM and AFM) have confirmed that at least a part of the formed polymer accumulates at the LC/substrate interface.

The polymerisation can be carried out in one step. It is also possible firstly to carry out the polymerisation, optionally while applying a voltage, in a first step in order to produce a pretilt angle, and subsequently, in a second polymerisation step without an applied voltage, to polymerise or crosslink the compounds which have not reacted in the first step ("end curing").

Suitable and preferred polymerisation methods are, for example, thermal or photopolymerisation, preferably photopolymerisation, in particular UV induced photopolymerisation, which can be achieved by exposure of the polymerisable compounds to UV radiation.

Optionally one or more polymerisation initiators are added to the LC medium. Suitable conditions for the polymerisation and suitable types and amounts of initiators are known to the person skilled in the art and are described in the literature. Suitable for free-radical polymerisation are, for example, the commercially available photoinitiators Irgacure651®, Irgacure184®, Irgacure907®, Irgacure369® or Darocure1173® (Ciba AG). If a polymerisation initiator is employed, its proportion is preferably 0.001 to 5% by weight, particularly preferably 0.001 to 1% by weight.

The polymerisable compounds according to the invention are also suitable for polymerisation without an initiator, which is accompanied by considerable advantages, such, for example, lower material costs and in particular less contamination of the LC medium by possible residual amounts of the initiator or degradation products thereof. The polymerisation can thus also be carried out without the addition of an initiator. In a preferred embodiment, the LC medium thus does not contain a polymerisation initiator.

The LC medium may also comprise one or more stabilisers in order to prevent undesired spontaneous polymerisation of the RMs, for example during storage or transport. Suitable types and amounts of stabilisers are known to the person skilled in the art and are described in the literature. Particularly suitable are, for example, the commercially available stabilisers from the Irganox® series (Ciba AG), such as, for example, Irganox® 1076. If stabilisers are employed, their proportion, based on the total amount of RMs or the polymerisable component (component A), is preferably 10-500,000 ppm, particularly preferably 50-50,000 ppm.

The polymerisable compounds of formula I do in particular show good UV absorption in, and are therefore especially suitable for, a process of preparing a PSA display including one or more of the following features:
 the polymerisable medium is exposed to UV light in the display in a 2-step process, including a first UV exposure step ("UV-1 step") to generate the tilt angle, and a second UV exposure step ("UV-2 step") to finish polymerization,
 the polymerisable medium is exposed to UV light in the display generated by an energy-saving UV lamp (also known as "green UV lamps"). These lamps are characterized by a relative low intensity (1/100-1/10 of a conventional UV1 lamp) in their absorption spectra from 300-380 nm, and are preferably used in the UV2 step, but are optionally also used in the UV1 step when avoiding high intensity is necessary for the process.
 the polymerisable medium is exposed to UV light in the display generated by a UV lamp with a radiation spectrum that is shifted to longer wavelengths, preferably 340 nm or more, to avoid short UV light exposure in the PS-VA process.

Both using lower intensity and a UV shift to longer wavelengths protect the organic layer against damage that may be caused by the UV light.

A preferred embodiment of the present invention relates to a process for preparing a PSA display as described above and below, comprising one or more of the following features:
 the polymerisable LC medium is exposed to UV light in a 2-step process, including a first UV exposure step ("UV-1 step") to generate the tilt angle, and a second UV exposure step ("UV-2 step") to finish polymerization,
 the polymerisable LC medium is exposed to UV light generated by a UV lamp having an intensity of from 0.5 mW/cm$^2$ to 10 mW/cm$^2$ in the wavelength range from 300-380 nm, preferably used in the UV2 step, and optionally also in the UV1 step,
 the polymerisable LC medium is exposed to UV light having a wavelength of 340 nm or more, and preferably 400 nm or less.

This preferred process can be carried out for example by using the desired UV lamps or by using a band pass filter and/or a cut-off filter, which are substantially transmissive for UV light with the respective desired wavelength(s) and are substantially blocking light with the respective undesired wavelengths. For example, when irradiation with UV light of wavelengths λ of 300-400 nm is desired, UV exposure can be carried out using a wide band pass filter being substantially transmissive for wavelengths 300 nm<λ<400 nm. When irradiation with UV light of wavelength λ of more than 340 nm is desired, UV exposure can be carried out using a cut-off filter being substantially transmissive for wavelengths λ>340 nm.

"Substantially transmissive" means that the filter transmits a substantial part, preferably at least 50% of the intensity, of incident light of the desired wavelength(s). "Substantially blocking" means that the filter does not transmit a substantial part, preferably at least 50% of the intensity, of incident light of the undesired wavelengths. "Desired (undesired) wavelength" e.g. in case of a band pass filter means the wavelengths inside (outside) the given range of λ, and in case of a cut-off filter means the wavelengths above (below) the given value of λ.

This preferred process enables the manufacture of displays by using longer UV wavelengths, thereby reducing or even avoiding the hazardous and damaging effects of short UV light components.

UV radiation energy is in general from 6 to 100 J, depending on the production process conditions.

Preferably the LC medium according to the present invention does essentially consist of a polymerisable component A) and an LC component B), or LC host mixture, as described above and below. However, the LC medium may additionally comprise one or more further components or additives, preferably selected from the list including but not limited to co-monomers, chiral dopants, polymerisation initiators, inhibitors, stabilizers, surfactants, wetting agents, lubricating agents, dispersing agents, hydrophobing agents, adhesive agents, flow improvers, defoaming agents, deaerators, diluents, reactive diluents, auxiliaries, colourants, dyes, pigments and nanoparticles.

Particular preference is given to LC media comprising one, two or three polymerisable compounds of formula I.

Preference is furthermore given to LC media in which the polymerisable component A) comprises exclusively polymerisable compounds of formula I.

Preference is furthermore given to LC media in which the LC component B), or the LC host mixture, has a nematic LC phase, and preferably has no chiral liquid crystal phase.

Preference is furthermore given to achiral compounds of formula I, and to LC media in which the compounds of component A and/or B are selected exclusively from the group consisting of achiral compounds.

Preferably the proportion of the polymerisable component A) in the LC medium is from >0 to <5%, very preferably from >0 to <1%, most preferably from 0.01 to 0.5%.

Preferably the proportion of compounds of formula I in the LC medium is from >0 to <5%, very preferably from >0 to <1%, most preferably from 0.01 to 0.5%.

Preferably the proportion of the LC component B) in the LC medium is from 95 to <100%, very preferably from 99 to <100%.

In a preferred embodiment the polymerisable compounds of the polymerisable component A) are exclusively selected from formula I.

In another preferred embodiment the polymerisable component A) comprises, in addition to the compounds of formula I, one or more further polymerisable compounds ("co-monomers"), preferably selected from RMs.

Suitable and preferred mesogenic comonomers are selected from the following formulae:

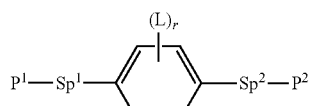
M1

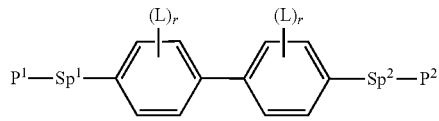
M2

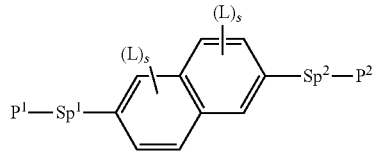
M3

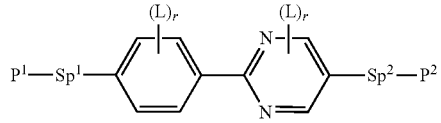
M4

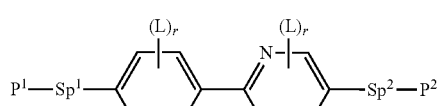
M5

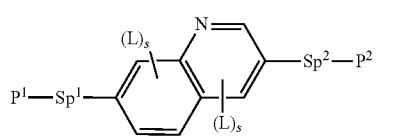
M6

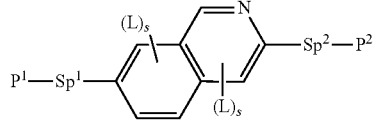
M7

-continued

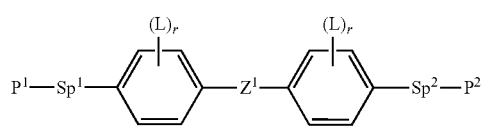
M8

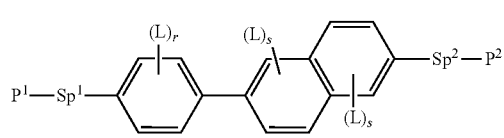
M9

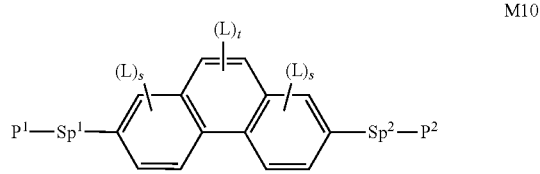
M10

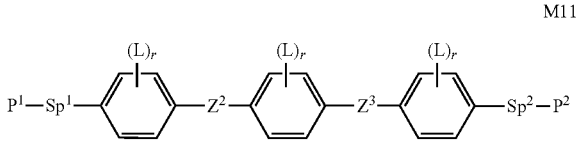
M11

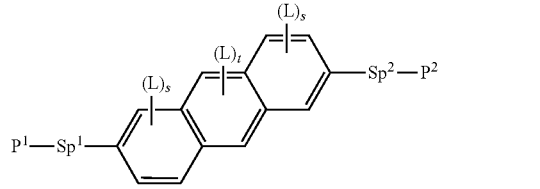
M12

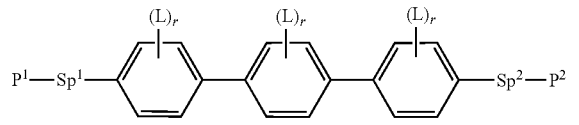
M13

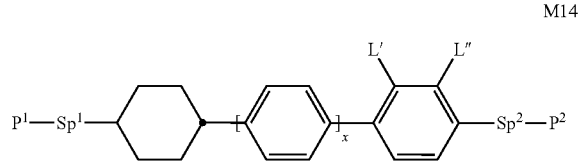
M14

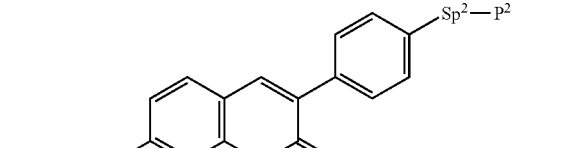
M15

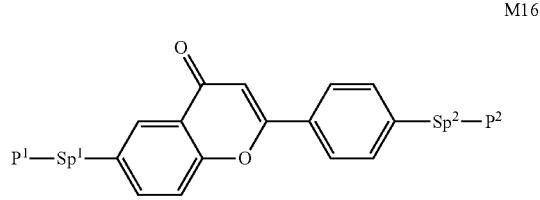
M16

-continued
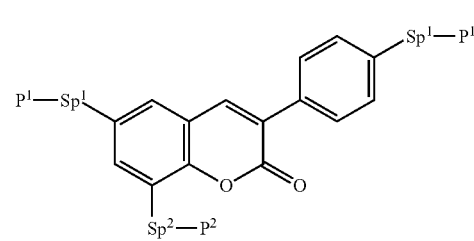 M17
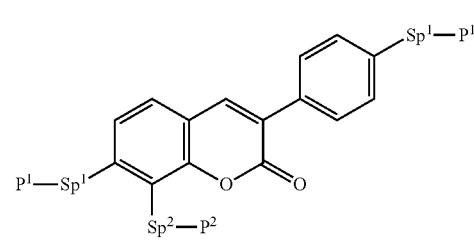 M18
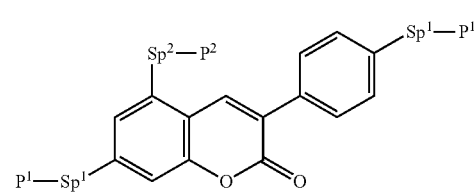 M19
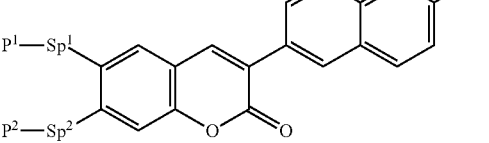 M20
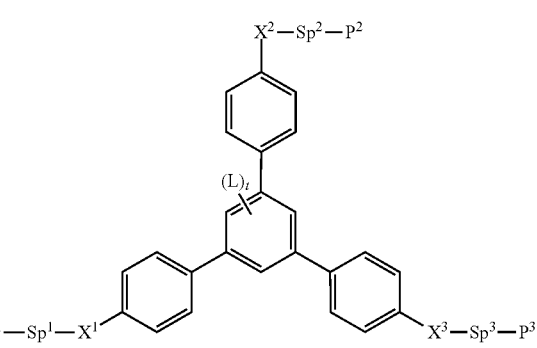 M21
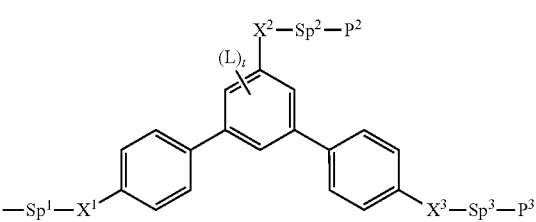 M22
-continued
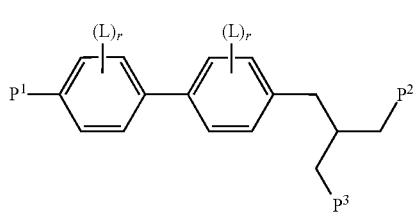 M23
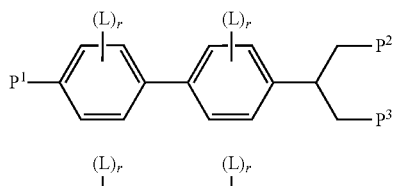 M24
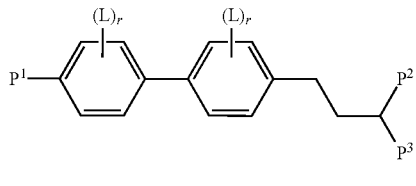 M25
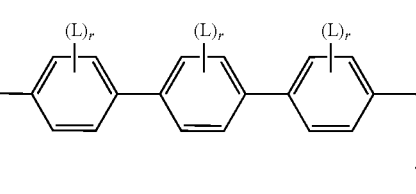 M26
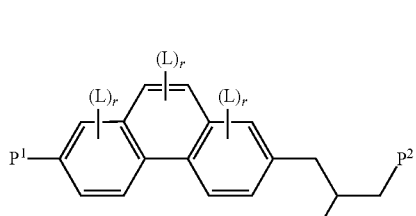 M27
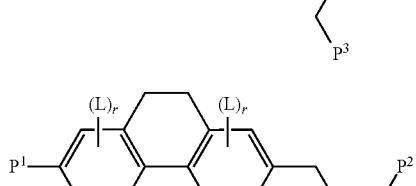 M28
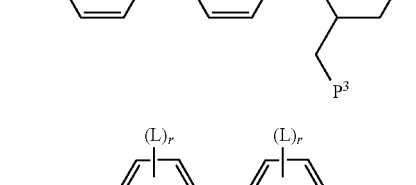 M29
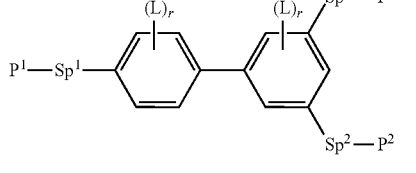 M30
in which the individual radicals have the following meanings:

P$^1$, P$^2$ and P$^3$ each, independently of one another, denote an acrylate or methacrylate group, Sp$^1$, Sp$^2$ and Sp$^3$ each, independently of one another, denote a single bond or a spacer group having one of the meanings indicated above and below for Sp$^1$, and particularly preferably denote —(CH$_2$)$_{p1}$—, —(CH$_2$)$_{p1}$—O—, —(CH$_2$)$_{p1}$—CO—O—, —(CH$_2$)$_{p1}$—O—CO— or —(CH$_2$)$_{p1}$—O—CO—O—, in which p1 is an integer from 1 to 12, where, in addition, one or more of the radicals P$^1$-Sp$^1$-, P$^1$-Sp$^2$- and P$^3$-Sp$^3$- may denote R$^{aa}$, with the proviso that at least one of the radicals P$^1$-Sp$^1$-, P$^2$-Sp$^2$ and P$^3$-Sp$^3$- present is different from R$^{aa}$, R$^{aa}$ denotes H, F, Cl, CN or straight-chain or branched alkyl having 1 to 25 C atoms, in which, in addition, one or more non-adjacent CH$_2$ groups may each be replaced, independently of one another, by C(R$^0$)=C(R$^{00}$)—, —C≡C—, —N(R$^0$)—, —O—, —S—, —CO—, —CO—O—, —O—CO—, —O—CO—O— in such a way that O and/or S atoms are not linked directly to one another, and in which, in addition, one or more H atoms may be replaced by F, Cl, CN or P$^1$-Sp$^1$-, particularly preferably straight-chain or branched, optionally mono- or polyfluorinated alkyl, alkoxy, alkenyl, alkynyl, alkylcarbonyl, alkoxycarbonyl, alkylcarbonyloxy or alkoxycarbonyloxy having 1 to 12 C atoms (where the alkenyl and alkynyl radicals have at least two C atoms and the branched radicals have at least three C atoms), R$^0$, R$^{00}$ each, independently of one another and identically or differently on each occurrence, denote H or alkyl having 1 to 12 C atoms, R$^y$ and R$^z$ each, independently of one another, denote H, F, CH$_3$ or CF$_3$, X$^1$, X$^2$ and X$^3$ each, independently of one another, denote —CO—O—, —O—CO— or a single bond, Z$^1$ denotes —O—, —CO—, —C(R$^y$R$^z$)— or —CF$_2$CF$_2$—, Z$^2$ and Z$^3$ each, independently of one another, denote —CO—O—, —O—CO—, —CH$_2$O—, —OCH$_2$—, —CF$_2$O—, —OCF$_2$— or —(CH$_2$)$_n$—, where n is 2, 3 or 4, L on each occurrence, identically or differently, denotes F, Cl, CN or straight-chain or branched, optionally mono- or polyfluorinated alkyl, alkoxy, alkenyl, alkynyl, alkylcarbonyl, alkoxycarbonyl, alkylcarbonyloxy or alkoxycarbonyloxy having 1 to 12 C atoms, preferably F, L' and L" each, independently of one another, denote H, F or Cl, r denotes 0, 1, 2, 3 or 4, s denotes 0, 1, 2 or 3, t denotes 0, 1 or 2, x denotes 0 or 1.

Especially preferred are compounds of formulae M2, M13, M17, M22, M23 and M29.

Further preferred are trireactive compounds M15 to M30, in particular M17, M18, M19, M22, M23, M24, M25, M29 and M30.

In the compounds of formulae M1 to M30 the group

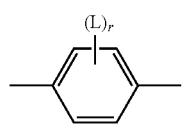

is preferably

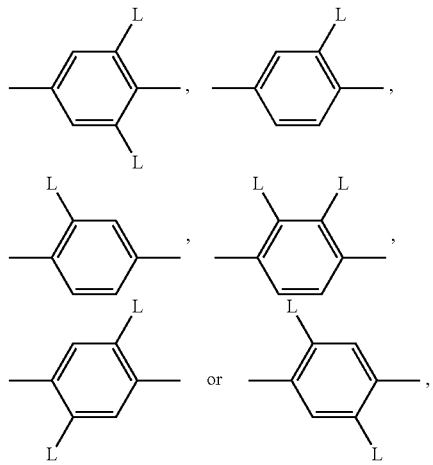

wherein L on each occurrence, identically or differently, has one of the meanings given above or below, and is preferably F, Cl, CN, NO$_2$, CH$_3$, C$_2$H$_5$, C(CH$_3$)$_3$, CH(CH$_3$)$_2$, CH$_2$CH (CH$_3$)C$_2$H$_5$, OCH$_3$, OC$_2$H$_5$, COCH$_3$, COC$_2$H$_5$, COOCH$_3$, COOC$_2$H$_5$, CF$_3$, OCF$_3$, OCHF$_2$, OC$_2$F$_5$ or P-Sp-, very preferably F, Cl, CN, CH$_3$, C$_2$H$_5$, OCH$_3$, COCH$_3$, OCF$_3$ or P-Sp-, more preferably F, Cl, CH$_3$, OCH$_3$, COCH$_3$ oder OCF$_3$, especially F or CH$_3$.

Besides the polymerisable compounds described above, the LC media for use in the LC displays according to the invention comprise an LC component B), or LC "host mixture" comprising, or consisting of, one or more, preferably two or more LC compounds which are selected from low-molecular-weight compounds that are unpolymerisable. These LC compounds are selected such that they stable and/or unreactive to a polymerisation reaction under the conditions applied to the polymerisation of the polymerisable compounds.

In principle, any LC mixture which is suitable for use in conventional displays is suitable as host mixture. Suitable LC mixtures are known to the person skilled in the art and are described in the literature, for example mixtures in VA displays in EP 1 378 557 A1 and mixtures for OCB displays in EP 1 306 418 A1 and DE 102 24 046 A1.

In addition to the polymerisable compounds the LC medium according to the present invention comprises one or more mesogenic or liquid crystalline compounds comprising an alkenyl group, ("alkenyl compound"), where this alkenyl group is preferably stable to a polymerisation reaction under the conditions used for the polymerisation of the polymerisable compounds of formula I or of the other polymerisable compounds contained in the LC medium.

The polymerisable compounds of formula I are especially suitable for use in an LC host mixture that comprises one or more mesogenic or LC compounds comprising an alkenyl group (hereinafter also referred to as "alkenyl compounds"), wherein said alkenyl group is stable to a polymerisation reaction under the conditions used for polymerisation of the compounds of formula I and of the other polymerisable compounds contained in the LC medium. Compared to RMs known from prior art the compounds of formula I do in such an LC host mixture exhibit improved properties, like solubility, reactivity or capability of generating a tilt angle.

The LC host mixture is preferably a nematic LC mixture.

The alkenyl groups in the alkenyl compounds are preferably selected from straight-chain, branched or cyclic alkenyl, in particular having 2 to 25 C atoms, particularly preferably having 2 to 12 C atoms, in which, in addition, one or more non-adjacent CH$_2$ groups may be replaced by —O—, —S—, —CO—, —CO—O—, —O—CO—, —O—CO—O— in such a way that O and/or S atoms are not linked directly to one another, and in which, in addition, one or more H atoms may be replaced by F and/or Cl.

Preferred alkenyl groups are straight-chain alkenyl having 2 to 7 C atoms and cyclohexenyl, in particular ethenyl, propenyl, butenyl, pentenyl, hexenyl, heptenyl, 1,4-cyclohexen-1-yl and 1,4-cyclohexen-3-yl.

The concentration of compounds containing an alkenyl group in the LC host mixture (i.e. without any polymerisable compounds) is preferably from 5% to 100%, very preferably from 20% to 60%.

Especially preferred are LC mixtures containing 1 to 5, preferably 1, 2 or 3 compounds having an alkenyl group.

The mesogenic and LC compounds containing an alkenyl group are preferably selected from the following formulae:

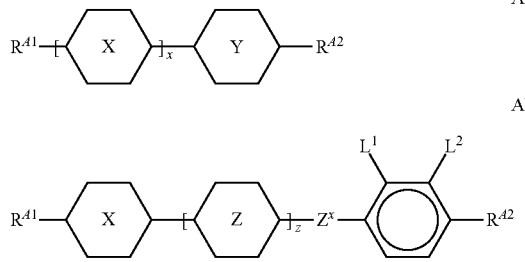

AN

AY in which the individual radicals, on each occurrence identically or differently, each, independently of one another, have the following meaning:

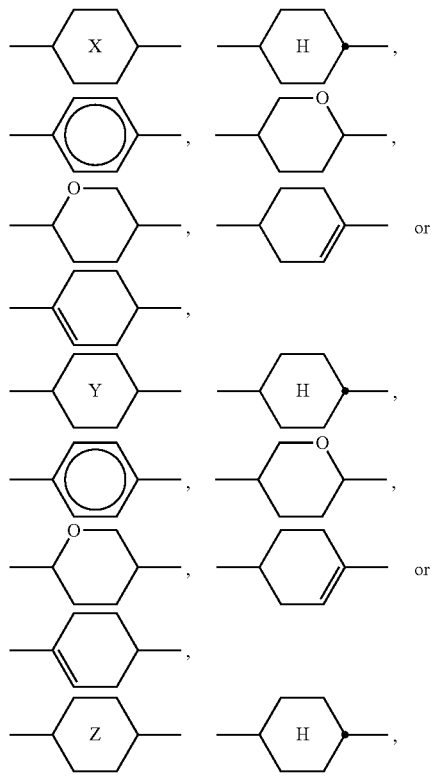

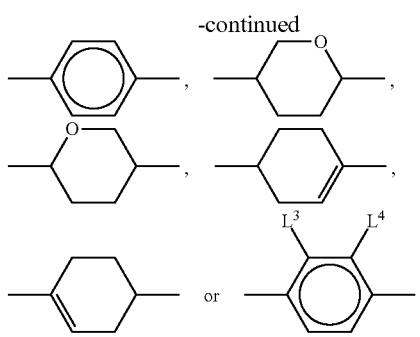

$R^{A1}$ alkenyl having 2 to 9 C atoms or, if at least one of the rings X, Y and Z denotes cyclohexenyl, also one of the meanings of $R^{A2}$, $R^{A2}$ alkyl having 1 to 12 C atoms, in which, in addition, one or two non-adjacent CH$_2$ groups may be replaced by —O—, —CH=CH—, —CO—, —OCO— or —COO— in such a way that O atoms are not linked directly to one another, $Z^x$ —CH$_2$CH$_2$—, —CH=CH—, —CF$_2$O—, —OCF$_2$—, —CH$_2$O—, —OCH$_2$—, —CO—O—, —O—CO—, —C$_2$F$_4$—, —CF=CF—, —CH=CH—CH$_2$O—, or a single bond, preferably a single bond, $L^{1-4}$ each, independently of one another, H, F, Cl, OCF$_3$, CF$_3$, CH$_3$, CH$_2$F or CHF$_2$H, preferably H, F or Cl, x 1 or 2, z 0 or 1.

$R^{A2}$ is preferably straight-chain alkyl or alkoxy having 1 to 8 C atoms or straight-chain alkenyl having 2 to 7 C atoms.

The LC medium preferably comprises no compounds containing a terminal vinyloxy group (—O—CH=CH$_2$), in particular no compounds of the formula AN or AY in which $R^{A1}$ or $R^{A2}$ denotes or contains a terminal vinyloxy group (—O—CH=CH$_2$).

Preferably, $L^1$ and $L^2$ denote F, or one of $L^1$ and $L^2$ denotes F and the other denotes Cl, and $L^3$ and $L^4$ denote F, or one of $L^3$ and $L^4$ denotes F and the other denotes Cl.

The compounds of the formula AN are preferably selected from the following sub-formulae:

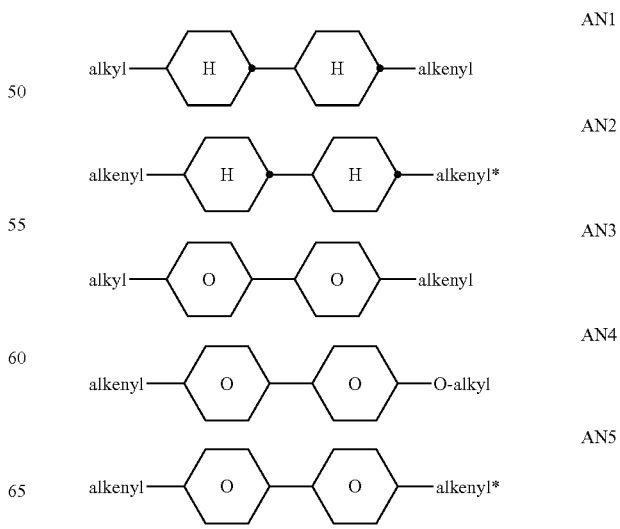

AN6
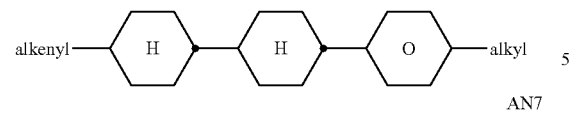

AN7
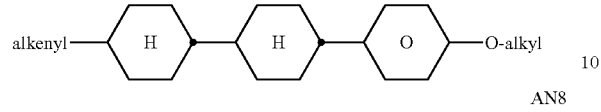

AN8
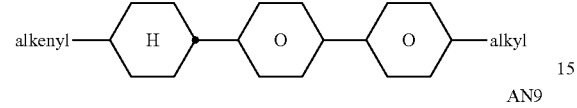

AN9
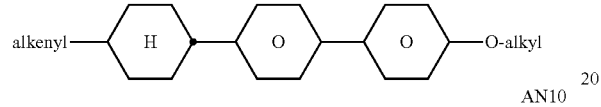

AN10
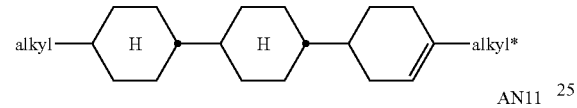

AN11
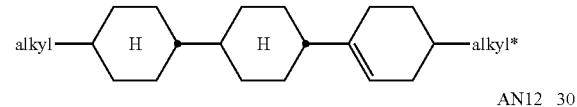

AN12
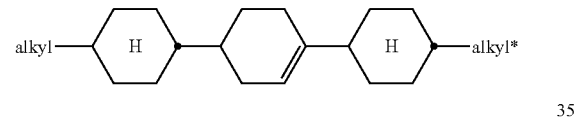

in which alkyl and alkyl* each, independently of one another, denote a straight-chain alkyl radical having 1-6 C atoms, and alkenyl and alkenyl* each, independently of one another, denote a straight-chain alkenyl radical having 2-7 C atoms. Alkenyl and alkenyl* preferably denote $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

The compounds of the formula AY are preferably selected from the following sub-formulae:

AY1
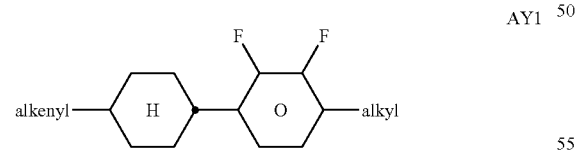

AY2
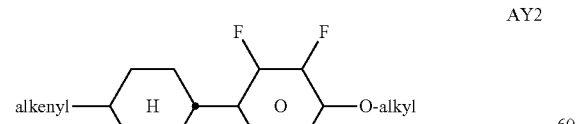

AY3
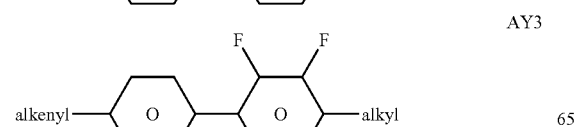

AY4
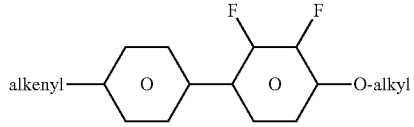

AY5
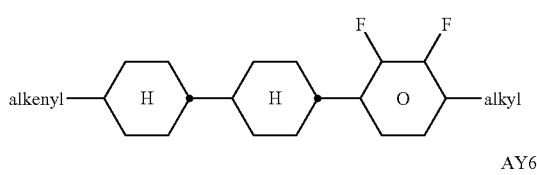

AY6
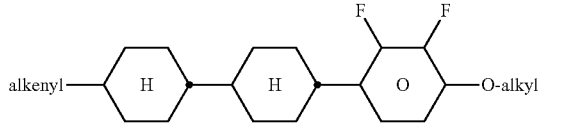

AY7
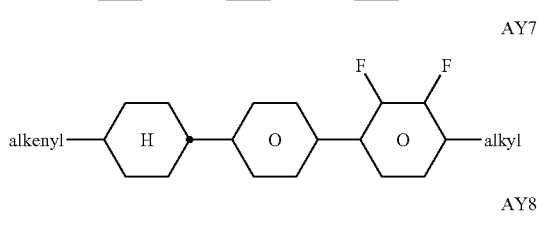

AY8
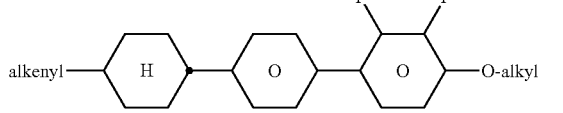

AY9
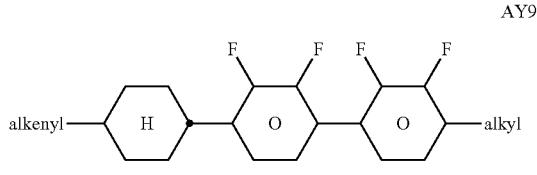

AY10
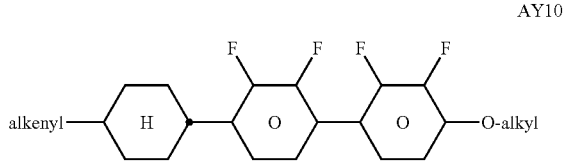

AY11
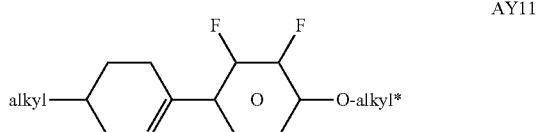

AY12
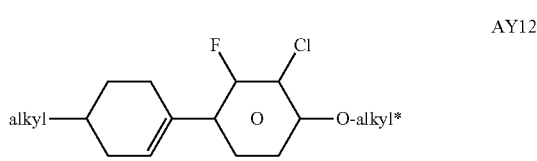

AY13

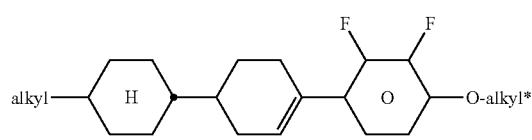
AY14

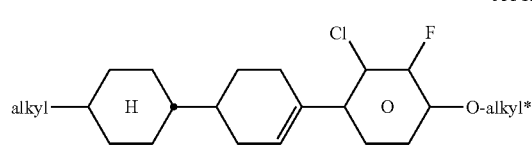
AY15

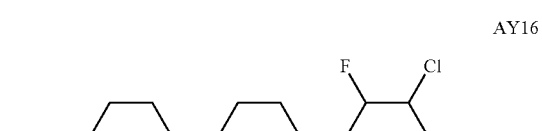
AY16

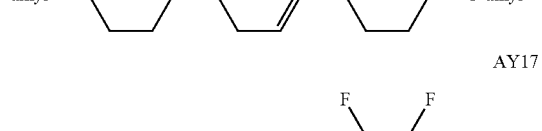
AY17

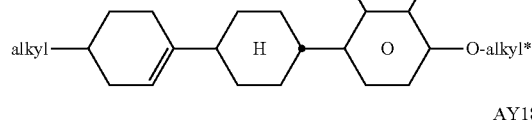
AY18

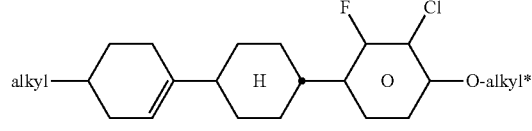
AY19

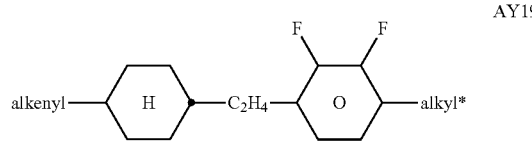
AY20

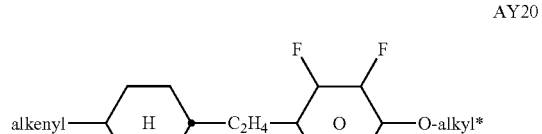
AY21

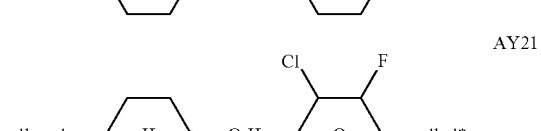
AY22

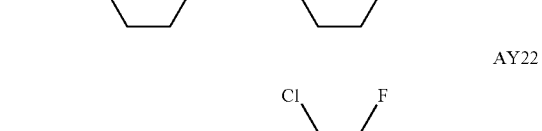
AY23

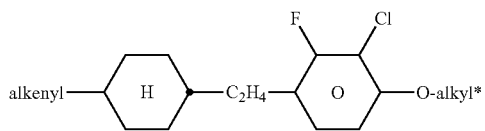
AY24

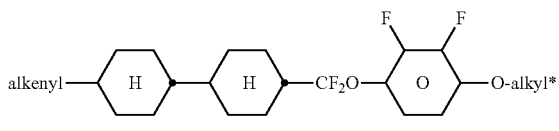
AY25

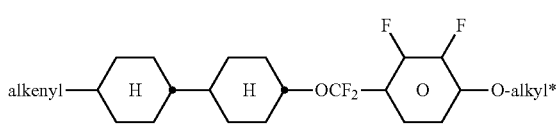
AY26

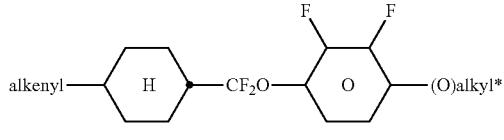
AY27

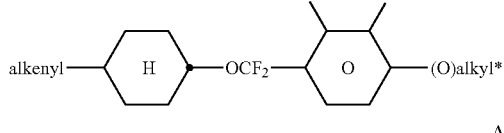
AY28

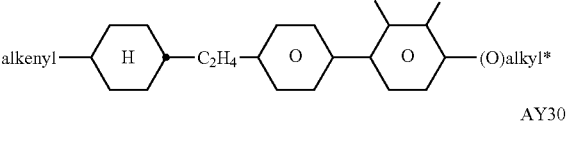
AY29

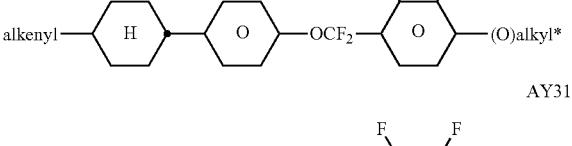
AY30

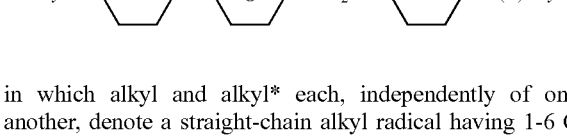
AY31 in which alkyl and alkyl* each, independently of one another, denote a straight-chain alkyl radical having 1-6 C atoms, and alkenyl and alkenyl* each, independently of one another, denote a straight-chain alkenyl radical having 2-7 C atoms. Alkenyl and alkenyl* preferably denote $CH_2$=CH—, $CH_2$=$CHCH_2CH_2$—, $CH_3$—CH=CH—, $CH_3$—$CH_2$—CH=CH—, $CH_3$—$(CH_2)_2$—CH=CH—, $CH_3$—$(CH_2)_3$—CH=CH— or $CH_3$—CH=CH—$(CH_2)_2$—.

Very preferred compounds of the formula AN are selected from the following sub-formulae:

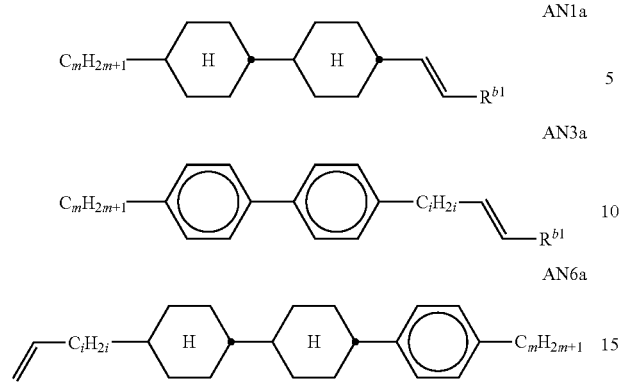

ANla

AN3a

AN6a in which m denotes 1, 2, 3, 4, 5 or 6, i denotes 0, 1, 2 or 3, and $R^{b1}$ denotes H, $CH_3$ or $C_2H_5$.

Very particularly preferred compounds of the formula AN are selected from the following sub-formulae:

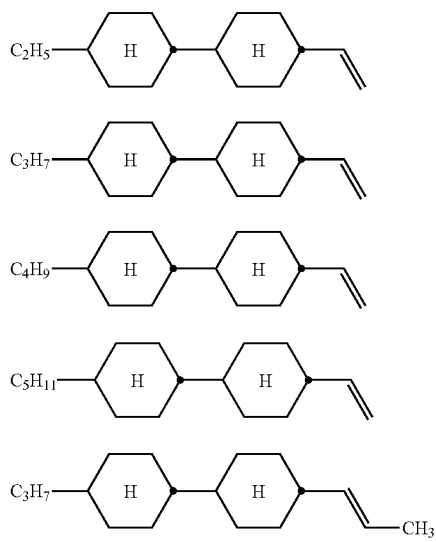

AN1a1

AN1a2

AN1a3

AN1a4

AN1a5

Most preferred are compounds of formula AN1a2 and AN1a5.

Very particularly preferred compounds of the formula AY are selected from the following sub-formulae:

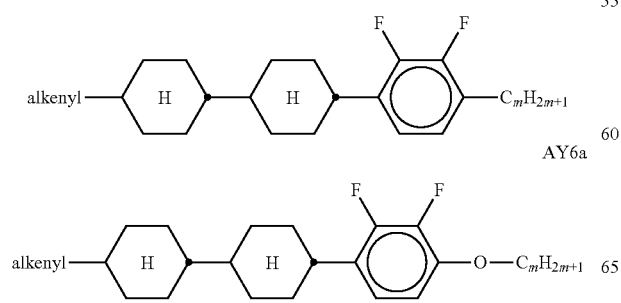

AY5a

AY6a

-continued

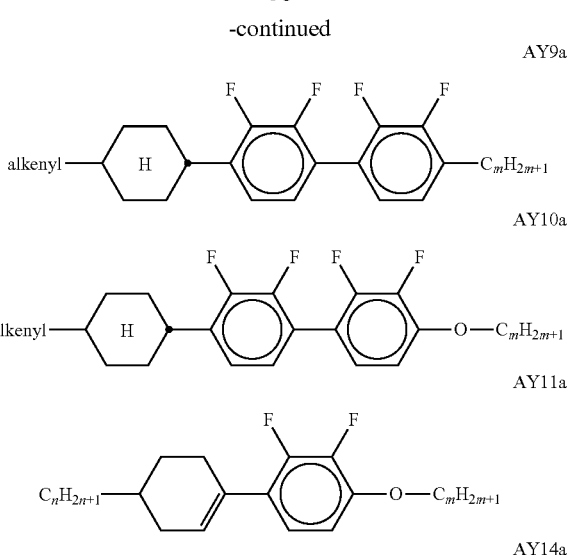

AY9a

AY10a

AY11a

AY14a in which m and n each, independently of one another, denote 1, 2, 3, 4, 5 or 6, and alkenyl denotes $CH_2{=}CH{-}$, $CH_2{=}CHCH_2CH_2{-}$, $CH_3{-}CH{=}CH{-}$, $CH_3{-}CH_2{-}CH{=}CH{-}$, $CH_3{-}(CH_2)_2{-}CH{=}CH{-}$, $CH_3{-}(CH_2)_3{-}CH{=}CH{-}$ or $CH_3{-}CH{=}CH{-}(CH_2)_2{-}$.

In a first preferred embodiment the LC medium contains an LC component B), or LC host mixture, based on compounds with negative dielectric anisotropy. Such LC media are especially suitable for use in PS-VA and PS-UB-FFS displays. Particularly preferred embodiments of such an LC medium are those of sections a)-z) below:

a) LC medium which comprises one or more compounds of the formulae CY and/or PY:

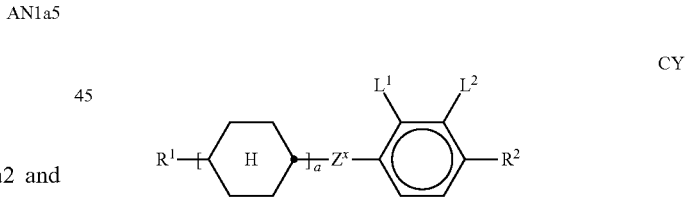

CY

PY wherein
a denotes 1 or 2,
b denotes 0 or 1,

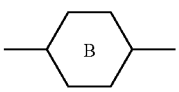

denotes

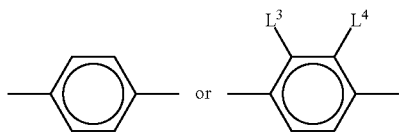

- $R^1$ and $R^2$ each, independently of one another, denote alkyl having 1 to 12 C atoms, where, in addition, one or two non-adjacent $CH_2$ groups may be replaced by —O—, —CH=CH—, —CO—, —OCO— or —COO— in such a way that O atoms are not linked directly to one another, preferably alkyl or alkoxy having 1 to 6 C atoms,
- $Z^x$ and $Z^y$ each, independently of one another, denote —$CH_2CH_2$—, —CH=CH—, —$CF_2O$—, —$OCF_2$—, —$CH_2O$—, —$OCH_2$—, —CO—O—, —O—CO—, —$C_2F_4$—, —CF=CF—, —CH—$CH_2O$— or a single bond, preferably a single bond,
- $L^{1-4}$ each, independently of one another, denote F, Cl, $OCF_3$, $CF_3$, $CH_3CH_2F$, $CHF_2$.
- Preferably, both $L^1$ and $L^2$ denote F or one of $L^1$ and $L^2$ denotes F and the other denotes Cl, or both $L^3$ and $L^4$ denote F or one of $L^3$ and $L^4$ denotes F and the other denotes Cl.

The compounds of the formula CY are preferably selected from the group consisting of the following sub-formulae:

CY1
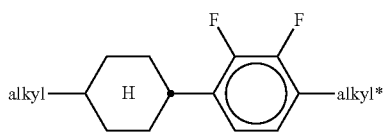

CY2
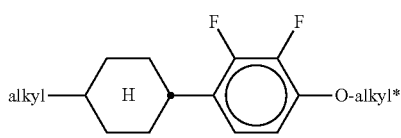

CY3
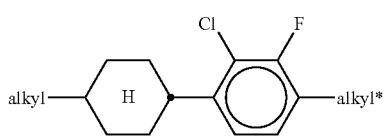

CY4
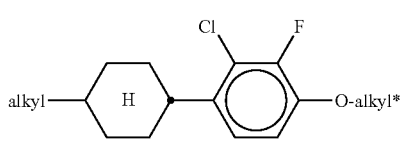

CY5
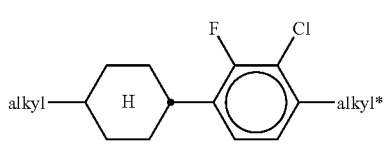

CY6
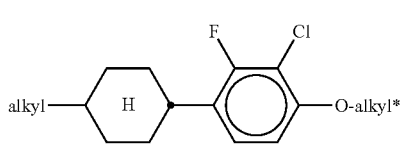

CY7
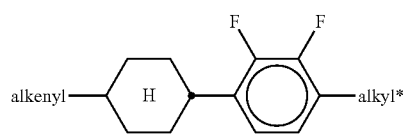

CY8
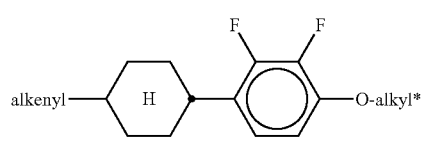

CY9
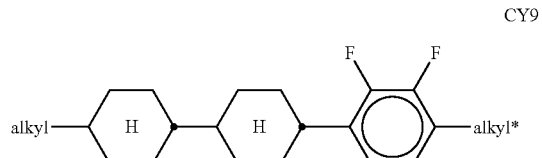

CY10
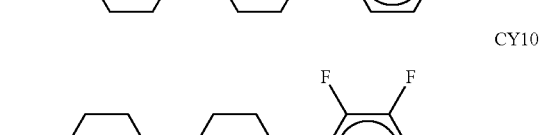

CY11
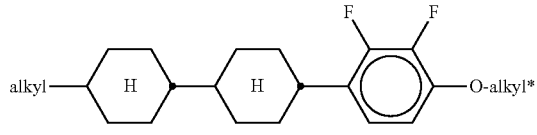

CY12
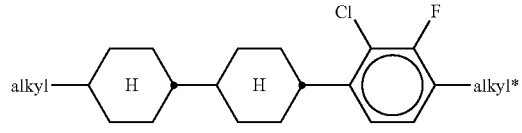

CY13
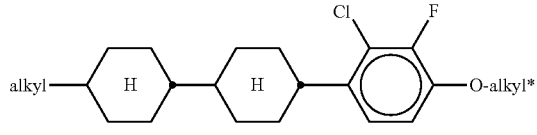

CY14
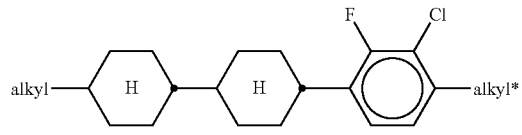

CY15
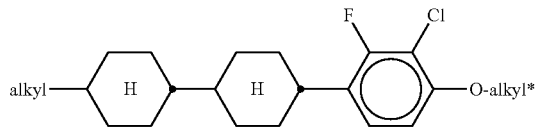

CY16
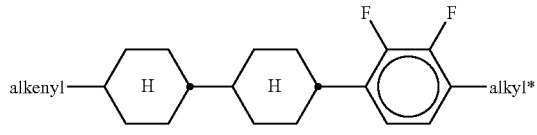

CY17
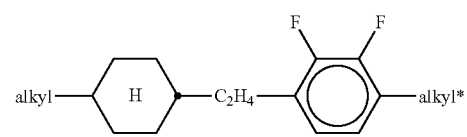

CY18
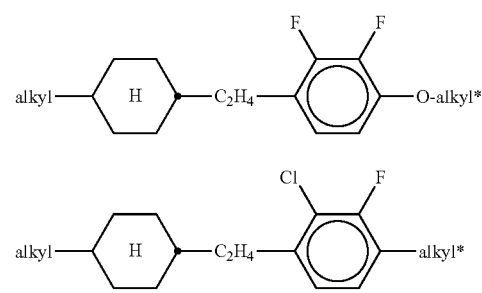

CY19

CY20
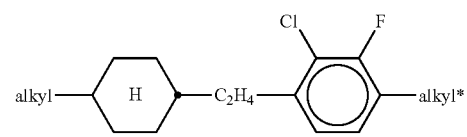

CY21
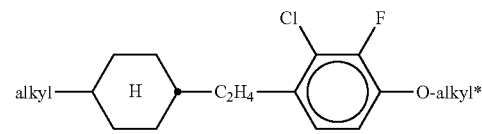

CY22
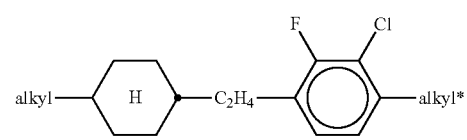

CY23
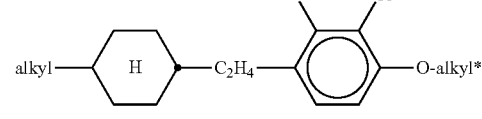

CY24
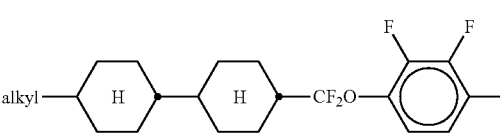

CY25
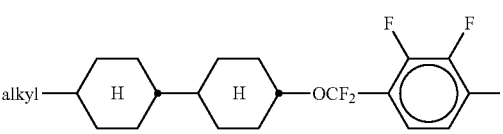

CY26
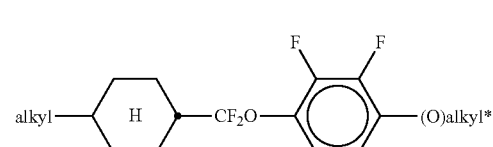
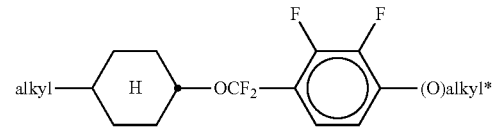

CY27
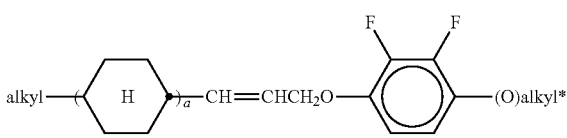

CY28
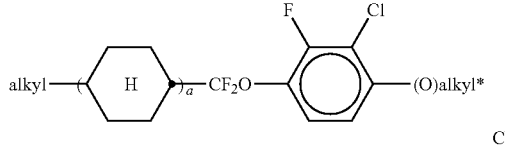

CY29
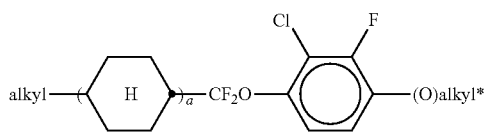

CY30
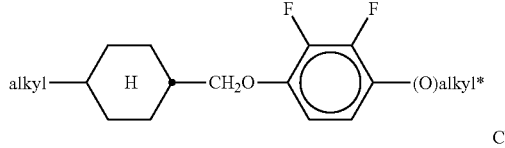

CY31
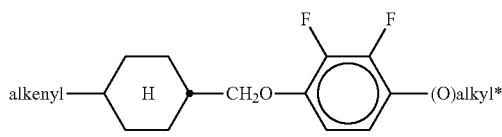

CY32
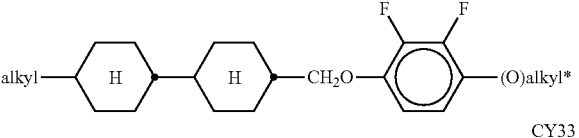

CY33
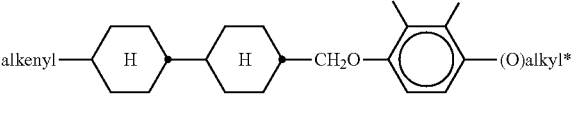

in which a denotes 1 or 2, alkyl and alkyl* each, independently of one another, denote a straight-chain alkyl radical having 1-6 C atoms, and alkenyl denotes a straight-chain alkenyl radical having 2-6 C atoms, and (O) denotes an oxygen atom or a single bond. Alkenyl preferably denotes $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

The compounds of the formula PY are preferably selected from the group consisting of the following sub-formulae:

PY1
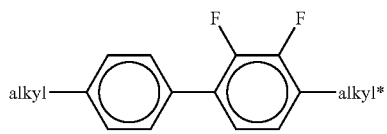

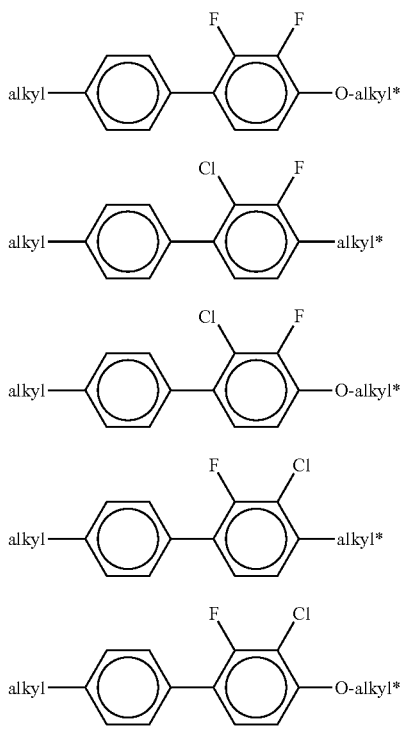

PY2
PY3
PY4
PY5
PY6
PY7
PY8
PY9
PY10
PY11
PY12

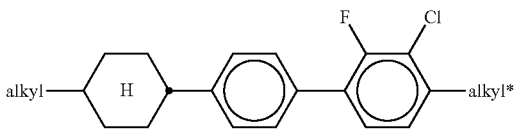

PY13

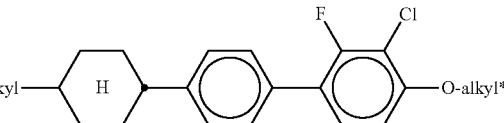

PY14

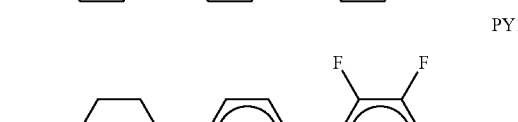

PY15

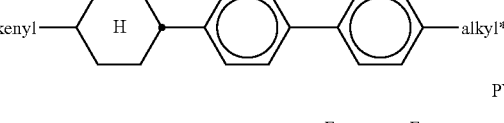

PY16

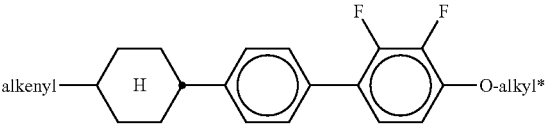

PY17

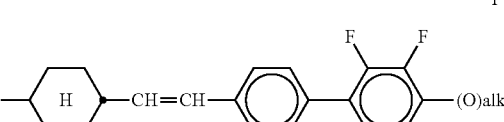

PY18

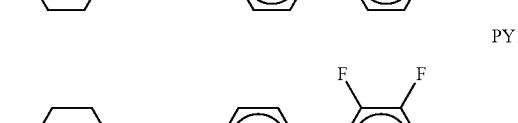

PY19

PY20

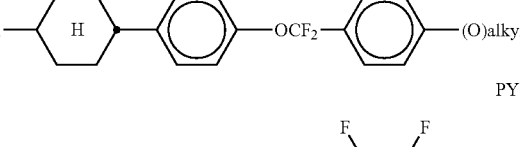

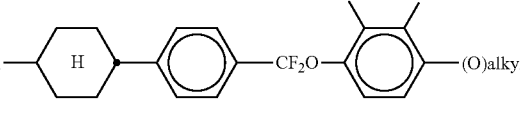

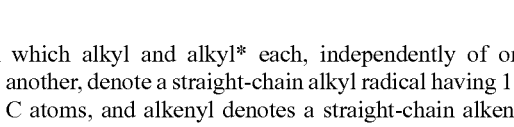

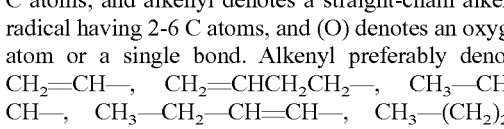

in which alkyl and alkyl* each, independently of one another, denote a straight-chain alkyl radical having 1-6 C atoms, and alkenyl denotes a straight-chain alkenyl radical having 2-6 C atoms, and (O) denotes an oxygen atom or a single bond. Alkenyl preferably denotes $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

b) LC medium which additionally comprises one or more compounds of the following formula:

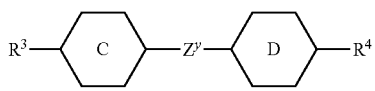

in which the individual radicals have the following meanings:

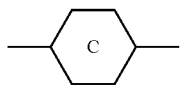

denotes

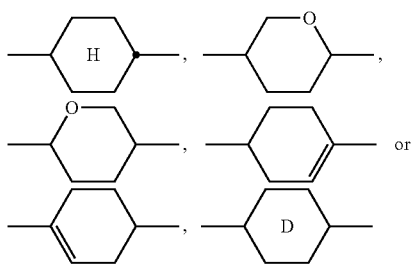

denotes

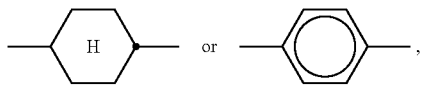

- $R^3$ and $R^4$ each, independently of one another, denote alkyl having 1 to 12 C atoms, in which, in addition, one or two non-adjacent $CH_2$ groups may be replaced by —O—, —CH=CH—, —CO—, —O—CO— or —CO—O— in such a way that O atoms are not linked directly to one another,
- $Z^y$ denotes —$CH_2CH_2$—, —CH=CH—, —$CF_2O$—, —$OCF_2$—, —$CH_2O$—, —$OCH_2$—, —CO—O—, —O—CO—, —$C_2F_4$—, —CF=CF—, —CH=CH—$CH_2O$— or a single bond, preferably a single bond.

The compounds of the formula ZK are preferably selected from the group consisting of the following sub-formulae:

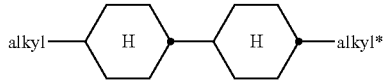

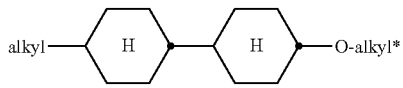

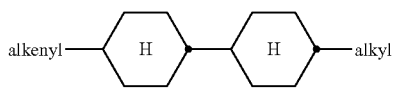

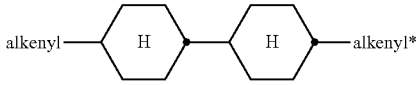

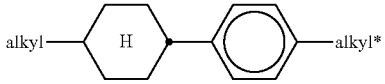

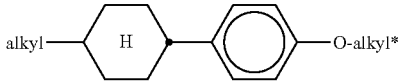

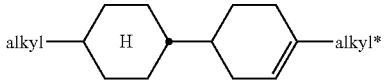

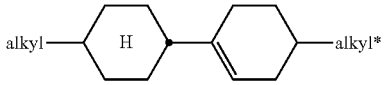

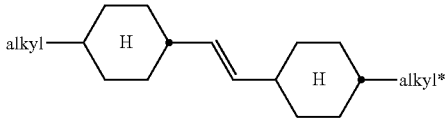

in which alkyl and alkyl* each, independently of one another, denote a straight-chain alkyl radical having 1-6 C atoms, and alkenyl denotes a straight-chain alkenyl radical having 2-6 C atoms. Alkenyl preferably denotes $CH_2$=CH—, $CH_2$=$CHCH_2CH_2$—, $CH_3$—CH=CH—, $CH_3$—$CH_2$—CH=CH—, $CH_3$—$(CH_2)_2$—CH=CH—, $CH_3$—$(CH_2)_3$—CH=CH— or $CH_3$—CH=CH—$(CH_2)_2$—.

Especially preferred are compounds of formula ZK1.

Particularly preferred compounds of formula ZK are selected from the following sub-formulae:

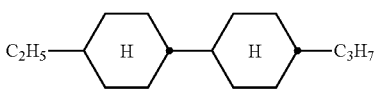

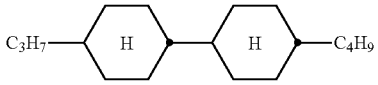

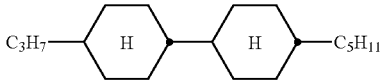

wherein the propyl, butyl and pentyl groups are straight-chain groups.

Most preferred are compounds of formula ZK1a.

c) LC medium which additionally comprises one or more compounds of the following formula:

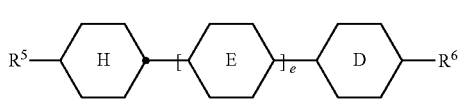
DK in which the individual radicals on each occurrence, identically or differently, have the following meanings:
R⁵ and R⁶ each, independently of one another, denote alkyl having 1 to 12 C atoms, where, in addition, one or two non-adjacent CH₂ groups may be replaced by —O—, —CH=CH—, —CO—, —OCO— or —COO— in such a way that O atoms are not linked directly to one another, preferably alkyl or alkoxy having 1 to 6 C atoms,

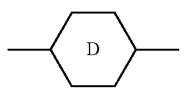

denotes

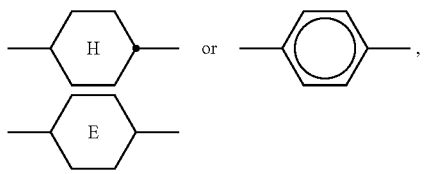

denotes

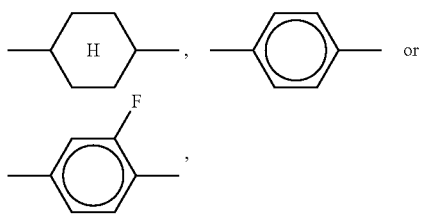

and
  e denotes 1 or 2.
  The compounds of the formula DK are preferably selected from the group consisting of the following sub-formulae:

DK1

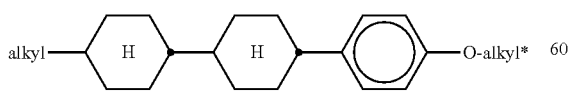
DK2

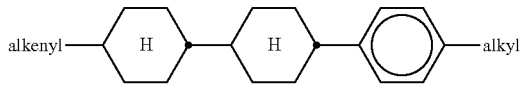
DK3

DK4

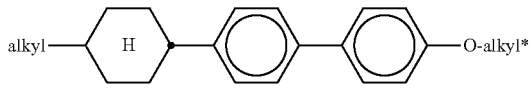
DK5

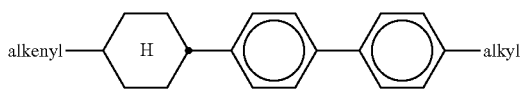
DK6

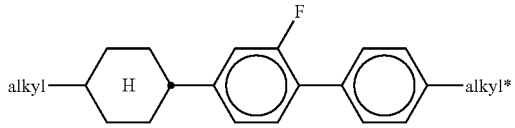
DK7

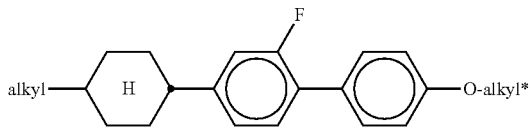
DK8

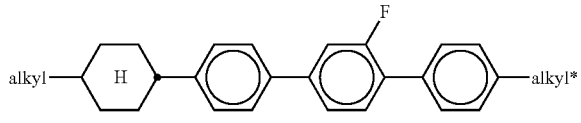
DK9

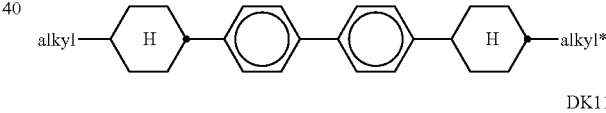
DK10

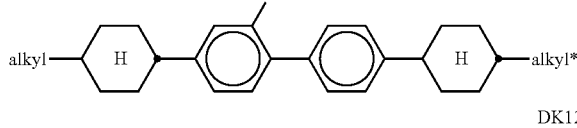
DK11

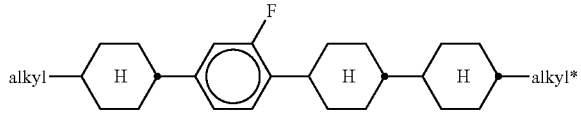
DK12 in which alkyl and alkyl* each, independently of one another, denote a straight-chain alkyl radical having 1-6 C atoms, and alkenyl denotes a straight-chain alkenyl radical having 2-6 C atoms. Alkenyl preferably denotes CH₂=CH—, CH₂=CHCH₂CH₂—, CH₃—CH=CH—, CH₃—CH₂—CH=CH—, CH₃—(CH₂)₂—CH=CH—, CH₃—(CH₂)₃—CH=CH— or CH₃—CH=CH—(CH₂)₂—.

d) LC medium which additionally comprises one or more compounds of the following formula:

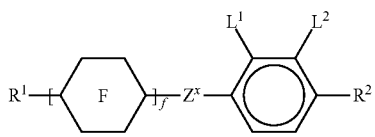
LY in which the individual radicals have the following meanings:

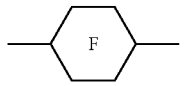

denotes

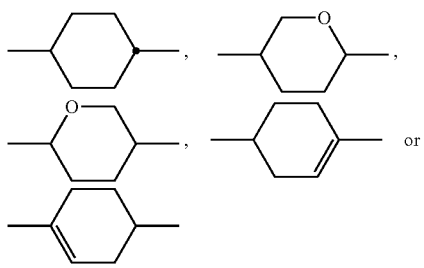

with at least one ring F being different from cyclohexylene, f denotes 1 or 2, $R^1$ and $R^2$ each, independently of one another, denote alkyl having 1 to 12 C atoms, where, in addition, one or two non-adjacent $CH_2$ groups may be replaced by —O—, —CH=CH—, —CO—, —OCO— or —COO— in such a way that O atoms are not linked directly to one another, $Z^x$ denotes —$CH_2CH_2$—, —CH=CH—, —$CF_2O$—, —$OCF_2$—, —$CH_2O$—, —$OCH_2$—, —CO—O—, —O—CO—, —$C_2F_4$—, —CF=CF—, —CH=CH—$CH_2O$— or a single bond, preferably a single bond, $L^1$ and $L^2$ each, independently of one another, denote F, Cl, $OCF_3$, $CF_3$, $CH_3$, $CH_2F$, $CHF_2$.

Preferably, both radicals $L^1$ and $L^2$ denote F or one of the radicals $L^1$ and $L^2$ denotes F and the other denotes Cl.

The compounds of the formula LY are preferably selected from the group consisting of the following sub-formulae:

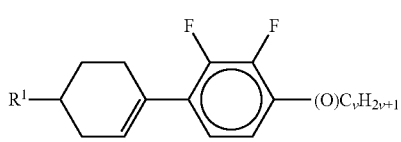
LY1

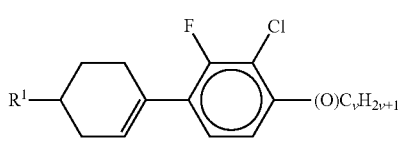
LY2

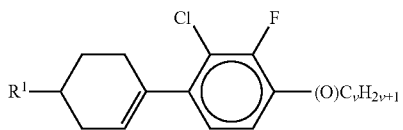
LY3

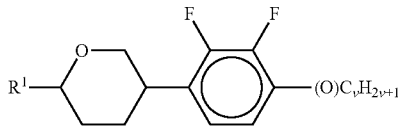
LY4

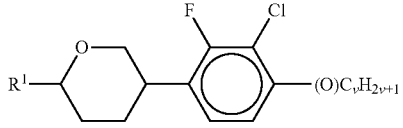
LY5

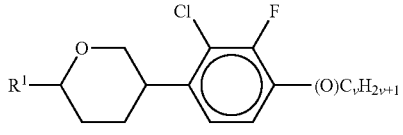
LY6

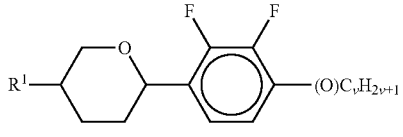
LY7

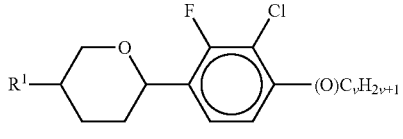
LY8

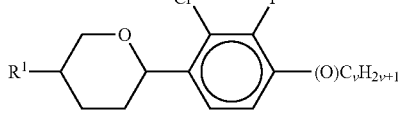
LY9

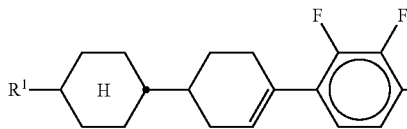
LY10

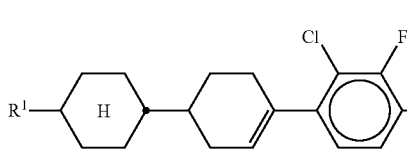
LY11

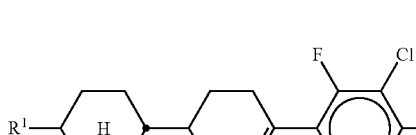
LY12

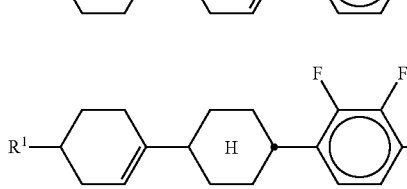
LY13

LY14
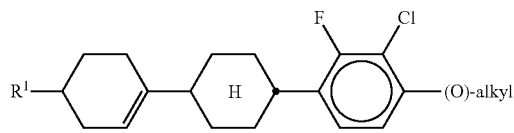

LY15
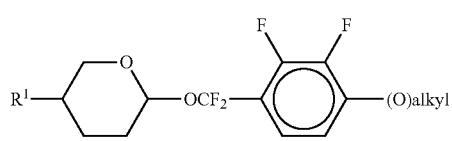

LY16
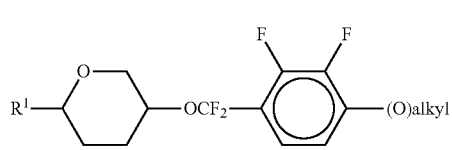

LY17
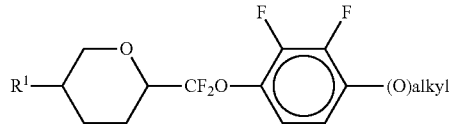

LY18
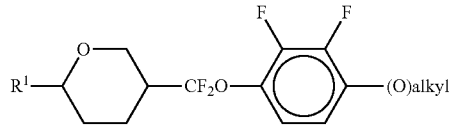

LY19
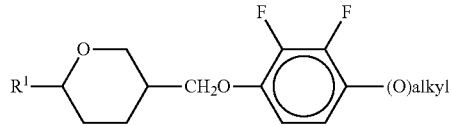

LY20
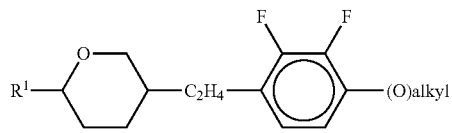

LY21
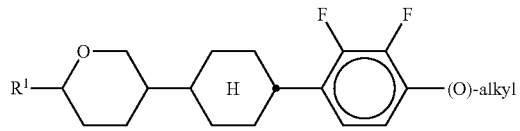

LY22
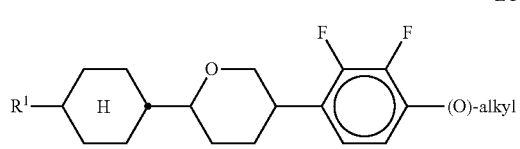

LY23
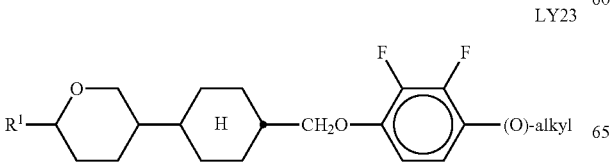

LY24
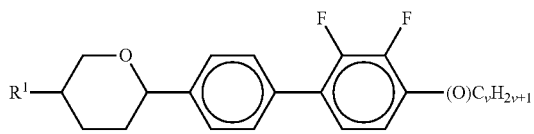

in which $R^1$ has the meaning indicated above, alkyl denotes a straight-chain alkyl radical having 1-6 C atoms, (O) denotes an oxygen atom or a single bond, and v denotes an integer from 1 to 6. $R^1$ preferably denotes straight-chain alkyl having 1 to 6 C atoms or straight-chain alkenyl having 2 to 6 C atoms, in particular $CH_3$, $C_2H_5$, n-$C_3H_7$, n-$C_4H_9$, n-$C_5H_{11}$, $CH_2$=CH—, $CH_2$=CHCH$_2$CH$_2$—, $CH_3$—CH=CH—, $CH_3$—CH$_2$—CH=CH—, $CH_3$—(CH$_2$)$_2$—CH=CH—, $CH_3$—(CH$_2$)$_3$—CH=CH— or $CH_3$—CH=CH—(CH$_2$)$_2$—.

e) LC medium which additionally comprises one or more compounds selected from the group consisting of the following formulae:

G1
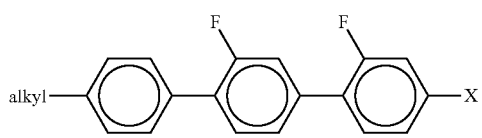

G2
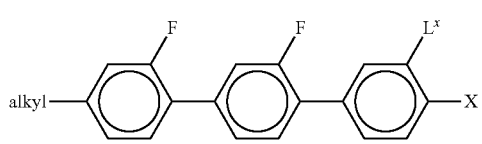

G3
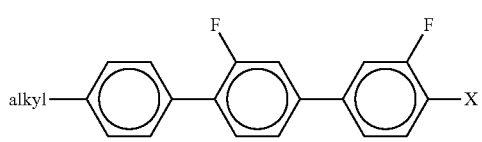

G4
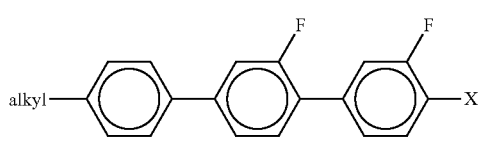

in which alkyl denotes $C_{1-6}$-alkyl, $L^x$ denotes H or F, and X denotes F, Cl, $OCF_3$, $OCHF_2$ or $OCH$=$CF_2$. Particular preference is given to compounds of the formula G1 in which X denotes F.

f) LC medium which additionally comprises one or more compounds selected from the group consisting of the following formulae:

Y1
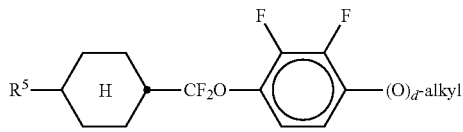

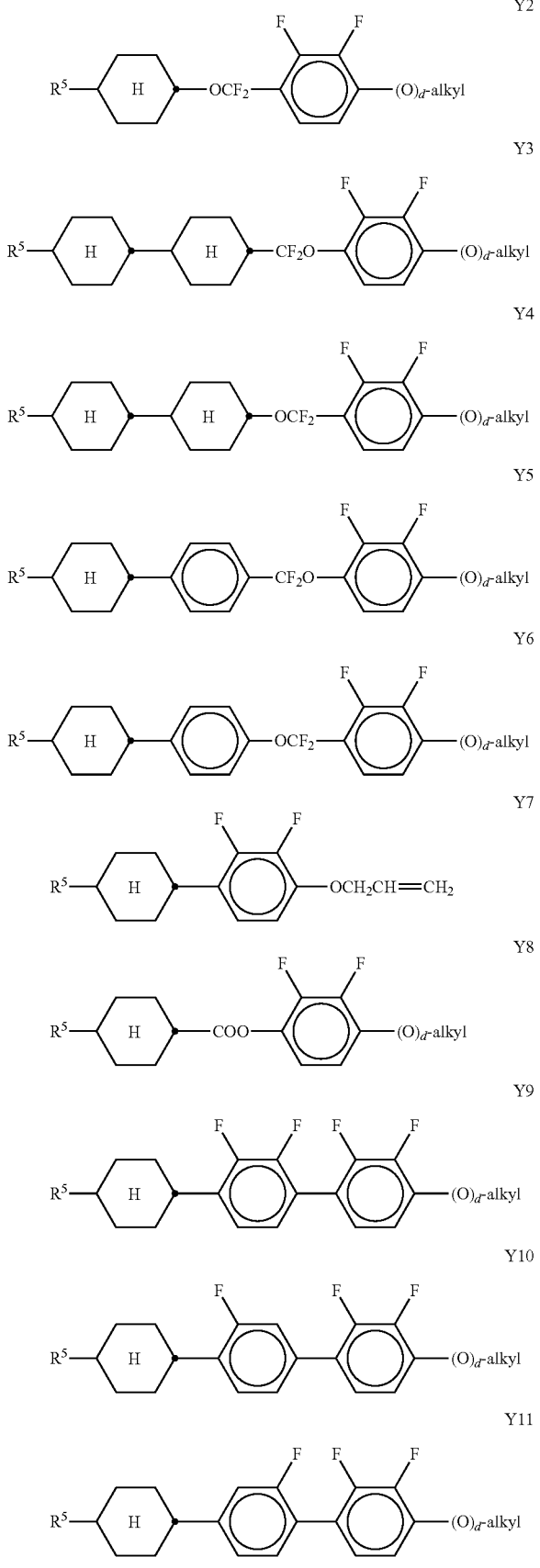
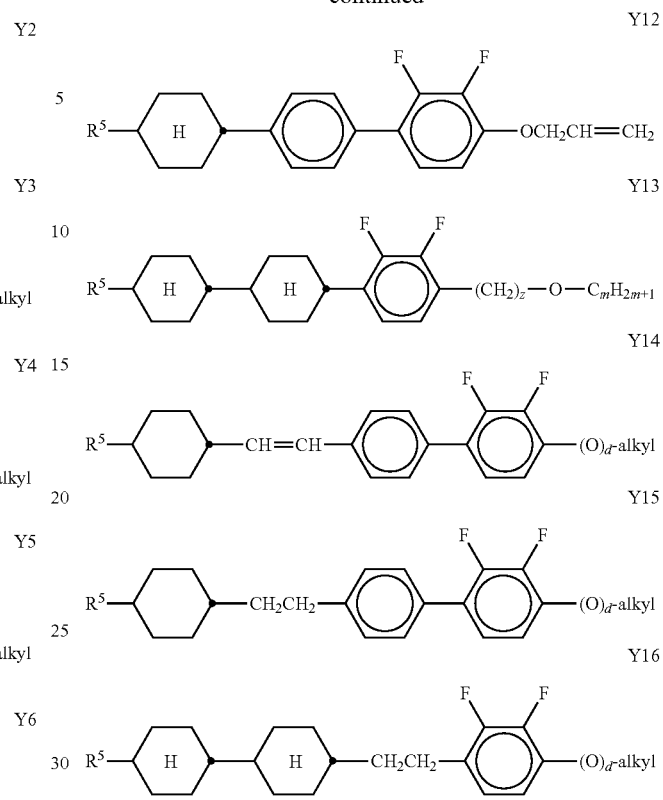

in which R⁵ has one of the meanings indicated above for R¹, alkyl denotes $C_{1-6}$-alkyl, d denotes 0 or 1, and z and m each, independently of one another, denote an integer from 1 to 6. R⁵ in these compounds is particularly preferably $C_{1-6}$-alkyl or -alkoxy or $C_{2-6}$-alkenyl, d is preferably 1. The LC medium according to the invention preferably comprises one or more compounds of the above-mentioned formulae in amounts of 5% by weight.

g) LC medium which additionally comprises one or more biphenyl compounds selected from the group consisting of the following formulae:

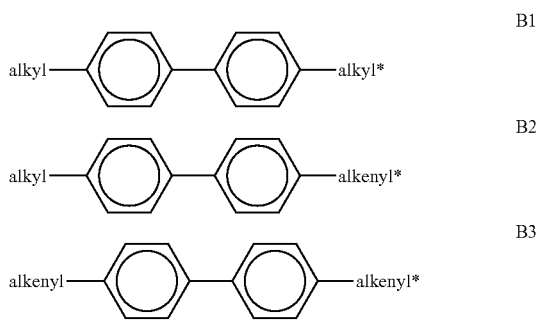

in which alkyl and alkyl* each, independently of one another, denote a straight-chain alkyl radical having 1-6 C atoms, and alkenyl and alkenyl* each, independently of one another, denote a straight-chain alkenyl radical having 2-6 C atoms. Alkenyl and alkenyl* preferably denote $CH_2=CH-$, $CH_2=CHCH_2CH_2-$, $CH_3-CH=CH-$, $CH_3-CH_2-CH=CH-$, $CH_3-$ (CH$_2$)$_2$—CH=CH—, CH$_3$—(CH$_2$)$_3$—CH=CH— or CH$_3$—CH=CH—(CH$_2$)$_2$—.

The proportion of the biphenyls of the formulae B1 to B3 in the LC mixture is preferably at least 3% by weight, in particular ≥5% by weight.

The compounds of the formula B2 are particularly preferred.

The compounds of the formulae B1 to B3 are preferably selected from the group consisting of the following sub-formulae:

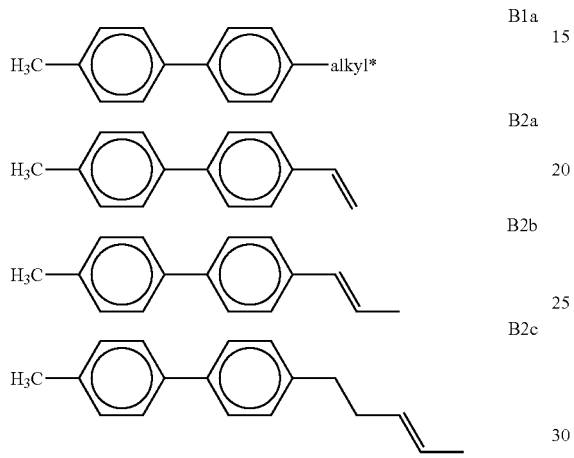

in which alkyl* denotes an alkyl radical having 1-6 C atoms. The medium according to the invention particularly preferably comprises one or more compounds of the formulae B1a and/or B2c.

h) LC medium which additionally comprises one or more terphenyl compounds of the following formula:

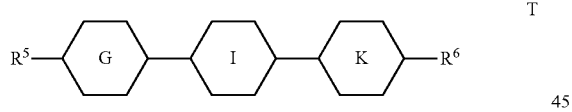

in which R$^5$ and R$^6$ each, independently of one another, have one of the meanings indicated above, and

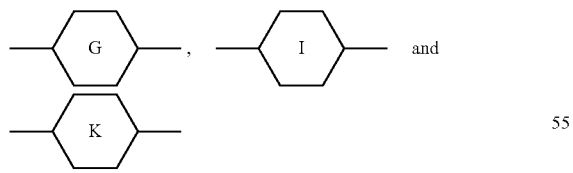

each, independently of one another, denote

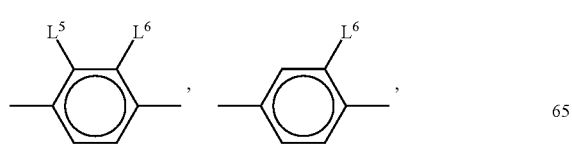

-continued

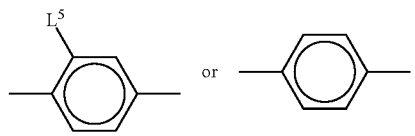

in which L$^5$ denotes F or Cl, preferably F, and L$^6$ denotes F, Cl, OCF$_3$, CF$_3$, CH$_3$, CH$_2$F or CHF$_2$, preferably F.

The compounds of the formula T are preferably selected from the group consisting of the following sub-formulae:

T1

T2

T3

T4

T5

T6
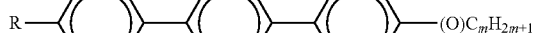

T7
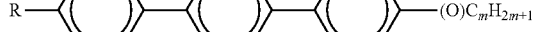

T8

T9
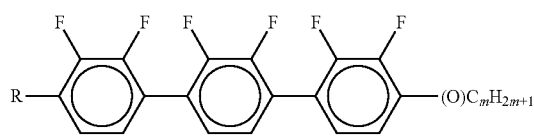

T10
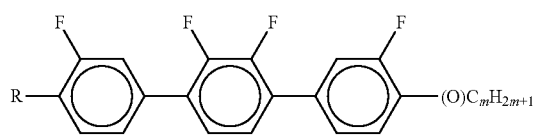

T11
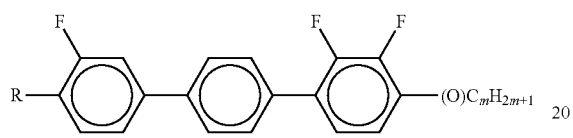

T12
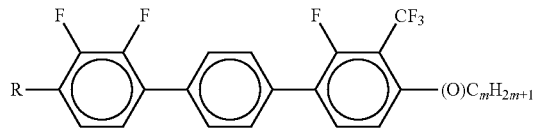

T13
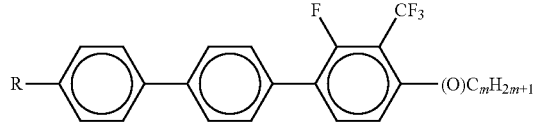

T14
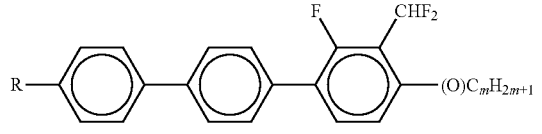

T15
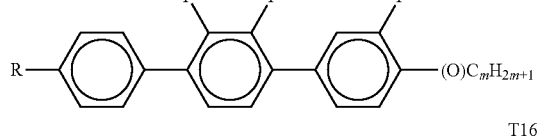

T16
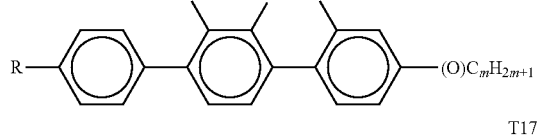

T17
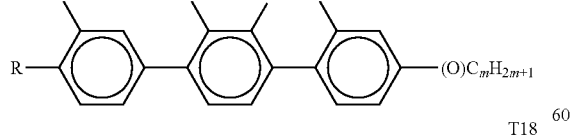

T18
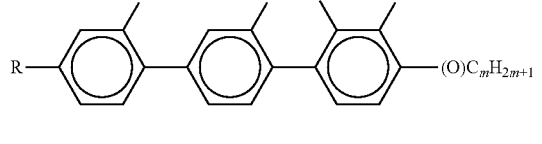

T19
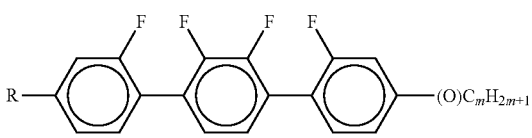

T20
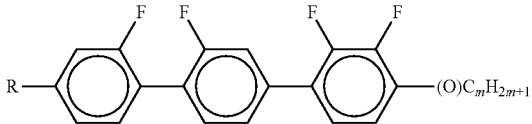

T21
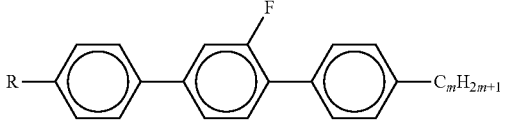

T22
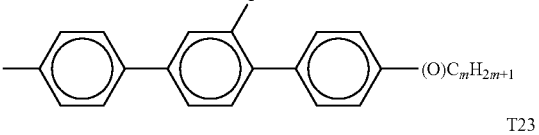

T23
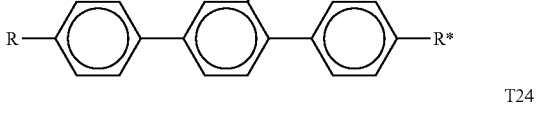

T24
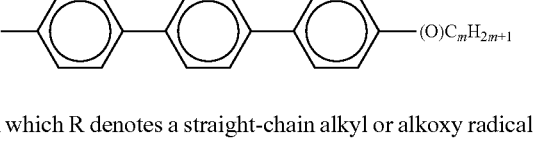

in which R denotes a straight-chain alkyl or alkoxy radical having 1-7 C atoms, R* denotes a straight-chain alkenyl radical having 2-7 C atoms, (O) denotes an oxygen atom or a single bond, and m denotes an integer from 1 to 6. R* preferably denotes $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

R preferably denotes methyl, ethyl, propyl, butyl, pentyl, hexyl, methoxy, ethoxy, propoxy, butoxy or pentoxy.

The LC medium according to the invention preferably comprises the terphenyls of the formula T and the preferred sub-formulae thereof in an amount of 0.5-30% by weight, in particular 1-20% by weight.

Particular preference is given to compounds of the formulae T1, T2, T3 and T21. In these compounds, R preferably denotes alkyl, furthermore alkoxy, each having 1-5 C atoms.

The terphenyls are preferably employed in mixtures according to the invention if the Δn value of the mixture is to be ≥0.1. Preferred mixtures comprise 2-20% by weight of one or more terphenyl compounds of the formula T, preferably selected from the group of compounds T1 to T22.

i) LC medium which additionally comprises one or more quaterphenyl compounds selected from the group consisting of the following formulae:

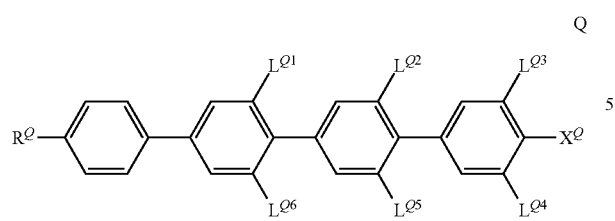

Q wherein
- $R^Q$ is alkyl, alkoxy, oxaalkyl or alkoxyalkyl having 1 to 9 C atoms or alkenyl or alkenyloxy having 2 to 9 C atoms, all of which are optionally fluorinated,
- $X^Q$ is F, Cl, halogenated alkyl or alkoxy having 1 to 6 C atoms or halogenated alkenyl or alkenyloxy having 2 to 6 C atoms,
- $L^{Q1}$ to $L^{Q6}$ independently of each other are H or F, with at least one of $L^{Q1}$ to $L^{Q6}$ being F.

Preferred compounds of formula Q are those wherein $R^Q$ denotes straight-chain alkyl with 2 to 6 C-atoms, very preferably ethyl, n-propyl or n-butyl.

Preferred compounds of formula Q are those wherein $L^{Q3}$ and $L^{Q4}$ are F. Further preferred compounds of formula Q are those wherein $L^{Q3}$, $L^{Q4}$ and one or two of $L^{Q1}$ and $L^{Q2}$ are F.

Preferred compounds of formula Q are those wherein $X^Q$ denotes F or $OCF_3$, very preferably F.

The compounds of formula Q are preferably selected from the following subformulae

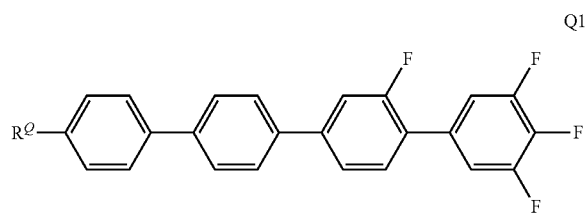

Q1

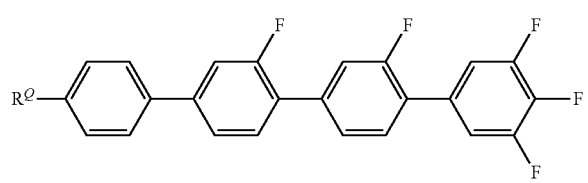

Q2 wherein $R^Q$ has one of the meanings of formula Q or one of its preferred meanings given above and below, and is preferably ethyl, n-propyl or n-butyl.

Especially preferred are compounds of formula Q1, in particular those wherein $R^Q$ is n-propyl.

Preferably the proportion of compounds of formula Q in the LC medium is from >0 to ≤5% by weight, very preferably from 0.1 to 2% by weight, most preferably from 0.2 to 1.5% by weight.

Preferably the LC medium contains 1 to 5, preferably 1 or 2 compounds of formula Q.

The addition of quaterphenyl compounds of formula Q to the LC medium mixture enables to reduce ODF mura, whilst maintaining high UV absorption, enabling quick and complete polymerisation, enabling strong and quick tilt angle generation, and increasing the UV stability of the LC medium.

Besides. the addition of compounds of formula Q, which have positive dielectric anisotropy, to the LC medium with negative dielectric anisotropy allows a better control of the values of the dielectric constants $\in_{\parallel}$ and $\in_{\perp}$, and in particular enables to achieve a high value of the dielectric constant $\in_{\parallel}$ while keeping the dielectric anisotropy $\Delta\in$ constant, thereby reducing the kick-back voltage and reducing image sticking.

k) LC medium which additionally comprises one or more compounds selected from the group consisting of the following formulae:

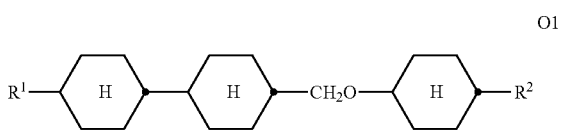

O1

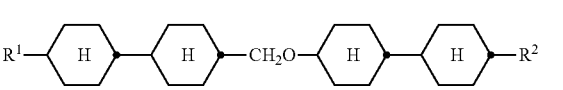

O2

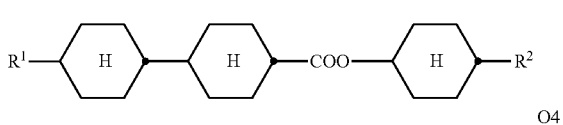

O3

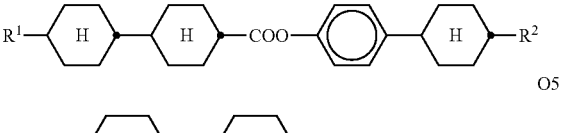

O4

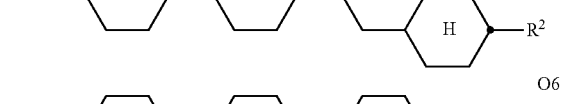

O5

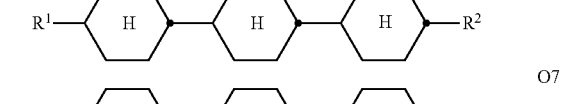

O6

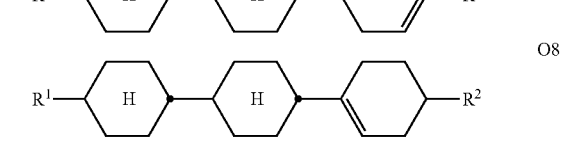

O7

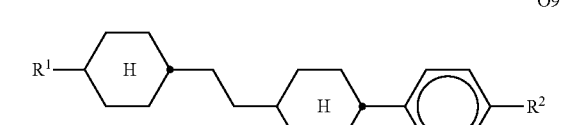

O8

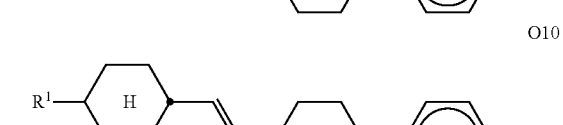

O9

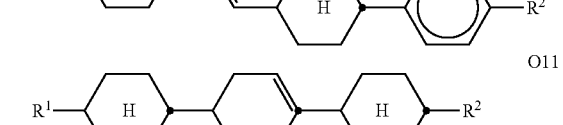

O10

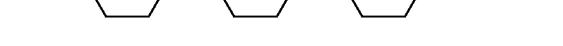

O11 in which R¹ and R² have the meanings indicated above and preferably each, independently of one another, denote straight-chain alkyl having 1 to 6 C atoms or straight-chain alkenyl having 2 to 6 C atoms.

Preferred media comprise one or more compounds selected from the formulae O1, O3 and O4.

l) LC medium which additionally comprises one or more compounds of the following formula:

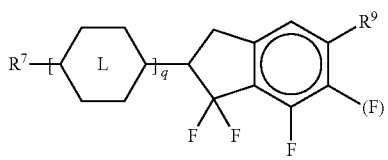

FI in which

denotes

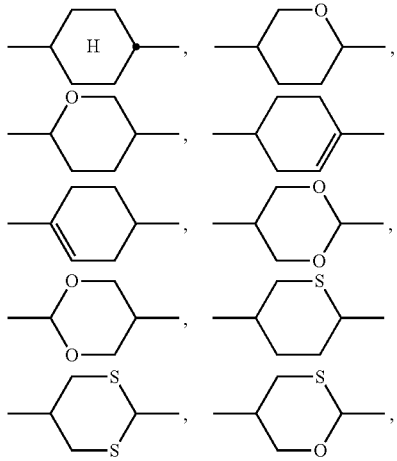

R⁹ denotes H, CH₃, C₂H₅ or n-C₃H₇, (F) denotes an optional fluorine substituent, and q denotes 1, 2 or 3, and R⁷ has one of the meanings indicated for R¹, preferably in amounts of >3% by weight, in particular 5% by weight and very particularly preferably 5-30% by weight.

Particularly preferred compounds of the formula FI are selected from the group consisting of the following sub-formulae:

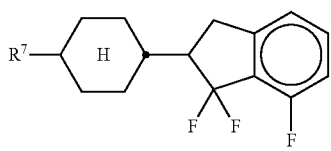
FI1

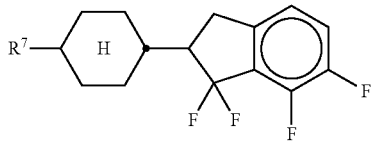
FI2

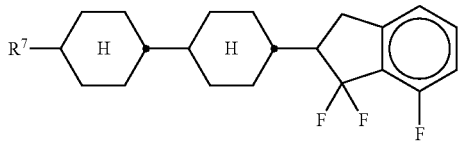
FI3

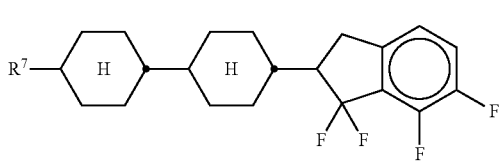
FI4

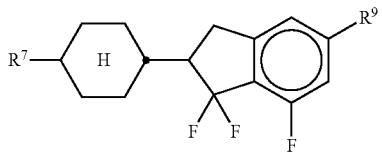
FI5

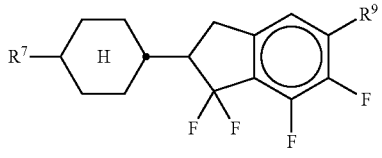
FI6

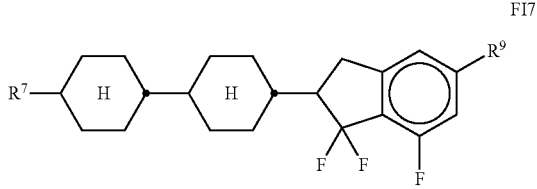
FI7

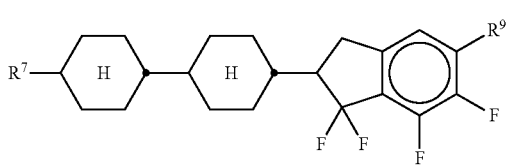
FI8 in which R⁷ preferably denotes straight-chain alkyl, and R⁹ denotes CH₃, C₂H₅ or n-C₃H₇. Particular preference is given to the compounds of the formulae F11, F12 and F13.

m) LC medium which additionally comprises one or more compounds selected from the group consisting of the following formulae:

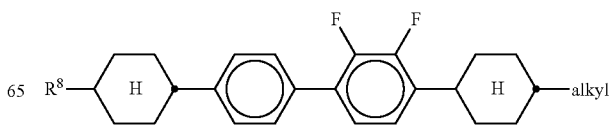
VK1

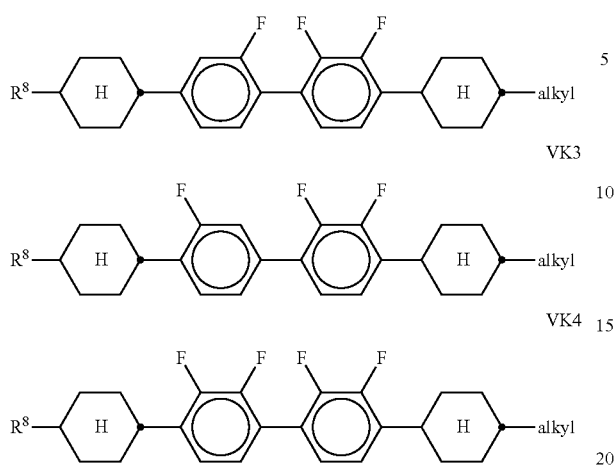

in which R⁸ has the meaning indicated for $R^1$, and alkyl denotes a straight-chain alkyl radical having 1-6 C atoms.

n) LC medium which additionally comprises one or more compounds which contain a tetrahydronaphthyl or naphthyl unit, such as, for example, the compounds selected from the group consisting of the following formulae:

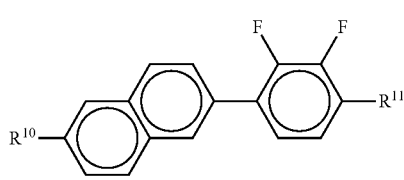

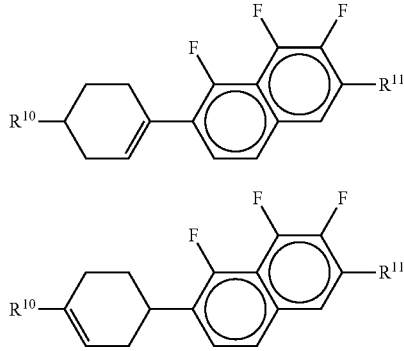

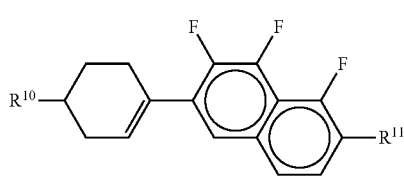

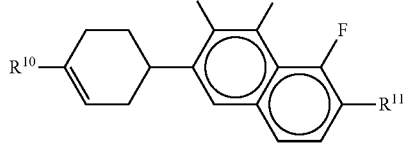

in which $R^{10}$ and $R^{11}$ each, independently of one another, denote alkyl having 1 to 12 C atoms, where, in addition, one or two non-adjacent $CH_2$ groups may be replaced by —O—, —CH=CH—, —CO—, —OCO— or —COO— in such a way that O atoms are not linked directly to one another, preferably alkyl or alkoxy having 1 to 6 C atoms, and $R^{10}$ and $R^{11}$ preferably denote straight-chain alkyl or alkoxy having 1 to 6 C atoms or straight-chain alkenyl having 2 to 6 C atoms, and $Z^1$ and $Z^2$ each, independently of one another, denote —$C_2H_4$—, —CH=CH—, —$(CH_2)_4$—, —$(CH_2)_3O$—, —$O(CH_2)_3$—, —CH=CH—$CH_2CH_2$—, —$CH_2CH_2$CH=CH—, —$CH_2O$—, —$OCH_2$—, —CO—O—, —O—CO—, —$C_2F_4$—, —CF=CF—, —CF=CH—, —CH=CF—, —$CH_2$— or a single bond.

o) LC medium which additionally comprises one or more difluorodibenzo-chromans and/or chromans of the following formulae:

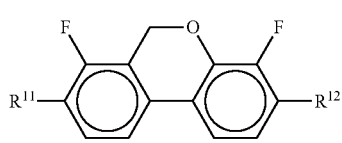

CR

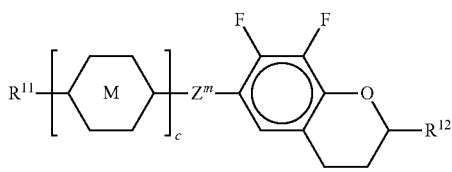

RC

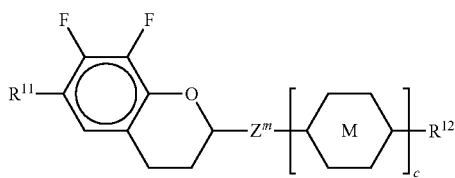

in which
R$^{11}$ and R$^{12}$ each, independently of one another, have one of the meanings indicated above for R$^{11}$,
ring M is trans-1,4-cyclohexylene or 1,4-phenylene,
Z$^m$ —C$_2$H$_4$—, —CH$_2$O—, —OCH$_2$—, —CO—O— or —O—CO—,
c is 0, 1 or 2,
preferably in amounts of 3 to 20% by weight, in particular in amounts of 3 to 15% by weight.
Particularly preferred compounds of the formulae BC, CR and RC are selected from the group consisting of the following sub-formulae:

BC1
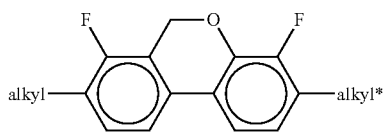

BC2
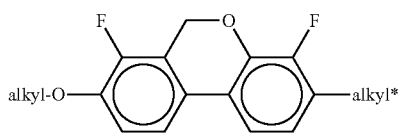

BC3
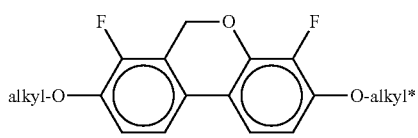

BC4
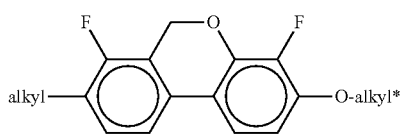

BC5
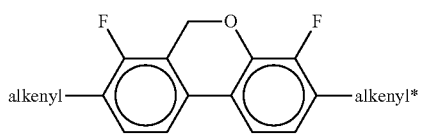

BC6
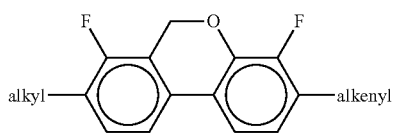

BC7
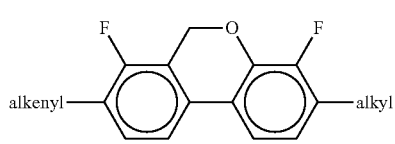

CR1
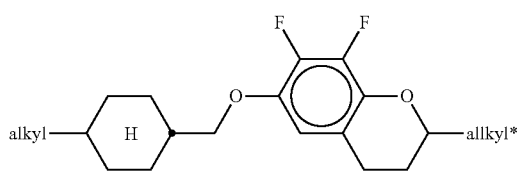

CR2
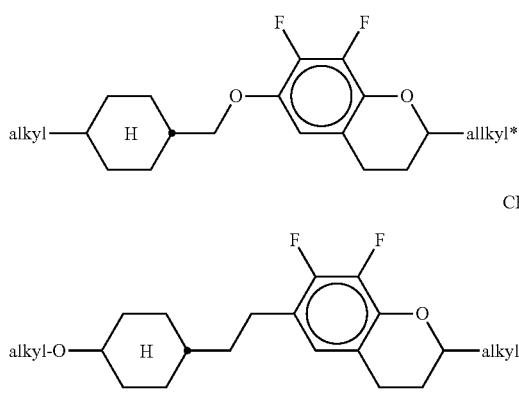

CR3

CR4
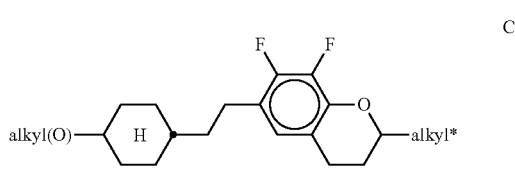

CR5
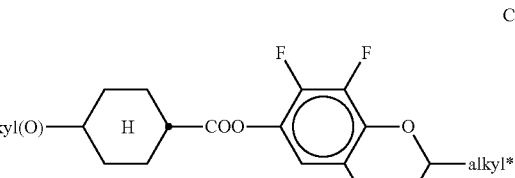

CR6
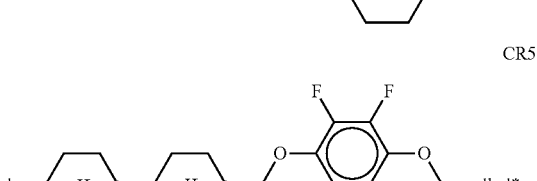

CR7
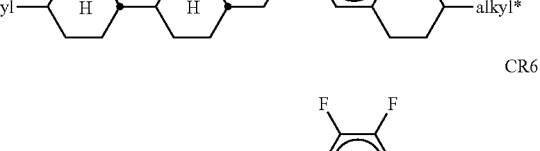

CR8
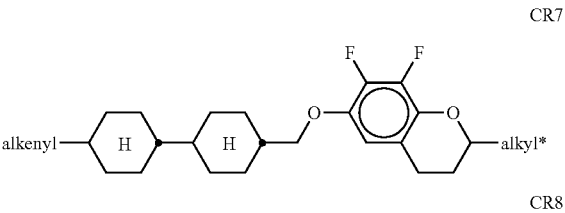

-continued

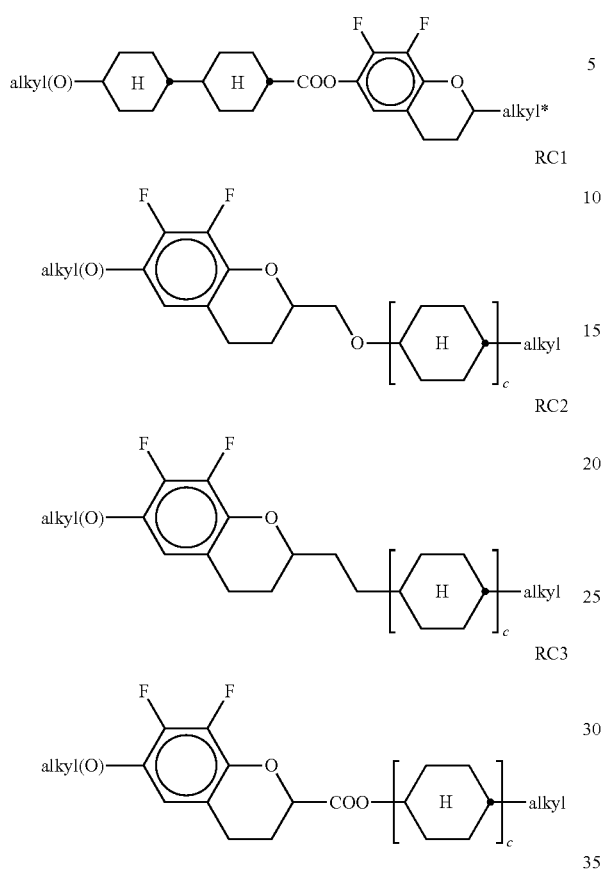

in which alkyl and alkyl* each, independently of one another, denote a straight-chain alkyl radical having 1-6 C atoms, (O) denotes an oxygen atom or a single bond, c is 1 or 2, and alkenyl and alkenyl* each, independently of one another, denote a straight-chain alkenyl radical having 2-6 C atoms. Alkenyl and alkenyl* preferably denote $CH_2$=CH—, $CH_2$=CHCH$_2$CH$_2$—, $CH_3$—CH=CH—, $CH_3$—CH$_2$—CH=CH—, $CH_3$—(CH$_2$)$_2$—CH=CH—, $CH_3$—(CH$_2$)$_3$—CH=CH— or $CH_3$—CH=CH—(CH$_2$)$_2$—.

Very particular preference is given to mixtures comprising one, two or three compounds of the formula BC-2.

p) LC medium which additionally comprises one or more fluorinated phenanthrenes and/or dibenzofurans of the following formulae:

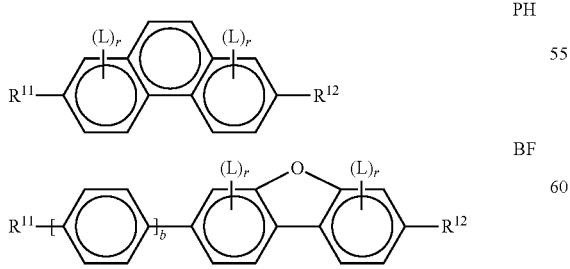

in which $R^{11}$ and $R^{12}$ each, independently of one another, have one of the meanings indicated above for $R^{11}$, b denotes 0 or 1, L denotes F, and r denotes 1, 2 or 3.

Particularly preferred compounds of the formulae PH and BF are selected from the group consisting of the following sub-formulae:

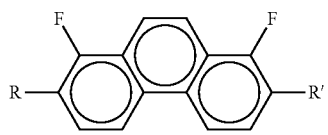

PH1

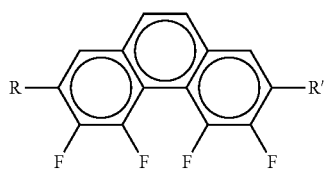

PH2

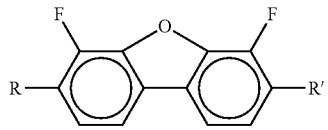

BF1

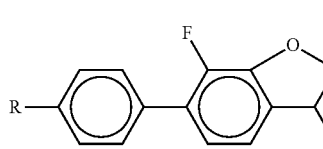

BF2 in which R and R' each, independently of one another, denote a straight-chain alkyl or alkoxy radical having 1-7 C atoms.

q) LC medium which additionally comprises one or more monocyclic compounds of the following formula

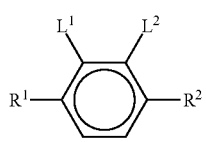

Y wherein $R^1$ and $R^2$ each, independently of one another, denote alkyl having 1 to 12 C atoms, where, in addition, one or two non-adjacent CH$_2$ groups may be replaced by —O—, —CH=CH—, —CO—, —OCO— or —COO— in such a way that O atoms are not linked directly to one another, preferably alkyl or alkoxy having 1 to 6 C atoms, $L^1$ and $L^2$ each, independently of one another, denote F, Cl, OCF$_3$, CF$_3$, CH$_3$, CH$_2$F, CHF$_2$.

Preferably, both $L^1$ and $L^2$ denote F or one of $L^1$ and $L^2$ denotes F and the other denotes Cl, The compounds of the formula Y are preferably selected from the group consisting of the following sub-formulae:

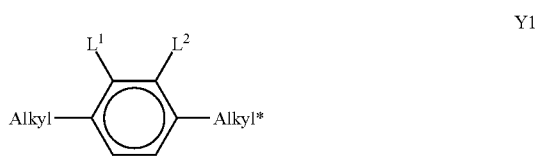

Y1

-continued

Y2: Alkyl—[ring with L¹, L²]—Alkoxy

Y3: Alkyl—[ring with L¹, L²]—Alkenyl

Y4: Alkenyl—[ring with L¹, L²]—Alkenyl*

Y5: Alkenyl—[ring with L¹, L²]—Alkoxy

Y6: Alkoxy—[ring with L¹, L²]—Alkoxy*

Y7: Alkyl—[ring with L¹, L²]—O-Alkenyl

Y8: Alkoxy—[ring with L¹, L²]—O-Alkenyl

Y9: Alkenyl—[ring with L¹, L²]—O-Alkenyl

Y10: Alkenyl-O—[ring with L¹, L²]—O-Alkenyl*, in which, Alkyl and Alkyl* each, independently of one another, denote a straight-chain alkyl radical having 1-6 C atoms, Alkoxy denotes a straight-chain alkoxy radical having 1-6 C atoms, Alkenyl and Alkenyl* each, independently of one another, denote a straight-chain alkenyl radical having 2-6 C atoms, and O denotes an oxygen atom or a single bond. Alkenyl and Alkenyl* preferably denote $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

Particularly preferred compounds of the formula Y are selected from the group consisting of the following sub-formulae:

Y6A: Alkoxy—[ring with F, F]—Alkoxy

Y6B: Alkoxy—[ring with Cl, F]—Alkoxy wherein Alkoxy preferably denotes straight-chain alkoxy with 3, 4, or 5 C atoms.

r) LC medium which, apart from the polymerisable compounds according to the invention, in particular of the formula I or sub-formulae thereof and the comonomers, comprises no compounds which contain a terminal vinyloxy group ($-O-CH=CH_2$).

s) LC medium which comprises 1 to 5, preferably 1, 2 or 3, polymerisable compounds, preferably selected from polymerisable compounds according to the invention, in particular of the formula I or sub-formulae thereof.

t) LC medium in which the proportion of polymerisable compounds, in particular of the formula I or sub-formulae thereof, in the mixture as a whole is 0.05 to 5%, preferably 0.1 to 1%.

u) LC medium which comprises 1 to 8, preferably 1 to 5, compounds of the formulae CY1, CY2, PY1 and/or PY2. The proportion of these compounds in the mixture as a whole is preferably 5 to 60%, particularly preferably 10 to 35%. The content of these individual compounds is preferably in each case 2 to 20%.

v) LC medium which comprises 1 to 8, preferably 1 to 5, compounds of the formulae CY9, CY10, PY9 and/or PY10. The proportion of these compounds in the mixture as a whole is preferably 5 to 60%, particularly preferably 10 to 35%. The content of these individual compounds is preferably in each case 2 to 20%.

w) LC medium which comprises 1 to 10, preferably 1 to 8, compounds of the formula ZK, in particular compounds of the formulae ZK1, ZK2 and/or ZK6. The proportion of these compounds in the mixture as a whole is preferably 3 to 25%, particularly preferably 5 to 45%. The content of these individual compounds is preferably in each case 2 to 20%.

x) LC medium in which the proportion of compounds of the formulae CY, PY and ZK in the mixture as a whole is greater than 70%, preferably greater than 80%.

y) LC medium in which the LC host mixture contains one or more compounds containing an alkenyl group, preferably selected from the group consisting of formula CY, PY and LY, wherein one or both of $R^1$ and $R^2$ denote straight-chain alkenyl having 2-6 C atoms, formula ZK and DK, wherein one or both of $R^3$ and $R^4$ or one or both of $R^5$ and $R^6$ denote straight-chain alkenyl having 2-6 C atoms, and formula B2 and B3, very preferably selected from formulae CY15, CY16, CY24, CY32, PY15, PY16, ZK3, ZK4, DK3, DK6, B2 and B3, most preferably selected from formulae ZK3, ZK4, B2 and B3. The concentration of these compounds in the LC host mixture is preferably from 2 to 70%, very preferably from 3 to 55%.

z) LC medium which contains one or more, preferably 1 to 5, compounds selected of formula PY1-PY8, very preferably of formula PY2. The proportion of these compounds in the mixture as a whole is preferably 1 to 30%, particularly preferably 2 to 20%. The content of these individual compounds is preferably in each case 1 to 20%.

z1) LC medium which contains one or more, preferably 1, 2 or 3, compounds of formula T2. The content of these compounds in the mixture as a whole is preferably 1 to 20%.

z2) LC medium in which the LC host mixture contains one or more, preferably 1, 2 or 3, compounds of formula BF1, and one or more, preferably 1, 2 or 3, compounds selected from formulae AY14, AY15 and AY16, very preferably of formula AY14. The proportion of the compounds of formula AY14-AY16 in the LC host mixture is preferably from 2 to 35%, very preferably from 3 to 30%. The proportion of the compounds of formula BF1 in the LC host mixture is preferably from 0.5 to 20%, very preferably from 1 to 15%. Further preferably the LC host mixture according to this preferred embodiment contains one or more, preferably 1, 2 or 3 compounds of formula T, preferably selected from formula T1, T2 and T5, very preferably from formula T2 or T5. The proportion of the compounds of formula T in the LC host mixture medium is preferably from 0.5 to 15%, very preferably from 1 to 10%.

In a second preferred embodiment the LC medium contains an LC host mixture based on compounds with positive dielectric anisotropy. Such LC media are especially suitable for use in PS-OCB-, PS-TN-, PS-Posi-VA-, PS-IPS- or PS-FFS-displays.

Particularly preferred is an LC medium of this second preferred embodiment, which contains one or more compounds selected from the group consisting of compounds of formula AA and BB

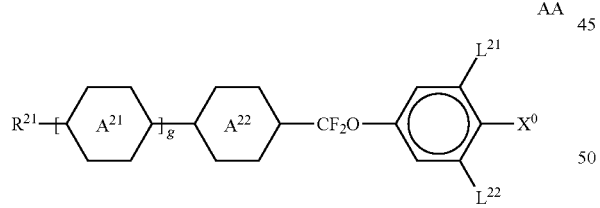

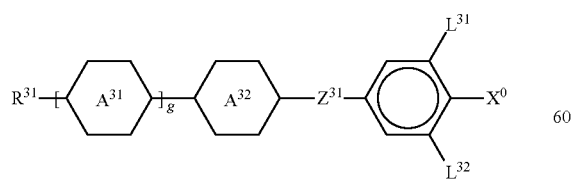

and optionally contains, in addition to the compounds of formula AA and/or BB, one or more compounds of formula CC

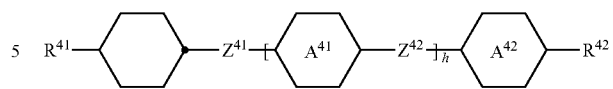

in which the individual radicals have the following meanings:

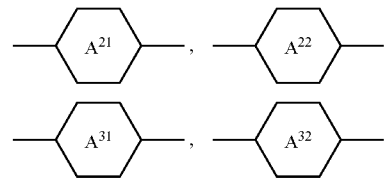

each, independently of one another, and on each occurrence, identically or differently

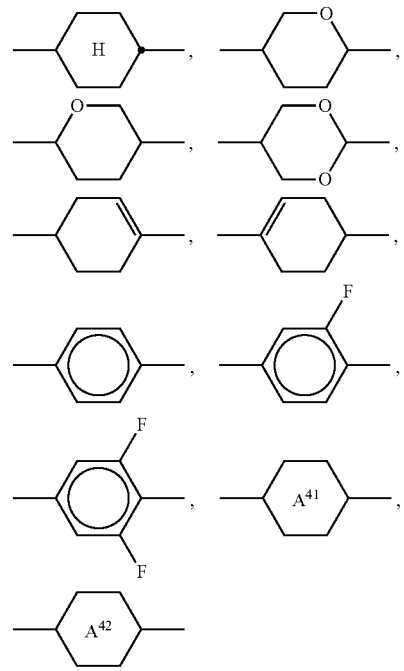

each, independently of one another, and on each occurrence, identically or differently

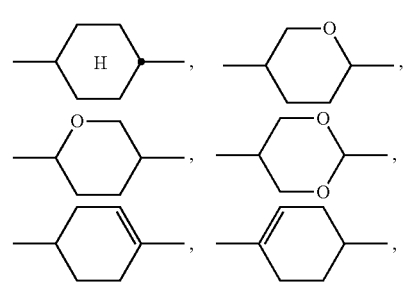

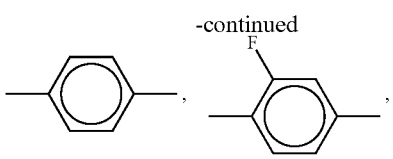

$R^{21}$, $R^{31}$, $R^{41}$, $R^{42}$ each, independently of one another, alkyl, alkoxy, oxaalkyl or alkoxyalkyl having 1 to 9 C atoms or alkenyl or alkenyloxy having 2 to 9 C atoms, all of which are optionally fluorinated, $X^0$ F, Cl, halogenated alkyl or alkoxy having 1 to 6 C atoms or halogenated alkenyl or alkenyloxy having 2 to 6 C atoms, $Z^{31}$ —CH$_2$CH$_2$—, —CF$_2$CF$_2$—, —COO—, trans-CH=CH—, trans-CF=CF—, —CH$_2$O— or a single bond, preferably —CH$_2$CH$_2$—, —COO—, trans-CH=CH— or a single bond, particularly preferably —COO—, trans-CH=CH— or a single bond, $Z^{41}$, $Z^{42}$ —CH$_2$CH$_2$—, —COO—, trans-CH=CH—, trans-CF=CF—, —CH$_2$O—, —CF$_2$O—, —C≡C— or a single bond, preferably a single bond, $L^{21}$, $L^{22}$, $L^{31}$, $L^{32}$ H or F, g 0, 1, 2 or 3, h 0, 1, 2 or 3.

$X^0$ is preferably F, Cl, CF$_3$, CHF$_2$, OCF$_3$, OCHF$_2$, OCFHCF$_3$, OCFHCHF$_2$, OCFHCHF$_2$, OCF$_2$CH$_3$, OCF$_2$CHF$_2$, OCF$_2$CHF$_2$, OCF$_2$CF$_2$CHF$_2$, OCF$_2$CF$_2$CHF$_2$, OCFHCF$_2$CF$_3$, OCFHCF$_2$CHF$_2$, OCF$_2$CF$_2$CF$_3$, OCF$_2$CF$_2$CClF$_2$, OCClFCF$_2$CF$_3$ or CH=CF$_2$, very preferably F or OCF$_3$ The compounds of formula AA are preferably selected from the group consisting of the following formulae:

in which $A^{21}$, $R^{21}$, $X^0$, $L^{21}$ and $L^{22}$ have the meanings given in formula AA, $L^{23}$ and $L^{24}$ each, independently of one another, are H or F, and $X^0$ is preferably F. Particularly preferred are compounds of formulae AA1 and AA2.

Particularly preferred compounds of formula AA1 are selected from the group consisting of the following subformulae:

AA1a

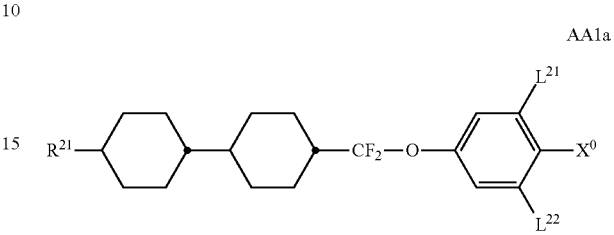

AA1b

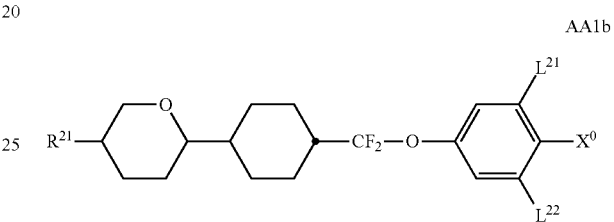

AA1c

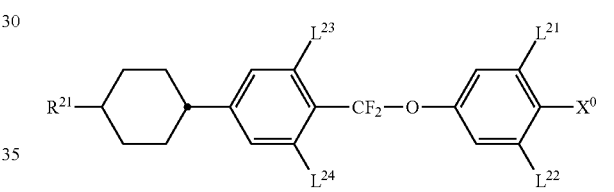

AA1

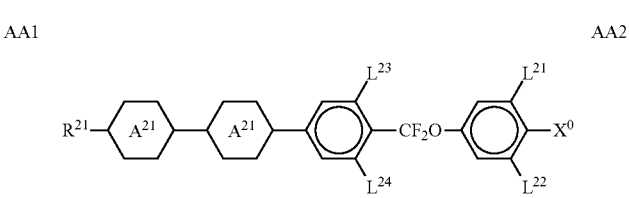

AA2

AA3

AA4

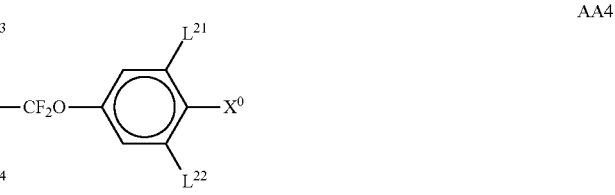

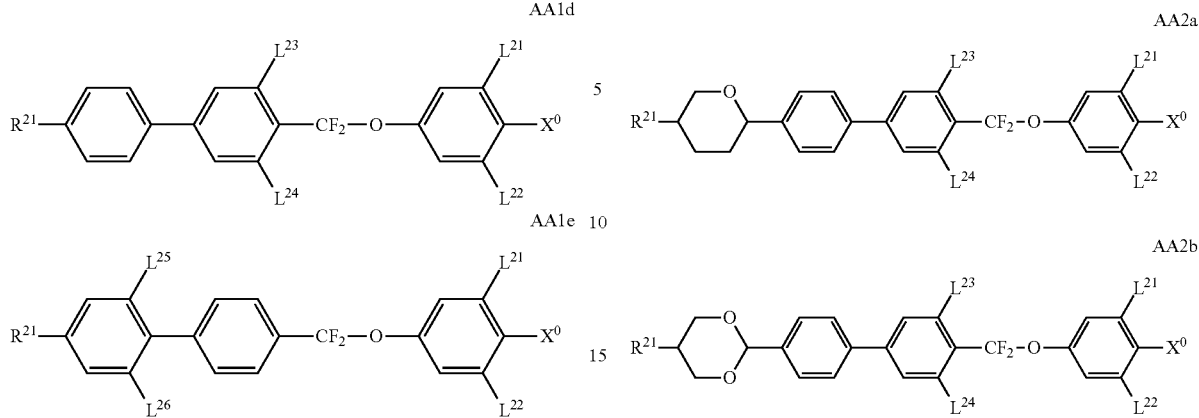

in which $R^{21}$, $X^0$, $L^{21}$ and $L^{22}$ have the meaning given in formula AA1, $L^{23}$, $L^{24}$, $L^{25}$ and $L^{26}$ are each, independently of one another, H or F, and $X^0$ is preferably F.

Very particularly preferred compounds of formula AA1 are selected from the group consisting of the following subformulae:

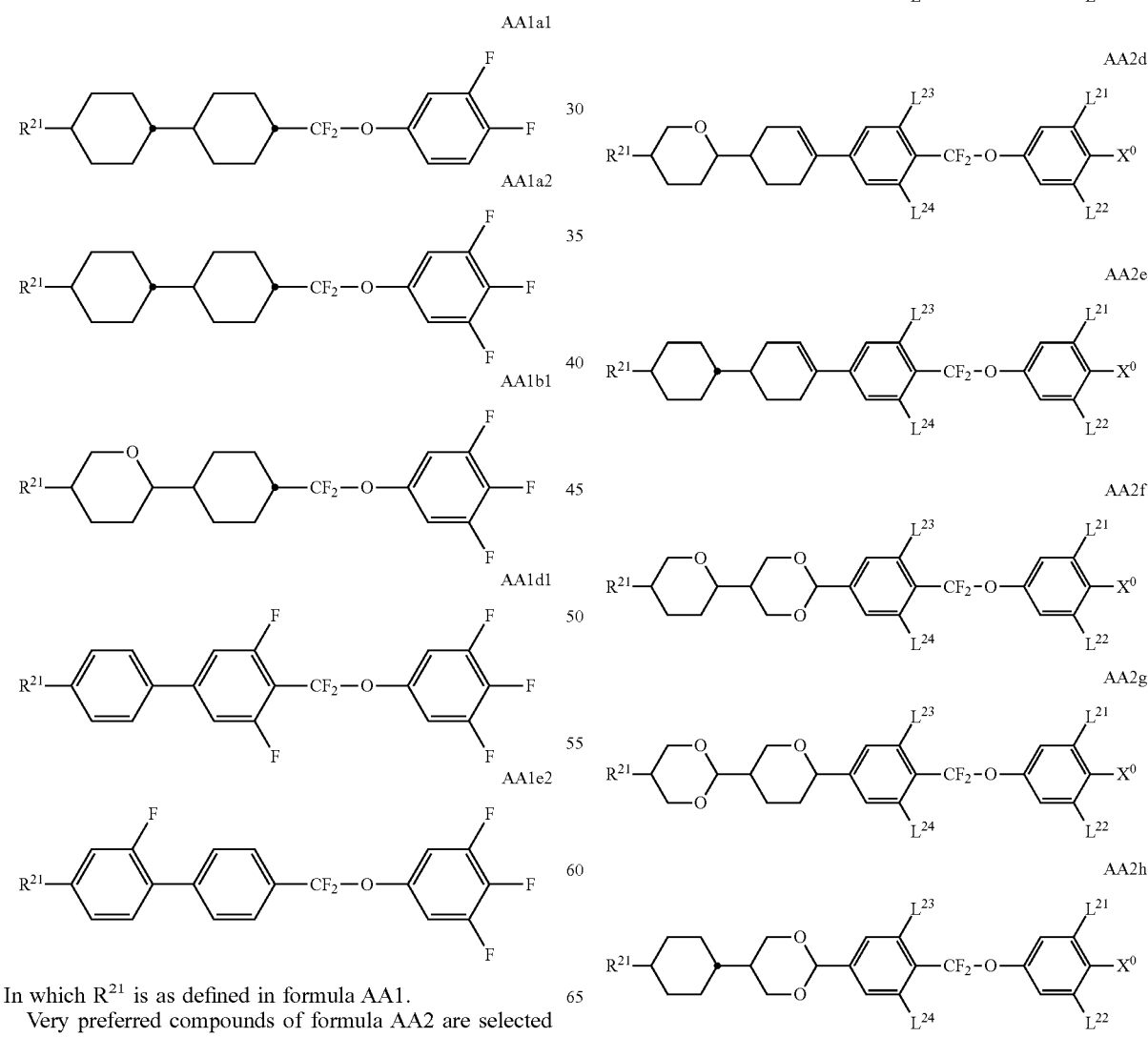

In which $R^{21}$ is as defined in formula AA1.

Very preferred compounds of formula AA2 are selected from the group consisting of the following subformulae:

AA2i
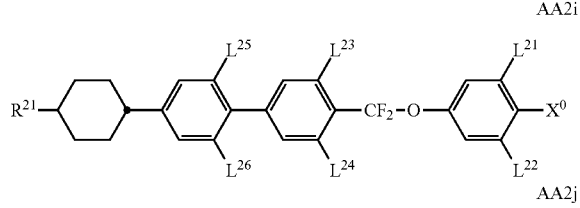

AA2j
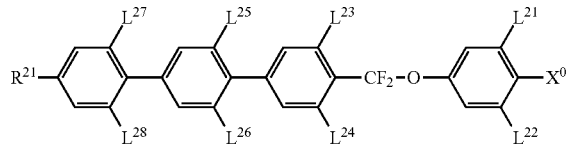

in which $R^{21}$, $X^0$, $L^{21}$ and $L^{22}$ have the meaning given in formula AA2, $L^{23}$, $L^{24}$, $L^{25}$ and $L^{26}$ each, independently of one another, are H or F, and $X^0$ is preferably F.

Very particularly preferred compounds of formula AA2 are selected from the group consisting of the following subformulae:

AA2a1
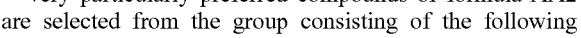

AA2c1

AA2d1
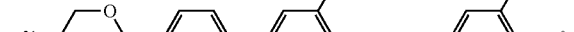

AA2e1
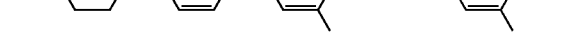

AA2f1
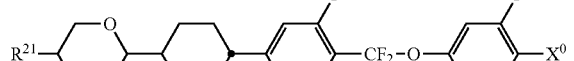

AA2h1
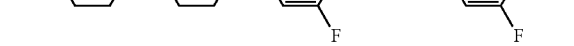

AA2i1

AA2i2

AA2j1
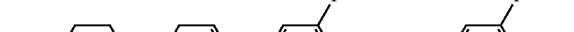

AA2j2

in which $R^{21}$ and $X^0$ are as defined in formula AA2.

Particularly preferred compounds of formula AA3 are selected from the group consisting of the following subformulae:

AA3a

AA3b

AA3c

in which $R^{21}$, $X^0$, $L^{21}$ and $L^{22}$ have the meaning given in formula AA3, and $X^0$ is preferably F.

Particularly preferred compounds of formula AA4 are selected from the group consisting of the following subformulae:

AA4a

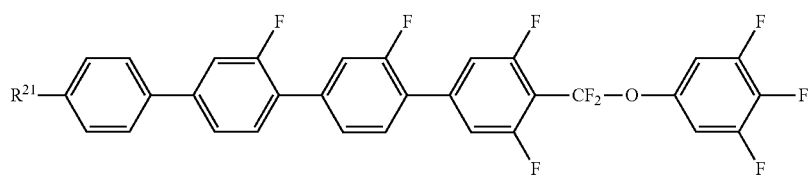

in which $R^{21}$ is as defined in formula AA4.

The compounds of formula BB are preferably selected from the group consisting of the following formulae:

BB1

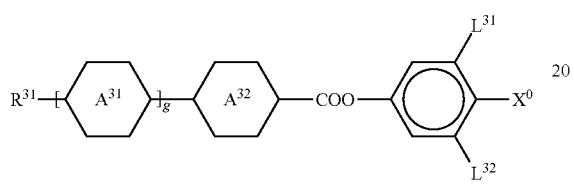

BB2

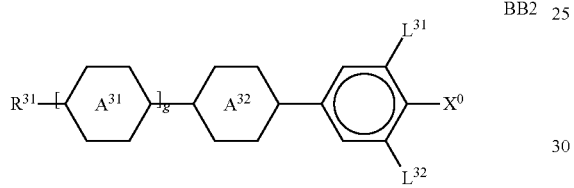

BB3

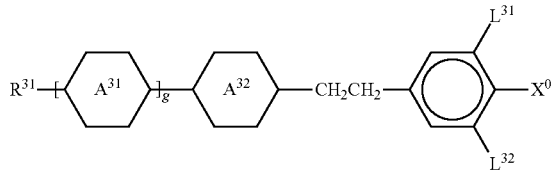

in which g, $A^{31}$, $A^{32}$, $R^{31}$, $X^0$, $L^{31}$ and $L^{32}$ have the meanings given in formula BB, and $X^0$ is preferably F. Particularly preferred are compounds of formulae BB1 and BB2.

Particularly preferred compounds of formula BB1 are selected from the group consisting of the following subformulae:

BB1a

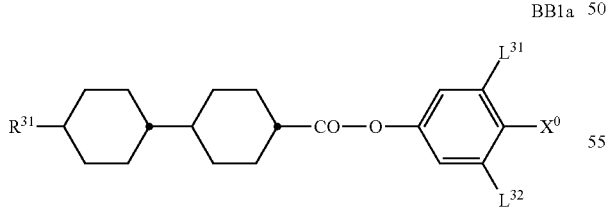

BB1b

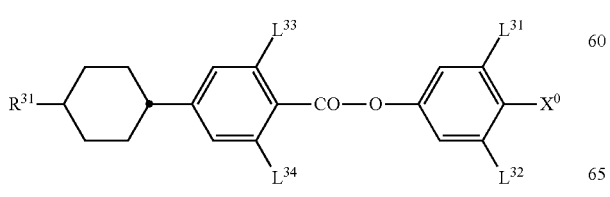

in which $R^{31}$, $X^0$, $L^{31}$ and $L^{32}$ have the meaning given in formula BB1, and $X^0$ is preferably F.

Very particularly preferred compounds of formula BB1a are selected from the group consisting of the following subformulae:

BB1a1

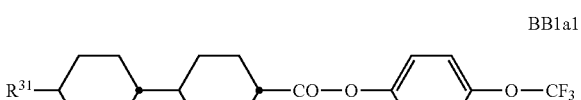

BB1a2

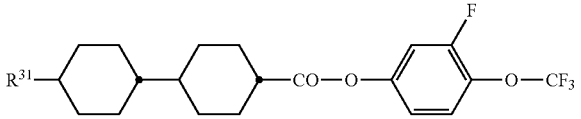

BB1a3

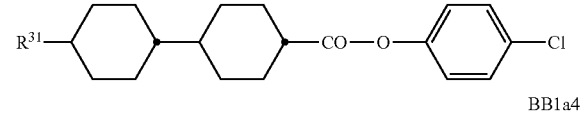

BB1a4

BB1a5

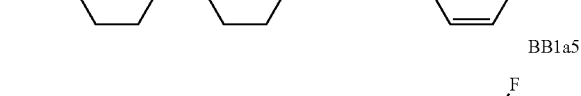

BB1a6 in which $R^{31}$ is as defined in formula BB1.

Very particularly preferred compounds of formula BB1b are selected from the group consisting of the following subformulae:

BB1b1

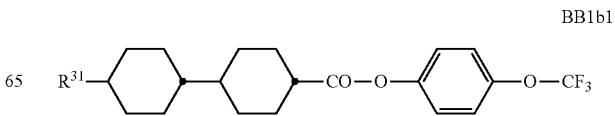

BB1b2
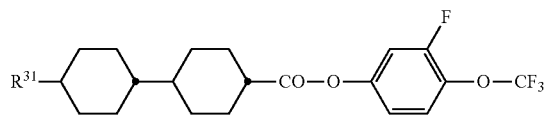

BB1b3
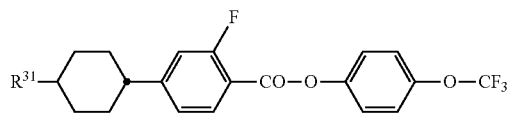

BB1b4
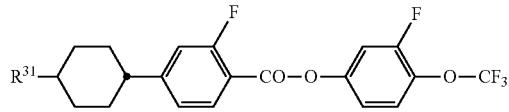

in which R³¹ is as defined in formula BB1.

Particularly preferred compounds of formula BB2 are selected from the group consisting of the following subformulae:

BB2a
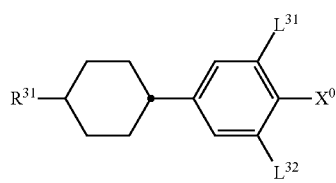

BB2b
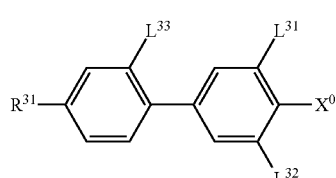

BB2c
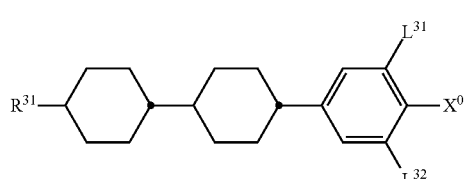

BB2d
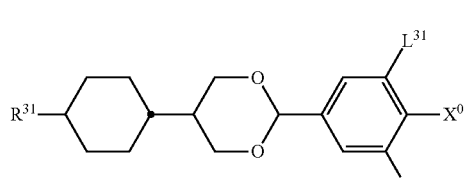

BB2e
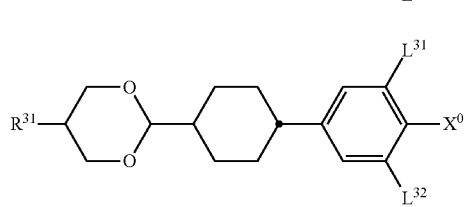

BB2f
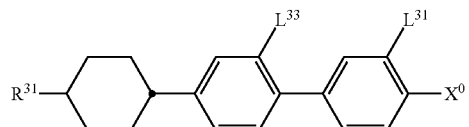

BB2g
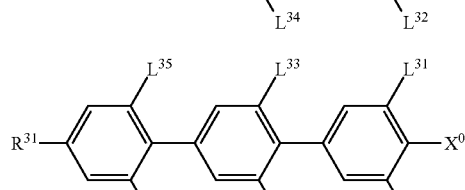

BB2h
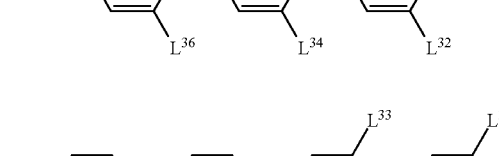

BB2i
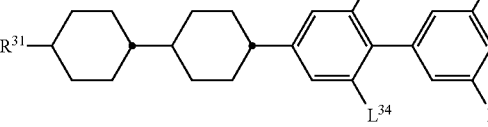

BB2k
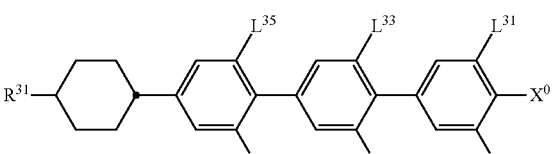

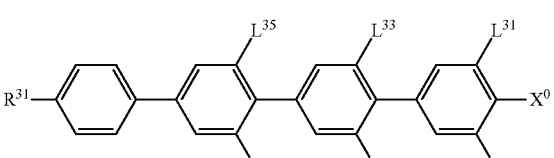

in which $R^{31}$, $X^0$, $L^{31}$ and $L^{32}$ have the meaning given in formula BB2, $L^{00}$, $L^{34}$, $L^{35}$ and $L^{36}$ are each, independently of one another, H or F, and $X^0$ is preferably F.

Very particularly preferred compounds of formula BB2 are selected from the group consisting of the following subformulae:

BB2a1
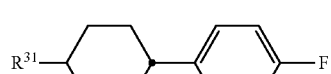

BB2a2
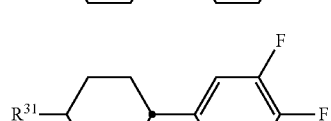

BB2a3
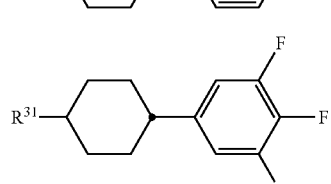

BB2a4

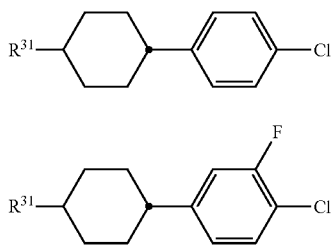

BB2a5

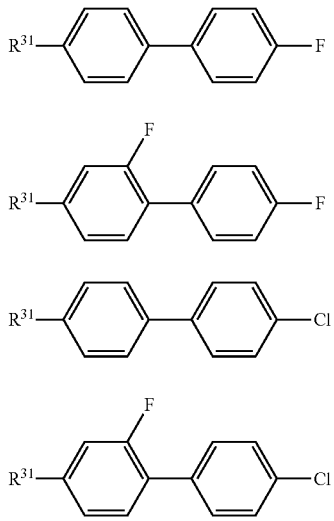

in which R³¹ is as defined in formula BB2.

Very particularly preferred compounds of formula BB2b are selected from the group consisting of the following subformulae BB2b1
BB2b2
BB2b3
BB2b4

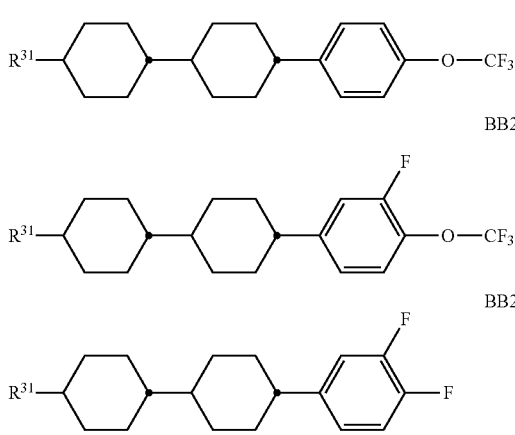

in which R³¹ is as defined in formula BB2.

Very particularly preferred compounds of formula BB2c are selected from the group consisting of the following subformulae:

BB2c1

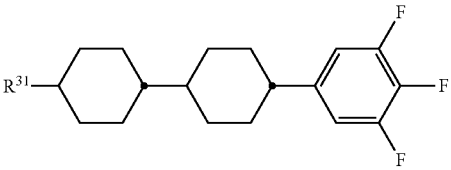

BB2c2

BB2c3

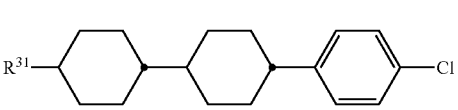

BB2c4

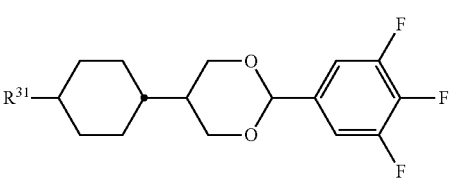

BB2c5

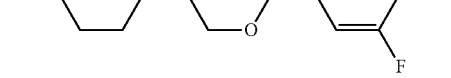

in which R³¹ is as defined in formula BB2.

Very particularly preferred compounds of formula BB2d and BB2e are selected from the group consisting of the following subformulae:

BB2d1

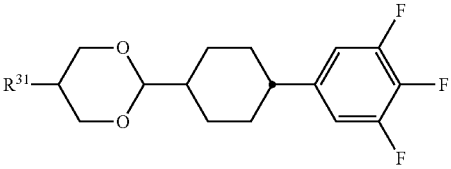

BB2e1

in which R³¹ is as defined in formula BB2.

Very particularly preferred compounds of formula BB2f are selected from the group consisting of the following subformulae:

BB2f1

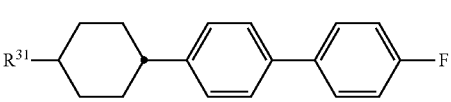

BB2f2

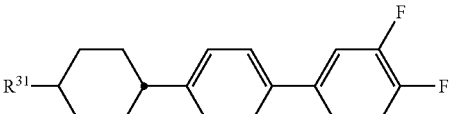

BB2f3

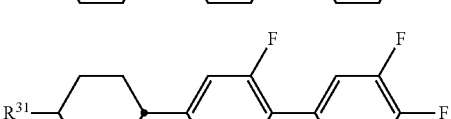

BB2f4

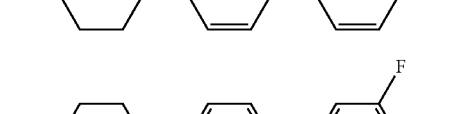

BB2f5

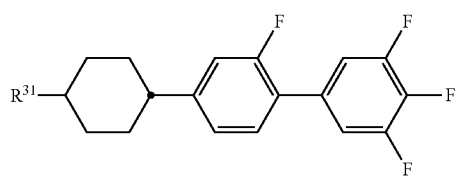

in which R³¹ is as defined in formula BB2.

Very particularly preferred compounds of formula BB2g are selected from the group consisting of the following subformulae:

BB2g1

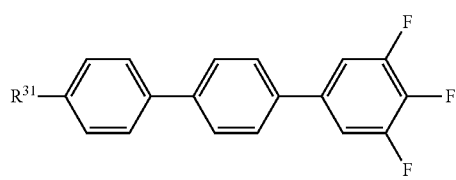

BB2g2

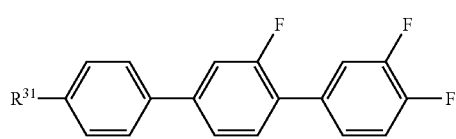

BB2g3

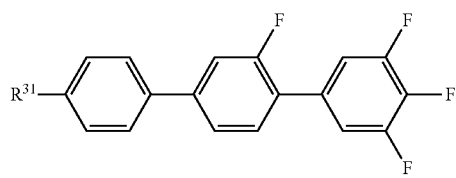

BB2g4

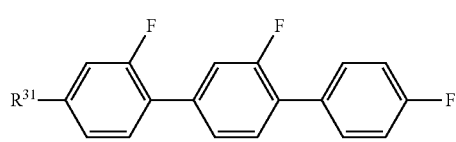

BB2g5

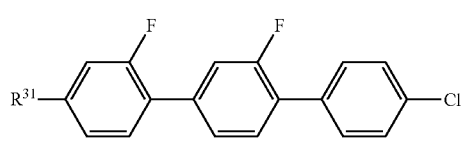

in which R³¹ is as defined in formula BB2.

Very particularly preferred compounds of formula BB2h are selected from the group consisting of the following subformulae:

BB2h1

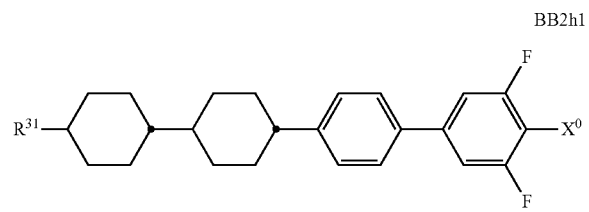

BB2h2

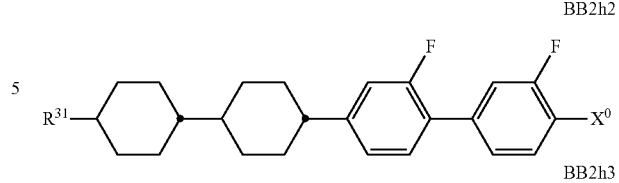

BB2h3

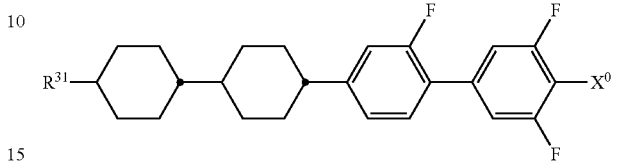

in which R³¹ and X⁰ are as defined in formula BB2.

Very particularly preferred compounds of formula BB2i are selected from the group consisting of the following subformulae:

BB2i1

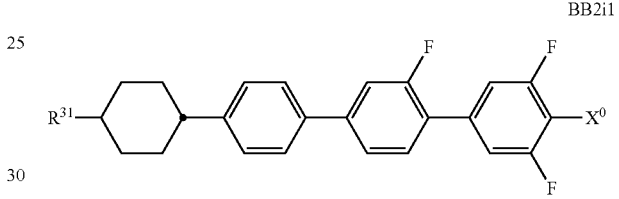

BB2i2

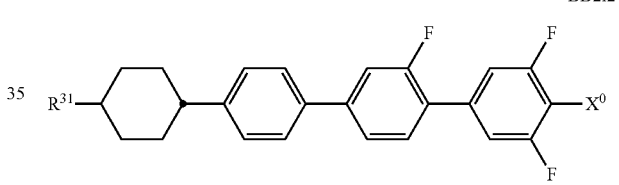

in which R³¹ and X⁰ are as defined in formula BB2.

Very particularly preferred compounds of formula BB2k are selected from the group consisting of the following subformulae:

BB2k1

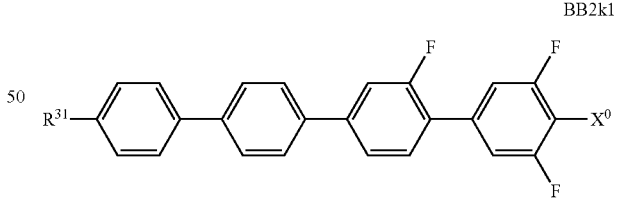

BB2k2

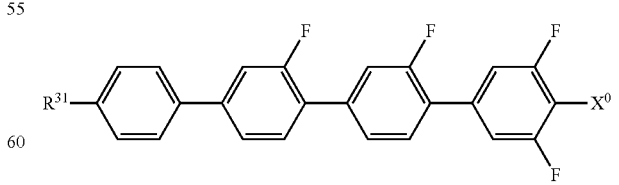

in which R³¹ and X⁰ are as defined in formula BB2.

Alternatively to, or in addition to, the compounds of formula BB1 and/or BB2 the LC media may also comprise one or more compounds of formula BB3 as defined above.

Particularly preferred compounds of formula BB3 are selected from the group consisting of the following subformulae:

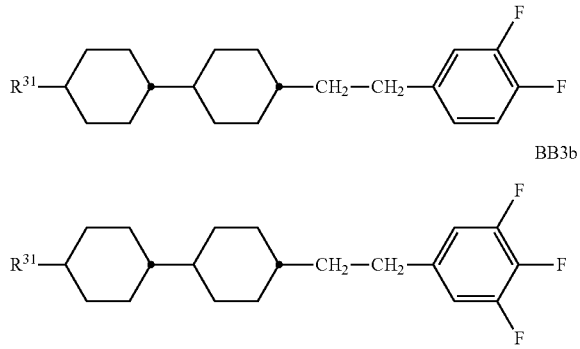

in which $R^{31}$ is as defined in formula BB3.

Preferably the LC media according to this second preferred embodiment comprise, in addition to the compounds of formula AA and/or BB, one or more dielectrically neutral compounds having a dielectric anisotropy in the range from −1.5 to +3, preferably selected from the group of compounds of formula CC as defined above.

Particularly preferred compounds of formula CC are selected from the group consisting of the following subformulae:

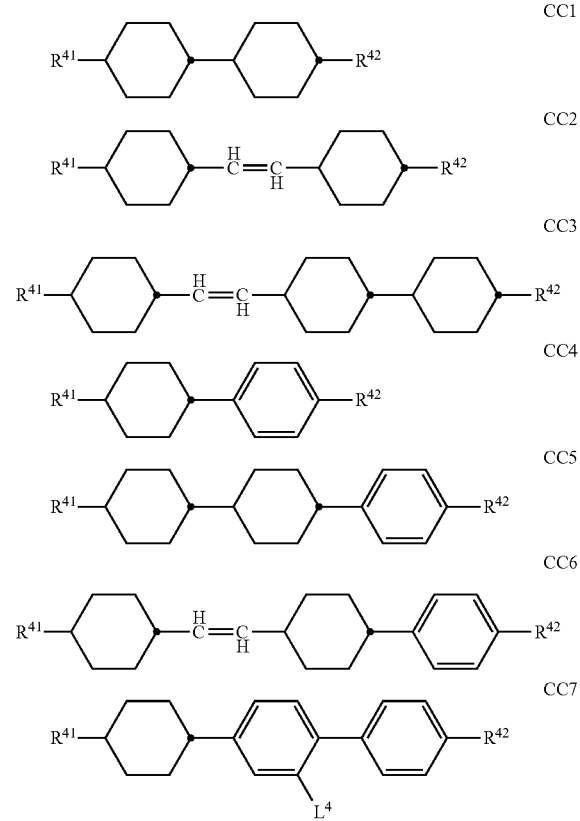

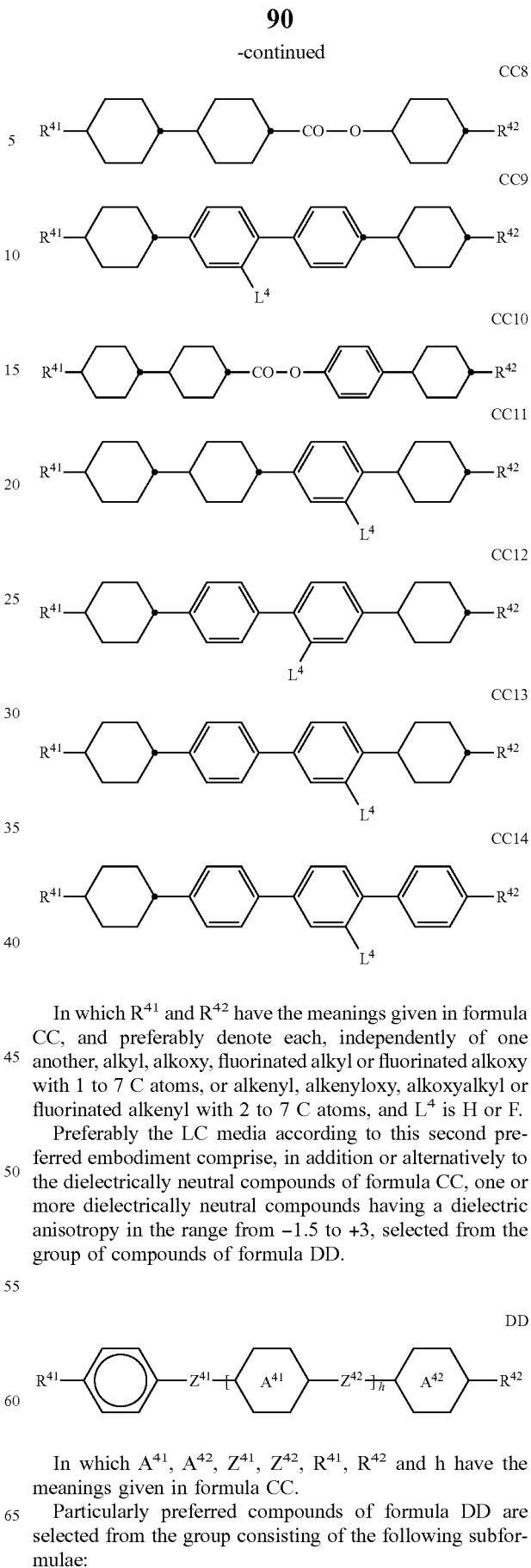

In which $R^{41}$ and $R^{42}$ have the meanings given in formula CC, and preferably denote each, independently of one another, alkyl, alkoxy, fluorinated alkyl or fluorinated alkoxy with 1 to 7 C atoms, or alkenyl, alkenyloxy, alkoxyalkyl or fluorinated alkenyl with 2 to 7 C atoms, and $L^4$ is H or F.

Preferably the LC media according to this second preferred embodiment comprise, in addition or alternatively to the dielectrically neutral compounds of formula CC, one or more dielectrically neutral compounds having a dielectric anisotropy in the range from −1.5 to +3, selected from the group of compounds of formula DD.

In which $A^{41}$, $A^{42}$, $Z^{41}$, $Z^{42}$, $R^{41}$, $R^{42}$ and h have the meanings given in formula CC.

Particularly preferred compounds of formula DD are selected from the group consisting of the following subformulae:

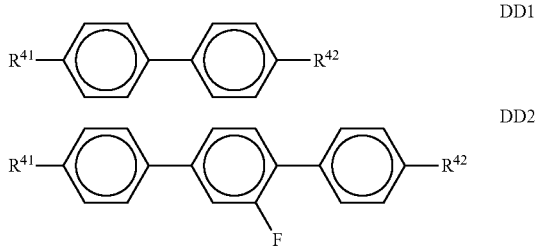

DD1

DD2 in which $R^{41}$ and $R^{42}$ have the meanings given in formula DD and $R^{41}$ preferably denotes alkyl bedeutet, and in formula DD1 $R^{42}$ preferably denotes alkenyl, particularly preferably —(CH$_2$)$_2$—CH═CH—CH$_3$, and in formula DD2 $R^{42}$ preferably denotes alkyl, —(CH$_2$)$_2$—CH═CH$_2$ or —(CH$_2$)$_2$—CH═CH—CH$_3$.

The compounds of formula AA and BB are preferably used in the LC medium according to the invention in a concentration from 2% to 60%, more preferably from 3% to 35%, and very particularly preferably from 4% to 30% in the mixture as a whole.

The compounds of formula CC and DD are preferably used in the LC medium according to the invention in a concentration from 2% to 70%, more preferably from 5% to 65%, even more preferably from 10% to 60%, and very particularly preferably from 10%, preferably 15%, to 55% in the mixture as a whole.

The combination of compounds of the preferred embodiments mentioned above with the polymerised compounds described above causes low threshold voltages, low rotational viscosities and very good low-temperature stabilities in the LC media according to the invention at the same time as constantly high clearing points and high HR values, and allows the rapid establishment of a particularly low pretilt angle in PSA displays. In particular, the LC media exhibit significantly shortened response times, in particular also the grey-shade response times, in PSA displays compared with the media from the prior art.

The LC media and LC host mixtures of the present invention preferably have a nematic phase range of at least 80 K, particularly preferably at least 100 K, and a rotational viscosity ≤250 mPa·s, preferably ≤200 mPa·s, at 20° C.

In the VA-type displays according to the invention, the molecules in the layer of the LC medium in the switched-off state are aligned perpendicular to the electrode surfaces (homeotropically) or have a tilted homeotropic alignment. On application of an electrical voltage to the electrodes, a realignment of the LC molecules takes place with the longitudinal molecular axes parallel to the electrode surfaces.

LC media according to the invention based on compounds with negative dielectric anisotropy according to the first preferred embodiment, in particular for use in displays of the PS-VA and PS-UB-FFS type, have a negative dielectric anisotropy Δ∈, preferably from −0.5 to −10, in particular from −2.5 to −7.5, at 20° C. and 1 kHz.

The birefringence Δn in LC media according to the invention for use in displays of the PS-VA and PS-UB-FFS type is preferably below 0.16, particularly preferably from 0.06 to 0.14, very particularly preferably from 0.07 to 0.12.

In the OCB-type displays according to the invention, the molecules in the layer of the LC medium have a "bend" alignment. On application of an electrical voltage, a realignment of the LC molecules takes place with the longitudinal molecular axes perpendicular to the electrode surfaces.

LC media according to the invention for use in displays of the PS-OCB, PS-TN, PS-IPS, PS-posi-VA and PS-FFS type are preferably those based on compounds with positive dielectric anisotropy according to the second preferred embodiment, and preferably have a positive dielectric anisotropy Δ∈ from +4 to +17 at 20° C. and 1 kHz.

The birefringence Δn in LC media according to the invention for use in displays of the PS-OCB type is preferably from 0.14 to 0.22, particularly preferably from 0.16 to 0.22.

The birefringence Δn in LC media according to the invention for use in displays of the PS-TN-, PS-posi-VA-, PS-IPS-oder PS-FFS-type is preferably from 0.07 to 0.15, particularly preferably from 0.08 to 0.13.

LC media according to the invention, based on compounds with positive dielectric anisotropy according to the second preferred embodiment, for use in displays of the PS-TN-, PS-posi-VA-, PS-IPS-oder PS-FFS-type, preferably have a positive dielectric anisotropy Δ∈ from +2 to +30, particularly preferably from +3 to +20, at 20° C. and 1 kHz.

The LC media according to the invention may also comprise further additives which are known to the person skilled in the art and are described in the literature, such as, for example, polymerisation initiators, inhibitors, stabilisers, surface-active substances or chiral dopants. These may be polymerisable or non-polymerisable. Polymerisable additives are accordingly ascribed to the polymerisable component or component A). Non-polymerisable additives are accordingly ascribed to the non-polymerisable component or component B).

In a preferred embodiment the LC media contain one or more chiral dopants, preferably in a concentration from 0.01 to 1%, very preferably from 0.05 to 0.5%. The chiral dopants are preferably selected from the group consisting of compounds from Table B below, very preferably from the group consisting of R- or S-1011, R- or S-2011, R- or S-3011, R- or S-4011, and R- or S-5011.

In another preferred embodiment the LC media contain a racemate of one or more chiral dopants, which are preferably selected from the chiral dopants mentioned in the previous paragraph.

Furthermore, it is possible to add to the LC media, for example, 0 to 15% by weight of pleochroic dyes, furthermore nanoparticles, conductive salts, preferably ethyldimethyldodecylammonium 4-hexoxybenzoate, tetrabutyl-ammonium tetraphenylborate or complex salts of crown ethers (cf., for example, Haller et al., Mol. Cryst. Liq. Cryst. 24, 249-258 (1973)), for improving the conductivity, or substances for modifying the dielectric anisotropy, the viscosity and/or the alignment of the nematic phases. Substances of this type are described, for example, in DE-A 22 09 127, 22 40 864, 23 21 632, 23 38 281, 24 50 088, 26 37 430 and 28 53 728.

The individual components of the preferred embodiments a)-z) of the LC media according to the invention are either known or methods for the preparation thereof can readily be derived from the prior art by the person skilled in the relevant art, since they are based on standard methods described in the literature. Corresponding compounds of the formula CY are described, for example, in EP-A-0 364 538. Corresponding compounds of the formula ZK are described, for example, in DE-A-26 36 684 and DE-A-33 21 373.

The LC media which can be used in accordance with the invention are prepared in a manner conventional per se, for example by mixing one or more of the above-mentioned compounds with one or more polymerisable compounds as defined above, and optionally with further liquid-crystalline compounds and/or additives. In general, the desired amount of the components used in lesser amount is dissolved in the components making up the principal constituent, advantageously at elevated temperature. It is also possible to mix solutions of the components in an organic solvent, for example in acetone, chloroform or methanol, and to remove the solvent again, for example by distillation, after thorough mixing. The invention furthermore relates to the process for the preparation of the LC media according to the invention.

It goes without saying to the person skilled in the art that the LC media according to the invention may also comprise compounds in which, for example, H, N, O, Cl, F have been replaced by the corresponding isotopes like deuterium etc.

The following examples explain the present invention without restricting it. However, they show the person skilled in the art preferred mixture concepts with compounds preferably to be employed and the respective concentrations thereof and combinations thereof with one another. In addition, the examples illustrate which properties and property combinations are accessible.

The following abbreviations are used:

(n, m, z: in each case, independently of one another, 1, 2, 3, 4, 5 or 6)

TABLE A

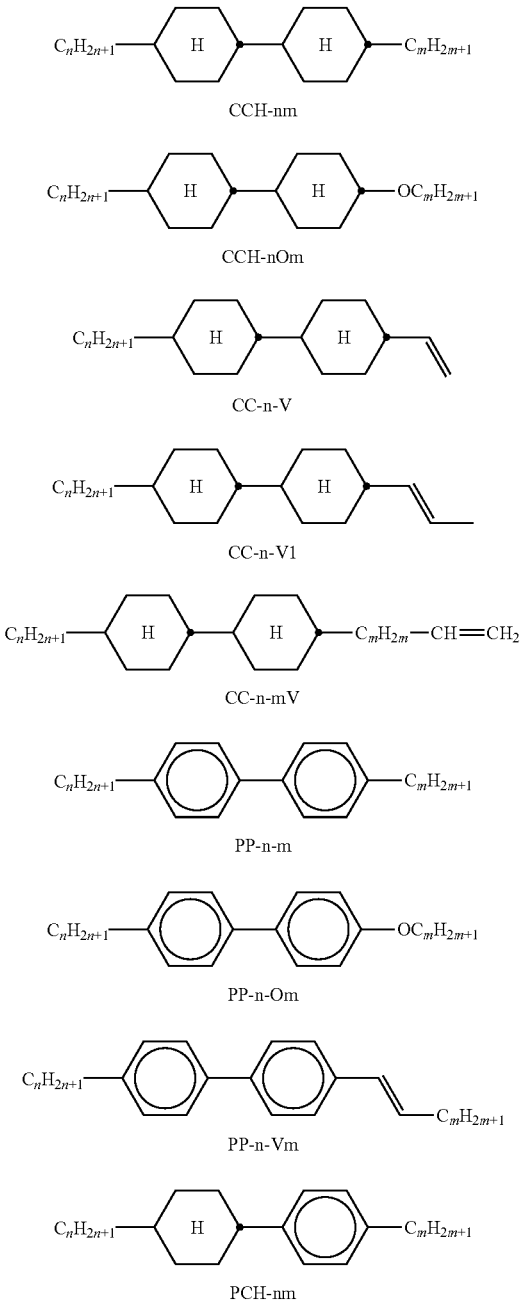

TABLE A-continued
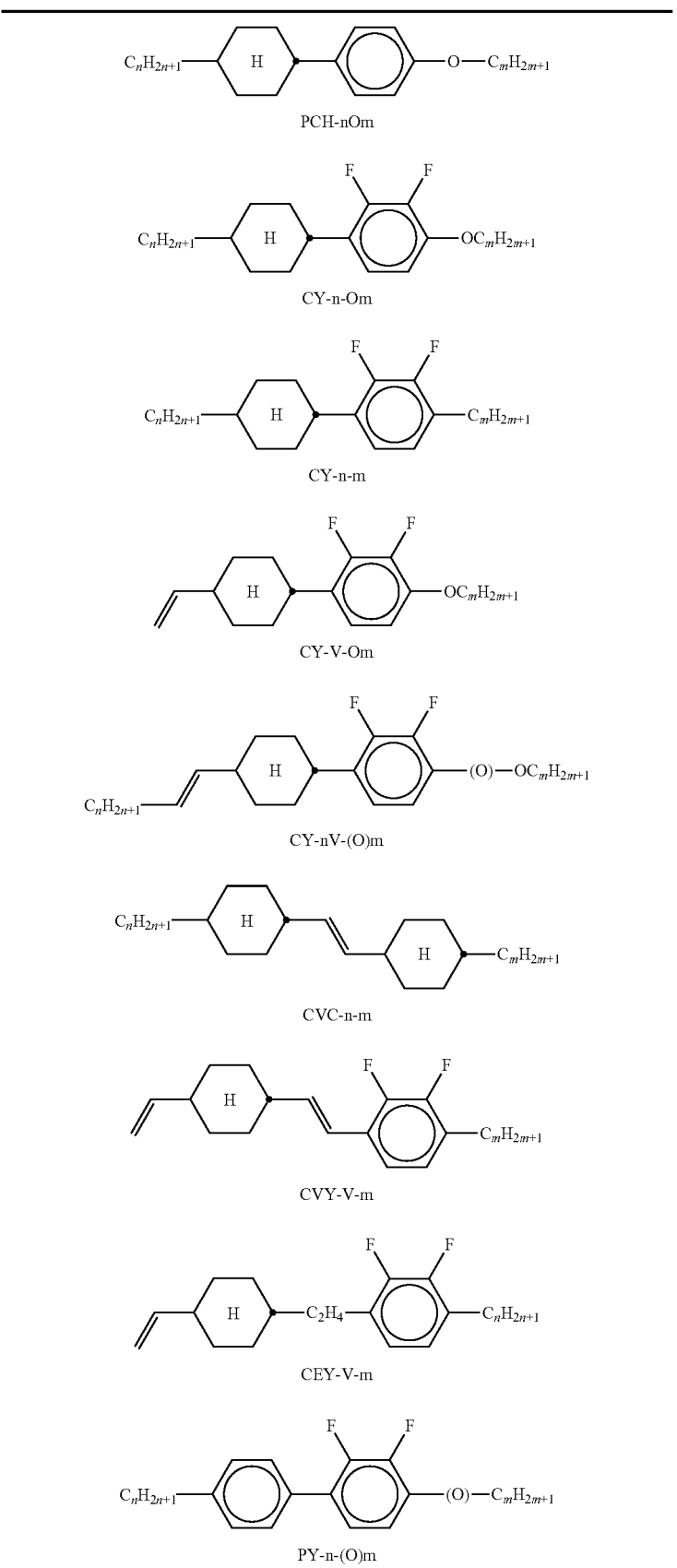

TABLE A-continued
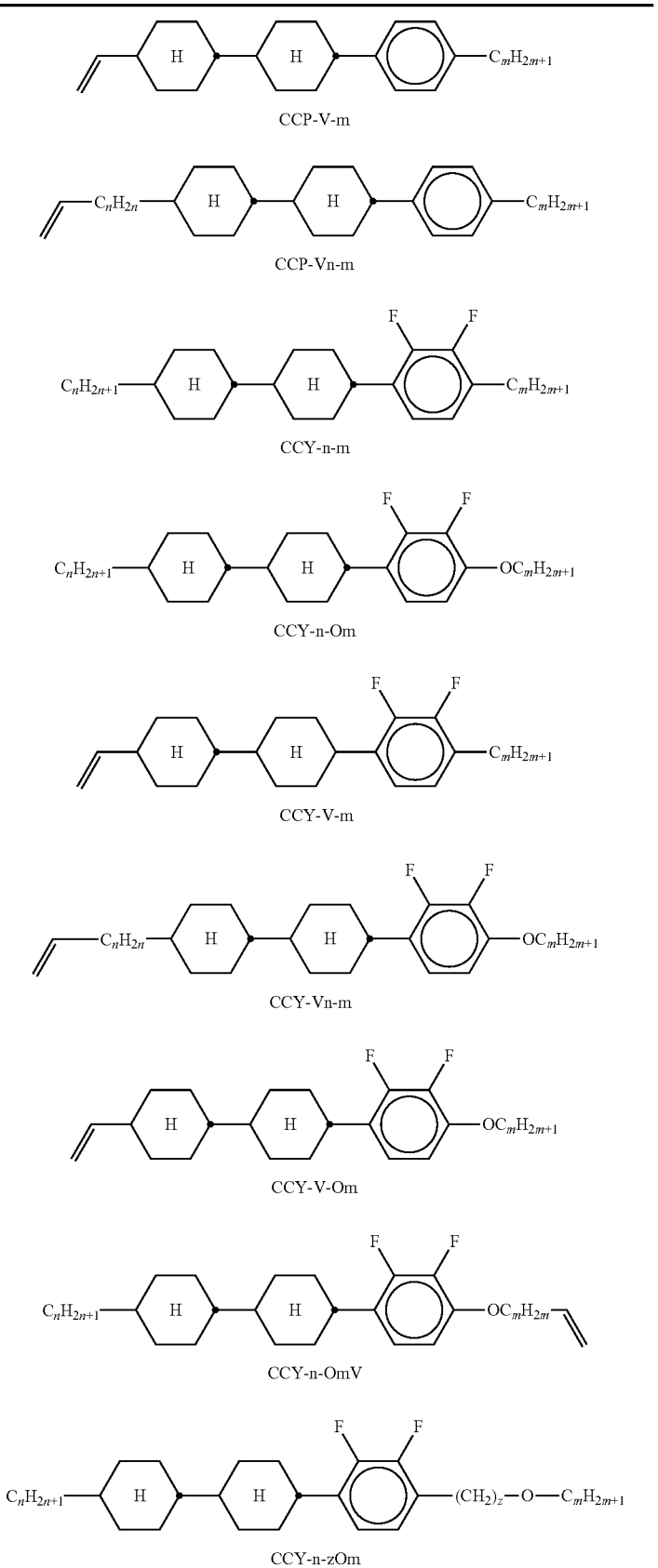

TABLE A-continued
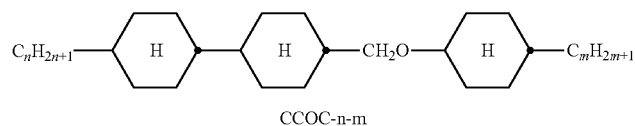
CCOC-n-m
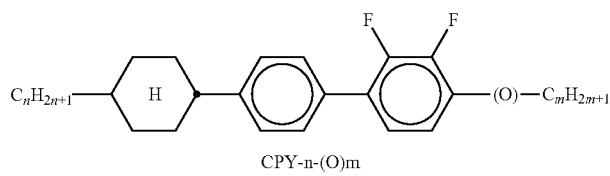
CPY-n-(O)m
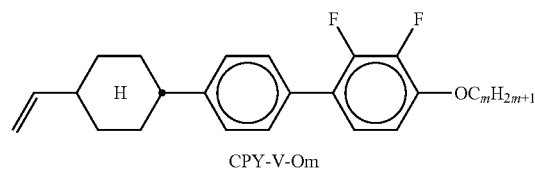
CPY-V-Om
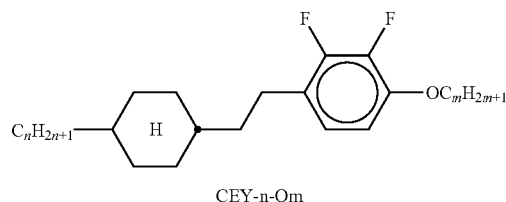
CEY-n-Om
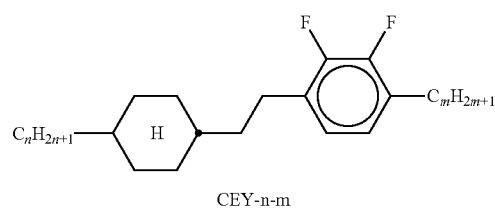
CEY-n-m
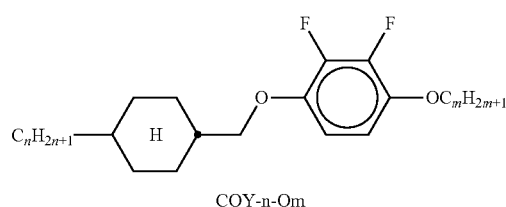
COY-n-Om
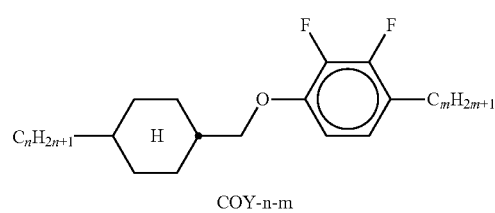
COY-n-m
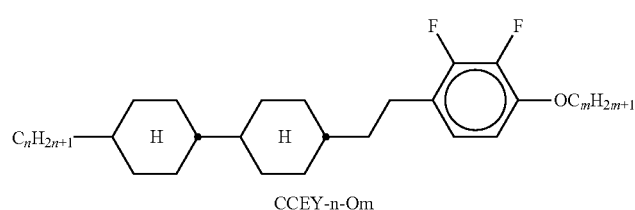
CCEY-n-Om TABLE A-continued
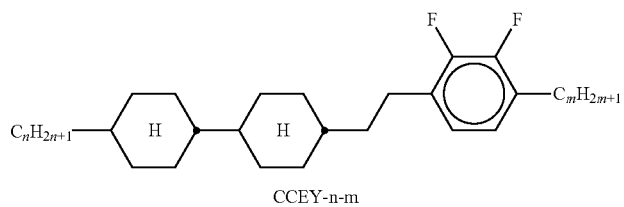
CCEY-n-m
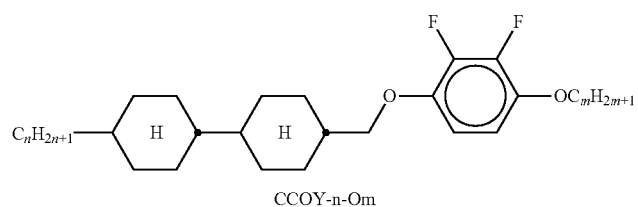
CCOY-n-Om
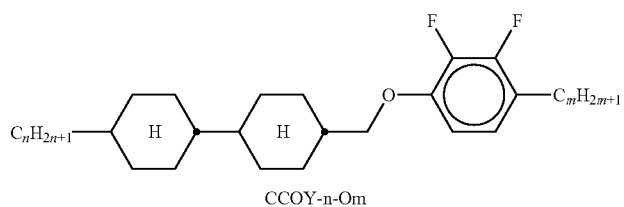
CCOY-n-Om
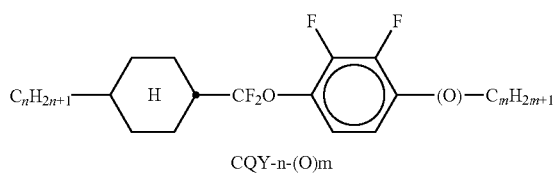
CQY-n-(O)m
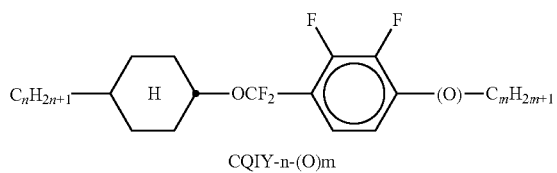
CQIY-n-(O)m
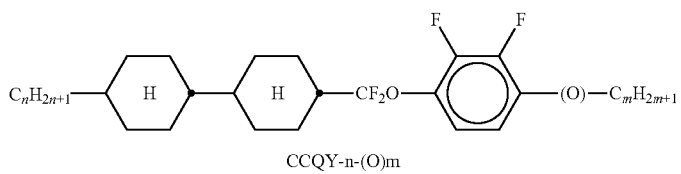
CCQY-n-(O)m
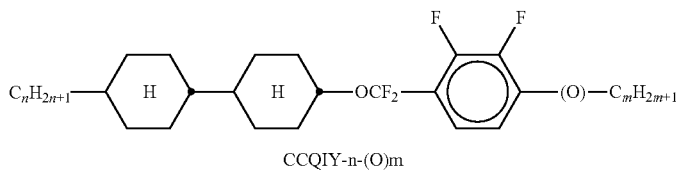
CCQIY-n-(O)m
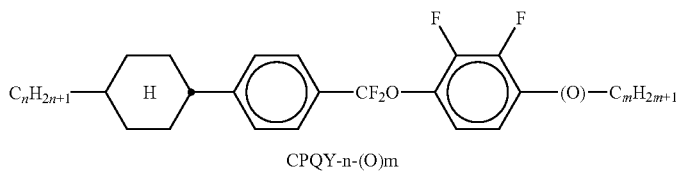
CPQY-n-(O)m TABLE A-continued
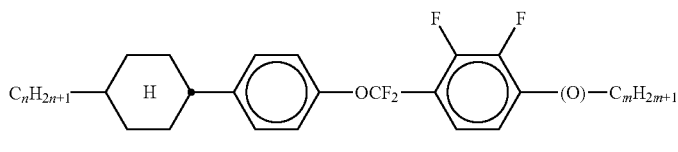
CPQIY-n-(O)m
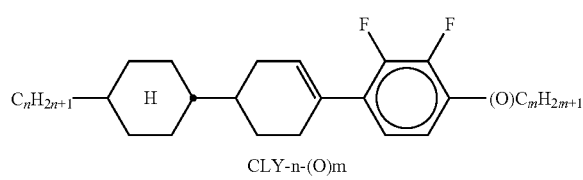
CLY-n-(O)m
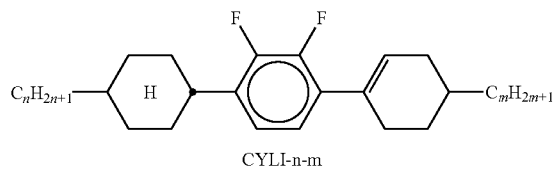
CYLI-n-m
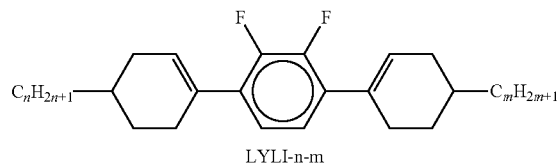
LYLI-n-m
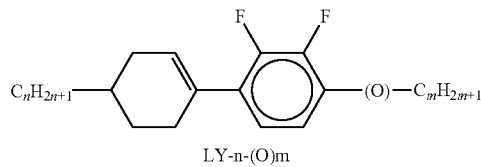
LY-n-(O)m
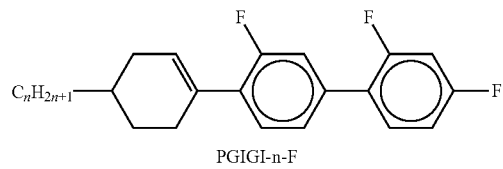
PGIGI-n-F
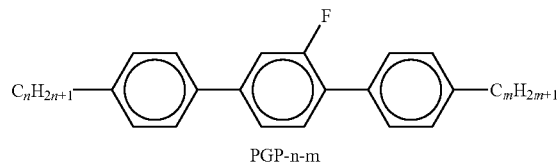
PGP-n-m
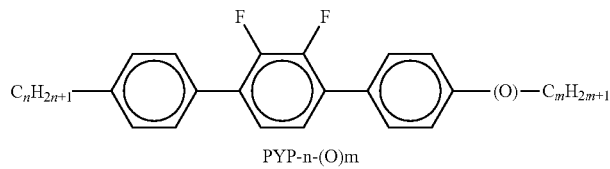
PYP-n-(O)m
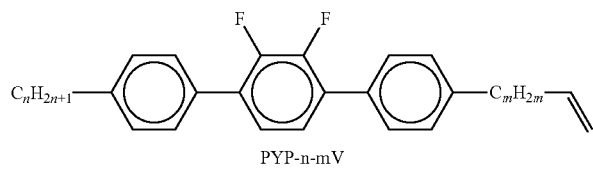
PYP-n-mV TABLE A-continued
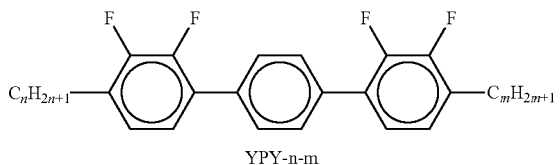
YPY-n-m
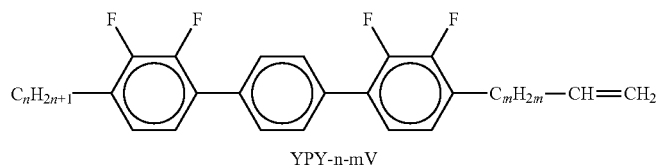
YPY-n-mV
BCH-nm
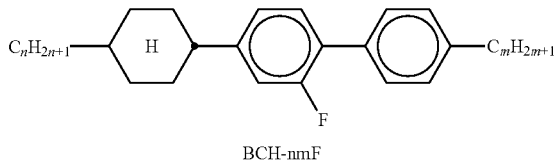
BCH-nmF
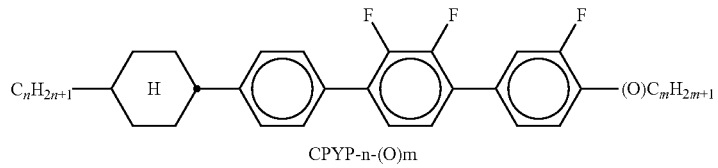
CPYP-n-(O)m
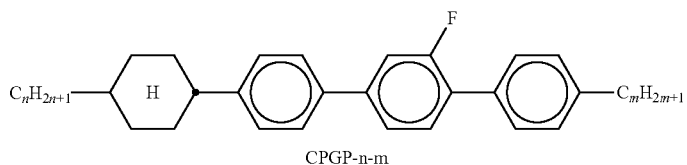
CPGP-n-m
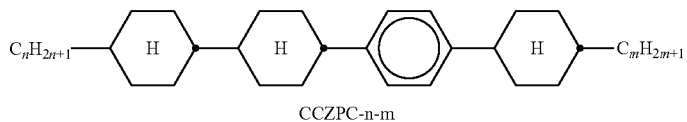
CCZPC-n-m
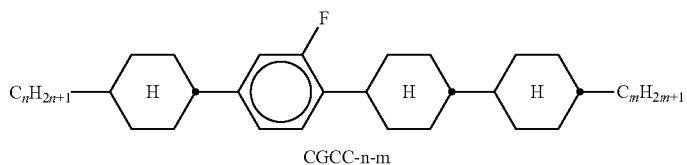
CGCC-n-m
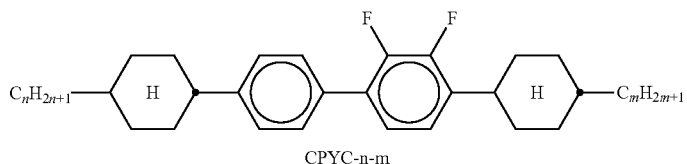
CPYC-n-m TABLE A-continued
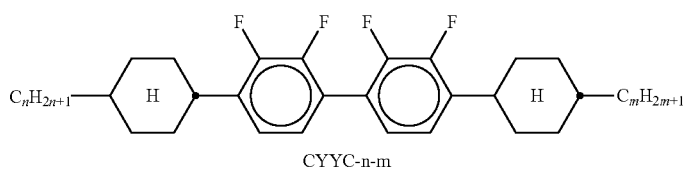
CYYC-n-m
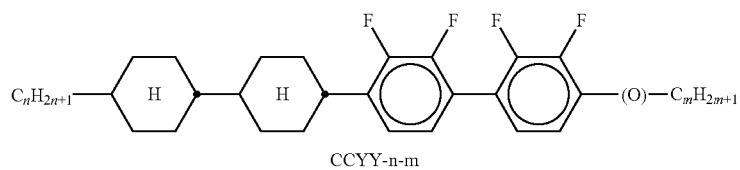
CCYY-n-m
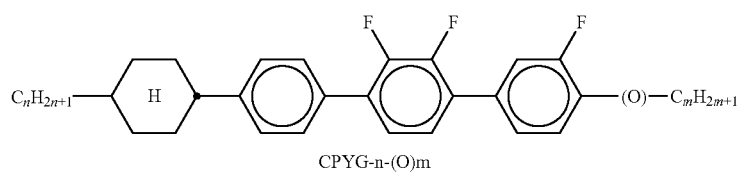
CPYG-n-(O)m
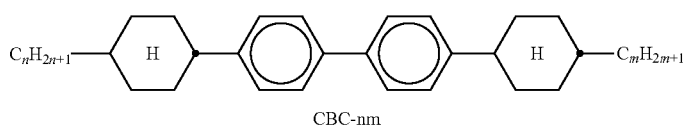
CBC-nm
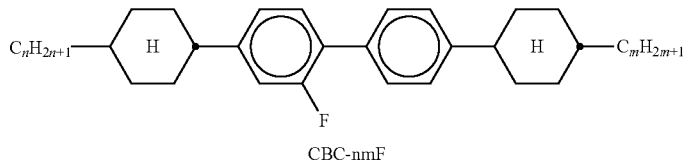
CBC-nmF
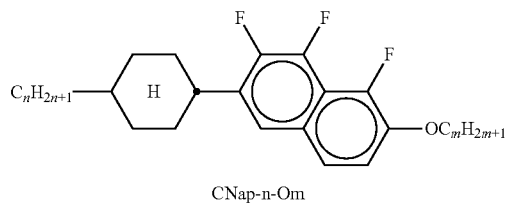
CNap-n-Om
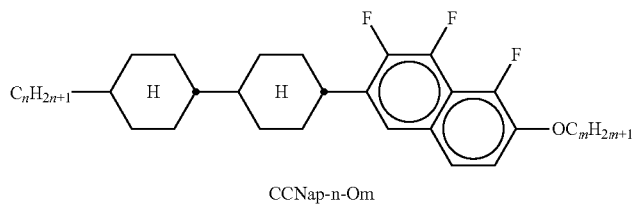
CCNap-n-Om
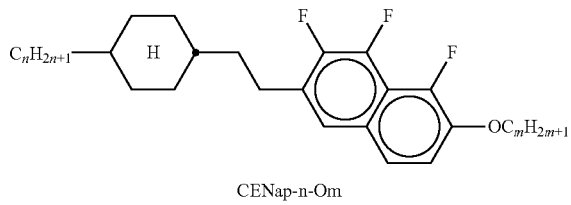
CENap-n-Om TABLE A-continued
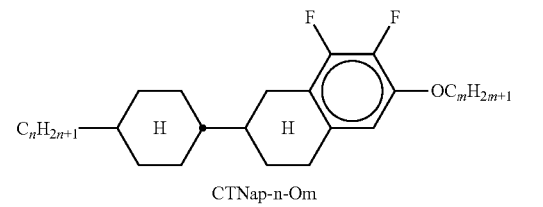
CTNap-n-Om
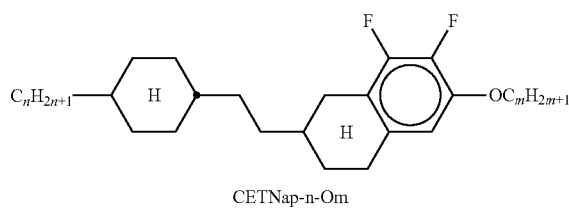
CETNap-n-Om
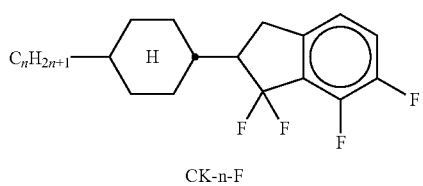
CK-n-F
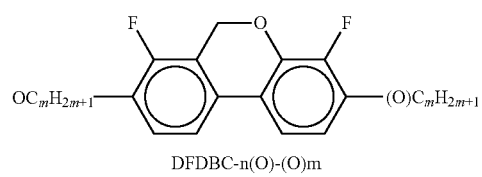
DFDBC-n(O)-(O)m
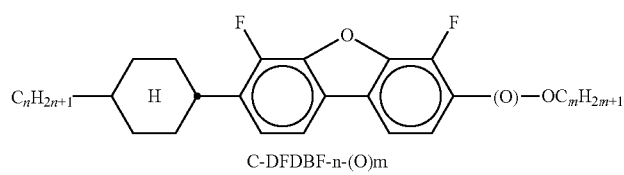
C-DFDBF-n-(O)m
In a preferred embodiment of the present invention, the LC media according to the invention comprise one or more compounds selected from the group consisting of compounds from Table A.
TABLE B
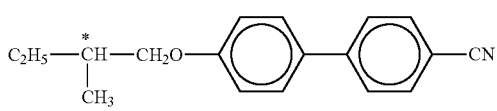
C 15
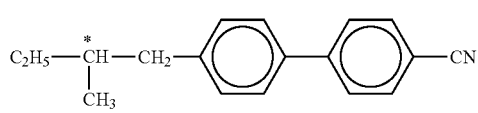
CB 15
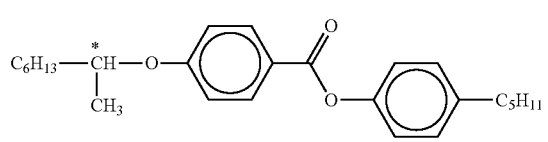
CM 21

TABLE B-continued
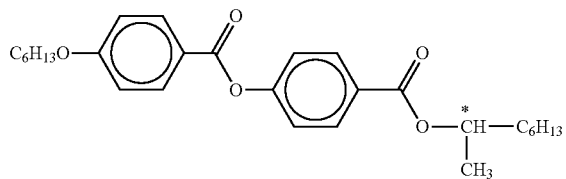 R/S-811
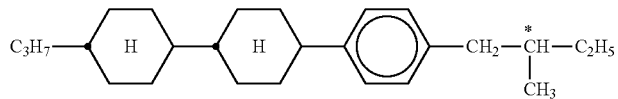 CM 44
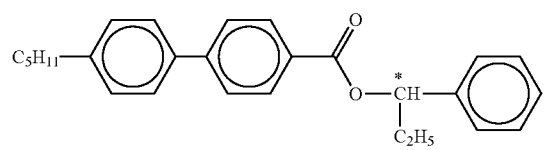 CM 45
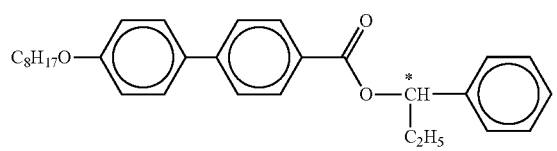 CM 47
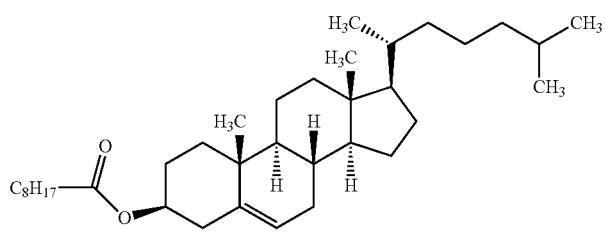 CN
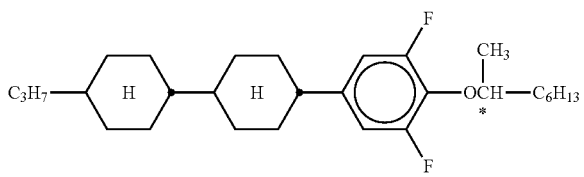 R/S-2011
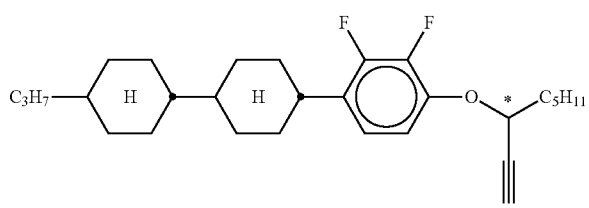 R/S-3011
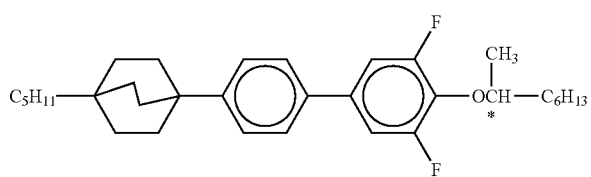 R/S-4011
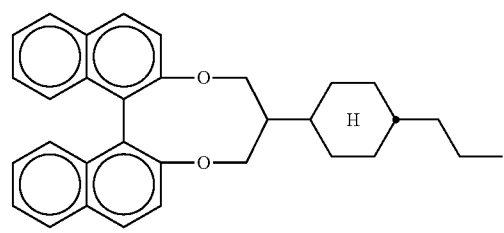 R/S-5011

TABLE B-continued

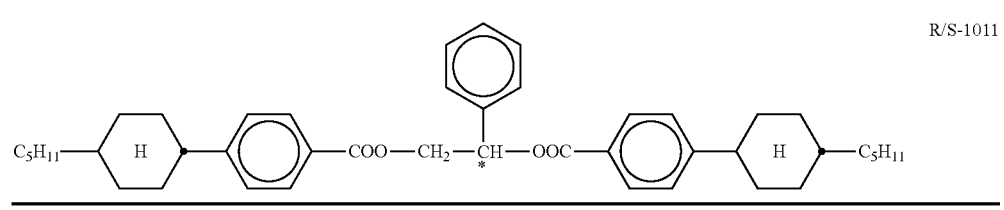

R/S-1011

Table B shows possible chiral dopants which can be added to the LC media according to the invention.

The LC media preferably comprise 0 to 10% by weight, in particular 0.01 to 5% by weight, particularly preferably 0.1 to 3% by weight, of dopants. The LC media preferably comprise one or more dopants selected from the group consisting of compounds from Table B.

TABLE C

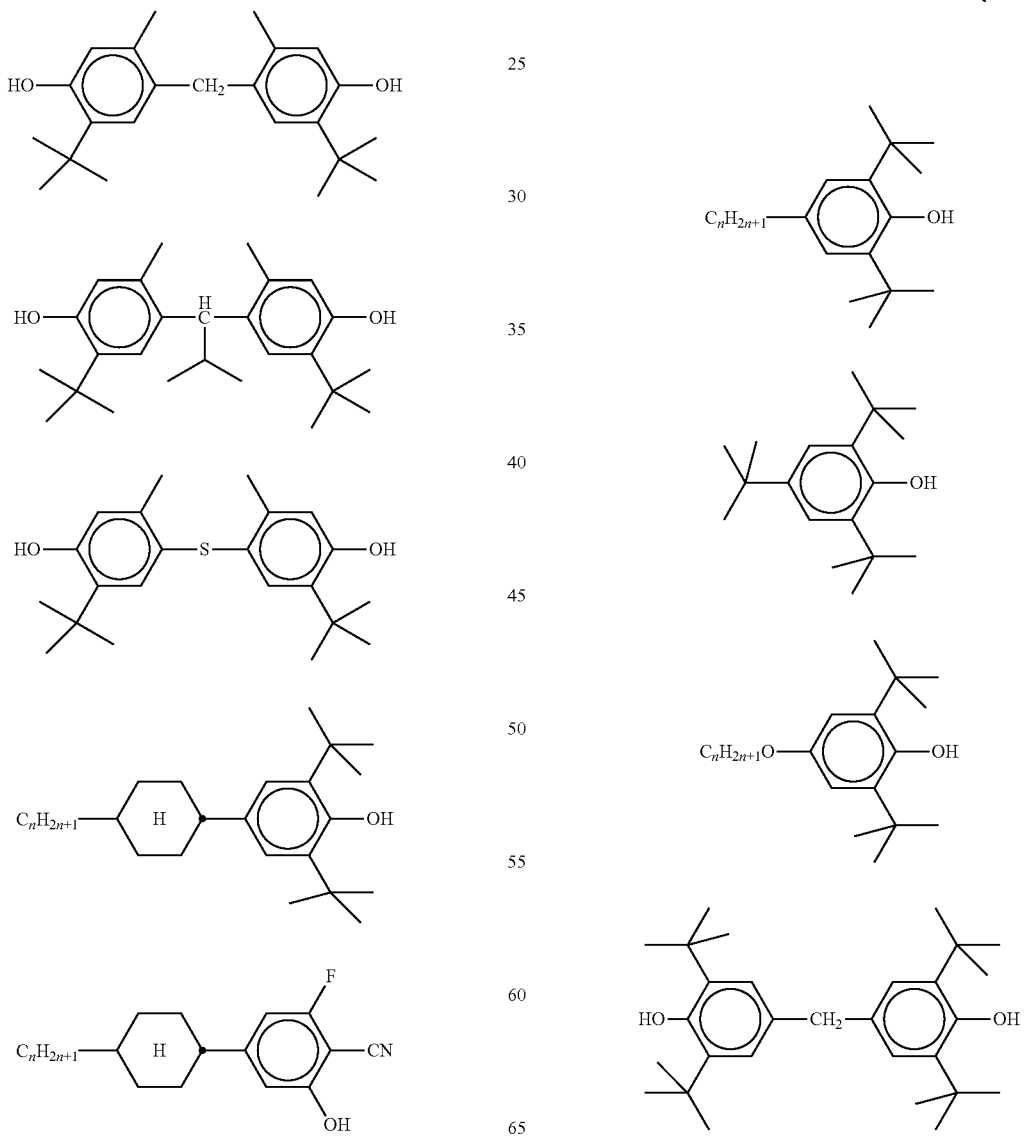

TABLE C-continued

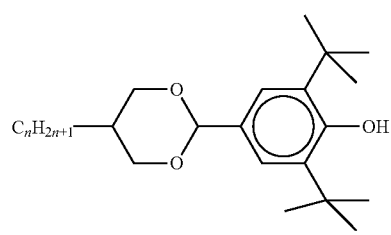

TABLE C-continued
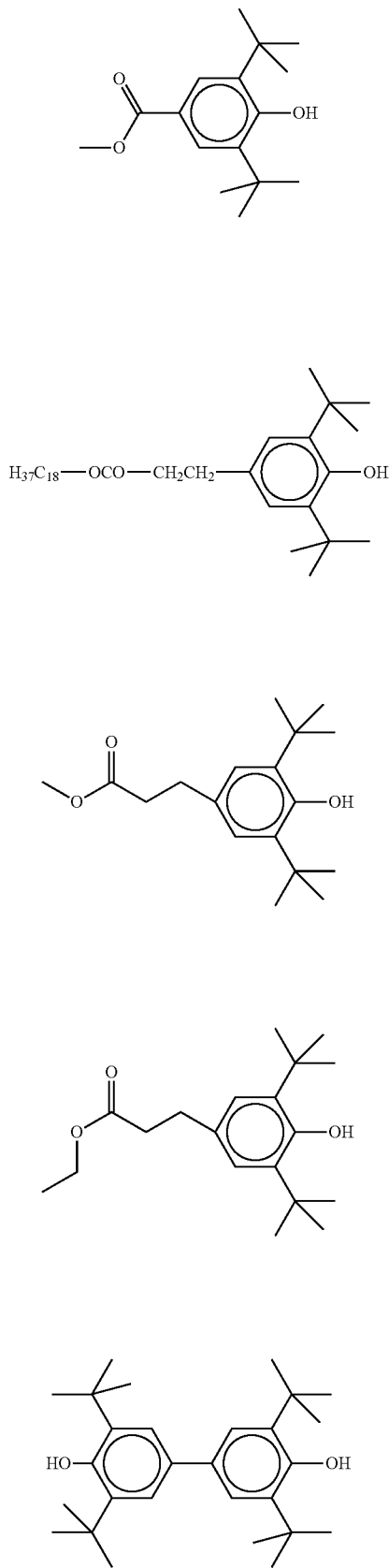

TABLE C-continued

TABLE C-continued
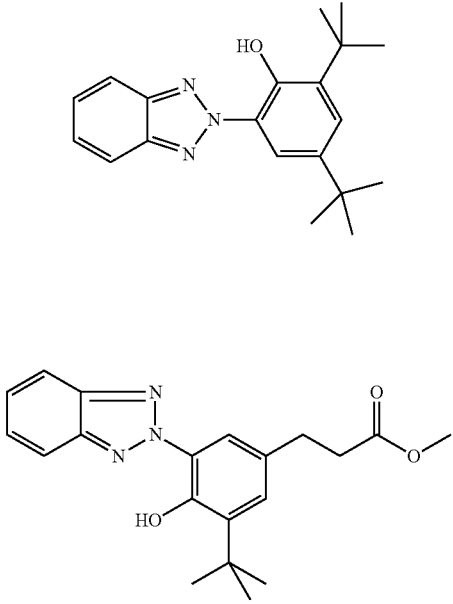
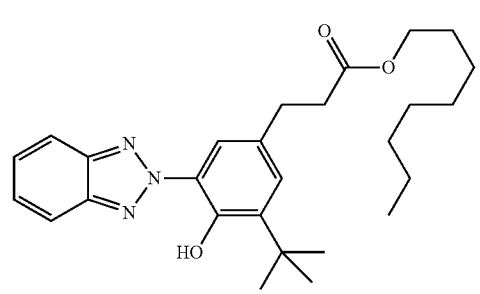 [SMILES: CCCCCCCCOC(=O)CCc1cc(-n2nc3ccccc3n2)c(O)c(C(C)(C)C)c1]
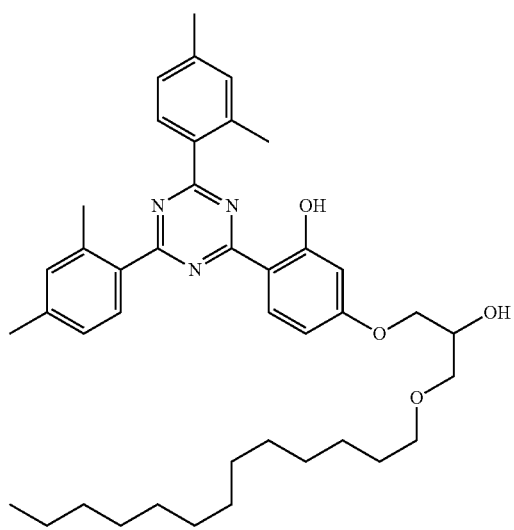 [SMILES: CCCCCCCCCCCCCOCC(O)COc1ccc(-c2nc(-c3ccc(C)cc3C)nc(-c3ccc(C)cc3C)n2)c(O)c1]
TABLE C-continued
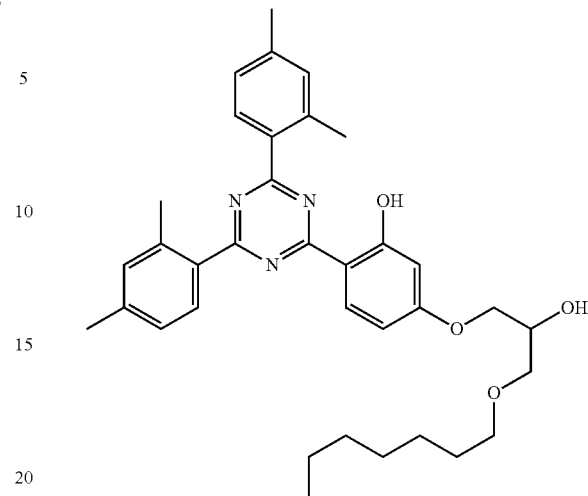
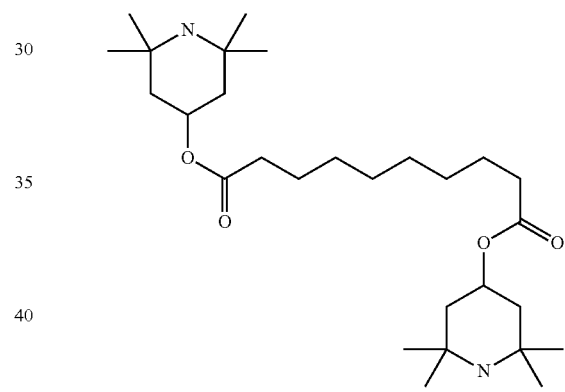
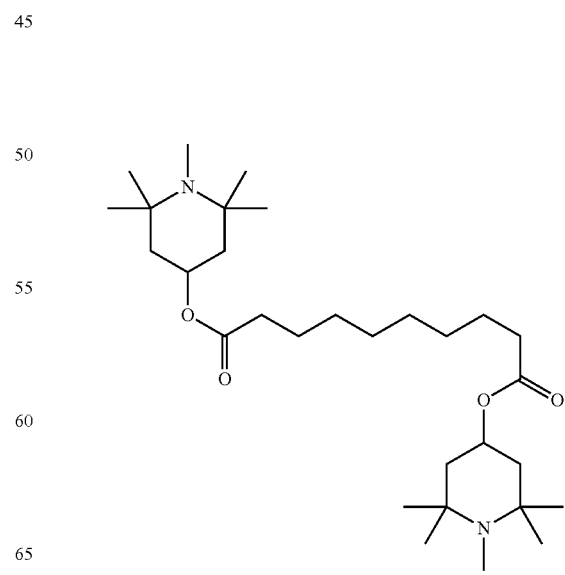

TABLE C-continued

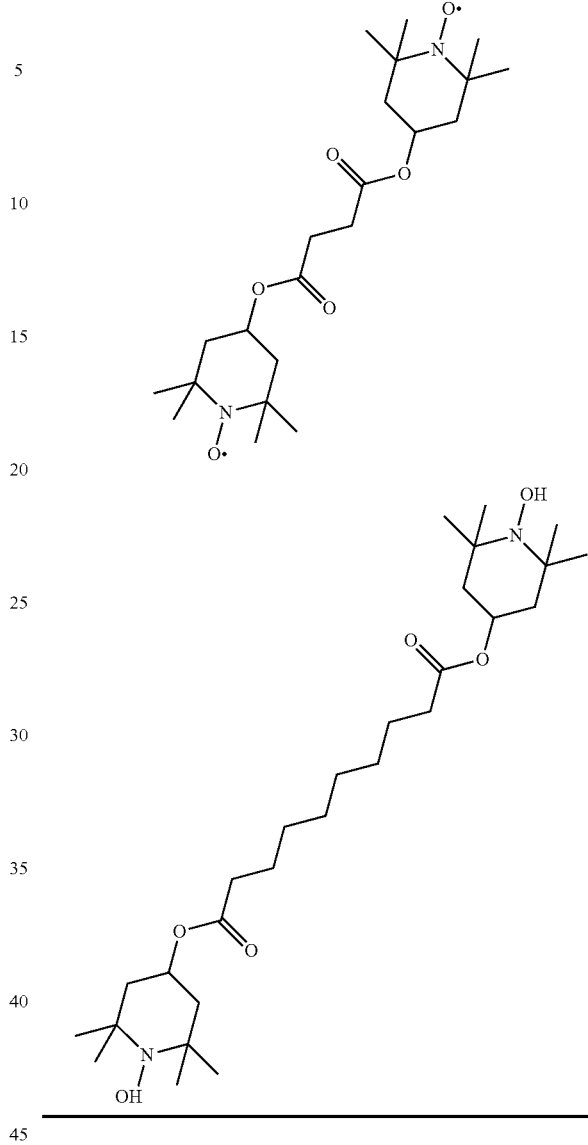

Table C shows possible stabilisers which can be added to the LC media according to the invention.
(n here denotes an integer from 1 to 12, preferably 1, 2, 3, 4, 5, 6, 7 or 8, terminal methyl groups are not shown).
O. denotes an oxygen free radical.

The LC media preferably comprise 0 to 10% by weight, in particular 1 ppm to 5% by weight, particularly preferably 1 ppm to 1% by weight, of stabilisers. The LC media preferably comprise one or more stabilisers selected from the group consisting of compounds from Table C.

TABLE D

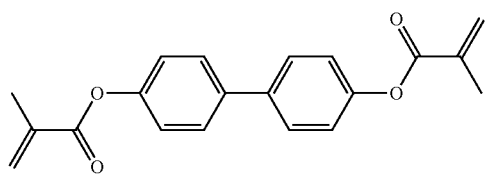 [SMILES: C=C(C)C(=O)Oc1ccc(-c2ccc(OC(=O)C(=C)C)cc2)cc1]

RM-1

TABLE D-continued
| | |
|---|---|
| 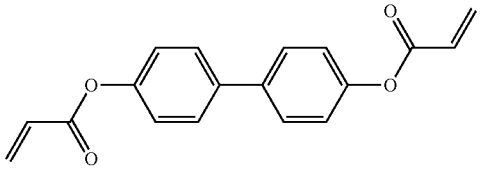 [SMILES: C=CC(=O)Oc1ccc(-c2ccc(OC(=O)C=C)cc2)cc1] | RM-2 |
| 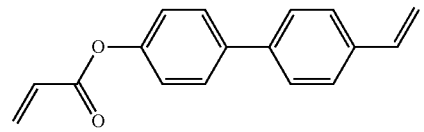 [SMILES: C=CC(=O)Oc1ccc(-c2ccc(C=C)cc2)cc1] | RM-3 |
| 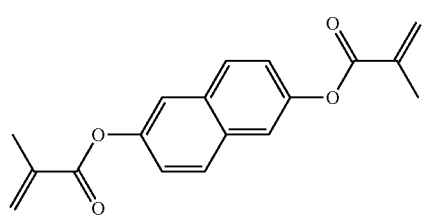 [SMILES: C=C(C)C(=O)Oc1ccc2cc(OC(=O)C(=C)C)ccc2c1] | RM-4 |
| 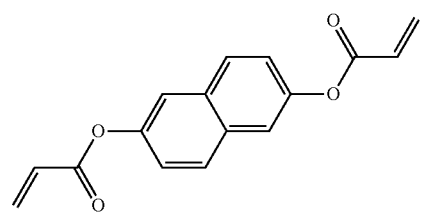 [SMILES: C=CC(=O)Oc1ccc2cc(OC(=O)C=C)ccc2c1] | RM-5 |
| 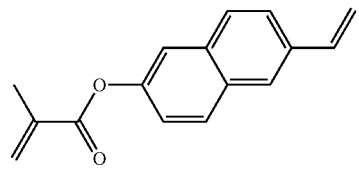 [SMILES: C=Cc1ccc2cc(OC(=O)C(=C)C)ccc2c1] | RM-6 |
| 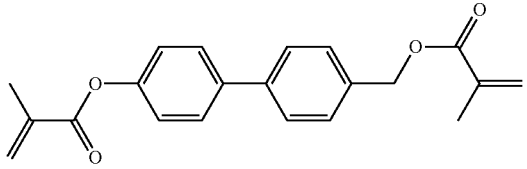 [SMILES: C=C(C)C(=O)OCc1ccc(-c2ccc(OC(=O)C(=C)C)cc2)cc1] | RM-7 |
| 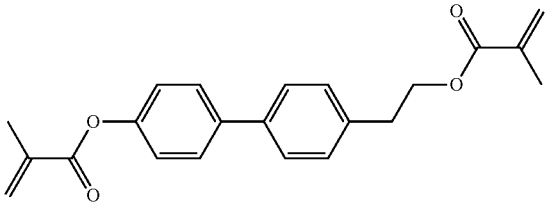 [SMILES: C=C(C)C(=O)OCCc1ccc(-c2ccc(OC(=O)C(=C)C)cc2)cc1] | RM-8 |
| 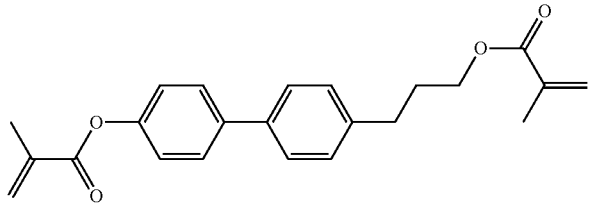 [SMILES: C=C(C)C(=O)OCCCc1ccc(-c2ccc(OC(=O)C(=C)C)cc2)cc1] | RM-9 |

TABLE D-continued
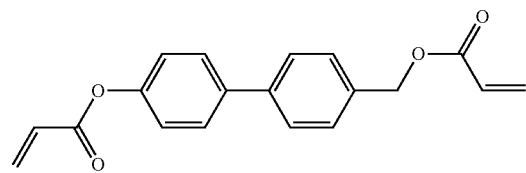 [SMILES: C=CC(=O)OCc1ccc(-c2ccc(OC(=O)C=C)cc2)cc1] RM-10
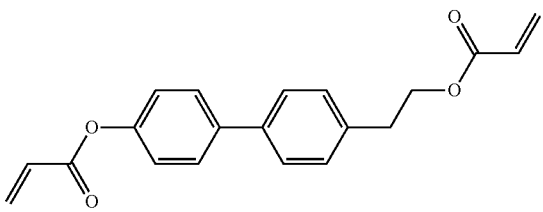 [SMILES: C=CC(=O)OCCc1ccc(-c2ccc(OC(=O)C=C)cc2)cc1] RM-11
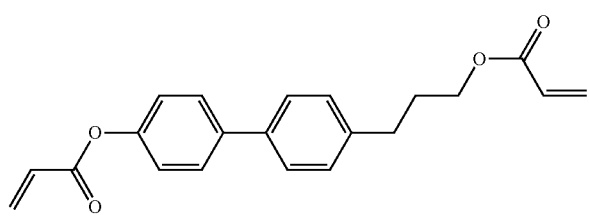 [SMILES: C=CC(=O)OCCCc1ccc(-c2ccc(OC(=O)C=C)cc2)cc1] RM-12
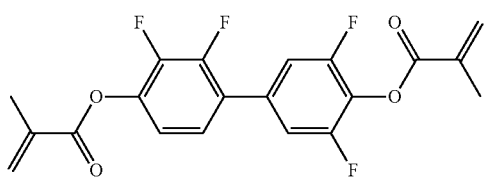 [SMILES: C=C(C)C(=O)Oc1ccc(-c2cc(F)c(OC(=O)C(=C)C)c(F)c2)c(F)c1F] RM-13
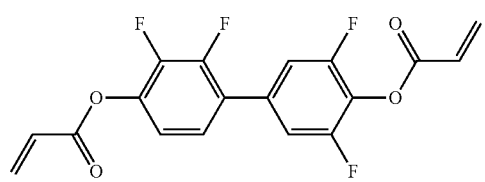 [SMILES: C=CC(=O)Oc1ccc(-c2cc(F)c(OC(=O)C=C)c(F)c2)c(F)c1F] RM-14
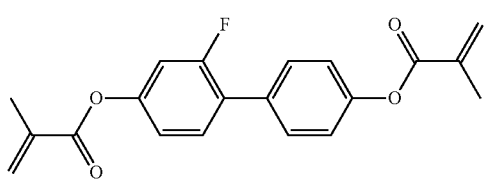 [SMILES: C=C(C)C(=O)Oc1ccc(-c2ccc(OC(=O)C(=C)C)cc2F)cc1] RM-15
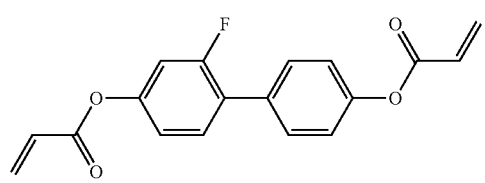 [SMILES: C=CC(=O)Oc1ccc(-c2ccc(OC(=O)C=C)cc2F)cc1] RM-16
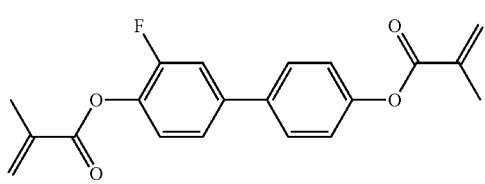 RM-17

TABLE D-continued

| | |
|---|---|
| (structure) | RM-18 |
| (structure) | RM-19 |
| (structure) | RM-20 |
| (structure) | RM-21 |
| (structure) | RM-22 |
| (structure) | RM-23 |
| (structure) | RM-24 |
| (structure) | RM-25 |
| (structure) | RM-26 |

TABLE D-continued
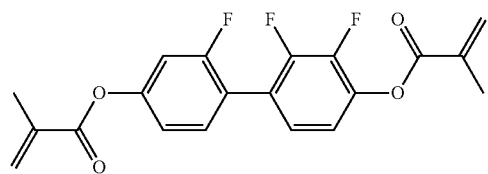 [SMILES: C=C(C)C(=O)Oc1ccc(-c2ccc(OC(=O)C(=C)C)c(F)c2F)c(F)c1] RM-27
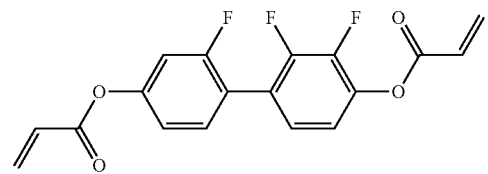 RM-28
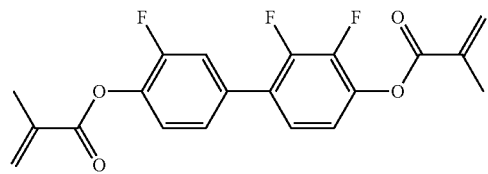 RM-29
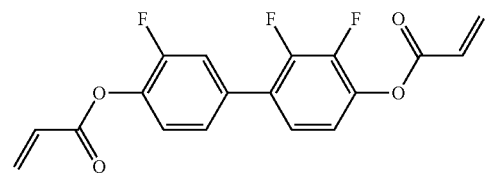 [SMILES: C=CC(=O)Oc1ccc(-c2ccc(OC(=O)C=C)c(F)c2F)c(F)c1] RM-30
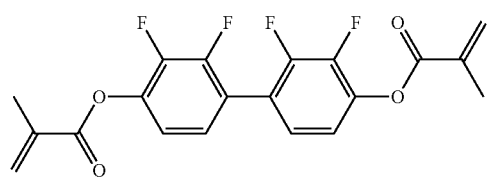 [SMILES: C=C(C)C(=O)Oc1ccc(-c2ccc(OC(=O)C(=C)C)c(F)c2F)c(F)c1F] RM-31
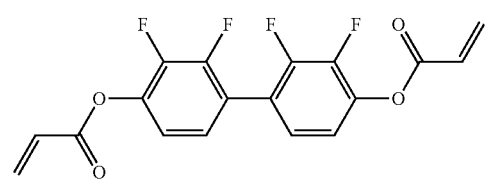 RM-32
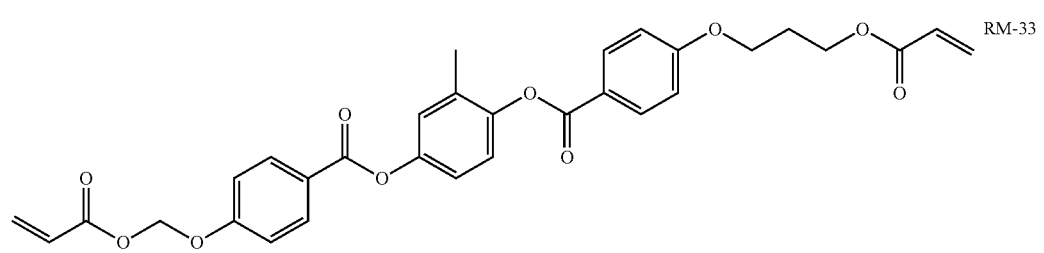 RM-33

TABLE D-continued
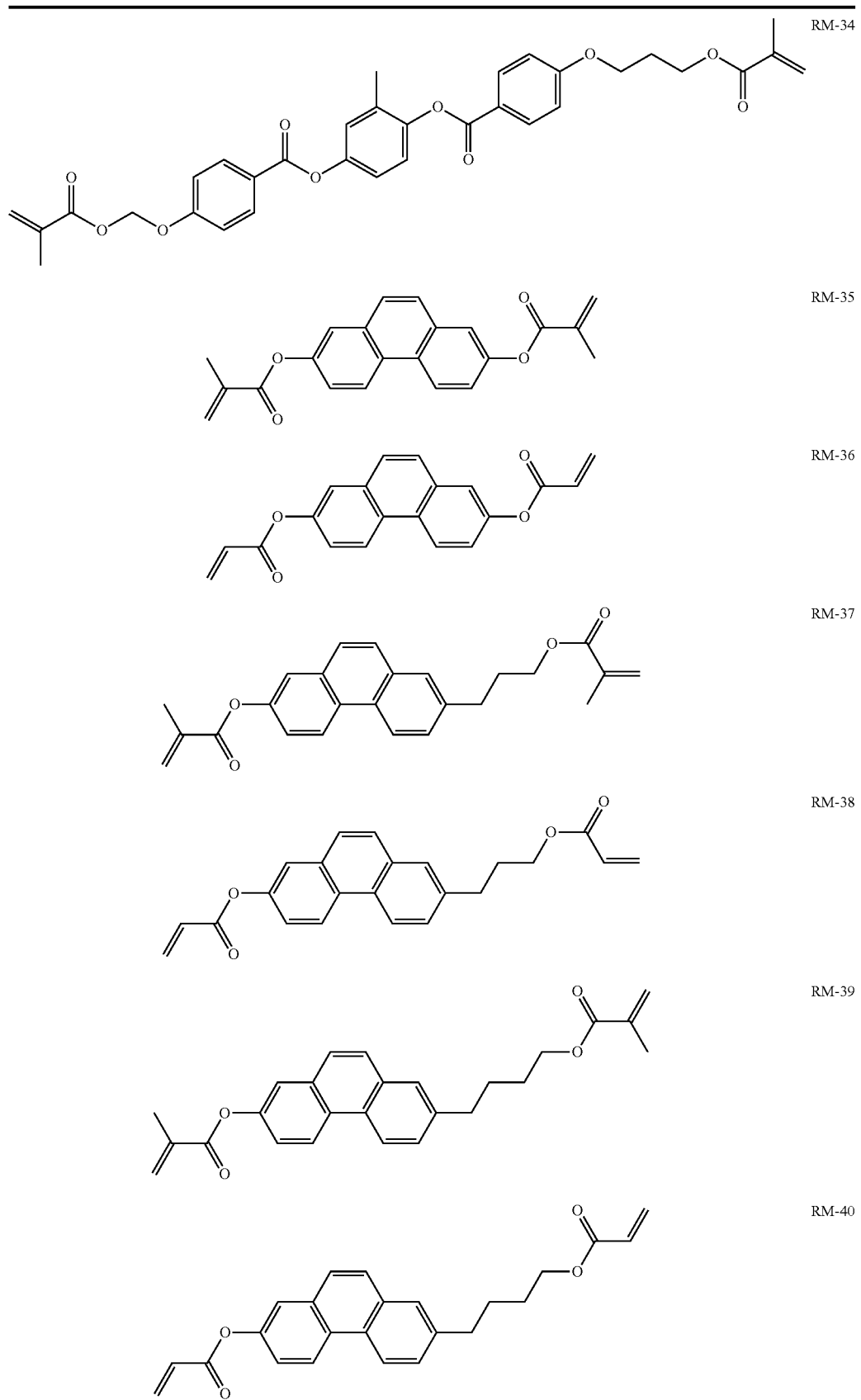
RM-34
RM-35
RM-36
RM-37
RM-38
RM-39
RM-40

TABLE D-continued
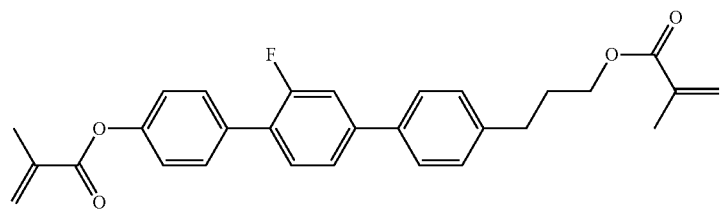 [SMILES: C=C(C)C(=O)OCCCc1ccc(-c2ccc(-c3ccc(OC(=O)C(=C)C)cc3)c(F)c2)cc1] RM-41
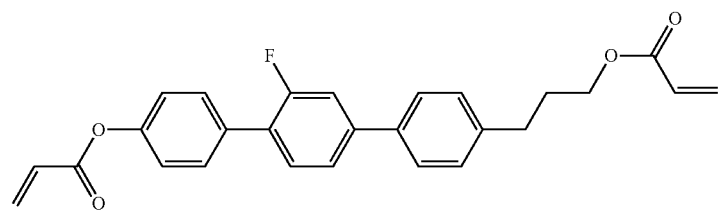 [SMILES: C=CC(=O)OCCCc1ccc(-c2ccc(-c3ccc(OC(=O)C=C)cc3)c(F)c2)cc1] RM-42
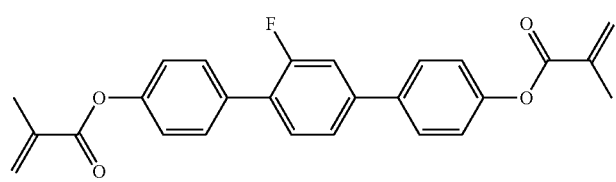 [SMILES: C=C(C)C(=O)Oc1ccc(-c2ccc(-c3ccc(OC(=O)C(=C)C)cc3)c(F)c2)cc1] RM-43
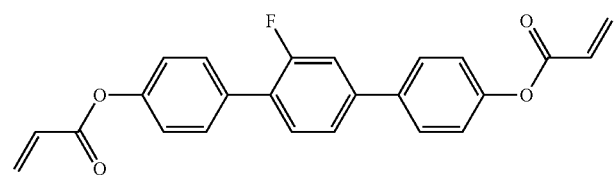 RM-44
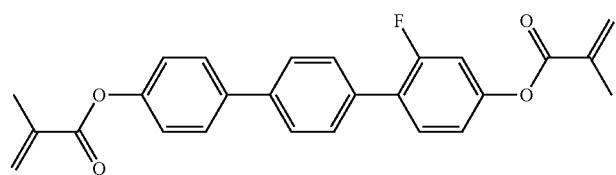 [SMILES: C=C(C)C(=O)Oc1ccc(-c2ccc(-c3ccc(OC(=O)C(=C)C)cc3F)cc2)cc1] RM-45
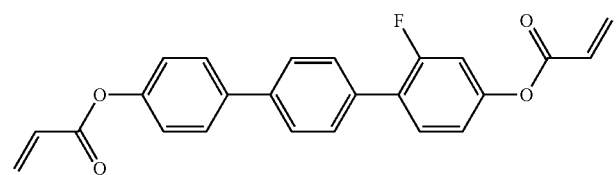 [SMILES: C=CC(=O)Oc1ccc(-c2ccc(-c3ccc(OC(=O)C=C)cc3F)cc2)cc1] RM-46
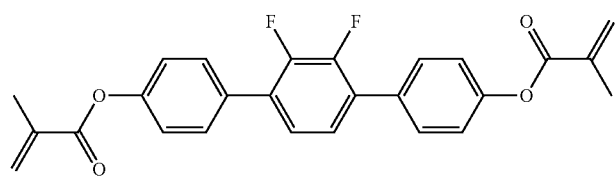 [SMILES: C=C(C)C(=O)Oc1ccc(-c2ccc(-c3ccc(OC(=O)C(=C)C)cc3)c(F)c2F)cc1] RM-47
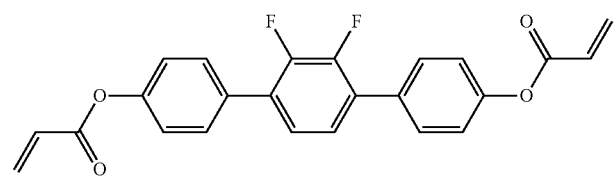 RM-48

TABLE D-continued
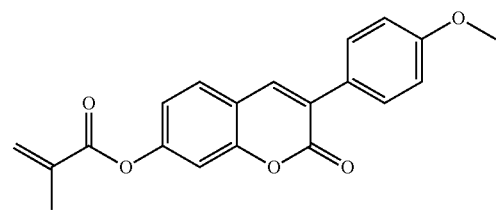 [SMILES: C=C(C)C(=O)Oc1ccc2cc(-c3ccc(OC)cc3)c(=O)oc2c1] RM-49
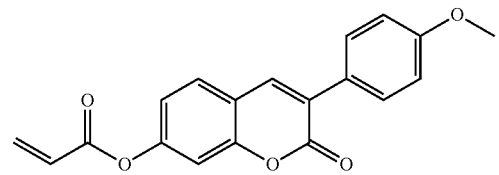 [SMILES: C=CC(=O)Oc1ccc2cc(-c3ccc(OC)cc3)c(=O)oc2c1] RM-50
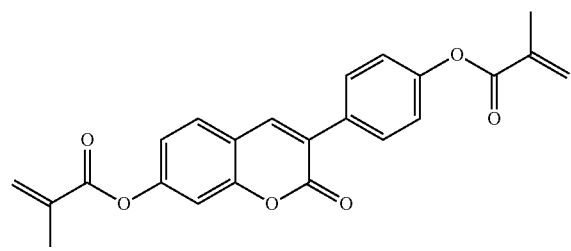 [SMILES: C=C(C)C(=O)Oc1ccc(-c2cc3ccc(OC(=O)C(=C)C)cc3oc2=O)cc1] RM-51
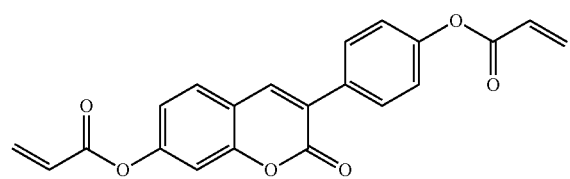 [SMILES: C=CC(=O)Oc1ccc(-c2cc3ccc(OC(=O)C=C)cc3oc2=O)cc1] RM-52
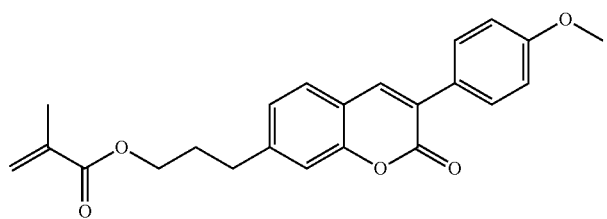 [SMILES: C=C(C)C(=O)OCCCc1ccc2cc(-c3ccc(OC)cc3)c(=O)oc2c1] RM-53
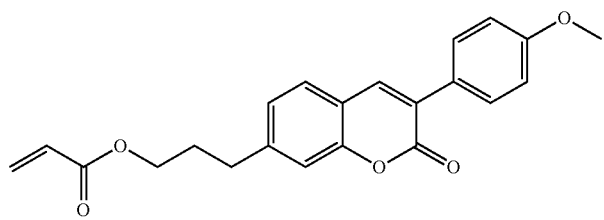 [SMILES: C=CC(=O)OCCCc1ccc2cc(-c3ccc(OC)cc3)c(=O)oc2c1] RM-54
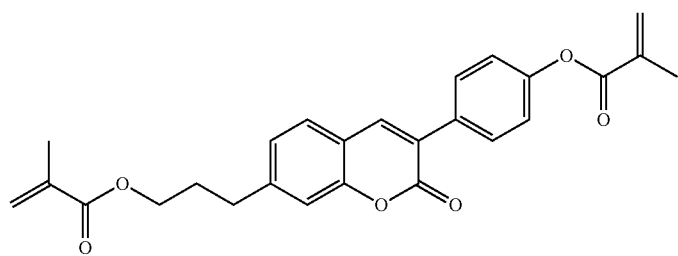 [SMILES: C=C(C)C(=O)OCCCc1ccc2cc(-c3ccc(OC(=O)C(=C)C)cc3)c(=O)oc2c1] RM-55

TABLE D-continued
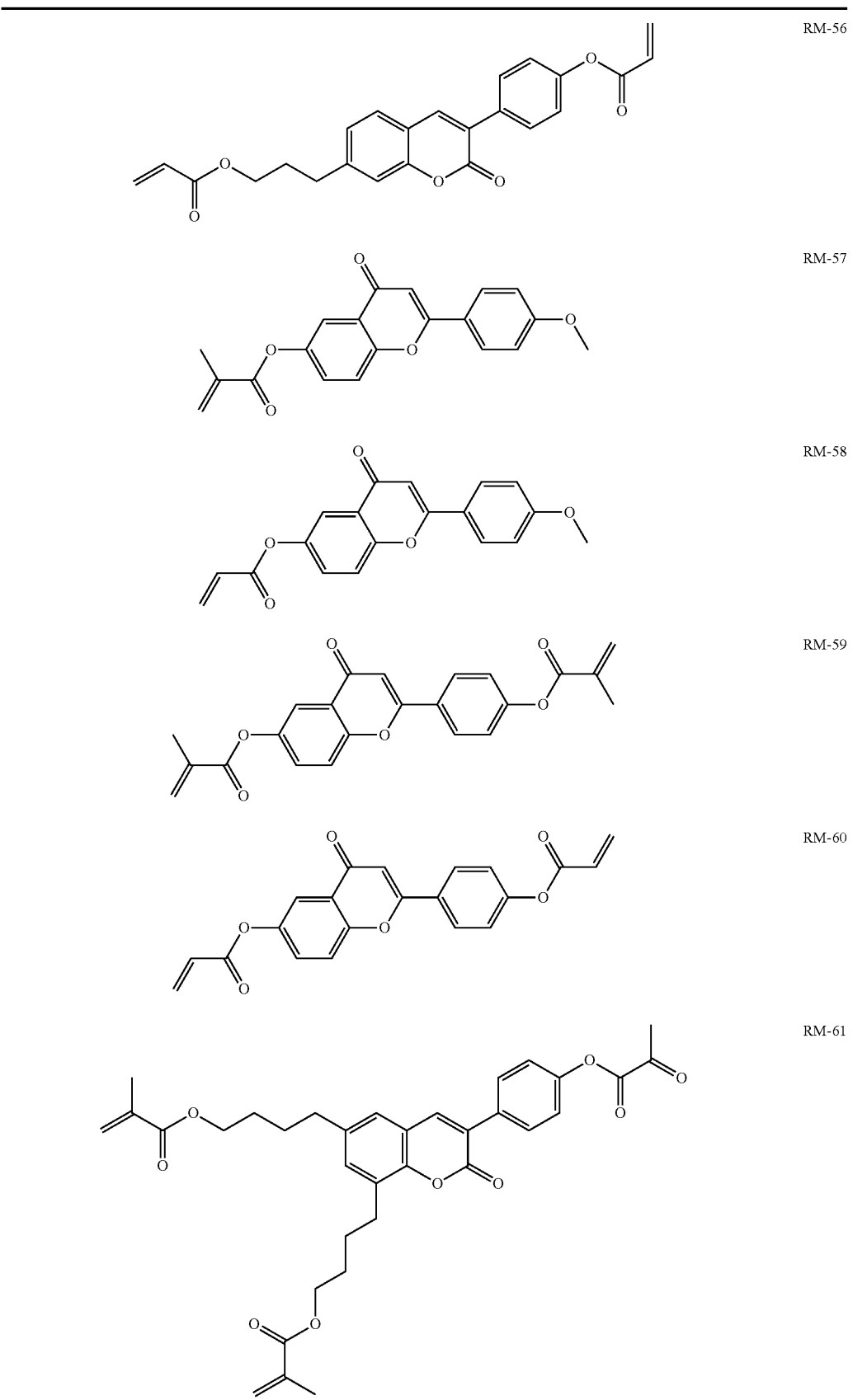
RM-56
RM-57
RM-58
RM-59
RM-60
RM-61

TABLE D-continued
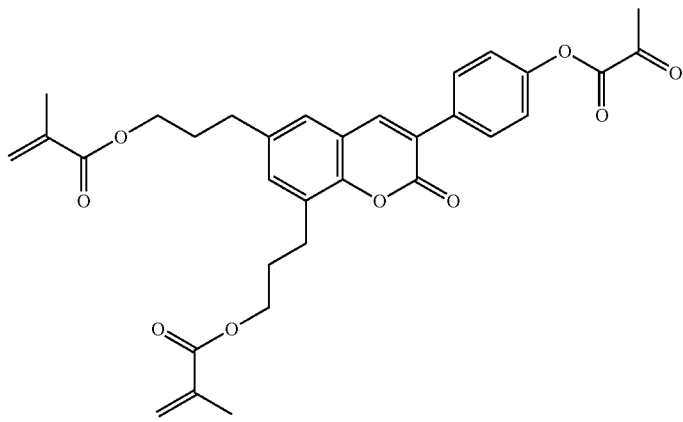 [SMILES: C=C(C)C(=O)OCCCc1cc(CCCOC(=O)C(=C)C)c2oc(=O)c(-c3ccc(OC(=O)C(C)=O)cc3)cc2c1]
RM-62
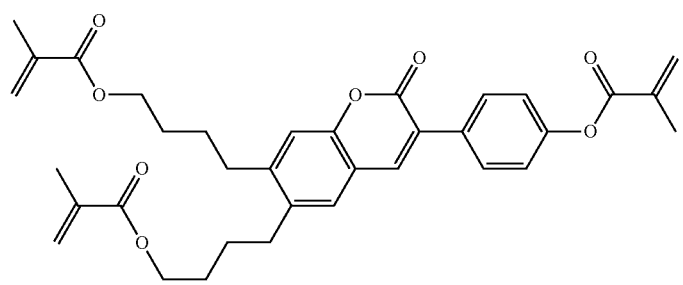 [SMILES: C=C(C)C(=O)OCCCCc1cc2cc(-c3ccc(OC(=O)C(=C)C)cc3)c(=O)oc2cc1CCCCOC(=O)C(=C)C]
RM-63
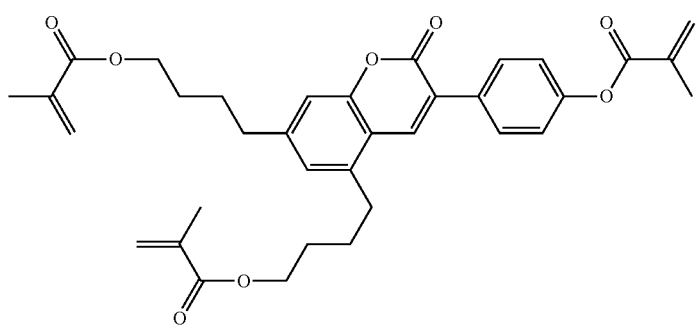 [SMILES: C=C(C)C(=O)OCCCCc1cc(CCCCOC(=O)C(=C)C)c2cc(-c3ccc(OC(=O)C(=C)C)cc3)c(=O)oc2c1]
RM-64
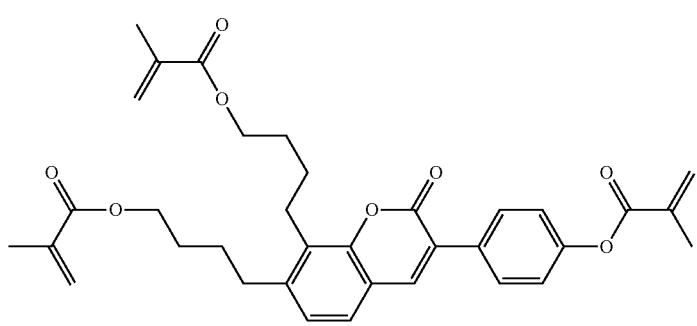 [SMILES: C=C(C)C(=O)OCCCCc1ccc2cc(-c3ccc(OC(=O)C(=C)C)cc3)c(=O)oc2c1CCCCOC(=O)C(=C)C]
RM-65

TABLE D-continued
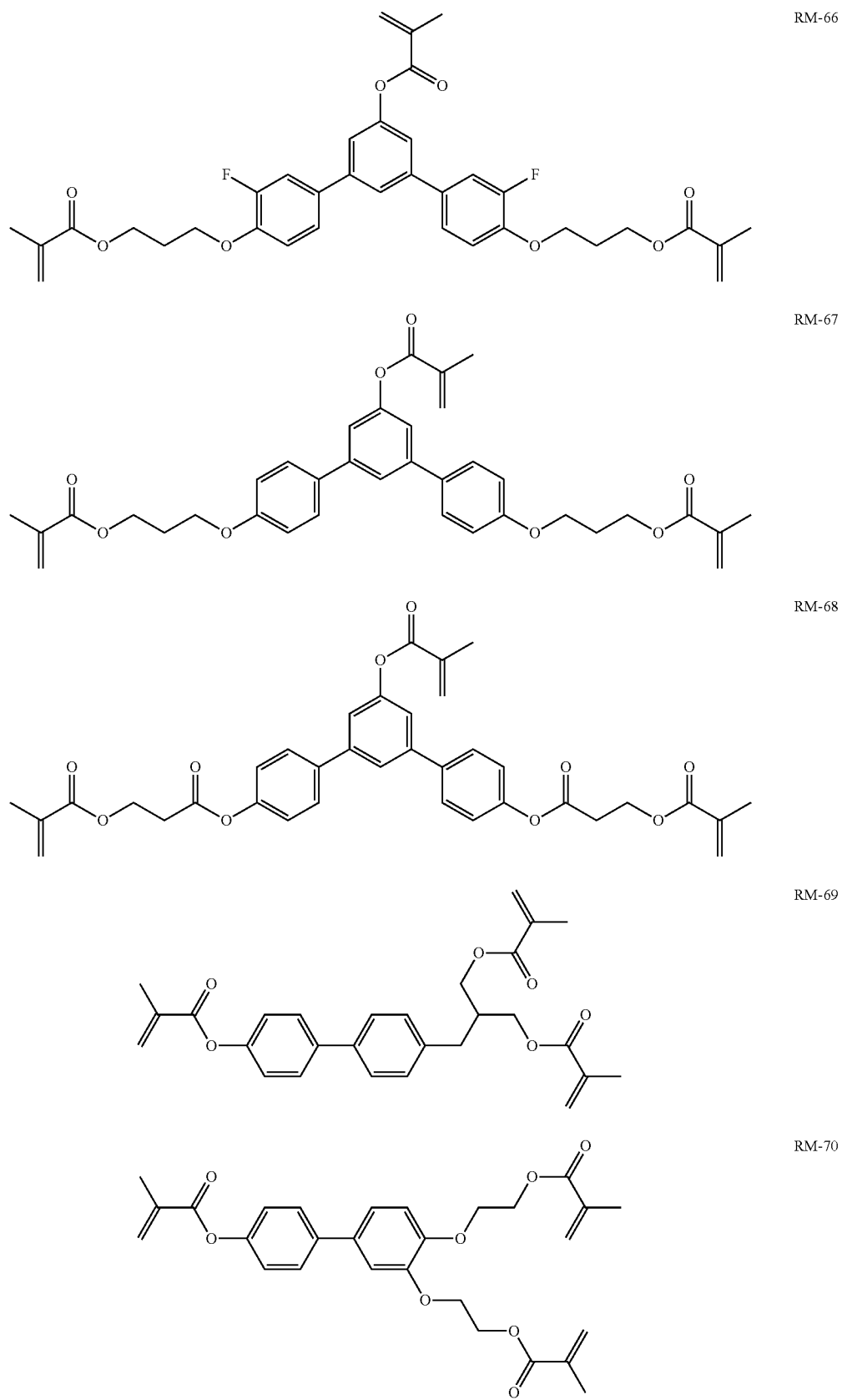
RM-66
RM-67
RM-68
RM-69
RM-70

TABLE D-continued

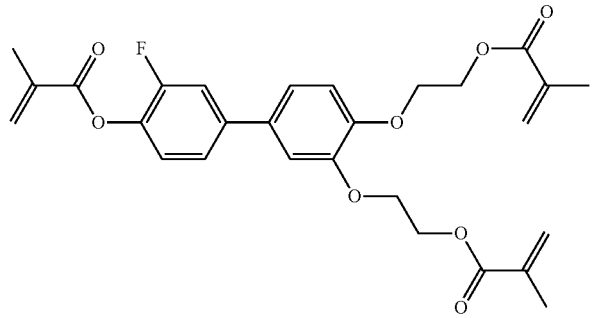 [SMILES: C=C(C)C(=O)OCCOc1ccc(-c2ccc(OC(=O)C(=C)C)cc2)cc1OCCOC(=O)C(=C)C]
RM-71

Table D shows illustrative compounds which can be used in the LC media in accordance with the present invention, preferably as reactive mesogenic compounds.

In a preferred embodiment of the present invention, the mesogenic media comprise one or more compounds selected from the group of the compounds from Table D.

In addition, the following abbreviations and symbols are used:

$V_0$ threshold voltage, capacitive [V] at 20° C.,
$n_e$ extraordinary refractive index at 20° C. and 589 nm,
$n_o$ ordinary refractive index at 20° C. and 589 nm,
$\Delta n$ optical anisotropy at 20° C. and 589 nm,
$\epsilon_\perp$ dielectric permittivity perpendicular to the director at 20° C. and 1 kHz,
$\epsilon_\parallel$ dielectric permittivity parallel to the director at 20° C. and 1 kHz,
$\Delta\epsilon$ dielectric anisotropy at 20° C. and 1 kHz,
cl.p., T(N,I) clearing point [° C.],
$\gamma_1$ rotational viscosity at 20° C. [mPa·s],
$K_1$ elastic constant, "splay" deformation at 20° C. [pN],
$K_2$ elastic constant, "twist" deformation at 20° C. [pN],
$K_3$ elastic constant, "bend" deformation at 20° C. [pN].

Unless explicitly noted otherwise, all concentrations in the present application are quoted in percent by weight and relate to the corresponding mixture as a whole, comprising all solid or liquid-crystalline components, without solvents.

Unless explicitly noted otherwise, all temperature values indicated in the present application, such as, for example, for the melting point T(C,N), the transition from the smectic (S) to the nematic (N) phase T(S,N) and the clearing point T(N,I), are quoted in degrees Celsius (° C.). M.p. denotes melting point, cl.p.=clearing point. Furthermore, C=crystalline state, N=nematic phase, S=smectic phase and I=isotropic phase. The data between these symbols represent the transition temperatures.

All physical properties are and have been determined in accordance with "Merck Liquid Crystals, Physical Properties of Liquid Crystals", Status November 1997, Merck KGaA, Germany, and apply for a temperature of 20° C., and $\Delta n$ is determined at 589 nm and $\Delta\epsilon$ at 1 kHz, unless explicitly indicated otherwise in each case.

The term "threshold voltage" for the present invention relates to the capacitive threshold ($V_0$), also known as the Freedericks threshold, unless explicitly indicated otherwise. In the examples, the optical threshold may also, as generally usual, be quoted for 10% relative contrast ($V_{10}$).

Unless stated otherwise, the process of polymerising the polymerisable compounds in the PSA displays as described above and below is carried out at a temperature where the LC medium exhibits a liquid crystal phase, preferably a nematic phase, and most preferably is carried out at room temperature.

Unless stated otherwise, methods of preparing test cells and measuring their electrooptical and other properties are carried out by the methods as described hereinafter or in analogy thereto.

The display used for measurement of the capacitive threshold voltage consists of two plane-parallel glass outer plates at a separation of 25 µm, each of which has on the inside an electrode layer and an unrubbed polyimide alignment layer on top, which effect a homeotropic edge alignment of the liquid-crystal molecules.

The display or test cell used for measurement of the tilt angles consists of two plane-parallel glass outer plates at a separation of 4 µm, each of which has on the inside an electrode layer and a polyimide alignment layer on top, where the two polyimide layers are rubbed antiparallel to one another and effect a homeotropic edge alignment of the liquid-crystal molecules.

The polymerisable compounds are polymerised in the display or test cell by irradiation with UVA light of defined intensity for a prespecified time, with a voltage simultaneously being applied to the display (usually 10 V to 30 V alternating current, 1 kHz). In the examples, unless indicated otherwise, a metal halide lamp and an intensity of 100 mW/cm² is used for polymerisation. The intensity is measured using a standard UVA meter (Hoenle UV-meter high end with UVA sensor).

The tilt angle is determined by crystal rotation experiment (Autronic-Melchers TBA-105). A low value (i.e. a large deviation from the 90° angle) corresponds to a large tilt here.

The VHR value is measured as follows: 0.3% of a polymerisable monomeric compound is added to the LC host mixture, and the resultant mixture is introduced into VA-VHR test cells which comprise an unrubbed VA-polyimide alignment layer. The LC-layer thickness d is approx. 6 µm, unless stated otherwise. The VHR value is determined after 5 min at 100° C. before and after UV exposure at 1 V, 60 Hz, 64 µs pulse (measuring instrument: Autronic-Melchers VHRM-105).

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding application No. EP 14002646.9 filed Jul. 30, 2014, is incorporated by reference herein.

Example 1

Polymerisable monomeric compound 1 is prepared as follows.

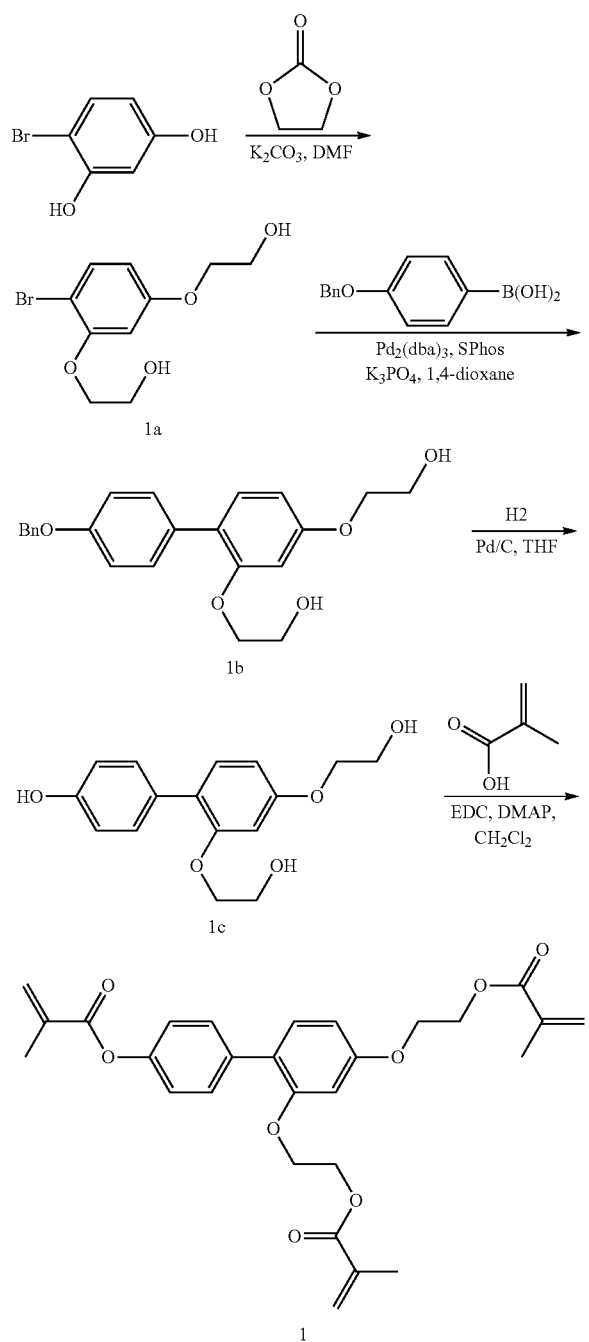

1a: To a solution of 4-bromoresorcinol (15.00 g, 79.4 mmol) and ethylenecarbonate (19.57 g. 222.2 mmol) in DMF (80 ml) is added dry potassium carbonate (4.39 g, 31.7 mmol). The reaction mixture is refluxed overnight. After cooling to room temperature, the reaction mixture is added into 100 ml water and neutralized carefully with 2 M HCl. The aqueous phase is extracted with ethylacetate. The organic phase is combined and washed with sat. aq. NaCl solution, dried over sodium sulfate. After removing solvent in vacuo, the solid residue is recrystallized with heptane/ethyl acetate 4:1 to provide 1a as white solid (9.1 g).

1b: To a solution of 1a (15.60 g, 56.3 mol) and 4-benzyloxylphenyl boronic acid (15.4 g, 67.5 mmol) in 350 ml 1,4-dioxane was added 73.9 g (320.8 mmol) potassium phosphate. The resulted suspension is degassed carefully with argon. Tris(dibenzylidene acetone)dipalladium(0) (1.55 g, 1.7 mmol) and 2-dicyclohexylphosphine-2',6'-dimethoxylbiphenyl (SPhos) (2.38 g, 5.6 mmol) is then added. The reaction mixture is heated to reflux and stirred overnight. After cooling to room temperature 400 ml dist. water and 150 ml ethylacetate and 150 ml THF is added, and the mixture is neutralized carefully with 6 M HCl acid under cooling to pH~4. The aqueous phase is extracted with ethylacetate. The organic phase is combined and washed with sat. aq. NaCl solution, dried over sodium sulfate. After removing solvent in vacuo, the solid residue is purified by column chromatography with THF/toluene 3:2 as eluent to provide 1b as white solid (16.8 g).

1c: A solution of 1b (16.7 g, 43.9 mmol) in tetrahydrofuran (160 ml) is treated with palladium (5%) on activated charcoal (2.0 g) and submitted to hydrogenation for 19 hs. The catalyst is then filtered off, and the remaining solution is concentrated in vacuo. The residue is recrystallized from toluene/ethylacetate solvent mixture to 1c as white solid (12.5 g).

1: Methacrylic acid (18.42 g, 214.0 mmol) and 4-(dimethylamino)pyridine (0.5 g, 4.1 mmol) is added to a suspension of 1c (12.5 g, 42.8 mmol) in dichloromethane (180 ml). The reaction mixture is treated dropwise at 0° C. with a solution of N-(3-dimethylaminopropyl)-N'-ethylcarbodiimide (34.50 g, 222.5 mmol) in dichloromethane (20 ml) and stirred for 20 h at room temperature. After removing solvent in vacuo, the oily residue is purified by silica gel chromatography with heptane/ethyl acetate 7:3 as eluent. The obtained product is recrystallized from ethanol to afford white crystals of 1 (10.1 g, mp. 42° C.).

Example 2

Polymerisable monomeric compound 2 is prepared from the commercially available 3-fluoro-4-benzyloxylphenyl boronic acid in analogy to Example 1 as follows.

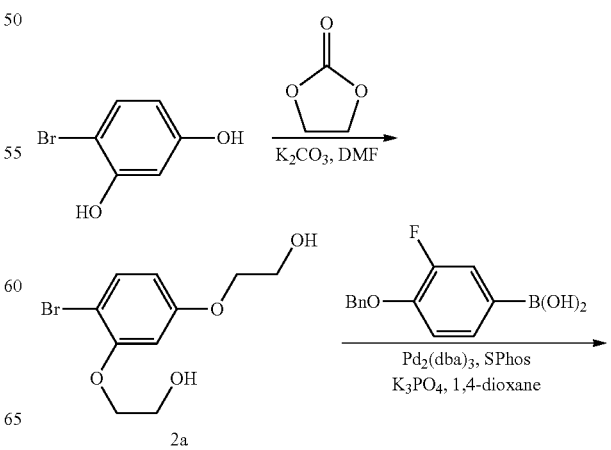

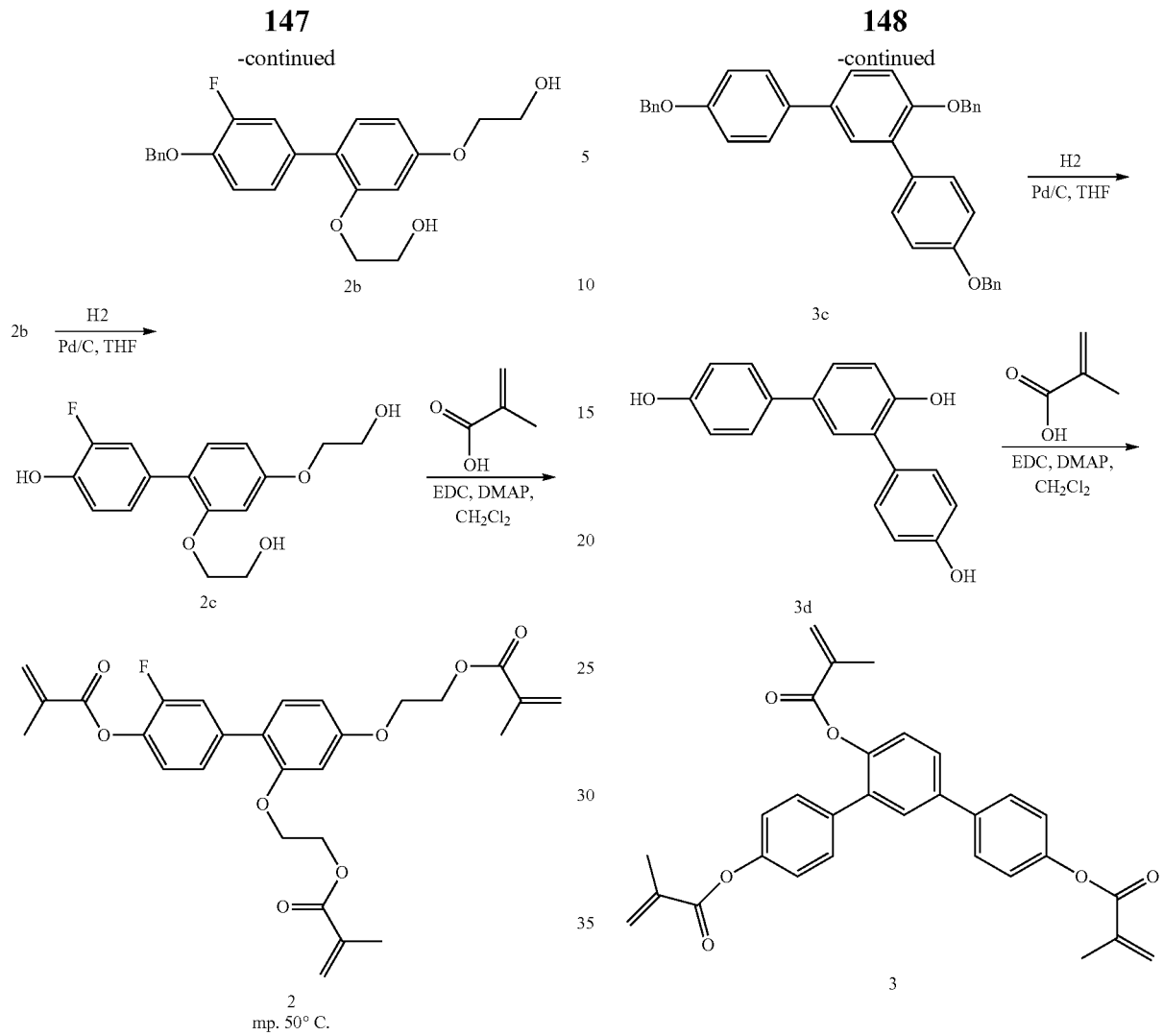

Example 3

Polymerisable monomeric compound 3 is prepared as follows.

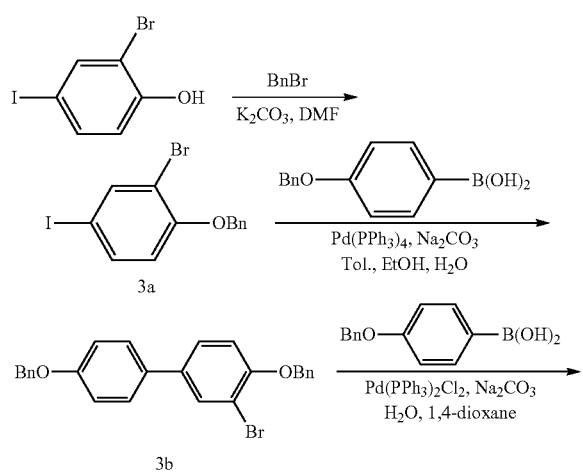

3a: To a solution of 2-bromo-4-iodio-phenol (75.00 g, 238.4 mmol) in 460 ml ethyl methylketone is added potassium carbonate (39.50 g. 286.0 mmol) in several portions. The reaction mixture is heated to reflux, to which benzyl-bromide (34.0 ml, 286.0 mmol) is added dropwise, and stirred overnight while refluxing. After cooling to room temperature, the reaction mixture is filtrated. The solid residue is washed thoroughly with aceton. After removing solvent in vacuo, the oily residue is purified by silica gel chromatography with heptane/toluene 7:3 as eluent. The crude product is further recrystallized from heptane to provide 3a as white solid (85.7 g).

3b: To a solution of 3a (85.50 g, 220.0 mmol) and 4-benzyloxylphenyl boronic acid (49.11 g, 215.3 mmol) in 1000 ml toluene was added 500 ml dist. water and 250 ml ethanol. Potassium carbonate (64.06 g, 604.4 mmol) is added. The resulted suspension is degassed carefully with argon. Tetrakis(triphenylphosphine)palladium(0) (9.11 g, 7.89 mmol) is then added. The reaction mixture is heated to reflux and stirred overnight. After cooling to room temperature, the reaction mixture is neutralized carefully with 6 M HCl acid under cooling to pH~7. The aqueous phase is extracted with ethylacetate. The organic phase is combined and washed with sat. aq. NaCl solution, dried over sodium sulfate. After removing solvent in vacuo, the solid residue is purified by column chromatography with THF/toluene 9:1 as eluent. The crude product is further recrystallized from toluene to provide 3b as grayish solid (76.3 g).

3c: To a solution of 3b (45.00 g, 99.0 mmol) and 4-benzyloxylphenyl boronic acid (15.81 g, 108.9 mmol) in 340 ml 1,4-dioxane was added 80 ml dist. water. Potassium carbonate (21.00 g, 198.0 mmol) is added. The resulted suspension is degassed carefully with argon. Bis(triphenylphosphine) palladium(II) dichloride (2.18 g, 2.97 mmol) is then added. The reaction mixture is heated to reflux and stirred overnight. After cooling to room temperature, the reaction mixture is neutralized carefully with 2 M HCl acid under cooling to pH~7. The aqueous phase is extracted with methyl t-butyl ether. The organic phase is combined and washed with sat. aq. NaCl solution, dried over sodium sulfate. After removing solvent in vacuo, the solid residue is recrystallized from isopropanol to provide 3c as white solid (41.3 g).

3d: A suspension of 3c (10.0 g, 21.8 mmol) in tetrahydrofuran (150 ml) is treated with palladium (5%) on activated charcoal (10.0 g) and submitted to hydrogenation for 30 hs. The catalyst is then filtered off. After removing solvent in vacuo, 3d is obtained as solid (6.3 g).

3: Methacrylic acid (9.39 g, 67.0 mmol) and 4-(dimethylamino)pyridine (0.23 g, 1.9 mmol) is added to a suspension of 3d (5.50 g, 19.1 mmol) in dichloromethane (200 ml). The reaction mixture is treated dropwise at 0° C. with a solution of N-(3-dimethylaminopropyl)-N'-ethylcarbodiimide (16.9 g, 109.0 mmol) in dichloromethane (60 ml) and stirred for 20 hs at room temperature. The reaction mixture is concentrated in vacuo, and the oily residue is purified by column chromatography on silica gel with chlorobutane/ethyl acetate 9:1 as eluent. The obtained product is recrystallized from ethanol to afford white crystals of 3 (2.7 g, mp. 105° C.).

Example 4

Polymerisable monomeric compound 4 is prepared as follows.

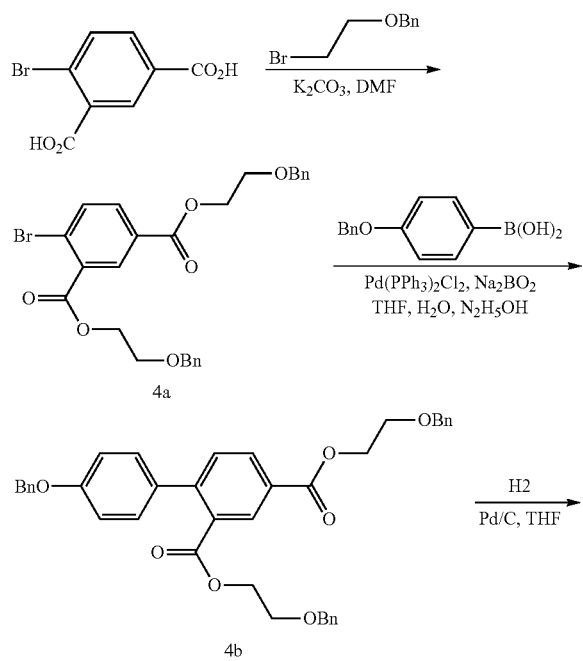

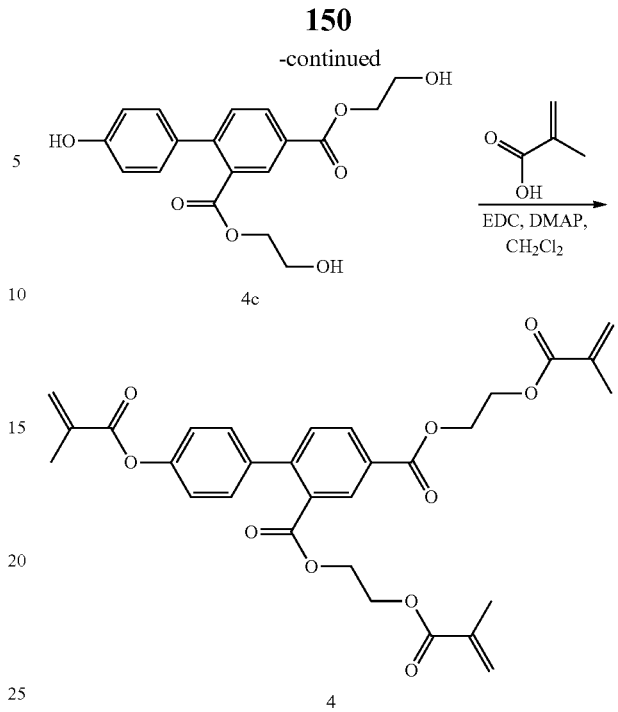

4a: To a solution of 4-bromo-isophthalic acid (21.00 g, 85.7 mmol) in DMF (200 ml) is added potassium carbonate (27.24 g, 197.1 mmol). To the resulted suspension (2-bromo-ethoxymethyl)-benzene (40.00 g, 186.00 mmol) is added. The reaction mixture is stirred at 70° C. for 4 hours. After cooling to room temperature, the reaction mixture is added into 1000 ml water and extracted with 3×300 ml methyl-t-butyl ether (MTBE). The organic phase is washed with sat. aq. NaCl solution, dried over sodium sulfate. After removing solvent in vacuo, the oily residue is purified by column chromatography on silica gel with heptane/ethyl acetate 3:2 as eluent to provide 4a as colorless oil (36.1 g).

4b: To a solution of sodium metaborate tetrahydrate (5.86 g, 42.1 mmol) in dist. water (20 ml) is added the solution of 4a (6.00 g, 26.3 mmol) and 4-(benzyloxy)phenyl boronic acid (12.00 g, 23.4 mmol) in 70 ml THF. After thoroughly degassing with argon, bis(triphenylphosphine)-palladium (II) chloride (1.24 g, 1.7 mmol) is added, followed by the addition of hydrazinium hydroxide (0.05 ml, 1 mmol). The reaction mixture is heated to reflux and stirred for 5 hours. After cooling to room temperature, the reaction mixture is carefully neutralized with 2 M HCl acid. The aqueous phase is separated and extracted with ethyl acetate. The organic phase is combined and dried over anhydrous sodium sulfate. After removing organic solvent, the oily residue is purified by column chromatography on silica gel with toluene/ethyl acetate 9:1 as eluent to afford 4b as brownish oil (13.2 g).

4c: A suspension of 4b (13.0 g, 20.4 mmol) in tetrahydrofuran (130 ml) is treated with palladium (5%) on activated charcoal (10.0 g) and submitted to hydrogenation for 30 hs. The catalyst is then filtered off. After removing solvent in vacuo, the solid residue is purified by column chromatography on silica gel with toluene/ethyl acetate 5:1 as elute to provide 4c as white solid (5.6 g).

4: Methacrylic acid (6.96 g, 80.8 mmol) and 4-(dimethylamino)pyridine (0.20 g, 1.6 mmol) is added to a suspension of 4c (5.60 g, 16.2 mmol) in dichloromethane (60 ml). The reaction mixture is treated dropwise at 0° C. with a solution of N-(3-dimethylaminopropyl)-N'-ethylcarbodiimide (12.9 g, 83.2 mmol) in dichloromethane (20 ml) and stirred for 20 hs at room temperature. The reaction mixture is concentrated in vacuo, and the oily residue is purified by column chromatography on silica gel with dichloromethane as eluent. The obtained product is recrystallized from ethanol to afford white crystals of 4 (3.0 g, mp. 54° C.).

Example 5

Polymerisable monomeric compound 5 is prepared from the commercially available 4-bromo-3-hydroxyl benzoic acid in analogy to Example 4 as follows.

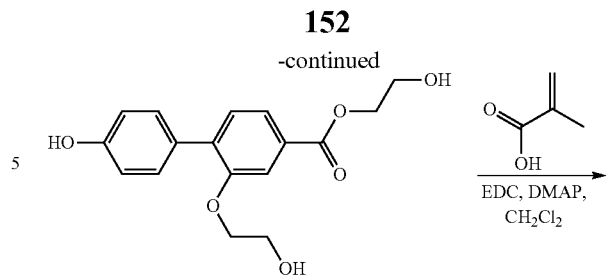

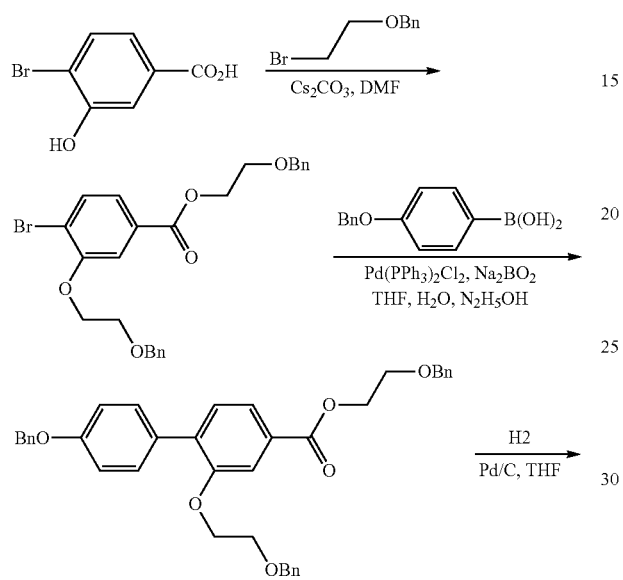

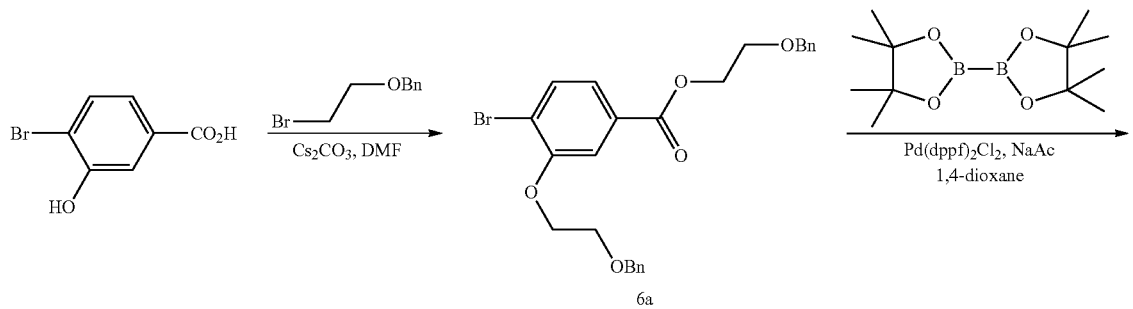

5
mp. 63° C.

Example 6

Polymerisable monomeric compound 6 is prepared as follows.

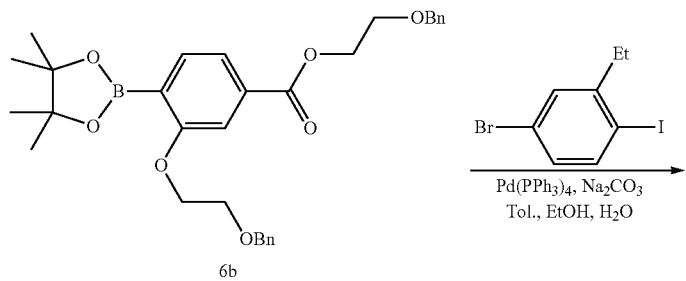

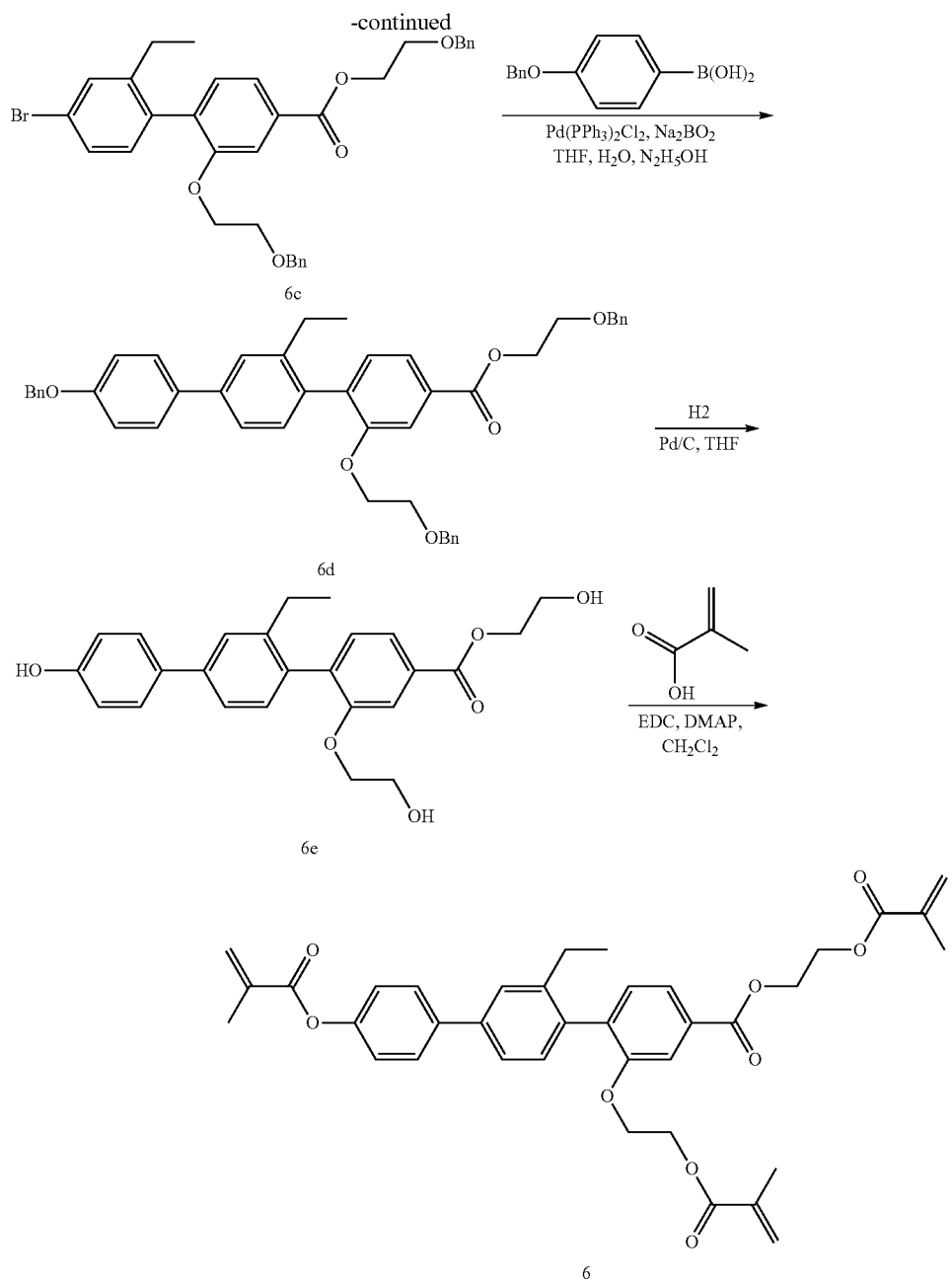

6a: To a solution of 4-bromo-3-hydroxy benzoic acid (9.8 g, 45.2 mmol) in DMF (140 ml) is added cesium carbonate (33.84 g, 103.9 mmol). To the resulted suspension (2-bromo-ethoxymethyl)-benzene (21.37 g, 99.3 mmol) is added. The reaction mixture is stirred at 110° C. for 3 hours. After cooling to room temperature, the reaction mixture is added into 800 ml water and extracted with 3×250 ml ethyl acetate. The organic phase is washed with sat. aq. NaCl solution, dried over sodium sulfate. After removing solvent in vacuo, the oily residue is purified by column chromatography on silica gel with heptane/ethyl acetate 7:3 as eluent to provide 6a as colorless oil (22.1 g).

6b: To a solution of 6a (8.00 g, 15.5 mmol) and bis(pinacolato)diboron (4.08 g, 16.1 mmol) in 70 ml 1,4-dioxane was added sodium acetate (4.56 g, 46.6 mmol). After thoroughly degassing with argon, bis(triphenylphosphine)-palladium(II) chloride (0.45 g, 0.62 mmol) is added. The reaction mixture is heated to reflux and stirred for 4 hours. After cooling to room temperature, 200 ml dist. water is added. The aqueous phase is separated and extracted with methyl t-butyl ether. The organic phase is combined and dried over anhydrous sodium sulfate, and filtrated through silica gel. After removing solvent in vacuo, the product 6b is obtained as brownish oil (9.0 g).

6c: To a solution of 6b (9.00 g, 15.0 mmol) and 4-bromo-2-ethyl iodobenzene (4.98 g, 16.0 mmol) in 100 ml toluene was added 50 ml dist. water and 25 ml ethanol. Potassium carbonate (4.24 g, 40.0 mmol) is added. The resulted suspension is degassed carefully with argon. Tetrakis(triphenylphosphine)palladium(0) (0.66 g, 0.57 mmol) is then added. The reaction mixture is heated to reflux and stirred overnight. After cooling to room temperature, the reaction mixture is neutralized carefully with 6 M HCl acid under cooling to pH~7. The aqueous phase is extracted with ethylacetate. The organic phase is combined and washed with sat. aq. NaCl solution, dried over sodium sulfate. After removing solvent in vacuo, the solid residue is purified by column chromatography with heptane/ethyl acetate 6:1 as eluent to provide 6c as yellowish oil (6.0 g).

6d: To a solution of sodium metaborate tetrahydrate (2.30 g, 16.5 mmol) in dist. water (20 ml) is added the solution of 6c (5.90 g, 9.19 mmol) and 4-(benzyloxy)phenyl boronic acid (2.51 g, 11.0 mmol) in 70 ml THF. After thoroughly degassing with argon, bis(triphenylphosphine)-palladium (II) chloride (0.37 g, 0.51 mmol) is added, followed by the addition of hydrazinium hydroxide (0.05 ml, 1 mmol). The reaction mixture is heated to reflux and stirred for 12 hours. After cooling to room temperature, the reaction mixture is carefully neutralized with 2 M HCl acid. The aqueous phase is separated and extracted with ethyl acetate. The organic phase is combined and dried over anhydrous sodium sulfate. After removing organic solvent, the oily residue is purified by column chromatography on silica gel with toluene/ethyl acetate 9:1 as eluent to afford 6d as colorless oil (4.4 g).

6e: A suspension of 6d (4.30 g, 6.0 mmol) in tetrahydrofuran (40 ml) is treated with palladium (5%) on activated charcoal (1.0 g) and submitted to hydrogenation for 18 hs. The catalyst is then filtered off. After removing solvent in vacuo, the oily residue is purified by column chromatography on silica gel with heptane/ethyl acetate solvent mixture as elute to provide 6e as colorless oil (2.3 g).

6: Methacrylic acid (2.11 g, 24.5 mmol) and 4-(dimethylamino)pyridine (0.10 g, 0.82 mmol) is added to a suspension of 6e (2.30 g, 5.44 mmol) in dichloromethane (30 ml). The reaction mixture is treated dropwise at 0° C. with a solution of N-(3-dimethylaminopropyl)-N'-ethylcarbodiimide (3.89 g, 25.0 mmol) in dichloromethane (10 ml) and stirred for 20 hs at room temperature. The reaction mixture is concentrated in vacuo, and the oily residue is purified by column chromatography on silica gel with heptanes/ethyl acetate solvent mixture as eluent. The obtained product is recrystallized from heptane/ethanol 1:2 to afford white crystals of 6 (2.1 g, mp. 67° C.).

Mixture Example 1

The nematic LC host mixture 1 is formulated as follows.

| CCH-501 | 9.00% | cl.p. | 70.0° C. |
|---|---|---|---|
| CCH-35 | 14.00% | Δn | 0.0825 |
| PCH-53 | 8.00% | Δε | −3.5 |
| PCH-304FF | 14.00% | $\epsilon_{\parallel}$ | 3.5 |
| PCH-504FF | 13.00% | $K_3/K_1$ | 1.00 |
| CCP-302FF | 8.00% | $\gamma_1$ | 141 mPa s |
| CCP-502FF | 8.00% | $V_0$ | 2.10 V |
| CCP-21FF | 9.00% | | |
| CCP-31FF | 9.00% | | |
| CPY-2-O2 | 8.00% | | |

Six polymerisable mixtures are prepared by adding each one of RM1 to RM6, respectively, to nematic LC host mixture 1 at a concentration of 0.3% by weight.

Mixture Example 2

The nematic LC host mixture 2 is formulated as follows.

| CY-3-O2 | 18.00% | cl.p. | +74.5° C. |
|---|---|---|---|
| CPY-2-O2 | 10.00% | Δn | 0.1021 |
| CPY-3-O2 | 10.00% | Δε | −3.1 |
| CCY-3-O2 | 9.00% | $\epsilon_{\parallel}$ | 3.5 |
| CCY-4-O2 | 4.00% | $K_3/K_1$ | 1.16 |
| CC-3-V | 40.00% | $\gamma_1$ | 86 mPa s |
| PYP-2-3 | 9.00% | $V_0$ | 2.29 V |

Six polymerisable mixtures are prepared by adding each one of RM1 to RM6, respectively, to nematic LC host mixture 2 at a concentration of 0.3% by weight.

Mixture Example 3

The nematic LC host mixture 3 is formulated as follows.

| CC-3-V | 20.00% | cl.p. | 74.5° C. |
|---|---|---|---|
| CC-3-V1 | 10.00% | Δn | 0.1084 |
| CCH-34 | 8.00% | Δε | −3.2 |
| CCH-35 | 4.00% | $V_0$ | 2.33 V |
| CCY-3-O1 | 5.50% | $K_3/K_1$ | 1.04 |
| CCY-3-O2 | 12.00% | $\gamma_1$ | 94 mPa s |
| CPY-2-O2 | 2.00% | | |
| CPY-3-O2 | 12.00% | | |
| PY-3-O2 | 15.00% | | |
| PY-4-O2 | 8.50% | | |
| PYP-2-3 | 3.00% | | |

Six polymerisable mixtures are prepared by adding each one of RM1 to RM6, respectively, to nematic LC host mixture 3 at a concentration of 0.3% by weight.

Mixture Example 4

The nematic LC host mixture 4 is formulated as follows.

| CC-3-V | 20.00% | cl.p. | 74.6° C. |
|---|---|---|---|
| CC-3-V1 | 10.00% | Δn | 0.1042 |
| CCH-35 | 9.00% | Δε | −3.1 |
| CCP-3-1 | 7.00% | $V_0$ | 2.48 V |
| CCY-3-O2 | 13.00% | $K_3/K_1$ | 1.13 |
| CPY-3-O2 | 13.00% | $\gamma_1$ | 94 mPa s |
| CY-3-O2 | 8.00% | | |
| PY-3-O2 | 15.00% | | |
| PY-4-O2 | 5.00% | | |

Six polymerisable mixtures are prepared by adding each one of RM1 to RM6, respectively, to nematic LC host mixture 4 at a concentration of 0.3% by weight.

Mixture Example 5

The nematic LC host mixture 5 is formulated as follows.

| CC-3-V | 27.50% | cl.p. | 74.8° C. |
|---|---|---|---|
| CC-3-V1 | 7.50% | Δn | 0.0986 |
| CCH-23 | 3.00% | Δε | −3.4 |
| CCP-3-1 | 3.75% | $V_0$ | 2.26 V |
| CCY-3-O2 | 12.50% | $K_3/K_1$ | 1.16 |
| CPY-2-O2 | 11.50% | $\gamma_1$ | 95 mPa s |
| CPY-3-O2 | 10.50% | | |
| CY-3-O2 | 15.50% | | |
| PY-3-O2 | 3.00% | | |
| PY-4-O2 | 5.25% | | |

Six polymerisable mixtures are prepared by adding each one of RM1 to RM6, respectively, to nematic LC host mixture 5 at a concentration of 0.3% by weight.

Mixture Example 6

The nematic LC host mixture 6 is formulated as follows.

| | | | |
|---|---|---|---|
| CC-3-V | 41.50% | cl.p. | 74.6° C. |
| CCP-3-1 | 2.00% | Δn | 0.0983 |
| CCY-3-O1 | 5.25% | Δε | −3.1 |
| CCY-3-O2 | 12.50% | $V_0$ | 2.28 V |
| CPY-2-O2 | 12.25% | $K_3/K_1$ | 1.11 |
| CPY-3-O2 | 7.50% | $\gamma_1$ | 85 mPa s |
| CY-3-O2 | 5.50% | | |
| PY-3-O2 | 3.50% | | |
| PY-4-O2 | 10.00% | | |

Six polymerisable mixtures are prepared by adding each one of RM1 to RM6, respectively, to nematic LC host mixture 6 at a concentration of 0.3% by weight.

Mixture Example 7

The nematic LC host mixture 7 is formulated as follows.

| | | | |
|---|---|---|---|
| CC-3-V | 27.50% | cl.p. | 75.6° C. |
| CC-3-V1 | 8.00% | Δn | 0.0989 |
| CCH-23 | 2.50% | Δε | −3.4 |
| CCP-3-1 | 3.00% | $V_0$ | 2.28 V |
| CCY-3-O2 | 12.00% | $K_3/K_1$ | 1.16 |
| CCY-4-O2 | 2.00% | $\gamma_1$ | 94 mPa s |
| CPY-2-O2 | 10.00% | | |
| CPY-3-O2 | 10.50% | | |
| CY-3-O2 | 15.50% | | |
| CY-3-O4 | 1.00% | | |
| PY-3-O2 | 15.00% | | |
| PY-4-O2 | 7.00% | | |
| PYP-2-3 | 1.00% | | |

Six polymerisable mixtures are prepared by adding each one of RM1 to RM6, respectively, to nematic LC host mixture 7 at a concentration of 0.3% by weight.

Mixture Example 8

The nematic LC host mixture 8 is formulated as follows.

| | | | |
|---|---|---|---|
| CC-3-V | 41.50% | cl.p. | 74.5° C. |
| CCY-3-O1 | 2.50% | Δn | 0.0984 |
| CCY-3-O2 | 11.50% | Δε | −3.3 |
| CCY-3-O3 | 5.00% | $V_0$ | 2.29 V |
| CPY-2-O2 | 5.00% | $K_3/K_1$ | 1.15 |
| CPY-3-O2 | 12.00% | $\gamma_1$ | 89 mPa s |
| CY-3-O2 | 9.50% | | |
| PY-3-O2 | 7.00% | | |
| PY-4-O2 | 3.00% | | |
| PYP-2-3 | 3.00% | | |

Six polymerisable mixtures are prepared by adding each one of RM1 to RM6, respectively, to nematic LC host mixture 8 at a concentration of 0.3% by weight.

Mixture Example 9

The nematic LC host mixture 9 is formulated as follows.

| | | | |
|---|---|---|---|
| CC-3-V | 28.00% | cl.p. | 74.9° C. |
| CCY-3-O1 | 10.00% | Δn | 0.1026 |
| CCY-3-O2 | 1.00% | Δε | −3.0 |
| CCY-3-O3 | 6.00% | $V_0$ | 2.47 V |
| CPY-2-O2 | 12.00% | $K_3/K_1$ | 1.19 |
| CPY-3-O2 | 3.00% | $\gamma_1$ | 90 mPa s |
| CY-3-O2 | 12.00% | | |
| PY-3-O2 | 10.00% | | |
| PY-4-O2 | 15.00% | | |
| PYP-2-3 | 3.00% | | |

Six polymerisable mixtures are prepared by adding each one of RM1 to RM6, respectively, to nematic LC host mixture 9 at a concentration of 0.3% by weight.

Mixture Example 10

The nematic LC host mixture 10 is formulated as follows.

| | | | |
|---|---|---|---|
| CC-3-V | 15.00% | cl.p. | 74.4° C. |
| CC-3-V1 | 9.00% | Δn | 0.1086 |
| CCH-23 | 8.00% | Δε | −3.2 |
| CCH-34 | 7.50% | $V_0$ | 2.33 V |
| CCY-3-O2 | 10.00% | $K_3/K_1$ | 1.10 |
| CCY-5-O2 | 8.00% | $\gamma_1$ | 102 mPa s |
| CPY-2-O2 | 3.00% | | |
| CPY-3-O2 | 8.50% | | |
| CY-3-O2 | 7.00% | | |
| PY-3-O2 | 16.00% | | |
| PYP-2-3 | 8.00% | | |

Six polymerisable mixtures are prepared by adding each one of RM1 to RM6, respectively, to nematic LC host mixture 10 at a concentration of 0.3% by weight.

Mixture Example 11

The nematic LC host mixture 11 is formulated as follows.

| | | | |
|---|---|---|---|
| CC-3-V | 42.00% | cl.p. | 73.5° C. |
| CCY-3-O1 | 5.00% | Δn | 0.1007 |
| CCY-3-O2 | 10.00% | Δε | −3.5 |
| CCY-4-O2 | 2.50% | $V_0$ | 2.15 V |
| CPY-2-O2 | 10.00% | $K_3/K_1$ | 1.13 |
| CPY-3-O2 | 10.00% | $\gamma_1$ | 85 mPa s |
| CY-3-O2 | 6.50% | | |
| PY-3-O2 | 11.00% | | |
| IS-18566 | 3.00% | | |

Six polymerisable mixtures are prepared by adding each one of RM1 to RM6, respectively, to nematic LC host mixture 11 at a concentration of 0.3% by weight.

Mixture Example 12

The nematic LC host mixture 12 is formulated as follows.

| | | | |
|---|---|---|---|
| CC-3-V | 45.50% | cl.p. | 73.0° C. |
| CCY-3-O1 | 3.00% | Δn | 0.1011 |
| CCY-3-O2 | 11.00% | Δε | −3.5 |
| CCY-4-O2 | 3.50% | $V_0$ | 2.15 V |
| CPY-2-O2 | 7.50% | $K_3/K_1$ | 1.09 |
| CPY-3-O2 | 10.00% | $\gamma_1$ | 79 mPa s |
| CY-3-O2 | 2.00% | | |
| PY-3-O2 | 11.50% | | |
| IS-18566 | 6.00% | | |

Six polymerisable mixtures are prepared by adding each one of RM1 to RM6, respectively, to nematic LC host mixture 12 at a concentration of 0.3% by weight.

Mixture Example 13

The nematic LC host mixture 13 is formulated as follows.

| | | | |
|---|---|---|---|
| CC-3-V | 34.50% | cl.p. | 75.0° C. |
| CC-3-V1 | 8.00% | $\Delta n$ | 0.1075 |
| CCY-3-O1 | 7.00% | $\Delta \epsilon$ | -3.1 |
| CCY-3-O2 | 11.50% | $V_0$ | 2.41 V |
| CCY-4-O2 | 3.50% | $K_3/K_1$ | 1.12 |
| CPY-3-O2 | 11.50% | $\gamma_1$ | 84 mPa s |
| PY-3-O2 | 13.00% | | |
| PP-1-2V1 | 6.00% | | |
| IS-18566 | 5.00% | | |

Six polymerisable mixtures are prepared by adding each one of RM1 to RM6, respectively, to nematic LC host mixture 13 at a concentration of 0.3% by weight.

Mixture Example 14

The nematic LC host mixture 14 is formulated as follows.

| | | | |
|---|---|---|---|
| CC-3-V | 37.50% | cl.p. | 75.5° C. |
| CC-3-V1 | 7.00% | $\Delta n$ | 0.1080 |
| CCY-3-O1 | 6.00% | $\Delta \epsilon$ | -3.0 |
| CCY-3-O2 | 11.00% | $V_0$ | 2.41 V |
| CPY-2-O2 | 4.50% | $K_3/K_1$ | 1.12 |
| CPY-3-O2 | 11.00% | $\gamma_1$ | 84 mPa s |
| PY-3-O2 | 17.00% | | |
| PGIY-2-O4 | 5.00% | | |
| PP-1-2V1 | 1.00% | | |

Six polymerisable mixtures are prepared by adding each one of RM1 to RM6, respectively, to nematic LC host mixture 14 at a concentration of 0.3% by weight.

Mixture Example 15

The nematic LC host mixture 15 is formulated as follows.

| | | | |
|---|---|---|---|
| CC-3-V | 39.00% | cl.p. | 75.0° C. |
| CC-3-V1 | 7.00% | $\Delta n$ | 0.1098 |
| CCY-3-O1 | 1.50% | $\Delta \epsilon$ | -3.0 |
| CCY-3-O2 | 5.00% | $V_0$ | 2.41 V |
| CPY-2-O2 | 9.00% | $K_3/K_1$ | 1.11 |
| CPY-3-O2 | 6.00% | $\gamma_1$ | 82 mPa s |
| PY-3-O2 | 11.50% | | |
| PGIY-2-O4 | 16.00% | | |
| PP-1-2V1 | 5.00% | | |

Six polymerisable mixtures are prepared by adding each one of RM1 to RM6, respectively, to nematic LC host mixture 15 at a concentration of 0.3% by weight.

Mixture Example 16

The nematic LC host mixture 16 is formulated as follows.

| | | | |
|---|---|---|---|
| CY-3-O2 | 16.50% | cl.p. | 74.0° C. |
| CCY-4-O2 | 10.50% | $\Delta n$ | 0.1069 |
| CCY-5-O2 | 6.00% | $\Delta \epsilon$ | -3.2 |
| CPY-2-O2 | 9.00% | $V_0$ | 2.18 |
| CPY-3-O2 | 9.00% | $K_3/K_1$ | 1.06 |
| CCH-34 | 9.00% | $\gamma_1$ | 117 mPa s |
| CCH-31 | 20.00% | | |
| CCP-3-1 | 2.00% | | |
| PYP-2-3 | 6.50% | | |
| PYP-2-4 | 6.50% | | |
| PCH-301 | 5.00% | | |

Six polymerisable mixtures are prepared by adding each one of RM1 to RM6, respectively, to nematic LC host mixture 16 at a concentration of 0.3% by weight.

Mixture Example 17

The nematic LC host mixture 17 is formulated as follows.

| | | | |
|---|---|---|---|
| CY-3-O2 | 16.50% | cl.p. | 74.5° C. |
| CCY-4-O2 | 9.50% | $\Delta n$ | 0.1070 |
| CCY-5-O2 | 4.00% | $\Delta \epsilon$ | -3.2 |
| CPY-2-O2 | 9.00% | $V_0$ | 2.19 |
| CPY-3-O2 | 9.00% | $K_3/K_1$ | 1.06 |
| CCH-34 | 9.00% | $\gamma_1$ | 117 mPa s |
| CCH-31 | 20.00% | | |
| CCP-3-1 | 5.00% | | |
| PYP-2-3 | 4.00% | | |
| PYP-2-4 | 4.00% | | |
| PCH-301 | 5.00% | | |
| PGIY-2-O4 | 5.00% | | |

Six polymerisable mixtures are prepared by adding each one of RM1 to RM6, respectively, to nematic LC host mixture 17 at a concentration of 0.3% by weight.

Mixture Example 18

The nematic LC host mixture 18 is formulated as follows.

| | | | |
|---|---|---|---|
| CY-3-O2 | 12.00% | cl.p. | 74.0° C. |
| CY-3-O4 | 10.00% | $\Delta n$ | 0.1064 |
| CCY-3-O2 | 6.00% | $\Delta \epsilon$ | -3.2 |
| CCY-4-O2 | 6.50% | $V_0$ | 2.19 |
| CCH-34 | 9.00% | $K_3/K_1$ | 0.99 |
| CCH-35 | 5.00% | $\gamma_1$ | 119 mPa s |
| CCP-3-1 | 14.50% | | |
| CCP-3-3 | 11.00% | | |
| PYP-2-3 | 9.00% | | |
| PYP-2-4 | 8.00% | | |
| Y-4O-O4 | 9.00% | | |

Six polymerisable mixtures are prepared by adding each one of RM1 to RM6, respectively, to nematic LC host mixture 18 at a concentration of 0.3% by weight.

Mixture Example 19

The nematic LC host mixture 19 is formulated as follows.

| | | | |
|---|---|---|---|
| CY-3-O2 | 12.00% | cl.p. | 73.5° C. |
| CY-3-O4 | 10.00% | $\Delta n$ | 0.1065 |
| CCY-3-O2 | 6.00% | $\Delta \epsilon$ | -3.3 |
| CCY-4-O2 | 5.50% | $V_0$ | 2.18 |
| CCH-34 | 8.50% | $K_3/K_1$ | 1.00 |
| CCH-35 | 5.00% | $\gamma_1$ | 119 mPa s |
| CCP-3-1 | 15.00% | | |
| CCP-3-3 | 11.50% | | |
| PYP-2-3 | 5.50% | | |
| PYP-2-4 | 5.00% | | |
| PP-1-2V1 | 2.00% | | |
| PGIY-2-O4 | 5.00% | | |
| Y-4O-O4 | 9.00% | | |

Six polymerisable mixtures are prepared by adding each one of RM1 to RM6, respectively, to nematic LC host mixture 19 at a concentration of 0.3% by weight.

Mixture Example 20

The nematic LC host mixture 20 is formulated as follows.

| | | | |
|---|---|---|---|
| CC-3-V | 28.50% | cl.p. | 74.5° C. |
| CCP-31 | 12.50% | Δn | 0.1077 |
| CCOY-2-O2 | 19.00% | Δε | −3.2 |
| CCOY-3-O2 | 11.50% | $V_0$ | 2.34 V |
| PY-3-O2 | 13.50% | $K_3/K_1$ | 0.91 |
| PP-1-3 | 10.00% | $\gamma_1$ | 99 mPa s |
| PYP-2-3 | 5.00% | | |

Six polymerisable mixtures are prepared by adding each one of RM1 to RM6, respectively, to nematic LC host mixture 20 at a concentration of 0.3% by weight.

Mixture Example 21

The nematic LC host mixture 21 is formulated as follows.

| | | | |
|---|---|---|---|
| CC-3-V1 | 9.00% | cl.p. | 75.4° C. |
| CCH-23 | 14.00% | Δn | 0.1056 |
| CCH-34 | 6.00% | Δε | −2.8 |
| CCH-35 | 6.00% | $V_0$ | 2.67 V |
| CCP-3-1 | 7.00% | $K_3/K_1$ | 1.07 |
| CCY-3-O1 | 5.00% | $\gamma_1$ | 102 mPa s |
| CCY-3-O2 | 10.00% | | |
| CPY-3-O2 | 12.00% | | |
| CY-3-O2 | 9.50% | | |
| PP-1-2V1 | 8.50% | | |
| PY-3-O2 | 12.00% | | |
| PY-4-O2 | 1.00% | | |

Six polymerisable mixtures are prepared by adding each one of RM1 to RM6, respectively, to nematic LC host mixture 21 at a concentration of 0.3% by weight.

Mixture Example 22

The nematic LC host mixture 22 is formulated as follows.

| | | | |
|---|---|---|---|
| CC-3-V | 37.00% | cl.p. | 75.0° C. |
| CC-3-V1 | 7.00% | Δn | 0.1090 |
| CCY-3-O2 | 5.00% | Δε | −3.2 |
| CLY-3-O2 | 10.00% | $V_0$ | 2.34 V |
| CPY-2-O2 | 10.50% | $K_3/K_1$ | 1.14 |
| CPY-3-O2 | 10.50% | $\gamma_1$ | 87 mPa s |
| PY-1-O4 | 10.00% | | |
| PY-3-O2 | 9.00% | | |
| PGIY-2-O4 | 1.00% | | |

Six polymerisable mixtures are prepared by adding each one of RM1 to RM6, respectively, to nematic LC host mixture 22 at a concentration of 0.3% by weight.

Mixture Example 23

The nematic LC host mixture 23 is formulated as follows.

| | | | |
|---|---|---|---|
| CC-3-V | 34.50% | cl.p. | 74.5° C. |
| CC-3-V1 | 8.00% | Δn | 0.1088 |
| CCY-3-O1 | 9.00% | Δε | −3.2 |
| CCY-3-O2 | 5.50% | $V_0$ | 2.33 V |
| CLY-3-O2 | 10.00% | $K_3/K_1$ | 1.12 |
| CPY-3-O2 | 5.00% | $\gamma_1$ | 90 mPa s |
| PY-1-O4 | 10.00% | | |
| PY-3-O2 | 10.00% | | |
| PYP-2-3 | 3.00% | | |
| PGIY-2-O4 | 5.00% | | |

Six polymerisable mixtures are prepared by adding each one of RM1 to RM6, respectively, to nematic LC host mixture 23 at a concentration of 0.3% by weight.

Mixture Example 24

The nematic LC host mixture 24 is formulated as follows.

| | | | |
|---|---|---|---|
| B-2O-O5 | 5.00% | cl.p. | 74.6° C. |
| CC-3-V1 | 38.00% | Δn | 0.1086 |
| CCY-3-O1 | 10.00% | Δε | −3.2 |
| CCY-3-O2 | 7.50% | $V_0$ | 2.34 V |
| CLY-3-O2 | 10.00% | $K_3/K_1$ | 1.11 |
| CPY-3-O2 | 9.50% | $\gamma_1$ | 82 mPa s |
| PY-3-O2 | 13.00% | | |
| PYP-2-3 | 2.00% | | |
| PGIY-2-O4 | 5.00% | | |

Six polymerisable mixtures are prepared by adding each one of RM1 to RM6, respectively, to nematic LC host mixture 24 at a concentration of 0.3% by weight.

Mixture Example 25

The nematic LC host mixture 25 is formulated as follows.

| | | | |
|---|---|---|---|
| CC-3-V | 34.00% | cl.p. | 74.3° C. |
| CC-3-V1 | 10.00% | Δn | 0.1091 |
| CCY-3-O1 | 4.50% | Δε | −3.2 |
| CLY-3-O2 | 10.00% | $V_0$ | 2.34 V |
| CPY-2-O2 | 10.50% | $K_3/K_1$ | 1.12 |
| CPY-3-O2 | 11.00% | $\gamma_1$ | 88 mPa s |
| PY-1-O4 | 9.00% | | |
| PY-3-O2 | 11.00% | | |

Six polymerisable mixtures are prepared by adding each one of RM1 to RM6, respectively, to nematic LC host mixture 25 at a concentration of 0.3% by weight.

For comparison purposes further individual polymerisable mixtures are prepared by adding direactive monomer C1 of prior art to each of nematic LC host mixtures 1-25 at a concentration of 0.3% by weight, respectively, and by adding direactive monomer C2 of prior art to each of nematic LC host mixtures 1-25 at a concentration of 0.3% by weight, respectively,

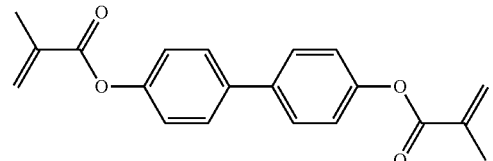

C1

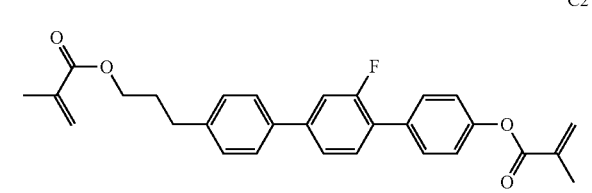

C2

-continued

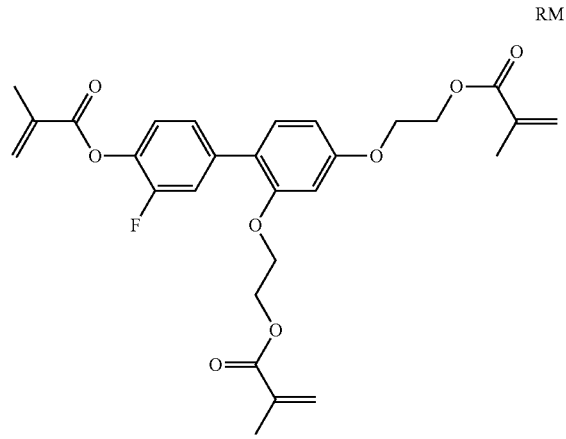
RM1

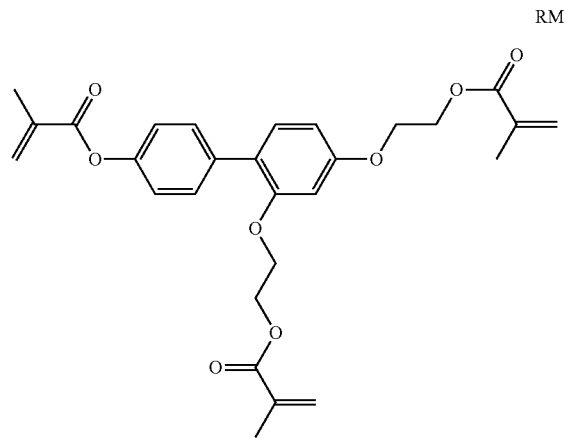
RM2

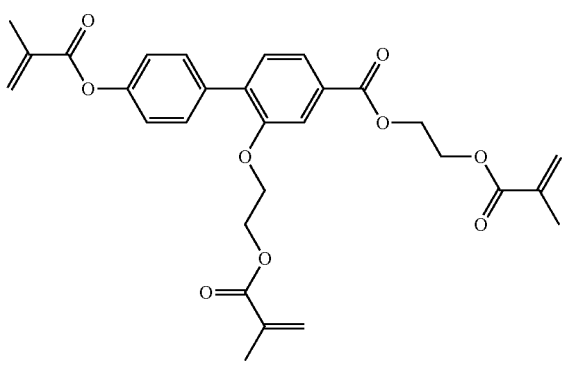
RM3

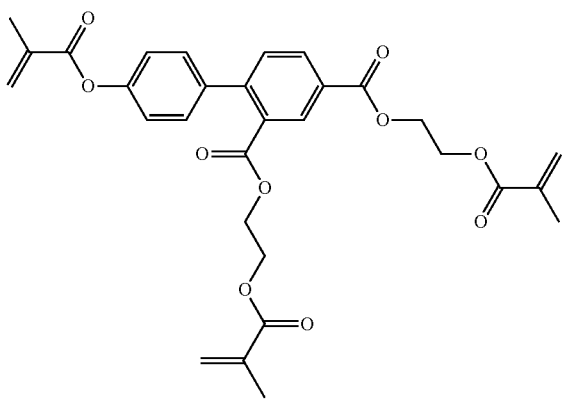
RM4

-continued

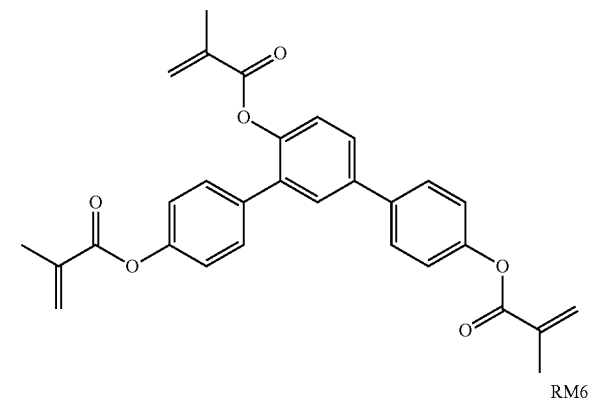
RM5

RM6

Use Examples

The polymerisable mixtures according to the invention and the polymerisable comparison mixtures are each inserted into a VA e/o test cell. The test cells comprise a VA-polyimide alignment layer (JALS-2096-R1) which is rubbed antiparallel (for the test cells with host mixture C the polyimide AL64101 was used). The LC-layer thickness d is approx. 4 µm.

Each test cell is irradiated with UV light having an intensity of 100 mW/cm$^2$ for the time indicated with application of a voltage of 24 V$_{rms}$ (alternating current), causing polymerisation of the polymerisable monomeric compound.

The VHR values of the polymerisable mixtures before and after UV exposure are measured as described above. The VHR values of the mixtures are shown in Table 1.

TABLE 1

| | VHR values | | | | | | |
|---|---|---|---|---|---|---|---|
| | Host 1 + C1 | Host 1 + RM1 | Host 1 + RM2 | Host 1 + RM3 | Host 1 + RM4 | Host 1 + RM5 | Host 1 + RM6 |
| | | | | VHR/% | | | |
| 0 min UV | 98.2 | 98.6 | 98.8 | 98.7 | 98.1 | 98.8 | 98.9 |
| 2 h Suntest[1] | 97.6 | 98.2 | 98.7 | 98.6 | 98.9 | 98.5 | 98.9 |
| | Host 2 + C1 | Host 2 + RM1 | Host 2 + RM2 | Host 2 + RM3 | Host 2 + RM4 | Host 2 + RM5 | Host 2 + RM6 |
| | | | | VHR/% | | | |
| 0 min UV | 98.3 | 97.5 | 98.3 | 89.0 | 95.8 | 97.6 | 98.5 |
| 2 h Suntest[1] | 85.6 | 89.2 | 93.0 | 93.4 | 94.7 | 90.1 | 92.5 |
| 10 min UV | 74.8 | 88.4 | 92.0 | 89.4 | 95.1 | 91.5 | 85.8 |

TABLE 1-continued

VHR values

|  | Host 3 + C1 | Host 3 + RM1 | Host 3 + RM2 | Host 3 + RM4 |
|---|---|---|---|---|
|  | VHR/% | | | |
| 0 min UV | 98.3 | 98.4 | 98.0 | 98.0 |
| 2 min UV | 94.8 | 97.5 | 96.7 | 96.8 |
| 15 min UV | 93.6 | 96.7 | 95.3 | 96.9 |
| 2 min UV + 2 h suntest[1),2)] | 95.5 | 96.4 | 96.1 | 97.2 |

|  | Host 4 + C1 | Host 4 + RM1 |
|---|---|---|
|  | VHR/% | |
| 0 min UV | 98.6 | 98.4 |
| 5 min UV | 96.3 | 97.6 |
| 15 min UV | 94.0 | 96.4 |
| 5 min UV + 2 h suntest[1),2)] | 96.0 | 97.2 |

[1)]"Suntest" means a second irradiation step with lower UV intensity but longer exposure time than the first step.
[2)]In the test cells for these mixtures the polyimide AL64101 was used.

As can be seen from Table 1, the VHR values of polymerisable mixtures comprising RM1 to RM6 according to the present invention after UV exposure are higher than the VHR values of polymerisable mixture comprising monomer C1, especially in polymerisable mixtures comprising host mixture 2 and 4 with alkenyl compounds.

In addition, RM1 to RM6 according to the present invention do either show only a very small decrease or even an increase of the VHR after 2h suntest compared to the initial VHR value.

In order to determine the polymerisation rate, the residual content of unpolymerised RM (in % by weight) in the test cells is measured by HPLC after various exposure times. For this purpose each mixture is polymerised in the test cell under the stated conditions. The mixture is then rinsed out of the test cell using MEK (methyl ethyl ketone) and measured.

The residual concentrations of the respective monomer in the mixture after different exposure times are shown in Table 2.

TABLE 2

Residual monomer content

| Time/min | Host 1 + C1 | Host 1 + RM1 | Host 1 + RM2 | Host 1 + RM3 | Host 1 + RM4 | Host 1 + RM5 | Host 1 + RM6 |
|---|---|---|---|---|---|---|---|
|  | | | Residual RM/% | | | | |
| 0 | 0.3 | 0.3 | 0.3 | 0.3 | 0.3 | 0.3 | 0.3 |
| 2 | 0.264 | 0.221 | 0.217 | 0.077 | 0.273 | 0.266 | 0.146 |
| 4 | 0.203 | 0.141 | 0.132 | 0.013 | 0.154 | 0.243 | 0.06 |
| 6 | 0.173 | 0.089 | 0.079 | 0.003 | 0.091 | 0.192 | 0.032 |

| Time/min | Host 2 + C1 | Host 2 + RM1 | Host 2 + RM2 | Host 2 + RM3 | Host 2 + RM4 | Host 2 + RM5 | Host 2 + RM6 |
|---|---|---|---|---|---|---|---|
|  | | | Residual RM/% | | | | |
| 0 | 0.3 | 0.3 | 0.3 | 0.3 | 0.3 | 0.3 | 0.3 |
| 2 | 0.185 | 0.141 | 0.136 | 0.058 | 0.164 | 0.198 | 0.118 |
| 6 | 0.067 | 0.054 | 0.046 | 0.007 | 0.064 | 0.073 | 0.022 |

TABLE 2-continued

Residual monomer content

| Time/min | Host 3 + C1 | Host 3 + RM1 | Host 3 + RM2 | Host 3 + RM3 | Host 3 + RM4 |
|---|---|---|---|---|---|
|  | | | Residual RM/% | | |
| 0 | 0.3 | 0.3 | 0.3 | 0.3 | 0.3 |
| 0.5 | 0.256 | 0.227 | 0.244 | 0.089 | 0.239 |
| 1 | 0.199 | 0.135 | 0.156 | 0.037 | 0.156 |
| 2 | 0.142 | 0.091 | 0.082 | 0.005 | 0.103 |
| 5 | 0.05 | 0.062 | 0.042 | 0.000 | 0.048 |

| Time/min | Host 4 + C1 | Host 4 + RM1 |
|---|---|---|
|  | Residual RM/% | |
| 0 | 0.3 | 0.3 |
| 1 | 0.278 | 0.232 |
| 2 | 0.249 | 0.162 |
| 3 | 0.209 | 0.101 |
| 5 | 0.146 | 0.043 |

As can be seen from Table 2, significantly more rapid and complete polymerisation is achieved in PSA displays containing a polymerisable mixture with RM1 to RM6 according to the present invention, compared to PSA displays containing a polymerisable mixture with monomer C1.

The tilt angle is determined before and after UV irradiation by a crystal rotation experiment (Autronic-Melchers TBA-105).

The tilt angles are shown in Table 3.

TABLE 3

Tilt angles

| UV-Time/sec | Host 1 + C1 | Host 1 + RM1 | Host 1 + RM2 | Host 1 + RM3 | Host 1 + RM4 | Host 1 + RM5 | Host 1 + RM6 |
|---|---|---|---|---|---|---|---|
|  | | | Pretilt Angle/° | | | | |
| 0 | 89.6 | 88.7 | 88.6 | 88.9 | 89.1 | 88.9 | 89.3 |
| 30 | 89.0 | 87.9 | 85.9 | 82.8 | 88.1 | 88.9 | 87.3 |
| 60 | 88.2 | 85.2 | 83.4 | 71.4 | 86.2 | 88.0 | 79.5 |
| 120 | 84.9 | 81.4 | 78.6 | 66.6 | 81.4 | 86.4 | 73.3 |

| UV-Time/sec | Host 2 + C1 | Host 2 + RM1 | Host 2 + RM2 | Host 2 + RM3 | Host 2 + RM4 | Host 2 + RM5 | Host 1 + RM6 |
|---|---|---|---|---|---|---|---|
|  | | | Pretilt Angle/° | | | | |
| 0 | 88.8 | 88.9 | 88.6 | 88.8 | 88.8 | 88.5 | 89.2 |
| 120 | 77.2 | 77.2 | 76.6 | 71.2 | 78.4 | 77.2 | 74.1 |

| UV-Time/sec | Host 3 + C1 | Host 3 + RM1 | Host 3 + RM2 | Host 3 + RM3 | Host 3 + RM4 |
|---|---|---|---|---|---|
|  | | | Pretilt Angle/° | | |
| 0 | 89.1 | 89.7 | 88.9 | 89.7 | 89.7 |
| 60 | 86.4 | 84.7 | 74.3 | 78.3 | 80.5 |
| 120 | 78.0 | 76.7 | 68.2 | 69.8 | 75.1 |
| 180 | 76.1 | 73.8 | 64.8 | 68.4 | 71.8 |
| 300 | 73.5 | 71.1 | 62.0 | 66.8 | 70.6 |

| UV-Time/sec | Host 4 + C1 | Host 4 + RM1 |
|---|---|---|
|  | Pretilt Angle/° | |
| 0 | 89.1 | 89.4 |
| 60 | 89.2 | 89.3 |
| 120 | 89.4 | 88.4 |

TABLE 3-continued

Tilt angles

| | | |
|---|---|---|
| 180 | 86.9 | 83.2 |
| 300 | 80.0 | 74.8 |

As can be seen from Table 3, a small tilt angle after polymerisation is achieved quickly in PSA displays containing a polymerisable mixture with RM1 to RM6 according to the present invention, which is smaller than in a PSA display containing a polymerisable mixture with monomer C1.

While the aforementioned values have been obtained after polymerisation of the polymerisable LC medium with a metal-halide UV lamp and a 320 nm UV filter, the following tables show values obtained after irradiation with the same UV lamp, but with a 340 nm UV filter.

This demonstrates the improved performance of the RMs according to the present invention when using UV lamps with emission spectra shifted to longer wavelengths and/or by using UV lamps with lower intensity.

Test cells and PI are similar to the example above, e.g. for the test cells with host mixture 3 the polyimide AL64101 was used etc.

TABLE 4

VHR values

| | Host 3 + C2 | Host 3 + RM3 |
|---|---|---|
| | VHR/% | |
| 0 min UV | 98.7 | 98.6 |
| 10 min UV | 93.9 | 97.7 |
| 20 min UV | 94.7 | 97.7 |

The VHR values of polymerisable mixtures comprising RM3 are compared with a polymerisable mixture comprising RM C2 instead of RM C1, because C2 has a polymerization speed that is better comparable to RM3. As shown in Table 5 below, C1 shows slower polymerization with the 340 nm filter and is therefore disadvantageous.

As shown in Table 4, after UV exposure the VHR values with RM3 are higher than the VHR values with monomer C2 of prior art.

TABLE 5

Residual monomer content

| Time/min | Host 3 + C1 | Host 3 + C2 | Host 3 + RM3 |
|---|---|---|---|
| | | Residual RM/% | |
| 0 | 0.3 | 0.3 | 0.3 |
| 5 | 0.279 | 0.145 | 0.053 |
| 10 | 0.188 | 0.054 | 0.015 |

As can be seen from Table 5, significantly more rapid and complete polymerisation is achieved in PSA displays containing a polymerisable mixture with RM3 according to the present invention, compared to PSA displays containing a polymerisable mixture with monomer C1 or C2.

TABLE 6

Tilt angles

| UV-Time/min | Host 3 + C1 | Host 3 + C2 | Host 3 + RM3 |
|---|---|---|---|
| | | Pretilt Angle/° | |
| 0 | 89.8 | 89.6 | 89.8 |
| 2 | 89.7 | 86.4 | 75.7 |
| 6 | 83.8 | 80.4 | 69.4 |

As can be seen from Table 6, a small tilt angle after polymerisation is achieved quickly in PSA displays containing a polymerisable mixture with RM3 according to the present invention, which is smaller than in a PSA display containing a polymerisable mixture with monomer C1 or C2.

For measuring the solubility, RM1 to RM4, respectively, and monomer C1 of prior art are each dissolved at various concentrations from 0.3 to 3.0% by weight in the commercially available nematic LC mixture MJ011412 (Merck Japan Ltd.). The samples are stored for 1000h at room temperature and checked if they remain a homogeneous solution. Afterwards the samples are centrifugated and filtrated, and the residual monomer concentration in the supernatant liquid is determined.

Maximum residual monomer concentration after 1000h at RT:
C1: 0.46%
RM1: 1.0%
RM2: 1.0%
RM3: 1.0%
RM4: 1.0%

It can be seen that RM1 to RM4 according to the present invention have better solubility in the LC host mixture than monomer C1 of prior art.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosures of all applications, patents and publications, cited herein and of corresponding EP application No. 14002646.9, filed Jul. 30, 2014, are incorporated by reference herein.

The invention claimed is:
1. A compound of formula I

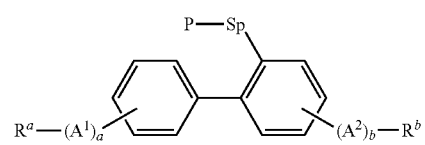

in which
- $A^1$, $A^2$ denote, independently of each other, aryl or heteroaryl having 4 to 30 ring atoms, which is mono- or polycyclic and is optionally substituted,
- $R^a$, $R^b$ denote, independently of each other, P-Sp-, H, F, Cl, CN, or straight chain, branched or cyclic alkyl having 1 to 25 C atoms, wherein one or more non-adjacent $CH_2$-groups are optionally replaced by —O—, —S—, —CO—, —CO—O—, —O—CO—, or —O—CO—O— in such a manner that O- and/or S-atoms are not directly connected with each other, and wherein one or more H atoms are each optionally replaced by F, Cl or P-Sp-,
- Sp denotes, on each occurrence identically or differently, a spacer group or a single bond,
- P denotes, on each occurrence identically or differently, a polymerisable group selected from the group consisting of $CH_2$=$CW^1$—CO—O—, $CH_2$=CH—O—, $(CH_2$=CH$)_2$CH—O—CO—, $(CH_2$=CH$)_2$CH—O—,

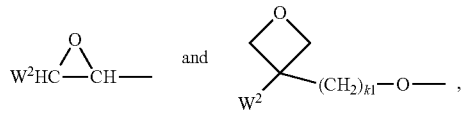

- $W^1$ denotes H, F, Cl or $CH_3$,
- $W^2$ denotes H or alkyl having 1 to 5 C atoms,
- $k_1$ denotes 0 or 1, and
- a, b denote, independently of each other, 0, 1 or 2,
- wherein all the benzene groups in the compound of formula I are optionally substituted by one or two groups L,
- wherein
- L denotes P—, P-Sp-, F, Cl, —CN, —$NO_2$, —NCO, —NCS, —OCN, —SCN, —C(=O)N($R^x)_2$, —C(=O)$Y^1$, —C(=O)$R^x$, —N($R^x)_2$, optionally substituted silyl, optionally substituted aryl or heteroaryl having 5 to 20 ring atoms, or straight-chain or branched alkyl having 1 to 25 C atoms, in which one or more non-adjacent $CH_2$ groups are optionally each replaced, independently of one another, b —C($R^0$)=C($R^{00}$)—, —C≡C—, —N($R^0$)—, —O—, —S—, —CO—, —CO—O—, —O—CO—, or —O—CO—O— in such a way that O and/or S atoms are not linked directly to one another, and in which one or more H atoms are optionally replaced by F, Cl, CN, P— or P-Sp-,
- $R^x$ denotes H, F, Cl, CN, or a straight chain, branched or cyclic alkyl having 1 to 25 C atoms, wherein one or more non-adjacent $CH_2$-groups are optionally replaced by —O—, —S—, —CO—, —CO—O—, —O—CO—, or —O—CO—O— in such a manner that O- and/or S-atoms are not directly connected with each other, and wherein one or more H atoms are each optionally replaced by F, Cl, P— or P-Sp-,
- $R^0$ and $R^{00}$ each, independently of one another, denote H or alkyl having 1 to 20 C atoms, and
- $Y^1$ is halogen,
- which compound of formula I contains exactly three polymerizable groups.

2. The compound of claim 1, wherein $A^1$ and $A^2$ are each independently benzene or naphthalene, wherein each benzene is independently optionally substituted by one or two groups L, and each naphthalene is independently optionally substituted by one or more groups L, wherein
- L denotes P—, P-Sp-, F, Cl, —CN, —$NO_2$, —NCO, —NCS, —OCN, —SCN, —C(=O)N($R^x)_2$, —C(=O)$Y^1$, —C(=O)$R^x$, —N($R^x)_2$, optionally substituted silyl, optionally substituted aryl or heteroaryl having 5 to 20 ring atoms, or straight-chain or branched alkyl having 1 to 25 C atoms, in which one or more non-adjacent $CH_2$ groups are optionally each replaced, independently of one another, by —C($R^0$)=C($R^{00}$)—, —C≡C—, —N($R^0$)—, —O—, —S—, —CO—, —CO—O—, —O—CO—, or —O—CO—O— in such a way that O and/or S atoms are not linked directly to one another, and in which one or more H atoms are optionally replaced by F, Cl, CN, P— or P-Sp-,
- $R^x$ denotes H, F, Cl, CN, or a straight chain, branched or cyclic alkyl having 1 to 25 C atoms, wherein one or more non-adjacent $CH_2$-groups are optionally replaced by —O—, —S—, —CO—, —CO—O—, —O—CO—, or —O—CO—O— in such a manner that O- and/or S-atoms are not directly connected with each other, and wherein one or more H atoms are each optionally replaced by F, Cl, P— or P-Sp-,
- $R^0$ and $R^{00}$ each, independently of one another, denote H or alkyl having 1 to 20 C atoms, and
- $Y^1$ is halogen.

3. The compound of claim 1, which is one of the following formulae

I1
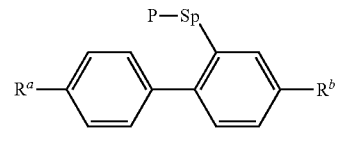

I2
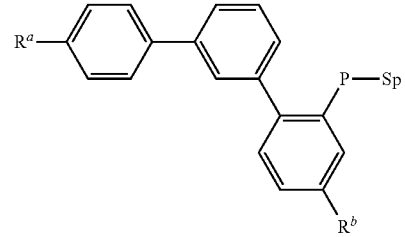

I3
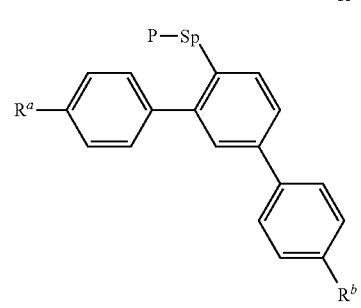

I4
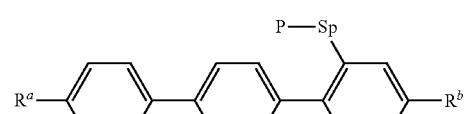

I5
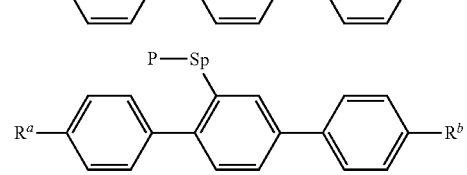

wherein $R^a$, $R^b$, P and Sp are as defined for the compound of formula I, and the benzene rings are optionally substituted by one or two groups L, wherein
L denotes P—, P-Sp-, F, Cl, —CN, —NO$_2$, —NCO, —NCS, —OCN, —SCN, —C(=O)N(R$^x$)$_2$, —C(=O)Y$^1$, —C(=O)R$^x$, —N(R$^x$)$_2$, optionally substituted silyl, optionally substituted aryl or heteroaryl having 5 to 20 ring atoms, or straight-chain or branched alkyl having 1 to 25 C atoms, in which one or more non-adjacent CH$_2$ groups are optionally each replaced, independently of one another, by —C(R$^0$)=C(R$^{00}$)—, —C≡C—, —N(R$^0$)—, —O—, —S—, —CO—, —CO—O—, —O—CO—, or —O—CO—O— in such a way that O and/or S atoms are not linked directly to one another, and in which one or more H atoms are optionally replaced by F, Cl, CN, P— or P-Sp-, R$^x$ denotes H, F, Cl, CN, or a straight chain, branched or cyclic alkyl having 1 to 25 C atoms, wherein one or more non-adjacent CH$_2$-groups are optionally replaced by —O—, —S—, —CO—, —CO—O—, —O—CO—, or —O—CO—O— in such a manner that O- and/or S-atoms are not directly connected with each other, and wherein one or more H atoms are each optionally replaced by F, Cl, P— or P-Sp-, R$^0$ and R$^{00}$ each, independently of one another, denote H or alkyl having 1 to 20 C atoms, and Y$^1$ is halogen.

4. The compound of claim 1, which is one of the following formulae

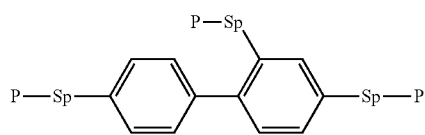

I1a

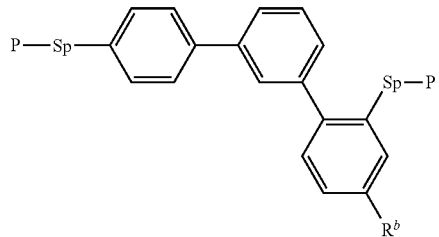

I2a

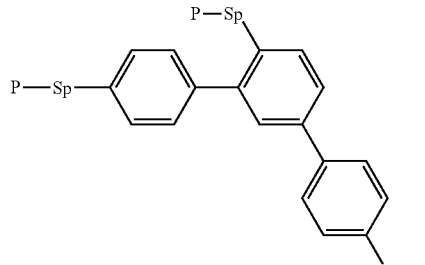

I3a

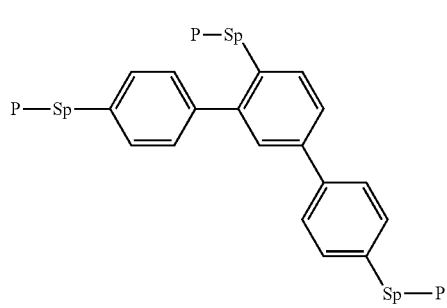

I3a

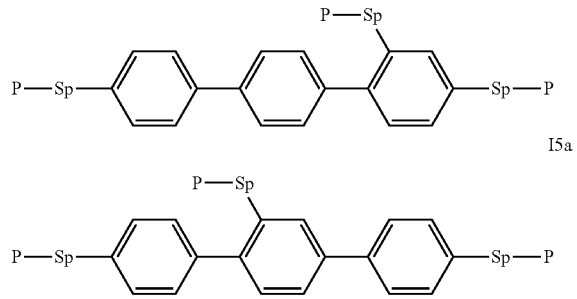

I4a

I5a wherein P and Sp are as defined for the compound of formula I, and the benzene rings are optionally substituted by one or two groups L, wherein
L denotes P—, P-Sp-, F, Cl, —CN, —NO$_2$, —NCO, —NCS, —OCN, —SCN, —C(=O)N(R$^x$)$_2$, —C(=O)Y$^1$, —C(=O)R$^x$, —N(R$^x$)$_2$, optionally substituted silyl, optionally substituted aryl or heteroaryl having 5 to 20 ring atoms, or straight-chain or branched alkyl having 1 to 25 C atoms, in which one or more non-adjacent CH$_2$ groups are optionally each replaced, independently of one another, by —C(R$^0$)=C(R$^{00}$)—, —C≡C—, —N(R$^0$)—, —O—, —S—, —CO—, —CO—O—, —O—CO—, or —O—CO—O— in such a way that O and/or S atoms are not linked directly to one another, and in which one or more H atoms are optionally replaced by F, Cl, CN, P— or P-Sp-, R$^x$ denotes H, F, Cl, CN, or a straight chain, branched or cyclic alkyl having 1 to 25 C atoms, wherein one or more non-adjacent CH$_2$-groups are optionally replaced by —O—, —S—, —CO—, —CO—O—, —O—CO—, or —O—CO—O— in such a manner that O- and/or S-atoms are not directly connected with each other, and wherein one or more H atoms are each optionally replaced by F, Cl, P— or P-Sp-, R$^0$ and R$^{00}$ each, independently of one another, denote H or alkyl having 1 to 20 C atoms, and Y$^1$ is halogen.

5. The compound of claim 1, which is one of the following formulae

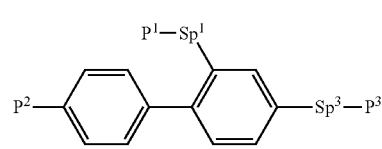

I1a1

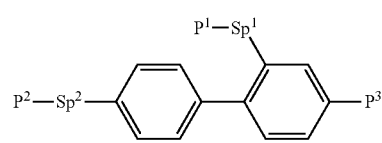

I1a2

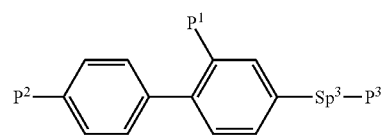

I1a3

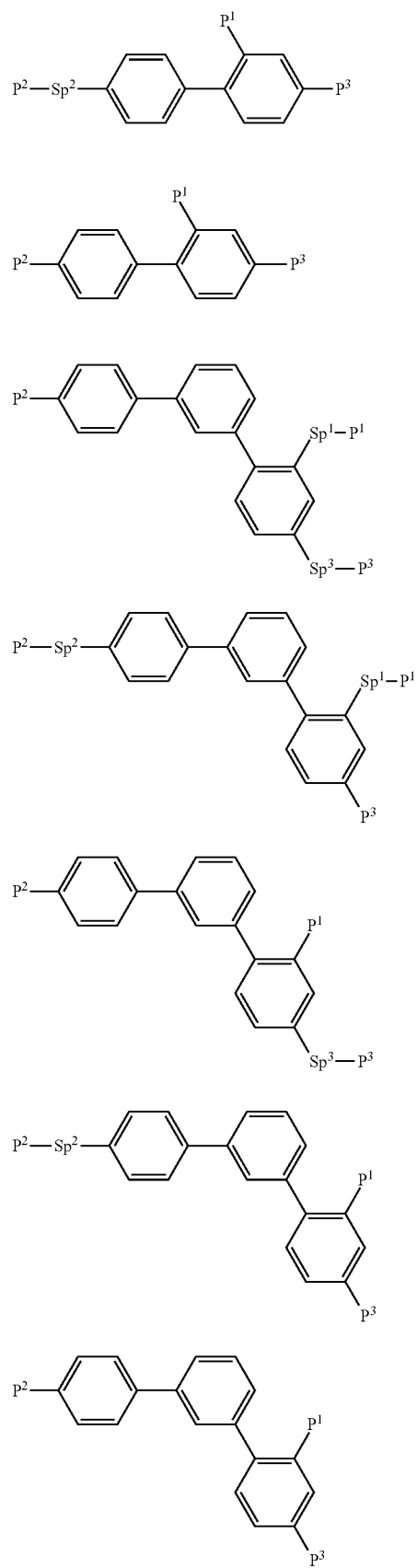
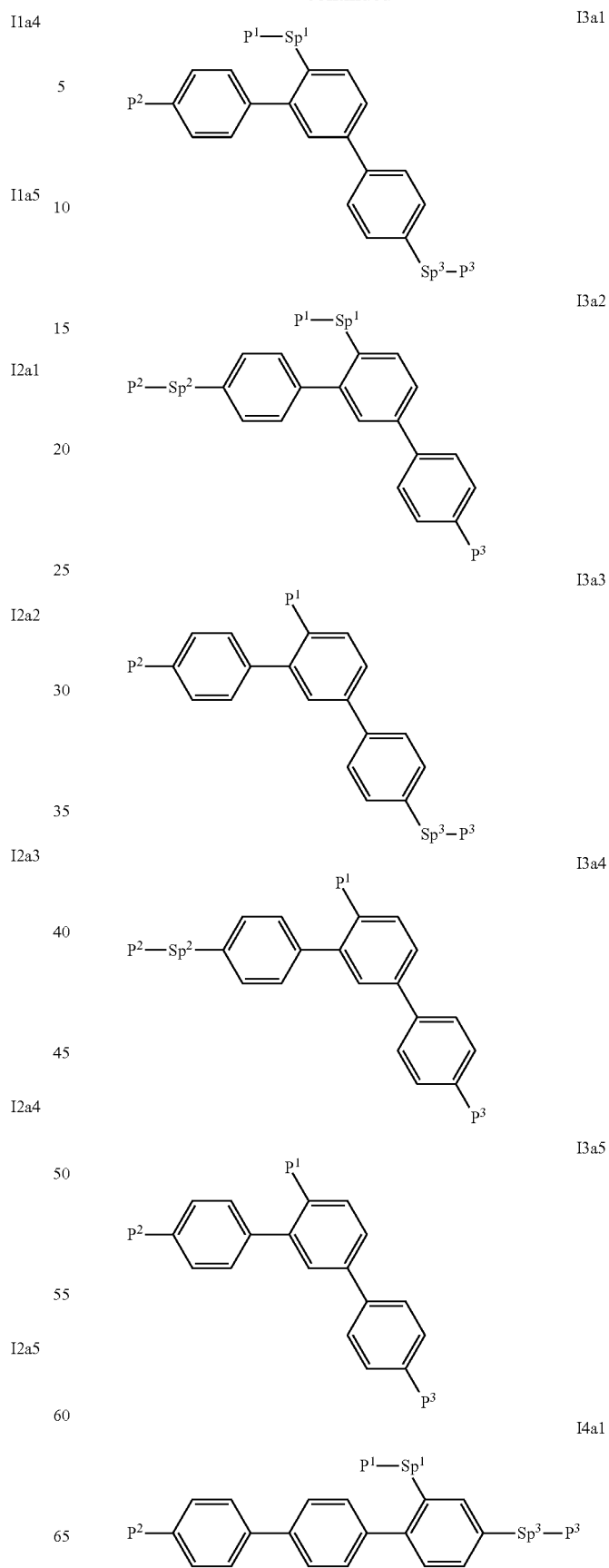

-continued

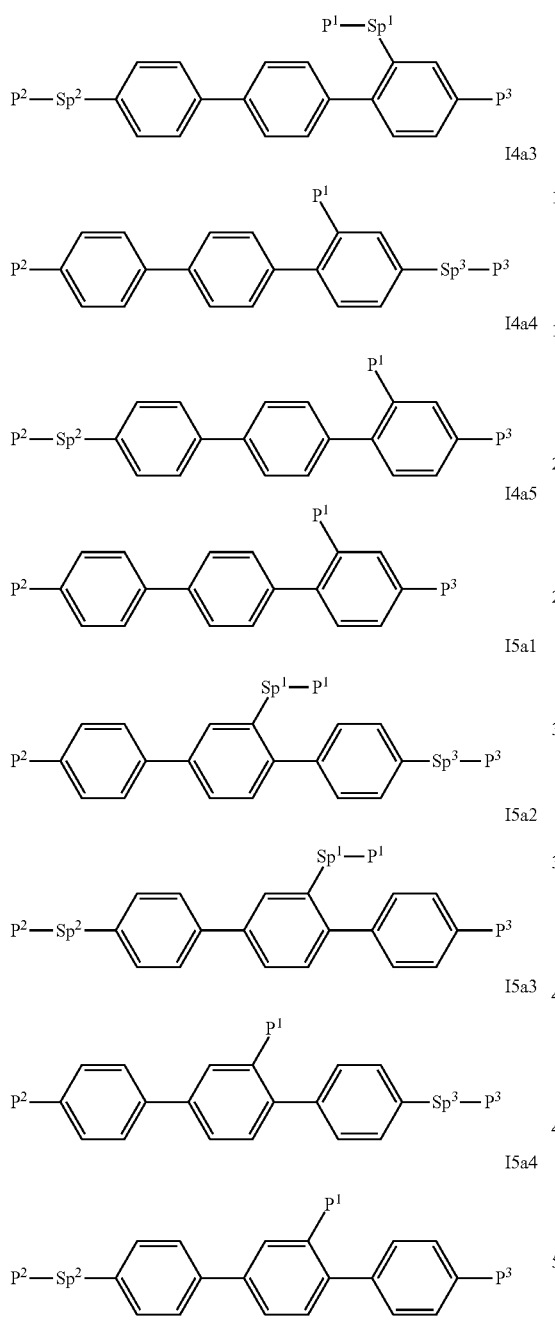

wherein P$^1$, P$^2$ and P$^3$ independently of each other have one of the meanings given for P for the compound of formula I, and Sp$^1$, Sp$^2$ and Sp$^3$ independently of each other have one of the meanings given for Sp for the compound of formula I which is different from a single bond.

6. A liquid crystal (LC) medium comprising one or more polymerisable compounds of formula I of claim 1.

7. The LC medium of claim 6, comprising
 a polymerisable component A) comprising one or more polymerisable compounds of formula I, and
 a liquid-crystalline LC component B) comprising one or more mesogenic or liquid-crystalline compounds.

8. The LC medium of claim 6, comprising one or more compounds of formulae CY and/or PY

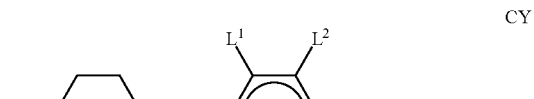

wherein
a denotes 1 or 2,
b denotes 0 or 1,

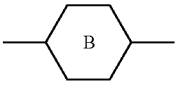

denotes

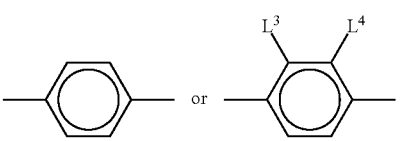

R$^1$ and R$^2$ each, independently of one another, denote alkyl having 1 to 12 C atoms, in which one or two non-adjacent CH$_2$ groups are optionally replaced by —O—, —CH=CH—, —CO—, —O—CO— or —CO—O— in such a way that O atoms are not linked directly to one another, Z$^x$
 denotes —CH=CH—, —CH$_2$O—, —OCH$_2$—, —OCF$_2$—, —O—, —CH$_2$—, —CH$_2$CH$_2$— or a single bond, and L$^{1-4}$ each, independently of one another, denote F, Cl, OCF$_3$, CF$_3$, CH$_3$, CH$_2$F, or CHF$_2$.

9. The LC medium of claim 7, comprising one or more compounds of the following formulae

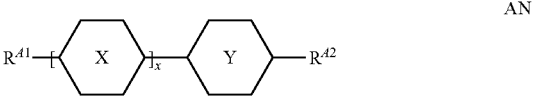

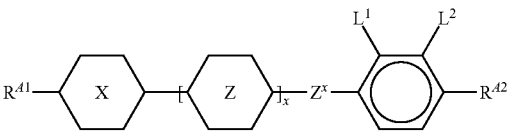

in which

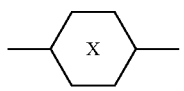

is each, on each occurrence identically or differently, and independently of one another,

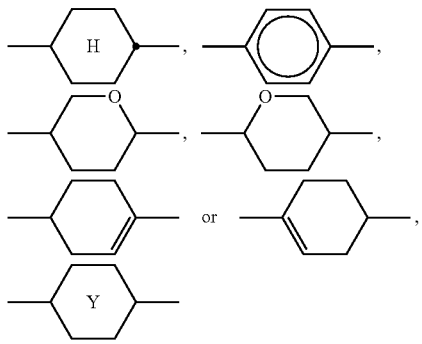

is each, on each occurrence identically or differently, and independently of one another,

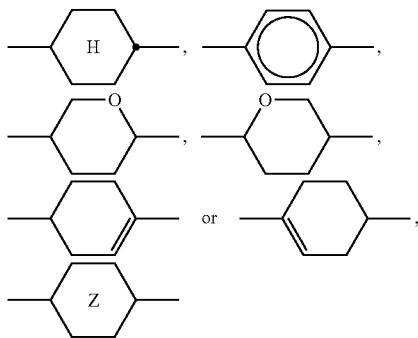

is each, on each occurrence identically or differently, and independently of one another,

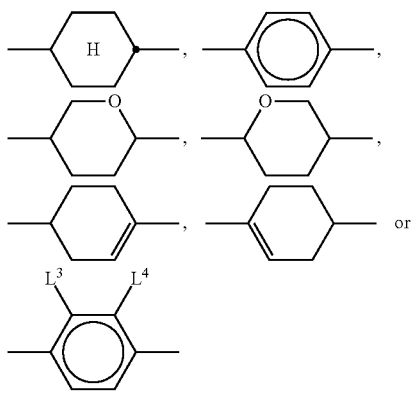

$R^{41}$ is each, on each occurrence identically or differently, and independently of one another, alkenyl having 2 to 9 C atoms or, if at least one of the rings X, Y and Z denotes cyclohexenyl, also has one of the meanings of $R^{42}$, $R^{42}$ is each, on each occurrence identically or differently, and independently of one another, alkyl having 1 to 12 C atoms, in which one or two non-adjacent $CH_2$ groups are optionally replaced by —O—, —CH=CH—, —CO—, —OCO— or —COO— in such a way that O atoms are not linked directly to one another, $Z^x$ —$CH_2CH_2$—, —CH=CH—, —$CF_2O$—, —$OCF_2$—, —$CH_2O$—, —$OCH_2$—, —CO—O—, —O—CO—, —$C_2F_4$—, —CF=CF—, —CH=CH—$CH_2O$—, or a single bond, $L^{1-4}$ each, independently of one another, H, F, Cl, $OCF_3$, $CF_3$, $CH_3$, $CH_2F$ or $CHF_2H$, x 1 or 2, z 0 or 1.

10. The LC medium of claim 6, comprising one or more compounds of the following formula

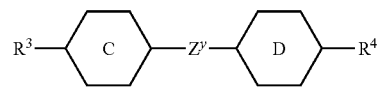

ZK in which

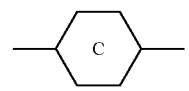

denotes

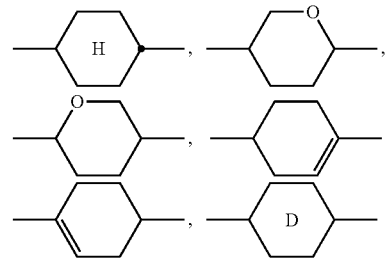

denotes

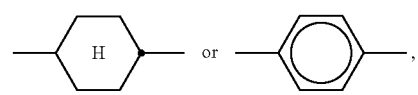

$R^3$ and $R^4$ each, independently of one another, denote alkyl having 1 to 12 C atoms, in which one or two non-adjacent $CH_2$ groups are optionally replaced by —O—, —CH=CH—, —CO—, —O—CO— or —CO—O— in such a way that O atoms are not linked directly to one another, $Z^y$ denotes —$CH_2CH_2$—, —CH=CH—, —$CF_2O$—, —$OCF_2$—, —$CH_2O$—, —O $CH_2$—, —COO—, —OCO—, —$C_2F_4$—, —CF=CF— or a single bond.

11. The LC medium of claim 6, in which the one or more polymerisable compounds of formula I are polymerised.

12. An LC display comprising one or more compounds of formula I of claim 1.

13. The LC display of claim 12, which is a PSA type display.

14. The LC display of claim 13, which is a PS-VA, PS-OCB, PS-IPS, PS-FFS, PS-UB-FFS, PS-posi-VA or PS-TN display.

15. The LC display of claim 13, comprising two substrates, at least one which is transparent to light, an electrode provided on each substrate or two electrodes provided on only one of the substrates, and located between the substrates a layer of an LC medium, which comprises one or more polymerisable compounds of formula I, wherein the polymerisable compounds are polymerised between the substrates of the display.

16. A process for the production of an LC display according to claim 15, comprising filling or otherwise providing an LC medium, which comprises one or more polymerisable compounds of formula I, between the substrates of the display, and polymerising the polymerisable compounds.

17. A compound of formula II

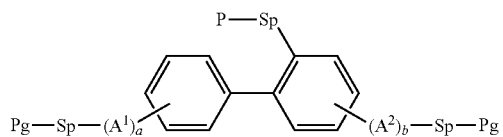

wherein $A^1$, $A^2$ denote, independently of each other, aryl or heteroaryl having 4 to 30 ring atoms, which is mono- or polycyclic and is optionally substituted, Sp denotes, on each occurrence identically or differently, a spacer group or a single bond, P denotes, on each occurrence identically or differently, a polymerisable group selected from the group consisting of $CH_2=CW^1-CO-O-$, $CH_2=CH-O-$, $(CH_2=CH)_2CH-O-CO-$, $(CH_2=CH)_2CH-O-$,

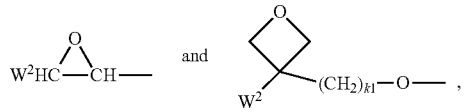

$W^1$ denotes H, F, Cl, CN, $CF_3$, phenyl or alkyl having 1 to 5 C atoms, $W^2$ denotes H or alkyl having 1 to 5 C atoms, $k_1$ denotes 0 or 1, and a, b denote, independently of each other, 0, 1 or 2, and Pg denotes OH, a protected hydroxyl group or a masked hydroxyl group.

18. A process for preparing a compound of formula I of claim 1, wherein P optionally denotes acrylate or methacrylate, comprising esterifying a compound of formula II

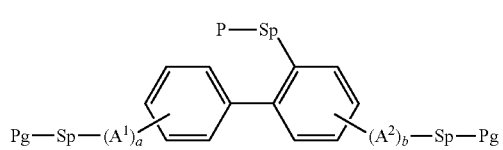

wherein $A^1$, $A^2$ denote, independently of each other, aryl or heteroaryl having 4 to 30 ring atoms, which is mono- or polycyclic and is optionally substituted, Sp denotes, on each occurrence identically or differently, a spacer group or a single bond, P denotes, on each occurrence identically or differently, a polymerisable group selected from the group consisting of $CH_2=CW^1-CO-O-$, $CH_2=CH-O-$, $(CH_2=CH)_2CH-O-CO-$, $(CH_2=CH)_2CH-O-$,

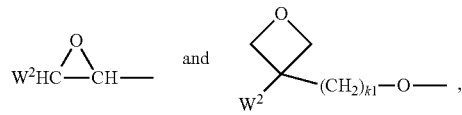

$W^1$ denotes H, F, Cl or $CH_3$, $W^2$ denotes H or alkyl having 1 to 5 C atoms, $k_1$ denotes 0 or 1, and a, b denote, independently of each other, 0, 1 or 2, and Pg denotes OH, by a corresponding acid, acid derivative, or halogenated compound containing a group P, in the presence of a dehydrating reagent.

19. A process of preparing an LC medium of claim 6, comprising mixing together one or more mesogenic or liquid-crystalline compounds, or a liquid-crystalline component B) which comprises one or more mesogenic or liquid-crystalline compounds, with one or more compounds of formula I, and optionally with further liquid-crystalline compounds and/or additives.

20. The compound of claim 1, wherein P denotes acrylate or methacrylate.

21. The compound of claim 1, wherein

Sp denotes a single bond or $-(CH_2)_{p1}-$, $-(CH_2CH_2O)_{q1}-CH_2CH_2-$, $-CH_2CH_2-S-CH_2CH_2-$, $-CH_2CH_2-NH-CH_2CH_2-$ or $-(SiR^0R^{00}-O)_{p1}-$, in which p1 is an integer from 1 to 12, q1 is an integer from 1 to 3, and $R^0$ and $R^{00}$ each, independently of one another, denote H or alkyl having 1 to 20 C atoms, and $A^1$ and $A^2$ are each independently benzene or naphthalene, wherein each benzene is independently optionally substituted by one or two groups L, and each naphthalene is independently optionally substituted by one or more groups L, and one of the benzene groups in formula I selected from the group consisting of the benzene group to which $R^a-(A^1)_a-$ is bonded and the benzene group to which $R^b-(A^2)_b-$ is bonded is optionally substituted by one or two groups L.

22. The compound of claim 21, wherein at least one benzene ring selected from the group consisting of the benzene group to which $R^a-(A^1)_a-$ is bonded, the benzene group to which $R^b-(A^2)_b-$ is bonded, the benzene group present as $A^1$ and the benzene group present as $A^2$ is substituted by one or two groups L, which L is F, Cl, $-CN$, a straight-chain or branched alkyl having 1 to 25 C atoms, in which one or more non-adjacent $CH_2$ groups are each optionally replaced, independently of one another, by $-C(R^{00})=C(R^{000})-$, $-C\equiv C-$, $-N(R^{00})-$, $-O-$, $-S-$, $-CO-$, $-CO-O-$, $-O-CO-$, or $-O-CO-O-$ in such a way that O and/or S atoms are not linked directly to one another, and in which one or more H atoms are optionally replaced by F, Cl, Br, I or CN.

23. The compound of claim 1, wherein each of the benzene groups in the compound of formula I that are substituted by one or two groups L are of the following formula

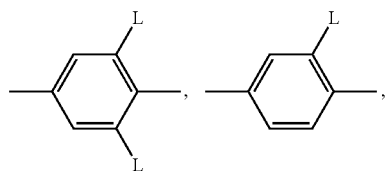

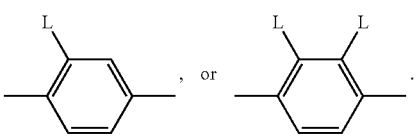

24. The compound of claim 1, which is one of the following compounds

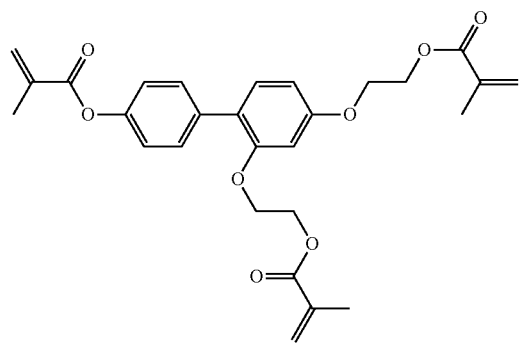

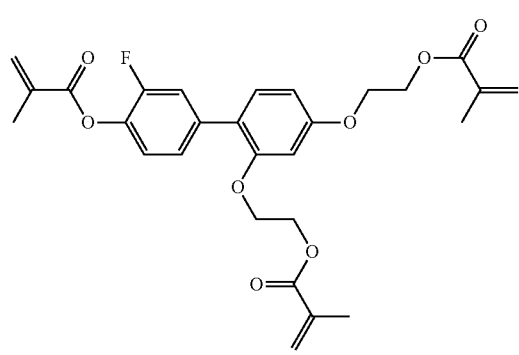

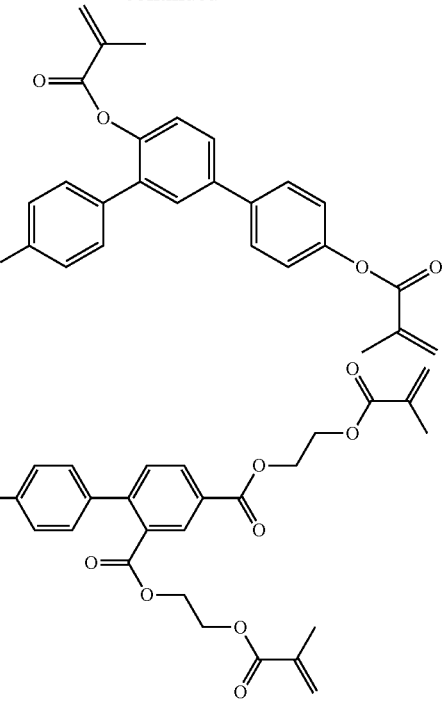

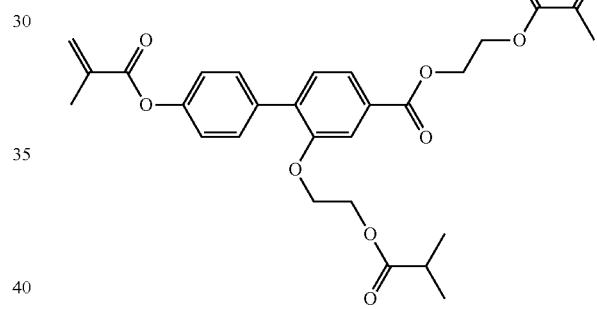

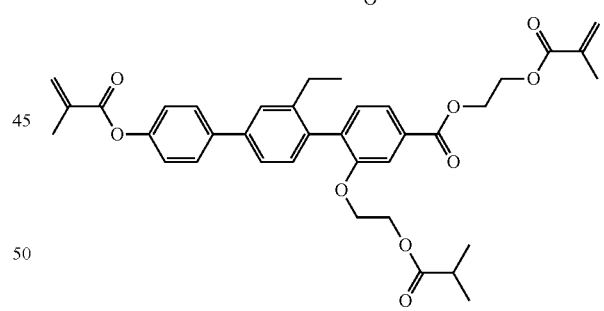

25. The compound of claim 1, wherein none of the benzene groups in the compound of formula I are substituted by a L.

* * * * *